(12) United States Patent
Yoakim et al.

(10) Patent No.: US 8,338,441 B2
(45) Date of Patent: Dec. 25, 2012

(54) INHIBITORS OF HUMAN IMMUNODEFICIENCY VIRUS REPLICATION

(75) Inventors: Christiane Yoakim, Laval (CA); Murray Bailey, Pierrefonds (CA); Francois Bilodeau, Laval (CA); Rebekah Carson, Mascouche (CA); Lee Fader, St-Lazare (CA); Stephen Kawai, Côte St-Luc (CA); Sebastien Morin, Montreal (CA); Carl Thibeault, Mascouche (CA); Bruno Simoneau, Laval (CA); Simon Surprenant, Laval (CA); Youla Tsantrizos, Montreal (CA); Steven Laplante, Laval (CA)

(73) Assignee: Gilead Sciences, Inc., Foster City, CA (US)

( * ) Notice: Subject to any disclaimer, the term of this patent is extended or adjusted under 35 U.S.C. 154(b) by 164 days.

(21) Appl. No.: 12/777,406

(22) Filed: May 11, 2010

(65) Prior Publication Data

US 2010/0292227 A1 Nov. 18, 2010

Related U.S. Application Data

(60) Provisional application No. 61/178,551, filed on May 15, 2009, provisional application No. 61/285,766, filed on Dec. 11, 2009.

(51) Int. Cl.
*A01N 43/40* (2006.01)
*A61K 31/435* (2006.01)

(52) U.S. Cl. .................................. 514/277; 546/341
(58) Field of Classification Search .................. 546/341; 514/277

See application file for complete search history.

(56) References Cited

U.S. PATENT DOCUMENTS

2006/0106070 A1* 5/2006 Rajagopalan et al. ........ 514/344

FOREIGN PATENT DOCUMENTS

| CA | 2262252 A1 | 8/1999 |
| WO | WO-2007131350 A1 | 11/2007 |
| WO | WO-2009062285 A1 | 5/2009 |
| WO | WO-2010130034 A1 | 11/2010 |

OTHER PUBLICATIONS

D.C. Montefiori, Current Protocols in Immunology,, 12.11.1-12.11.17 (2004).*
Doi, F. et al. (2004) "Synthesis of Chroman Derivatives by the Ring Expansion Reaction of Spirodienones, and an Assessment of their Plant Growth Inhibition," *Bulletin of the Chemical Society of Japan*, 77(12):2257-2263.
Kato, T. et al. (1978) "Studies on Ketene and Its Derivatives (XC). Reaction of Diketene with Ethyl Cyanoacetate and Malononitrile," *Heterocycles*, 9(7):841-844.
International Search Report for PCT/CA2010/000707, mailed Aug. 11, 2010, 5 pages.
International Written Opinion for PCT/CA2010/000707, mailed Aug. 11, 2010, 5 pages.
International Preliminary Report on Patentability for PCT/CA2010/000707, issued Nov. 15, 2011, 6 pages.
Michel, P. et al. (2003) "Synthesis of Enantiomers of Butane-1,2-diacetal-Protected Glyceraldehyde and of (R,R)-Butane-1,2-diacetal-Protected Glycolic Acid," *Synthesis*, 10:1598-1602.
Montefiori, D.C. (2004) "Evaluating Neutralizing Antibodies Against HIV, SIV, and SHIV in Luciferase Reporter Gene Assays," *Current Protocols in Immunology*, 12(11):1-17.
Nicolaou, K.C. et al. (1980) "Carbocyclic thromboxane A2," *Journal of the American Chemical Society*, 102(4):1404-1409.
Salahuddin, S. Z. et al. (1983) "Restricted expression of human T-cell leukemia-lymphoma virus (HTLV) in Transformed human umbilical cord blood lymphocytes," *Virology*, 129(1):51-64.
Sheradsky, T. et al. (1972) "Introduction of the aminooxy group on to nitroaromatic and heterocyclic rings: Synthesis and properties of O-(nitroaryl)hydroxylamines," *Tetrahedron*, 28(14):3833-3843.

* cited by examiner

Primary Examiner — James O Wilson
Assistant Examiner — Alexander R Pagano
(74) Attorney, Agent, or Firm — Allan Kutzenco

(57) ABSTRACT

Compounds of formula I:

wherein a, $R^1$, $R^2$, $R^3$, $R^4$, $R^5$ and $R^6$ are defined herein, are useful as inhibitors of HIV replication.

12 Claims, No Drawings

SEQUENCE LISTING

<160> NUMBER OF SEQ ID NOS: 1

<210> SEQ ID NO 1
<211> LENGTH: 288
<212> TYPE: PRT
<213> ORGANISM: Human immunodeficiency virus
<220> FEATURE:
<223> OTHER INFORMATION: NL4.3 strain

<400> SEQUENCE: 1

Phe Leu Asp Gly Ile Asp Lys Ala Gln Glu Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Val His Thr Asp Asn Gly Ser Asn Phe Thr Ser Thr Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Ile Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

-continued

```
Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
        210                 215                 220

Val Tyr Tyr Arg Asp Ser Arg Asp Pro Val Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
                260                 265                 270

Lys Gln Met Ala Gly Asp Asp Cys Val Ala Ser Arg Gln Asp Glu Asp
        275                 280                 285
```

INHIBITORS OF HUMAN IMMUNODEFICIENCY VIRUS REPLICATION

RELATED APPLICATIONS

This application claims benefit of U.S. Ser. No. 61/178,551, filed May 15, 2009, and U.S. Ser. No. 61/285,766, filed Dec. 11, 2009, which are herein incorporated by reference.

SEQUENCE LISTING

The instant application contains a Sequence Listing which has been submitted via EFS-Web and is hereby incorporated by reference in its entirety. Said ASCII copy, created on Jun. 1, 2010, is named 13-0157.txt, and is 3,141 bytes in size.

FIELD OF THE INVENTION

The present invention relates to compounds, compositions and methods for the treatment of human immunodeficiency virus (HIV) infection. In particular, the present invention provides novel inhibitors of the HIV integrase enzyme, pharmaceutical compositions containing such compounds and methods for using these compounds to reduce HIV replication and in the treatment of HIV infection.

BACKGROUND OF THE INVENTION

Acquired immune deficiency syndrome (AIDS) is caused by the human immunodeficiency virus (HIV), particularly the HIV-1 strain. Most currently approved therapies for HIV infection target the viral reverse transcriptase and protease enzymes. There are also two approved drugs targeting HIV entry and one approved drug targeting the integrase enzyme. Within the reverse transcriptase inhibitor and protease inhibitor classes, resistance of HIV to existing drugs is a problem. Therefore, it is important to discover and develop new antiretroviral compounds.

International patent application WO 2007/131350 and United States published patent application US 2006/0106070 describe compounds which are active against HIV replication.

SUMMARY OF THE INVENTION

The present invention provides a novel series of compounds having inhibitory activity against HIV replication. Therefore, the compounds of the invention may be used to inhibit the activity of HIV integrase and may be used to reduce HIV replication.

One aspect of the invention provides a compound of Formula I and a racemate, enantiomer or diastereomer of a compound of formula (I):

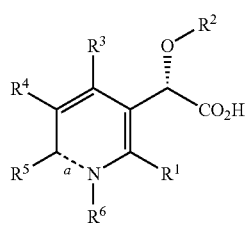

(I)

wherein $R^1$ is $(C_{1-6})$alkyl, $(C_{2-6})$alkenyl or $(C_{3-6})$cycloalkyl, wherein the $(C_{1-6})$alkyl is optionally substituted with —$O(C_{1-6})$alkyl or —$S(C_{1-6})$alkyl;

$R^2$ is $(C_{1-8})$alkyl or $(C_{3-8})$cycloalkyl, wherein the $(C_{3-8})$cycloalkyl is optionally substituted with $(C_{1-6})$alkyl;

$R^3$ is aryl, wherein the aryl is optionally fused to one or more cycles, at least one of which is a heterocycle, to form a heteropolycycle, and wherein the aryl or heteropolycycle is optionally substituted with 1 to 4 substituents each independently selected from $(C_{1-6})$alkyl, halo and —$O(C_{1-6})$alkyl;

$R^4$ is $(C_{1-6})$alkyl, —CN, halo, $(C_{1-6})$haloalkyl, $(C_{3-5})$cycloalkyl, or —$O(C_{1-6})$alkyl; and a is a double bond, $R^6$ is absent and $R^5$ is $R^{51}$ or —$(C_{1-3})$alkyl-$R^{51}$; or a is a single bond and $R^5$ and $R^6$ are joined, together with the atoms to which they are bonded, to form a 5-membered ring optionally having 1 to 3 further heteroatoms each independently selected from O, N and S, wherein the 5-membered ring is optionally substituted with 1 to 3 $R^{51}$ substituents;

wherein $R^{51}$ is in each case independently selected from $R^{52}$, —$OR^{53}$, —$N(R^{54})R^{53}$, —$C(\!=\!O)R^{52}$, —$C(\!=\!O)OR^{53}$, —$C(\!=\!O)N(R^{54})R^{53}$, —$OC(\!=\!O)N(R^{54})R^{53}$, —$N(R^{54})C(\!=\!O)R^{52}$, —$N(R^{54})C(\!=\!O)N(R^{54})R^{53}$ and —$N(R^{54})C(\!=\!O)OR^{53}$; wherein $R^{52}$ is in each case independently selected from $R^{53}$, $(C_{2-8})$alkenyl and $(C_{2-8})$alkynyl, $R^{53}$ is in each case independently selected from $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-, and $R^{54}$ is in each case independently selected from H and $(C_{1-3})$alkyl;

wherein each of $R^{52}$ and $R^{53}$ is optionally substituted with 1 to 3 substituents each independently selected from $R^{55}$, halo, —CN, —$OR^{56}$, —$SR^{56}$, —$SOR^{56}$, —$SO_2R^{56}$, —$N(R^{54})R^{56}$, —$N(R^{54})C(\!=\!O)R^{55}$, —$N(R^{54})C(\!=\!O)N(R^{54})R^{56}$, —$N(R^{54})C(\!=\!O)OR^{56}$, —$OC(\!=\!O)N(R^{54})R^{56}$, —$C(\!=\!O)R^{55}$, —$C(\!=\!O)OR^{56}$, and —$CON(R^{54})R^{56}$, wherein $R^{55}$ is in each case independently selected from $R^{56}$, $(C_{2-8})$alkenyl and $(C_{2-8})$alkynyl, and $R^{56}$ is in each case independently selected from H, $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-, wherein each of $R^{55}$ and $R^{56}$ is, where possible, in each case independently optionally substituted with 1 to 3 substituents each independently selected from $(C_{1-6})$alkyl, $(C_{1-6})$haloalkyl, halo, —OH, —$O(C_{1-6})$alkyl, —$NH_2$, —$NH(C_{1-6})$alkyl, —$N((C_{1-6})$alkyl$)_2$ and —$NH(C\!=\!O)(C_{1-6})$alkyl;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; or a salt thereof.

Another aspect of Formula (I) provides a compound of Formula II and a racemate, enantiomer or diastereomer of a compound of formula (II):

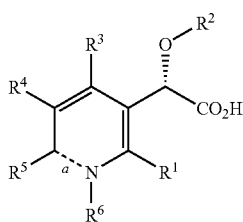

(II)

wherein
- R$^1$ is (C$_{1-6}$)alkyl, (C$_{2-6}$)alkenyl or (C$_{3-6}$)cycloalkyl, wherein the (C$_{1-6}$)alkyl is optionally substituted with —O(C$_{1-6}$)alkyl or —S(C$_{1-6}$)alkyl;
- R$^2$ is (C$_{1-8}$)alkyl or (C$_{3-8}$)cycloalkyl, wherein the (C$_{3-8}$)cycloalkyl is optionally substituted with (C$_{1-6}$)alkyl;
- R$^3$ is aryl, wherein the aryl is optionally fused to one or more cycles, at least one of which is a heterocycle, to form a heteropolycycle, and wherein the aryl or heteropolycycle is optionally substituted with 1 to 4 substituents each independently selected from (C$_{1-6}$)alkyl, halo and —O(C$_{1-6}$)alkyl;
- R$^4$ is (C$_{1-6}$)alkyl, —CN, halo, (C$_{1-6}$)haloalkyl, (C$_{3-5}$)cycloalkyl, or —O(C$_{1-6}$)alkyl; and
- a is a double bond, R$^6$ is absent and R$^5$ is R$^{51}$ or —(C$_{1-3}$)alkyl-R$^{51}$; or
- a is a single bond and R$^5$ and R$^6$ are joined, together with the atoms to which they are bonded, to form a 5-membered ring optionally having 1 to 3 further heteroatoms each independently selected from O, N and S, wherein the 5-membered ring is optionally substituted with 1 to 3 R$^{51}$ substituents;
- wherein R$^{51}$ is in each case independently selected from R$^{52}$, —OR$^{53}$, —N(R$^{54}$)R$^{53}$, —C(=O)R$^{52}$, —C(=O)OR$^{53}$, —C(=O)N(R$^{54}$)R$^{53}$, —OC(=O)N(R$^{54}$)R$^{53}$, —N(R$^{54}$)C(=O)R$^{52}$, —N(R$^{54}$)C(=O)N(R$^{54}$)R$^{53}$ and —N(R$^{54}$)C(=O)OR$^{53}$; wherein
  - R$^{52}$ is in each case independently selected from R$^{53}$, (C$_{2-8}$)alkenyl and (C$_{2-8}$)alkynyl,
  - R$^{53}$ is in each case independently selected from (C$_{1-8}$)alkyl, (C$_{3-8}$)cycloalkyl, (C$_{5-14}$)spirocycloalkyl, (C$_{3-8}$)cycloalkyl-(C$_{1-6}$)alkyl-, aryl, aryl-(C$_{1-6}$)alkyl-, Het, and Het-(C$_{1-6}$)alkyl-, and
  - R$^{54}$ is in each case independently selected from H and (C$_{1-3}$)alkyl;
- wherein each of R$^{52}$ and R$^{53}$ is optionally substituted with 1 to 3 substituents each independently selected from R$^{55}$, halo, —CN, —OR$^{56}$, —SR$^{56}$, —SOR$^{56}$, —SO$_2$R$^{56}$, —N(R$^{54}$)R$^{56}$, —N(R$^{54}$)C(=O)R$^{55}$, —N(R$^{54}$)C(=O)N(R$^{54}$)R$^{56}$, —N(R$^{54}$)C(=O)OR$^{56}$, —OC(=O)N(R$^{54}$)R$^{56}$, —C(=O)R$^{55}$, —C(=O)OR$^{56}$, and —CON(R$^{54}$)R$^{56}$, wherein
  - R$^{55}$ is in each case independently selected from R$^{56}$, (C$_{2-8}$)alkenyl and (C$_{2-8}$)alkynyl, and
  - R$^{56}$ is in each case independently selected from H, (C$_{1-8}$)alkyl, (C$_{3-8}$)cycloalkyl, (C$_{3-8}$)cycloalkyl-(C$_{1-6}$)alkyl-, aryl, aryl-(C$_{1-6}$)alkyl-, Het, and Het-(C$_{1-6}$)alkyl-,
    - wherein each of R$^{55}$ and R$^{56}$ is, where possible, in each case independently optionally substituted with 1 to 3 substituents each independently selected from (C$_{1-6}$)alkyl, (C$_{1-6}$)haloalkyl, halo, —OH, —O(C$_{1-6}$)alkyl, —NH$_2$, —NH(C$_{1-6}$)alkyl, —N((C$_{1-6}$)alkyl)$_2$ and —NH(C=O)(C$_{1-6}$)alkyl;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; or a salt thereof.

Another aspect of the invention provides one or more intermediates selected from the formulas:

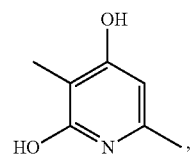

2c

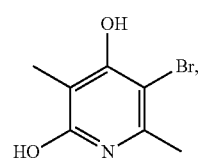

2d

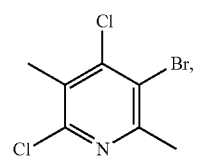

2e

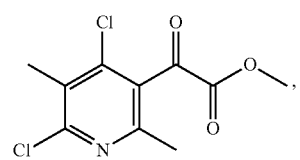

2f

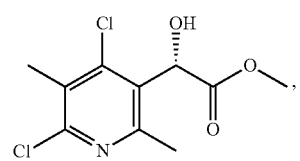

2g

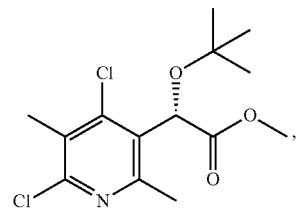

2h

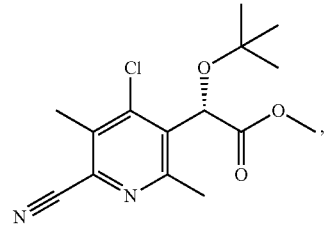

10a

-continued

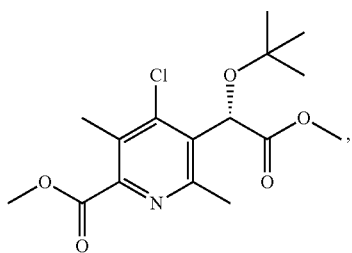
10b

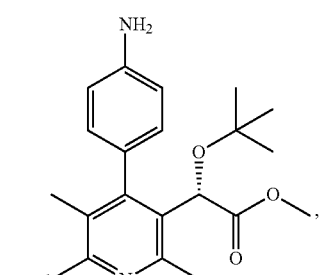
12a

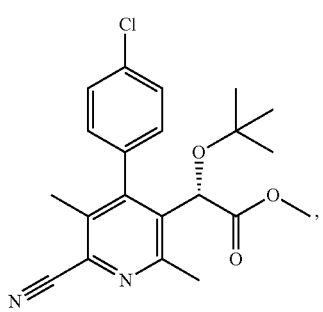
12b

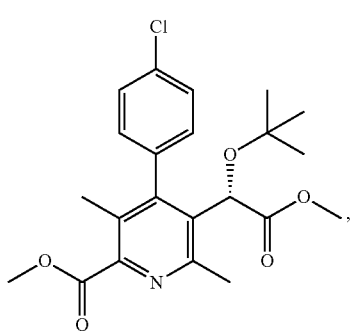
12c

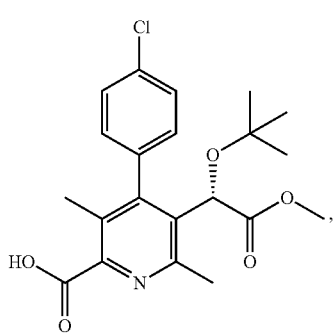
12d

-continued

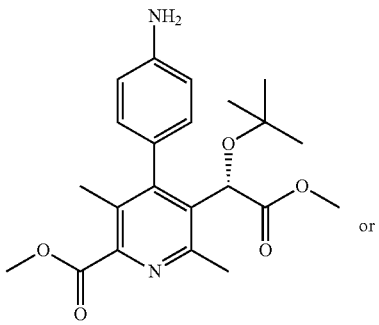
36a or

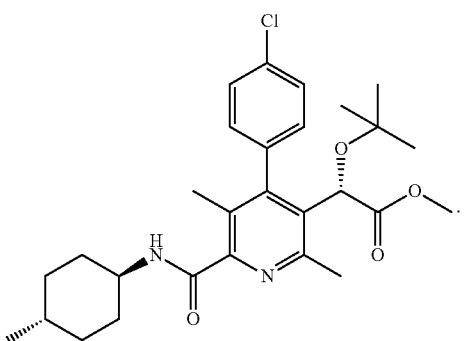
37a

Another aspect of this invention provides a compound of formula (I) or a pharmaceutically acceptable salt thereof, as a medicament.

Still another aspect of this invention provides a pharmaceutical composition comprising a therapeutically effective amount of a compound of formula (I) or a pharmaceutically acceptable salt thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of an HIV infection in a human being having or at risk of having the infection.

A further aspect of the invention involves a method of treating an HIV infection in a human being having or at risk of having the infection, the method comprising administering to the human being a therapeutically effective amount of a compound of formula (I), a pharmaceutically acceptable salt thereof, or a composition thereof as described hereinabove.

Another aspect of the invention involves a method of treating an HIV infection in a human being having or at risk of having the infection, the method comprising administering to the human being a therapeutically effective amount of a combination of a compound of formula (I) or a pharmaceutically acceptable salt thereof, and at least one other antiviral agent; or a composition thereof.

Also within the scope of this invention is the use of a compound of formula (I) as described herein, or a pharmaceutically acceptable salt thereof, for the treatment of an HIV infection in a human being having or at risk of having the infection.

Another aspect of this invention provides the use of a compound of formula (I) as described herein, or a pharmaceutically acceptable salt thereof, for the manufacture of a medicament for the treatment of an HIV infection in a human being having or at risk of having the infection.

An additional aspect of this invention refers to an article of manufacture comprising a composition effective to treat an HIV infection; and packaging material comprising a label which indicates that the composition can be used to treat infection by HIV; wherein the composition comprises a compound of formula (I) according to this invention or a pharmaceutically acceptable salt thereof.

Still another aspect of this invention relates to a method of inhibiting the replication of HIV comprising exposing the virus to an effective amount of the compound of formula (I), or a salt thereof, under conditions where replication of HIV is inhibited.

Further included in the scope of the invention is the use of a compound of formula (I) to inhibit the activity of the HIV integrase enzyme.

Further included in the scope of the invention is the use of a compound of formula (I), or a salt thereof, to inhibit the replication of HIV.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

Unless specifically indicated, throughout the specification and the appended claims, a given chemical formula or name shall encompass salts, including pharmaceutically acceptable salts thereof and solvates thereof, such as for instance hydrates, including solvates of the free compounds or solvates of a salt of the compound. For example, the compounds of the present invention can exist in unsolvated as well as solvated forms with pharmaceutically acceptable solvents such as water, ethanol and the like. In general, the solvated forms are considered equivalent to the unsolvated forms for the purpose of the present invention.

In one aspect the present invention also provides all pharmaceutically-acceptable isotopically labeled compounds of the present invention wherein one or more atoms are replaced by atoms having the same atomic number, but an atomic mass or mass number different from the atomic mass or mass number predominantly found in nature. Examples of isotopes suitable for inclusion in the compounds of the present invention include isotopes of hydrogen, for example 2H or 3H. Isotopically labeled compounds of the present invention, for example deuterated versions of the compounds, can be prepared by conventional techniques known to those skilled in the art or by synthetic processes analogous to those described in the present application using appropriate isotopically labeled reagents in place of the non-labeled reagent mentioned therein.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of $(C_{2-6})$alkenyl radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of $(C_{2-6})$alkynyl radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms. Examples of $(C_{3-7})$cycloalkyl radicals include, but are not limited to, cyclopropyl, cyclobutyl, cyclopentyl, cyclohexyl and cycloheptyl.

The term "$(C_{5-n})$spirocycloalkyl", wherein n is an integer, either alone or in combination with another radical, denotes a cycloalkyl multi-ring system having two rings linked by one common atom. Examples of $(C_{5-14})$spirocycloalkyl radicals include, but are not limited to,

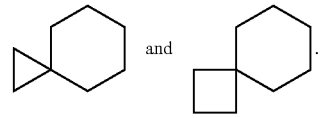

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise, such that the substitution would give rise to a chemically stable compound, such as are recognized by those skilled in the art.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-6})$alkyl- include, but are not limited to, phenylmethyl (benzyl), 1-phenylethyl, 2-phenylethyl and phenylpropyl. When an aryl-$(C_{1-n})$alkyl-group is substituted, it is understood that substituents may be attached to either the aryl or the alkyl portion thereof or both, unless specified otherwise, such that the substitution would give rise to a chemically stable compound, such as are recognized by those skilled in the art.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S, unless specified otherwise. When a Het group is substituted, it is understood that substituents may be attached to any carbon atom or heteroatom thereof which would otherwise bear a hydrogen atom, unless specified otherwise, such that the substitution would give rise to a chemically stable compound, such as are recognized by those skilled in the art.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-6})$alkyl-include, but are not limited to, thienylmethyl, furylmethyl, piperidinylethyl, 2-pyridinylmethyl, 3-pyridinylmethyl, 4-pyridinylmethyl, quinolinylpropyl, and the like. When an Het-$(C_{1-n})$alkyl- group is substituted, it is understood that substituents may be attached to either the Het or the alkyl portion thereof or both, unless specified otherwise, such that the substitution would give rise to a chemically stable compound, such as are recognized by those skilled in the art.

The term "heteroatom" as used herein is intended to mean O, S or N.

The term "carbocycle" as used herein, either alone or in combination with another radical, is intended to mean a 3- to 8-membered saturated, unsaturated or aromatic cyclic radical in which all of the ring members are carbon atoms, and which may be fused to one or more 3- to 8-membered saturated, unsaturated or aromatic carbocyclic groups. When a carbocycle is substituted, it is understood that substituents may be attached to any carbon atom which would otherwise bear a hydrogen atom, unless specified otherwise, such that the substitution would give rise to a chemically stable compound, such as are recognized by those skilled in the art.

The term "heterocycle" as used herein and unless specified otherwise, either alone or in combination with another radical, is intended to mean a 3- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine and pyrimidine, and saturated, unsaturated and aromatic derivatives thereof.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzopyran, benzodioxole, benzodioxane, benzothiazole, quinoline, isoquinoline, and naphthyridine, and saturated, unsaturated and aromatic derivatives thereof.

The term "halo" as used herein is intended to mean a halogen substituent selected from fluoro, chloro, bromo or iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. When two or more hydrogen atoms are replaced by halo substituents, the halo substituents may be the same or different. Examples of $(C_{1-6})$haloalkyl include but are not limited to chloromethyl, chloroethyl, dichloroethyl, bromomethyl, bromoethyl, dibromoethyl, chlorobromoethyl, fluoromethyl, difluoromethyl, trifluoromethyl, fluoroethyl and difluoroethyl.

The terms "—O—$(C_{1-n})$alkyl" as used herein interchangeably, wherein n is an integer, either alone or in combination with another radical, is intended to mean an oxygen atom further bonded to an alkyl radical having 1 to n carbon atoms as defined above. Examples of —O—$(C_{1-n})$alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—$(C_{1-n})$alkyl radical is substituted, it is understood to be substituted on the $(C_{1-n})$alkyl portion thereof, such that the substitution would give rise to a chemically stable compound, such as are recognized by those skilled in the art.

The terms "—S—$(C_{1-n})$alkyl" as used herein interchangeably, wherein n is an integer, either alone or in combination with another radical, is intended to mean an sulfur atom further bonded to an alkyl radical having 1 to n carbon atoms as defined above. Examples of —S—$(C_{1-n})$alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—$(C_{1-n})$ alkyl radical, or an oxidized derivative thereof, such as an —SO—$(C_{1-n})$alkyl radical or an —$SO_2$—$(C_{1-n})$alkyl radical, is substituted, each is understood to be substituted on the $(C_{1-n})$alkyl portion thereof, such that the substitution would give rise to a chemically stable compound, such as are recognized by those skilled in the art.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof, herein incorporated by reference.

The following designations

----- and ----┬---- are used interchangeably in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, aspartates, benzenesulfonates, benzoates, besylates, bicarbonates, bitartrates, bromides/hydrobromides, Ca-edetates/edetates, camsylates, carbonates, chlorides/hydrochlorides, citrates, cyclamates, edisylates, ethane disulfonates, estolates, esylates, fumarates, gentisates (salt of 2,5-dihydroxy benzoic acid), gluceptates, gluconates, glutamates, glycinates, glycolates, glycollylarsnilates, hexylresorcinates, hydrabamines, hydroxymaleates, hydroxynaphthoates, iodides, isethionates, lactates, lactobionates, malates, maleates, malonates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, saccharinates, salicylates, stearates subacetates, succinates, sulfamides, sulfates, tannates, tartrates, teoclates, toluenesulfonates, triethiodides, xinafoates (salt of 1-hydroxy-2-naphthoicacid), ammonium, arginine, benzathines, chloroprocaines, cholines, diethanolamines, ethylenediamines, lysine, meglumines, TRIS (C,C,C-tris(hydroxymethyl)-aminomethan or Trometamol) and procaines. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19 and Handbook of Pharmaceutical Salts, P. Heinrich Stahl, Camille G. Wermuth (Eds.), Wiley-VCH, 2002, both of which are herein incorporated by reference).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The term "HIV integrase" or "integrase", used herein interchangeably, means the integrase enzyme encoded by the human immunodeficiency virus type 1. The polypeptide sequence of the integrase enzyme of NL4.3 strain of HIV-1 is provided as SEQ ID NO: 1.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Preferred Embodiments

In the following preferred embodiments, groups and substituents of the compounds of formula (I):

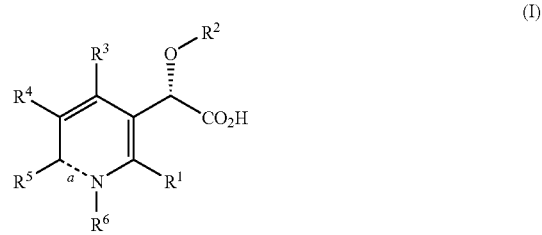

according to this invention are described in detail. Any and each individual definition as set out herein may be combined with any and each individual definition as set out herein.

R¹:

R¹-A:

In at least one embodiment, R¹ is $(C_{1-4})$alkyl, $(C_{2-4})$alkenyl or $(C_{3-5})$cycloalkyl, wherein the $(C_{1-4})$alkyl is optionally substituted with —$O(C_{1-3})$alkyl or —$S(C_{1-3})$alkyl.

R¹-B:

In at least one embodiment, R¹ is selected from: —$CH_3$, —$CH_2OMe$, —$CH_2OEt$, —$CH_2SMe$, —$CH=CH_2$ and

R¹-C:

In at least one embodiment, R¹ is $(C_{1-4})$alkyl.

R¹-D:

In at least one embodiment, R¹ is —$CH_3$.

R²:

R²-A:

In at least one embodiment, R² is $(C_{3-8})$alkyl or $(C_{3-8})$cycloalkyl wherein the $(C_{3-8})$cycloalkyl is optionally substituted with $(C_{1-6})$alkyl.

R²-B:

In at least one embodiment, R² is selected from:

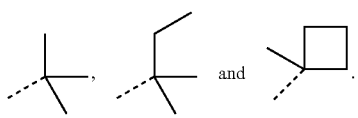

R²-C:

In at least one embodiment, R² is $(C_{3-8})$alkyl.

R²-D:

In at least one embodiment, R² is

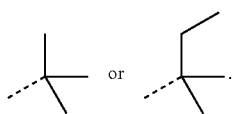

R³:

R³-A:

In at least one embodiment, R³ is phenyl or R³ is phenyl fused to one or more cycles, at least one of which is a heterocycle, to form a 9- to 13-membered heteropolycycle having 1 or 2 heteroatoms, each independently selected from N, O and S; wherein the phenyl or heteropolycycle is optionally substituted with 1 to 4 substituents each independently selected from $(C_{1-6})$alkyl, halo and —$O(C_{1-6})$alkyl.

R³-B:

In at least one embodiment, R³ is phenyl or a heteropolycycle selected from:

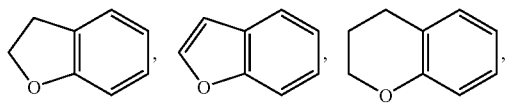

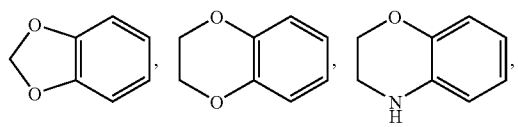

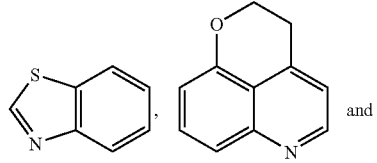

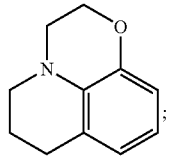

wherein the phenyl or heteropolycycle is optionally substituted with 1 to 4 substituents each independently selected from $(C_{1-6})$alkyl, halo and —$O(C_{1-6})$alkyl.

R³-C:

In at least one embodiment, R³ is selected from:

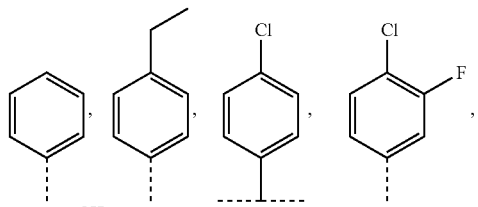

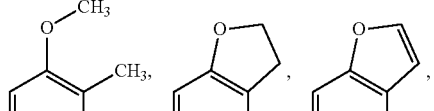

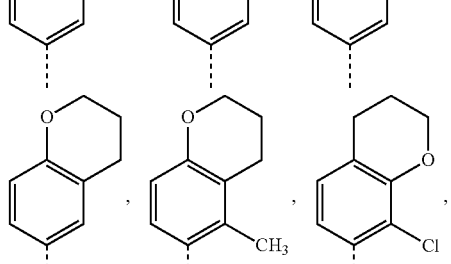

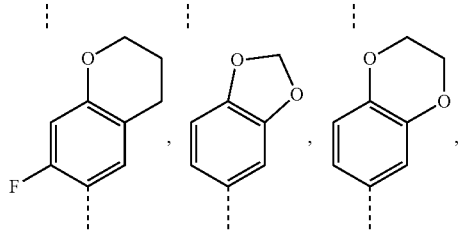

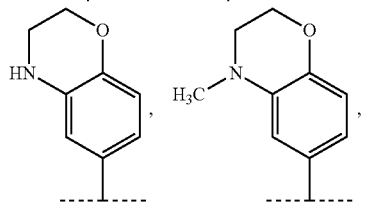

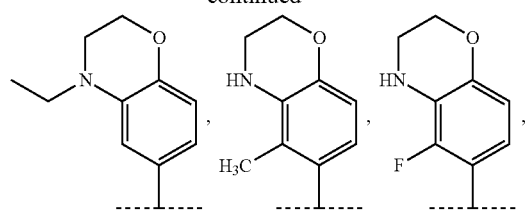
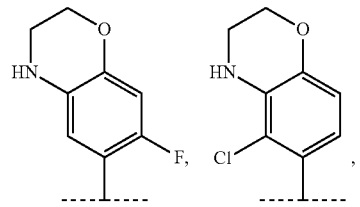
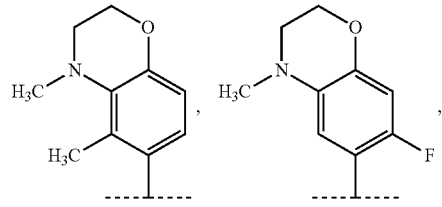
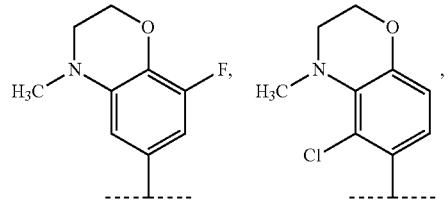
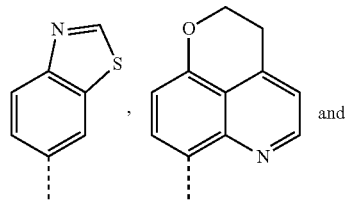
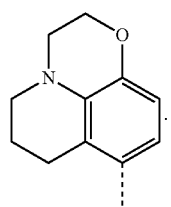
R³-D:
In at least one embodiment, R³ is selected from:
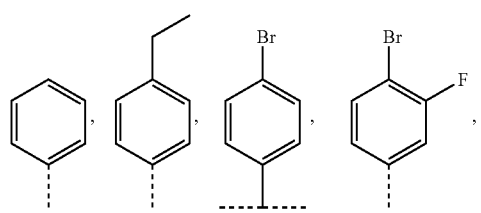
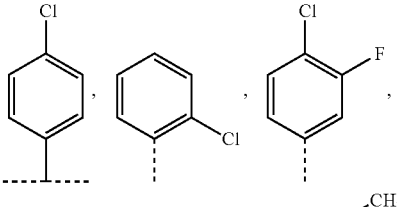
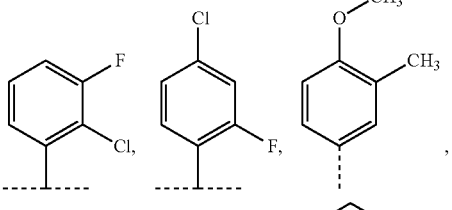
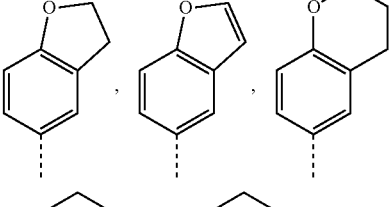
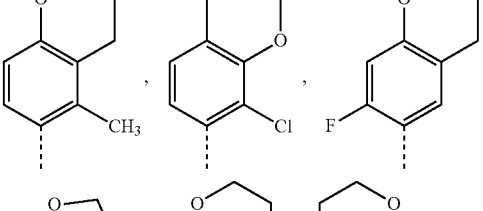
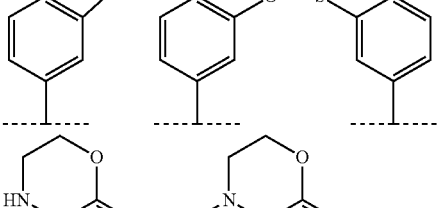
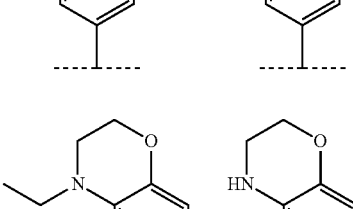
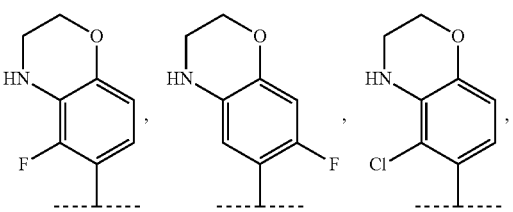
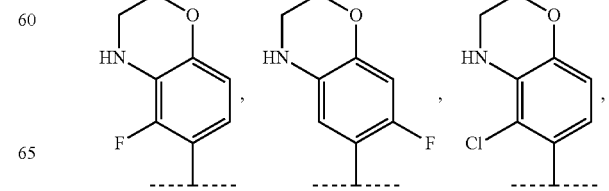

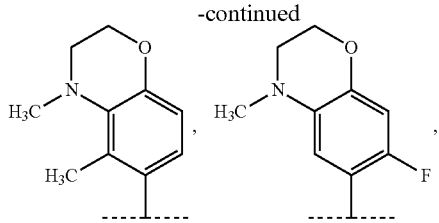

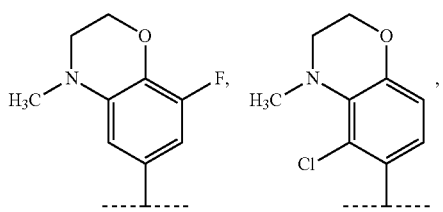

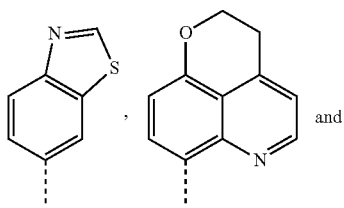

, and

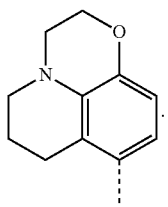

.

One skilled in the art will recognize that when the $R^3$ substituent is not symmetrically substituted about the axis of rotation of the bond attaching $R^3$ to Core, the compounds of the invention will have a rotational axis of asymmetry and thus rotational isomers are possible. When the energy barrier to rotation is relatively low, the rotational isomers rapidly interconvert at room temperature and are considered to be conformers. In contrast, when the energy barrier to rotation is relatively high, the rotational isomers interconvert so slowly at room temperature that they may be isolated and are considered to be atropisomers.

Because the compounds of the invention also posess at least one other chiral center, namely, the chiral carbon atom bonded to —$OR^2$, the rotational isomers will exist as diastereomers. For example, when the unsymmetrically substituted $R^3$ substituent bears a substituent $R^{3a}$ at a position ortho to the bond attaching $R^3$ to Core, wherein $R^{3a}$ is any atom or group other than hydrogen which is a substituent of $R^3$ by any definition of $R^3$ set forth herein, the following atropisomeric formulas A-1 and A-2 are possible, where, in conformance with accepted stereochemical notation, the darkened and/or solid wedge bonds indicate the side or edge of the $R^3$ substituent that is projecting towards the viewer:

A-1

A-2

Although for purposes of illustration, $R^3$ is shown as phenyl unsymmetrically substituted at the ortho position with a substituent $R^{3a}$ in formulas A-1 and A-2, it will be clear to the person skilled in the art that analogous atropisomers exist for other unsymmetrically substituted $R^3$ substituents.

It has been found that, when it is possible to separate the individual diastereomeric atropisomers so that their individual activities against HIV can be measured, the atropisomer with the formula similar to A-1 above, where the substituent on the $R^3$ group is on the opposite side of the plane of the pyridine ring from the —$OR^2$ group, is in some cases more active against HIV, when measured, for example, by the procedure of Example 48 below, than the atropisomer with the formula similar to A-2 above, where the substituent on the $R^3$ group is on the same side of the plane of the pyridine ring as the —$OR^2$ group.

$R^4$:

$R^4$-A:

In at least one embodiment, $R^4$ is $(C_{1-6})$alkyl, —CN, halo or $(C_{1-6})$haloalkyl.

$R^4$-B:

In at least one embodiment, $R^4$ is $(C_{1-6})$alkyl, —CN or halo.

$R^4$-C:

In at least one embodiment, $R^4$ is selected from —$CH_3$, —CN and —F.

$R^4$-D:

In at least one embodiment, $R^4$ is $(C_{1-6})$alkyl.

$R^4$-E:

In at least one embodiment, $R^4$ is —$CH_3$.

Core and $R^5/R^6$:

Core-A:

In at least one embodiment, a is a double bond and $R^6$ is absent such that the compound of the invention is a compound of formula (Ia):

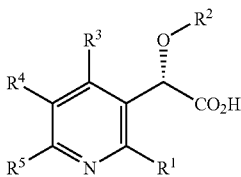

(Ia)

wherein $R^1$, $R^2$, $R^3$, $R^4$ and $R^5$ are as defined herein.

$R^5/R^6$-A:

In at least one embodiment, a is a double bond, $R^6$ is absent and $R^5$ is $R^{51}$ or —$(C_{1-3})$alkyl-$R^{51}$;
wherein $R^{51}$ is selected from $R^{52}$, —$OR^{53}$, —$N(R^{54})R^{53}$, —C(=O)$R^{52}$, —C(=O)$OR^{53}$, —C(=O)$N(R^{54})R^{53}$, —$N(R^{54})R^{53}$, —C(=O)$R^{52}$, —$N(R^{54})C(=O)N(R^{54})R^{53}$ and —$N(R^{54})C(=O)OR^{53}$; wherein $R^{52}$ is selected from $R^{53}$ and $(C_{2-8})$alkenyl, and $R^{53}$ is selected from $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-, and $R^{54}$ is in each case independently selected from H and $(C_{1-3})$alkyl;
wherein each of $R^{52}$ and $R^{53}$ is optionally substituted with 1 to 3 substituents each independently selected from $R^{56}$, halo, —CN, —$OR^{56}$, —$SR^{56}$, —$SO_2R^{56}$, —$N(R^{54})R^{56}$ and —$CON(R^{54})R^{56}$, wherein $R^{56}$ is in each case independently selected from H, $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-,
wherein $R^{56}$ is, where possible, in each case independently optionally substituted with 1 to 3 substituents each independently selected from $(C_{1-6})$alkyl, $(C_{1-6})$haloalkyl, halo, —$O(C_{1-6})$alkyl, —$N((C_{1-6})$alkyl$)_2$ and —$NH(C=O)(C_{1-6})$alkyl;
wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S.

$R^5/R^6$-B:

In at least one embodiment, a is a double bond, $R^6$ is absent and $R^5$ is $R^{51}$ or —$(C_{1-3})$alkyl-$R^{51}$;
wherein $R^{51}$ is selected from $R^{52}$, —$OR^{53}$, —$N(R^{54})R^{53}$, —C(=O)$R^{52}$, —C(=O)$OR^{53}$, —C(=O)$N(R^{54})R^{53}$, —$N(R^{54})C(=O)R^{52}$, —$N(R^{54})C(=O)N(R^{54})R^{53}$ and —$N(R^{54})C(=O)OR^{53}$; wherein $R^{52}$ is selected from $R^{53}$ and $(C_{2-8})$alkenyl, and $R^{53}$ is selected from $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-,
wherein Het and the Het portion of Het-$(C_{1-6})$alkyl- are in each case independently selected from a 5- or 6-membered saturated, unsaturated or aromatic heterocycle having 1 to 3 heteroatoms each independently selected from O, N and S, and an 8-9- or 10-membered saturated, unsaturated or aromatic heteropolycycle having 1 to 3 heteroatoms each independently selected from O, N and S; and $R^{54}$ is in each case independently selected from H and $(C_{1-3})$alkyl;
wherein each of $R^{52}$ and $R^{53}$ is optionally substituted with 1 to 3 substituents each independently selected from $R^{56}$, halo, —CN, —$OR^{56}$, —$SR^{56}$, —$SO_2R^{56}$, —$N(R^{54})R^{56}$, and —$CON(R^{54})R^{56}$, wherein $R^{56}$ is in each case independently selected from H, $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-,
wherein Het and the Het portion of Het-$(C_{1-6})$alkyl- are in each case independently selected from a 5- or 6-membered saturated, unsaturated or aromatic heterocycle having 1 to 3 heteroatoms each independently selected from O, N and S;
wherein $R^{56}$ is, where possible, in each case independently optionally substituted with 1 to 3 substituents each independently selected from $(C_{1-6})$alkyl, $(C_{1-6})$haloalkyl, halo, —$O(C_{1-6})$alkyl, —$N((C_{1-6})$alkyl$)_2$ and —$NH(C=O)(C_{1-6})$alkyl.

$R^5/R^6$-C:

In at least one embodiment, a is a double bond, $R^6$ is absent and $R^5$ is $R^{51}$ or —$(C_{1-3})$alkyl-$R^{51}$;
wherein $R^{51}$ is selected from $R^{52}$, —$OR^{53}$, —$N(R^{54})R^{53}$, —C(=O)$R^{52}$, —C(=O)$OR^{53}$, —C(=O)$N(R^{54})R^{53}$, —$N(R^{54})^C(=O)R^{52}$, —$N(R^{54})C(=O)N(R^{54})R^{53}$ and —$N(R^{54})C(=O)OR^{53}$; wherein $R^{52}$ is selected from $R^{53}$ and $(C_{2-8})$alkenyl, and $R^{53}$ is selected from $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-,
wherein Het and the Het portion of Het-$(C_{1-6})$alkyl- are in each case independently selected from:

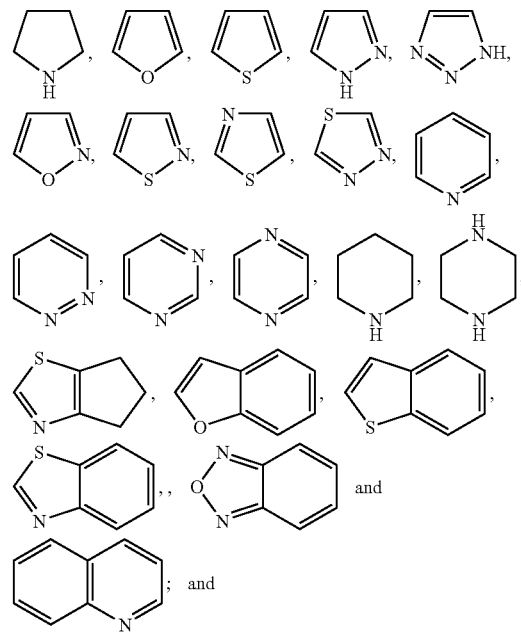

$R^{54}$ is in each case independently selected from H and $(C_{1-3})$alkyl;
wherein each of $R^{52}$ and $R^{53}$ is optionally substituted with 1 to 3 substituents each independently selected from $R^{56}$, halo, —CN, —$OR^{56}$, —$SR^{56}$, $SO_2R^{56}$, —$N(R^{54})R^{56}$ and —$CON(R^{54})R^{56}$, wherein $R^{56}$ is in each case independently selected from H, $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-, wherein Het and the Het portion of Het-($C_{1-6}$)alkyl- are in each case independently selected from:

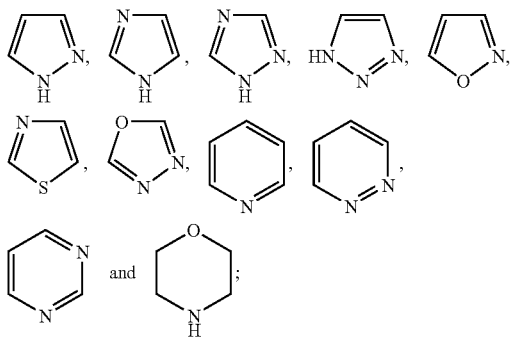

wherein $R^{56}$ is, where possible, in each case independently optionally substituted with 1 to 3 substituents each independently selected from ($C_{1-6}$)alkyl, ($C_{1-6}$)haloalkyl, halo, —O($C_{1-6}$)alkyl, —N(($C_{1-6}$)alkyl)$_2$ and —NH(C=O) ($C_{1-6}$)alkyl.

$R^5/R^6$-D:

In at least one embodiment, a is a double bond, $R^6$ is absent and $R^5$ is selected from:

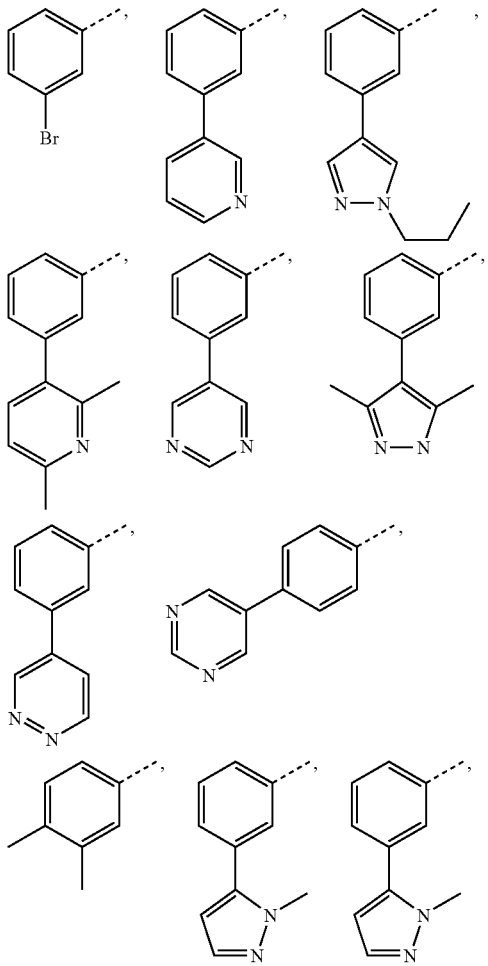

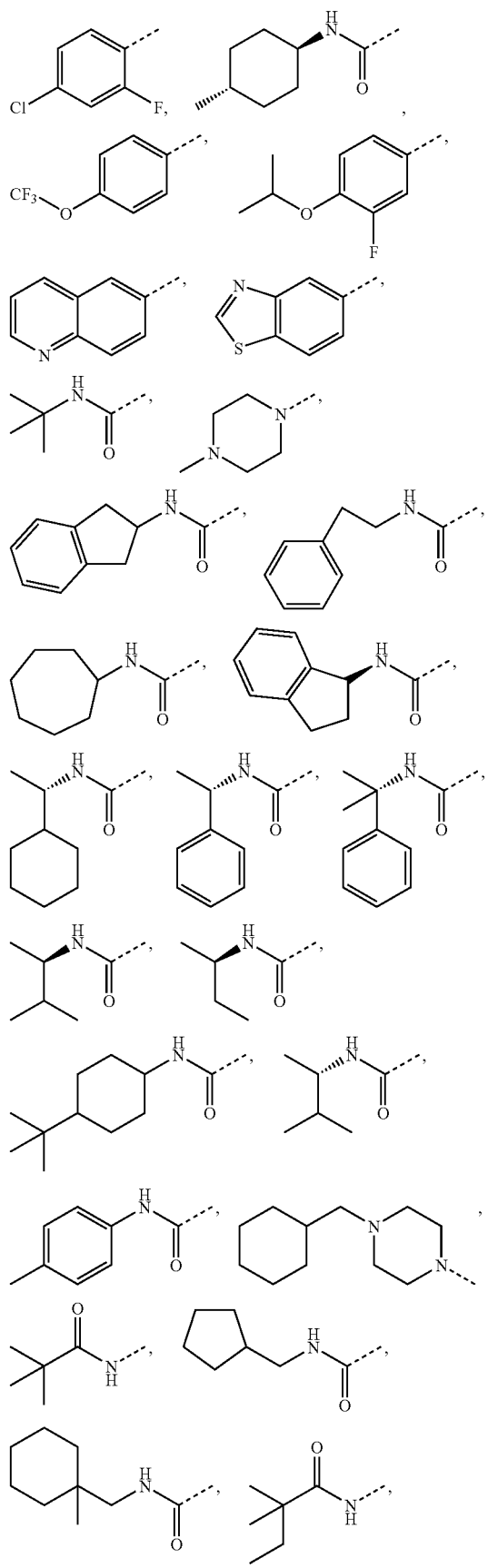

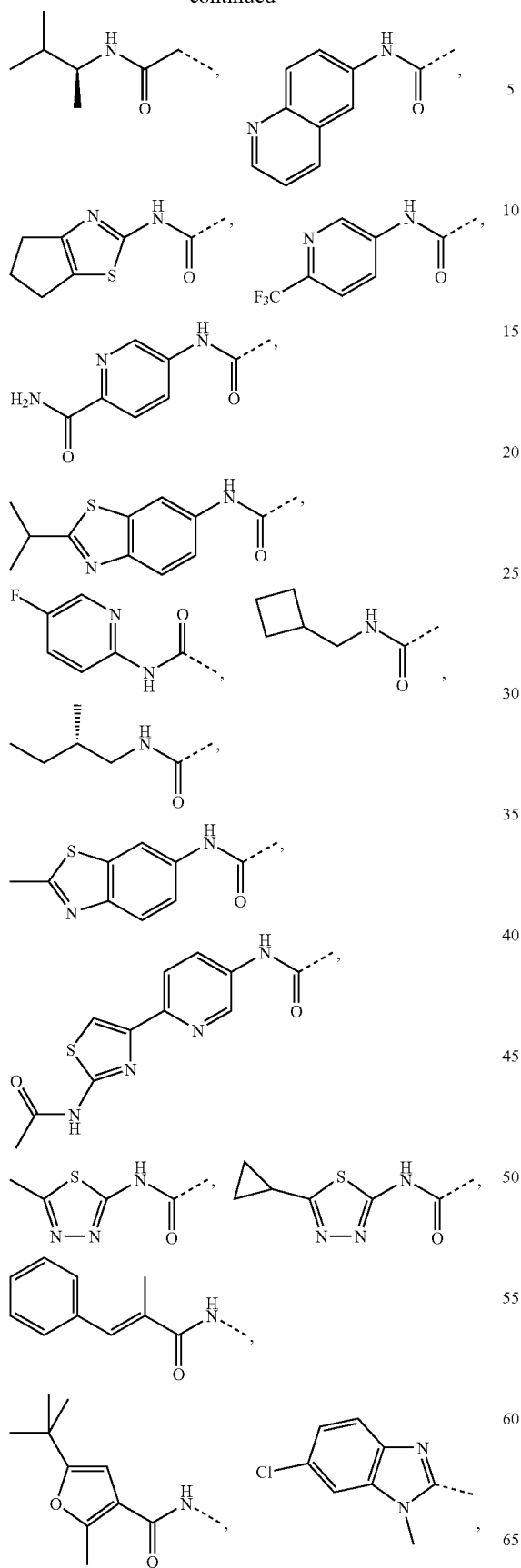
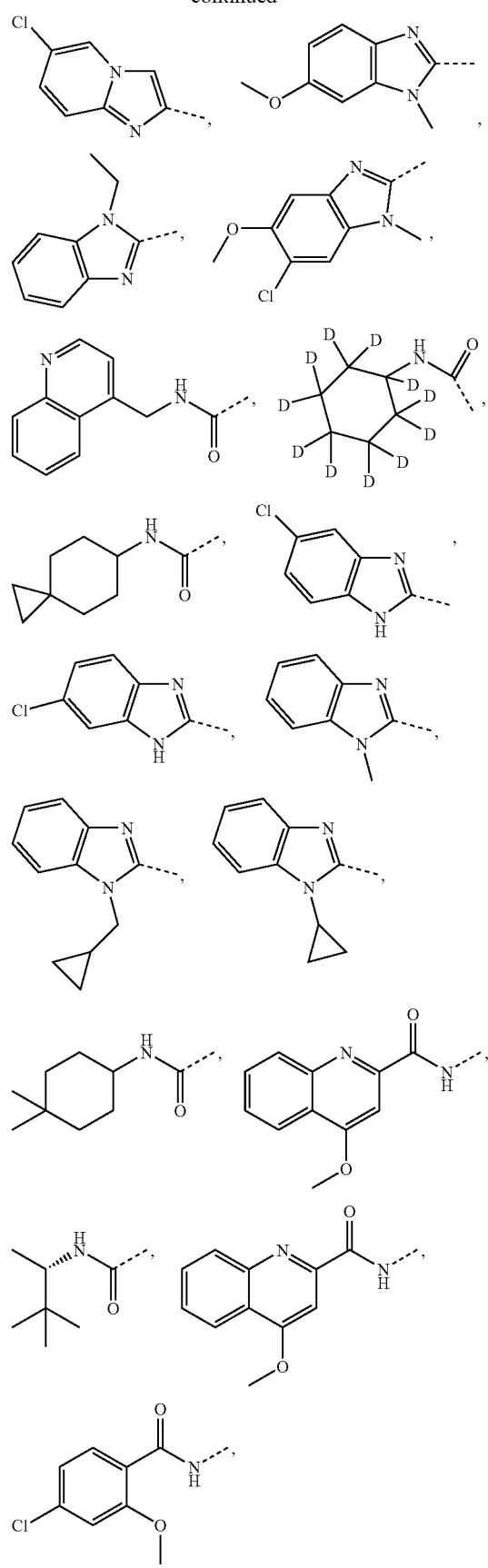

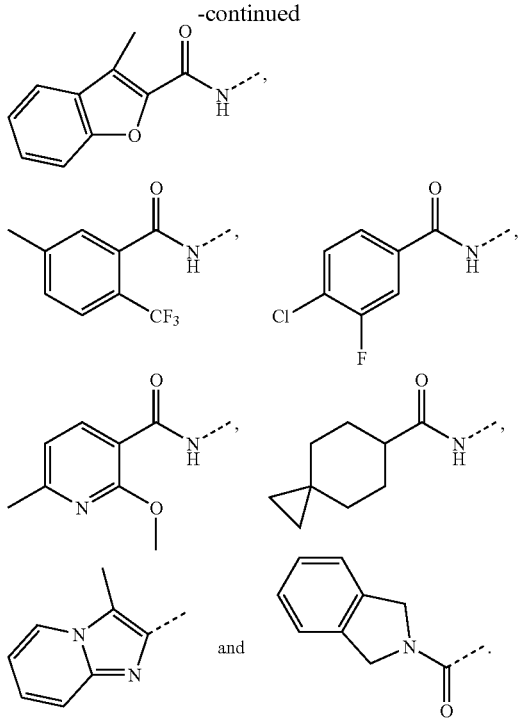

$R^5/R^6$-E:

In at least one embodiment, a is a double bond, $R^6$ is absent and $R^5$ is $R^{51}$ or $-(C_{1-3})$alkyl-$R^{51}$;

wherein $R^{51}$ is selected from $R^{52}$, $-OR^{53}$, $-C(=O)R^{52}$, $-C(=O)OR^{53}$, $-C(=O)N(R^{54})R^{53}$, $-N(R^{54})C(=O)R^{52}$, $-N(R^{54})C(=O)N(R^{54})R^{53}$ and $-N(R^{54})C(=O)OR^{53}$; wherein $R^{52}$ is selected from $R^{53}$ and $(C_{2-8})$alkenyl, and $R^{53}$ is selected from $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-, wherein Het and the Het portion of Het-$(C_{1-6})$alkyl- are in each case independently selected from:

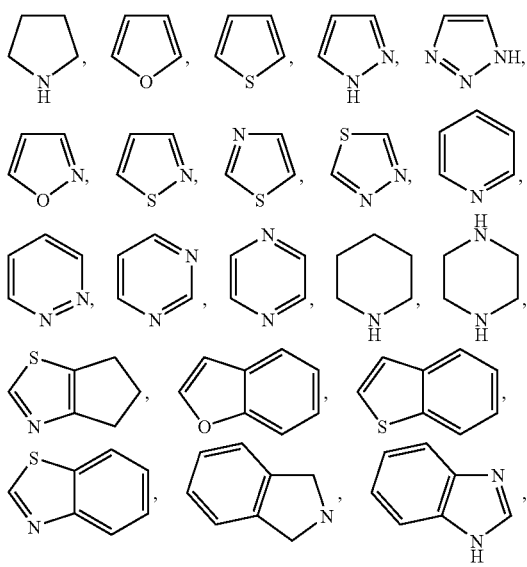

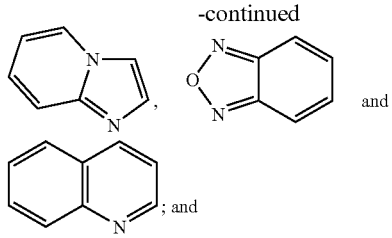

$R^{54}$ is in each case independently selected from H and $(C_{1-3})$alkyl;

wherein each of $R^{52}$ and $R^{53}$ is optionally substituted with 1 to 3 substituents each independently selected from $R^{56}$, halo, $-CN$, $-OR^{56}$, $-SR^{56}$, $-SO_2R^{56}$, $-N(R^{54})R^{56}$ and $-CON(R^{54})R^{56}$, wherein $R^{56}$ is in each case independently selected from H, $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-, wherein Het and the Het portion of Het-$(C_{1-6})$alkyl- are in each case independently selected from:

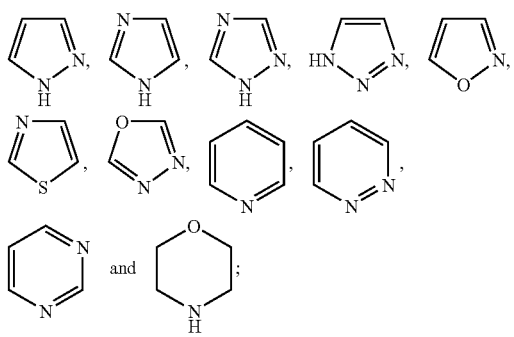

wherein $R^{56}$ is, where possible, in each case independently optionally substituted with 1 to 3 substituents each independently selected from $(C_{1-6})$alkyl, $(C_{1-6})$haloalkyl, halo, $-O(C_{1-6})$alkyl, $-N((C_{1-6})$alkyl$)_2$ and $-NH(C=O)(C_{1-6})$alkyl.

$R^5/R^6$-F:

In at least one embodiment, a is a double bond, $R^6$ is absent and $R^5$ is $R^{51}$ or $-(C_{1-3})$alkyl-$R^{51}$;

wherein $R^{51}$ is selected from $R^{52}$, $-OR^{53}$, $-C(=O)R^{52}$, $-C(=O)OR^{53}$, $-C(=O)N(R^{54})R^{53}$, $-N(R^{54})C(=O)R^{52}$, $-N(R^{54})C(=O)N(R^{54})R^{53}$ and $-N(R^{54})C(=O)OR^{53}$; wherein $R^{52}$ is selected from $R^{53}$ and $(C_{2-8})$alkenyl, and $R^{53}$ is selected from $(C_{1-8})$alkyl, $(C_{3-8})$cycloalkyl, $(C_{7-12})$spirocycloalkyl, $(C_{3-8})$cycloalkyl-$(C_{1-6})$alkyl-, aryl, aryl-$(C_{1-6})$alkyl-, Het, and Het-$(C_{1-6})$alkyl-, wherein Het and the Het portion of Het-$(C_{1-6})$alkyl- are in each case independently selected from:

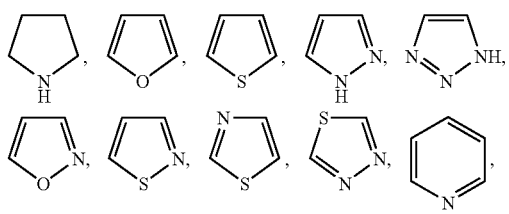

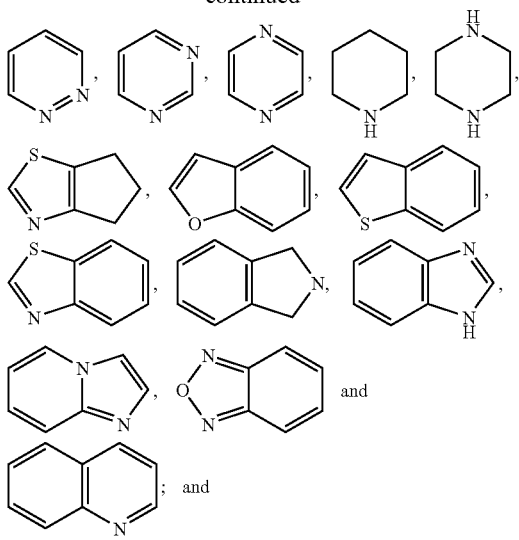

$R^{54}$ is in each case independently selected from H and $(C_{1-3})$alkyl;
wherein each of $R^{52}$ and $R^{53}$ is optionally substituted with 1 to 3 substituents each independently selected from $R^{56}$, halo, —CN, —OR$^{56}$, —SR$^{56}$, —SO$_2$R$^{56}$, —N(R$^{54}$)R$^{56}$ and —CON(R$^{54}$)R$^{56}$, wherein
$R^{56}$ is in each case independently selected from H, $(C_{1-6})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-,
wherein Het and the Het portion of Het-$(C_{1-6})$alkyl- are in each case independently selected from:

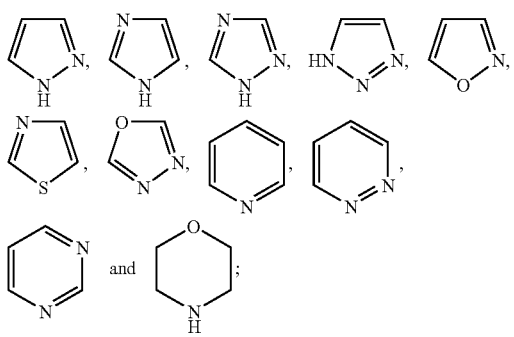

wherein $R^{56}$ is, where possible, in each case independently optionally substituted with 1 to 3 substituents each independently selected from $(C_{1-6})$alkyl, $(C_{1-6})$haloalkyl, halo, —O$(C_{1-6})$alkyl, —N$((C_{1-6})$alkyl)$_2$ and —NH(C=O)$(C_{1-6})$alkyl.

Examples of preferred subgeneric embodiments of the present invention are set forth in the following table, wherein each substituent group of each embodiment is defined according to the definitions set forth above:

| Embodiment | $R^1$ | $R^2$ | $R^3$ | $R^4$ | Core | $R^5/R^6$ |
|---|---|---|---|---|---|---|
| E-1 | $R^1$-A | $R^2$-A | $R^3$-A | $R^4$-A | Core-A | $R^5/R^6$-A |
| E-2 | $R^1$-A | $R^2$-A | $R^3$-A | $R^4$-A | Core-A | $R^5/R^6$-B |
| E-3 | $R^1$-A | $R^2$-A | $R^3$-A | $R^4$-B | Core-A | $R^5/R^6$-A |
| E-4 | $R^1$-A | $R^2$-A | $R^3$-A | $R^4$-B | Core-A | $R^5/R^6$-B |
| E-5 | $R^1$-A | $R^2$-A | $R^3$-A | $R^4$-D | Core-A | $R^5/R^6$-A |
| E-6 | $R^1$-A | $R^2$-A | $R^3$-A | $R^4$-D | Core-A | $R^5/R^6$-B |
| E-7 | $R^1$-A | $R^2$-C | $R^3$-A | $R^4$-A | Core-A | $R^5/R^6$-A |
| E-8 | $R^1$-A | $R^2$-C | $R^3$-A | $R^4$-A | Core-A | $R^5/R^6$-B |
| E-9 | $R^1$-A | $R^2$-C | $R^3$-A | $R^4$-B | Core-A | $R^5/R^6$-A |
| E-10 | $R^1$-A | $R^2$-C | $R^3$-A | $R^4$-B | Core-A | $R^5/R^6$-B |
| E-11 | $R^1$-A | $R^2$-C | $R^3$-A | $R^4$-D | Core-A | $R^5/R^6$-A |
| E-12 | $R^1$-A | $R^2$-C | $R^3$-A | $R^4$-D | Core-A | $R^5/R^6$-B |
| E-13 | $R^1$-B | $R^2$-B | $R^3$-D | $R^4$-E | Core-A | $R^5/R^6$-C |
| E-14 | $R^1$-B | $R^2$-B | $R^3$-D | $R^4$-E | Core-A | $R^5/R^6$-E |
| E-15 | $R^1$-B | $R^2$-D | $R^3$-B | $R^4$-B | Core-A | $R^5/R^6$-D |
| E-16 | $R^1$-B | $R^2$-A | $R^3$-B | $R^4$-D | Core-A | $R^5/R^6$-D |
| E-17 | $R^1$-B | $R^2$-D | $R^3$-D | $R^4$-D | Core-A | $R^5/R^6$-A |
| E-18 | $R^1$-C | $R^2$-A | $R^3$-A | $R^4$-A | Core-A | $R^5/R^6$-A |
| E-19 | $R^1$-C | $R^2$-A | $R^3$-A | $R^4$-A | Core-A | $R^5/R^6$-B |
| E-20 | $R^1$-C | $R^2$-A | $R^3$-A | $R^4$-B | Core-A | $R^5/R^6$-A |
| E-21 | $R^1$-C | $R^2$-A | $R^3$-A | $R^4$-B | Core-A | $R^5/R^6$-B |
| E-22 | $R^1$-C | $R^2$-A | $R^3$-A | $R^4$-D | Core-A | $R^5/R^6$-A |
| E-23 | $R^1$-C | $R^2$-A | $R^3$-A | $R^4$-D | Core-A | $R^5/R^6$-B |
| E-24 | $R^1$-C | $R^2$-C | $R^3$-A | $R^4$-A | Core-A | $R^5/R^6$-A |
| E-25 | $R^1$-C | $R^2$-C | $R^3$-A | $R^4$-A | Core-A | $R^5/R^6$-B |
| E-26 | $R^1$-C | $R^2$-C | $R^3$-A | $R^4$-B | Core-A | $R^5/R^6$-A |
| E-27 | $R^1$-C | $R^2$-C | $R^3$-A | $R^4$-B | Core-A | $R^5/R^6$-B |
| E-28 | $R^1$-C | $R^2$-C | $R^3$-A | $R^4$-D | Core-A | $R^5/R^6$-A |
| E-29 | $R^1$-C | $R^2$-C | $R^3$-A | $R^4$-D | Core-A | $R^5/R^6$-B |
| E-30 | $R^1$-C | $R^2$-B | $R^3$-B | $R^4$-A | Core-A | $R^5/R^6$-C |
| E-31 | $R^1$-C | $R^2$-A | $R^3$-A | $R^4$-B | Core-A | $R^5/R^6$-F |
| E-32 | $R^1$-D | $R^2$-B | $R^3$-B | $R^4$-E | Core-A | $R^5/R^6$-C |
| E-33 | $R^1$-D | $R^2$-D | $R^3$-C | $R^4$-E | Core-A | $R^5/R^6$-E |
| E-34 | $R^1$-D | $R^2$-D | $R^3$-C | $R^4$-B | Core-A | $R^5/R^6$-E |
| E-35 | $R^1$-D | $R^2$-B | $R^3$-C | $R^4$-B | Core-A | $R^5/R^6$-B |
| E-36 | $R^1$-D | $R^2$-D | $R^3$-C | $R^4$-E | Core-A | $R^5/R^6$-F |
| E-37 | $R^1$-D | $R^2$-D | $R^3$-C | $R^4$-B | Core-A | $R^5/R^6$-F |

Examples of most preferred compounds according to this invention are each single compound listed in the following Tables 1 to 6.

Unless specifically indicated, throughout the specification and the appended claims, a given chemical formula or name shall encompass tautomers, and all stereo, optical and geometrical isomers (e.g. enantiomers, diastereomers, E/Z isomers, atropisomers) resulting from all possible stereochemistry at a chiral center for which specific stereochemistry is not otherwise described, and racemates thereof, as well as mixtures in different proportions of the separate enantiomers, mixtures of diastereomers, or mixtures of any of the foregoing forms where such isomers and enantiomers exist.

It is well-known in the art that the biological and pharmacological activity of a compound is sensitive to the stereochemistry of the compound. Thus, for example, enantiomers often exhibit strikingly different biological activity including but not limited to differences in pharmacokinetic properties, including but not limited to metabolism, protein binding, and the like, and pharmacological properties, including but not limited to the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of Pure Stereoisomers, e.g. Enantiomers and Diastereomers, or Mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but are not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to the invention with known excipients, for example inert diluents, carriers, disintegrants, adjuvants, surfactants, binders and/or lubricants. The tablets may also consist of several layers.

When one enantiomer of a chiral active ingredient has a different biological activity than the other, it is contemplated that the pharmaceutical composition according to the invention may comprise a racemic mixture of the active ingredient, a mixture enriched in one enantiomer of the active ingredient or a pure enantiomer of the active ingredient. The mixture enriched in one enantiomer of the active ingredient is contemplated to contain from more than 50% to about 100% of one enantiomer of the active ingredient and from about 0% to less than 50% of the other enantiomer of the active ingredient. Preferably, when the composition comprises a mixture enriched in one enantiomer of the active ingredient or a pure enantiomer of the active ingredient, the composition comprises from more than 50% to about 100% of, or only, the more physiologically active enantiomer and/or the less toxic enantiomer. It is well known that one enantiomer of an active ingredient may be the more physiologically active for one therapeutic indication while the other enantiomer of the active ingredient may be the more physiologically active for a different therapeutic indication; therefore the preferred enantiomeric makeup of the pharmaceutical composition may differ for use of the composition in treating different therapeutic indications.

Therefore, according to one embodiment, the pharmaceutical composition according to the invention comprises a racemic mixture of the compound of formula (I), or a pharmaceutically acceptable salt thereof.

An alternative embodiment provides a pharmaceutical composition comprising a mixture enriched in one enantiomer of the compound of formula (I), or a pharmaceutically acceptable salt thereof.

A further embodiment provides a pharmaceutical composition comprising a pure enantiomer of the compound of formula (I), or a pharmaceutically acceptable salt thereof.

The dose range of the compounds of the invention applicable per day is usually from 0.001 to 100 mg/kg of body weight, preferably from 0.01 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

Combination Therapy

Combination therapy is contemplated wherein a compound according to the invention, or a pharmaceutically acceptable salt thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being. Such agents can be selected from:

NRTIs (nucleoside or nucleotide reverse transcriptase inhibitors) including but not limited to zidovudine/RETROVIR® (GSK), didanosine/VIDEX® (BMS), stavudine/ZERIT® (BMS), lamivudine/EPIVIR® (GSK/Shire), emtricitabine/EMTRIVA® (Gilead Sciences), abacavir/ZIAGEN® (GSK), and tenofovir/VIREAD® (Gilead Sciences), apricitabine (Avexa), elvucitabine (Achillion) and OBP-601 (Oncolys), amdoxovir (RFS Pharma);

NNRTIs (non-nucleoside reverse transcriptase inhibitors) including but not limited to nevirapine/VIRAMUNE® (Boehringer Ingelheim), delavirdine/RESCRIPTOR® (Pfizer), efavirenz/SUSTIVA® (BMS), etravirine/INTELENCE® (Johnson & Johnson), rilpivirine (Johnson & Johnson), UK-453,061 (Pfizer) and RDEA806 (Ardea Biosciences), IDX-899 (GSK);

protease inhibitors including but not limited to ritonavir/
NORVIR® (Abbott), tipranavir/APTIVUS® (Boehringer Ingelheim), saquinavir/INVIRASE® (Hoffmann LaRoche), nelfinavir/VIRACEPT® (Pfizer), indinavir/CRIXIVAN® (Merck), fosamprenavir/LEXIVA® (GSK/Vertex), atazanavir/REYATAZ® (BMS), lopinavir/KALETRA® (Abbott), and darunavir/PREZISTA® (Johnson & Johnson);

entry inhibitors including but not limited to
CCR5 antagonists including but not limited to maraviroc/SELZENTRY® (Pfizer), vicriviroc (Schering-Plough), INCB9471 (Incyte), PF-232798 (Pfizer), PRO-140 (Progenics Pharm), GSK706769 (GSK), PF-232798 (Pfizer), TBR-220 and TBR-652 (Tovira Therapeutics);
CXCR4 antagonists including but not limited to AMD-11070 (Genzyme),
fusion inhibitors including but not limited to enfuvirtide/FUZEON® (Trimeris), sifuvirtide (Fasogen), albuvirtide (Frontier Bio), FRI-1144 (Trimeris); and
others including but not limited to BMS-488043 (BMS);
integrase inhibitors including but not limited to raltegravir/ISENTRESS® (Merck), elvitegravir (Gilead Sciences), GSK1349572 and GSK1265744 (GSK), JTK-656 (Japan Tobacco);
TAT inhibitors;
maturation inhibitors including but not limited to bevirimat (Myriad Genetics), vivecon (Myriad Genetics); and
immunomodulating agents including but not limited to levamisole/ERGAMISOL® (Janssen-Ortho); and
other antiviral agents including hydroxyurea, ribavirin, IL-2, IL-12 and pensafuside.

Furthermore, a compound according to the invention can be used with at least one other compound according to the invention or with one or more antifungal or antibacterial agents (including but not limited to fluconazole).

Therefore, according to one embodiment, the pharmaceutical composition of this invention additionally comprises one or more antiviral agents.

A further embodiment provides the pharmaceutical composition of this invention wherein the one or more antiviral agent comprises at least one NNRTI.

According to another embodiment of the pharmaceutical composition of this invention, the one or more antiviral agent comprises at least one NRTI.

According to yet another embodiment of the pharmaceutical composition of this invention, the one or more antiviral agent comprises at least one protease inhibitor.

According to still another embodiment of the pharmaceutical composition of this invention, the one or more antiviral agent comprises at least one entry inhibitor.

According to a further embodiment of the pharmaceutical composition of this invention, the one or more antiviral agent comprises at least one integrase inhibitor.

Methodology and Synthesis

The synthesis of compounds of formula (I) according to this invention is conveniently accomplished following the general procedures outlined in the schemes below wherein a, $R^1$, $R^2$, $R^3$, $R^4$, $R^5$ and $R^6$ are as defined herein. Other procedures by which compounds of the invention may be prepared are well known in the art or are set forth in the examples below.

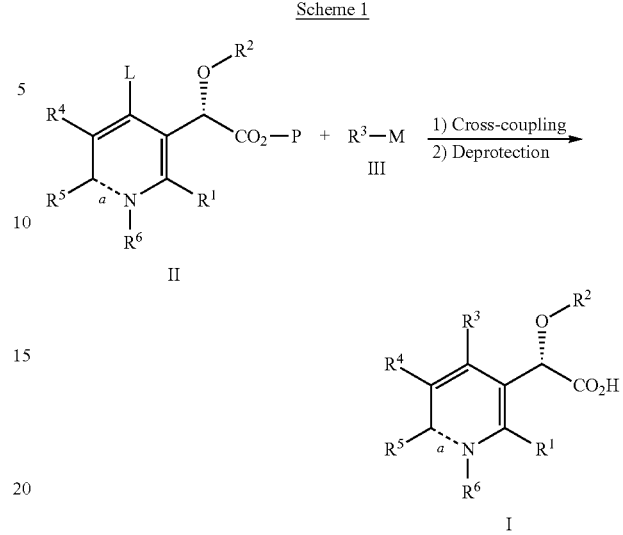

Scheme 1

Intermediates II, wherein a, $R^1$, $R^2$, $R^4$, $R^5$ and $R^6$ are as defined herein, L is a leaving group including but not limited to iodo, bromo, chloro or -OTf, and P is a protecting group chosen from commonly used protecting groups for carboxylic acids, including but not limited to a methyl or ethyl ester, and intermediates III, wherein $R^3$ is as defined herein and M is a group suitable for reacting with group L in a coupling reaction, such as are well known in the art, including but not limited to —B(OH)$_2$ or a boronate ester incuding but not limited to —B(OCH$_3$)$_2$ and —B(OC(CH$_3$)$_2$C(CH$_3$)$_2$O); —I; —SnR$_3$ wherein R is (C$_{1-6}$)alkyl; or —ZnX wherein X is halo, are commercially available or are prepared by reactions well known in the art or as set forth in the examples below. Protected derivatives of compounds of formula (I) can be prepared by well known coupling reactions of intermediates II and III, including but not limited to Suzuki cross-coupling between a boronic acid or boronate ester derivative III and a halo or triflate derivative II; copper catalyzed Ullmann cross-coupling between iodo derivatives II and III; Negishi cross-coupling between an arylzinc reagent III and an iodo or triflate derivative II; and Stille coupling between an arylltin reagent III and a bromo or iodo derivative II. The protected products of the coupling reaction are then deprotected, for example by saponification, to provide compounds of formula (I).

Alternatively, as shown in Scheme 2 below, intermediates IV and V, wherein a, $R^1$, $R^2$, $R^3$, $R^4$, $R^5$, $R^6$, L, M and P are as defined herein, may be coupled using the cross-coupling methods described above, followed by deprotection, to provide compounds of formula (I).

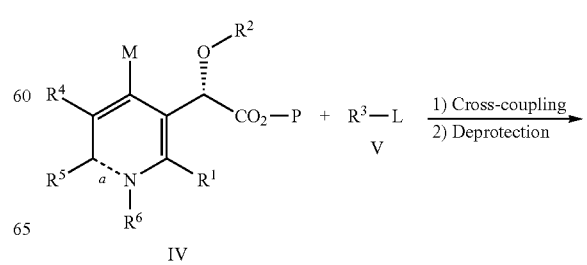

Scheme 2

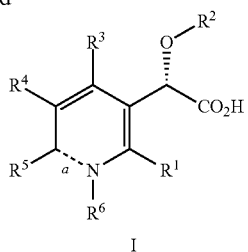

Furthermore, compounds of formula (Ia) wherein a is a single bond, $R^6$ is absent and $R^1$, $R^2$, $R^3$, $R^4$ and $R^5$ are as defined herein are conveniently prepared using the general procedure illustrated in Scheme 3 below.

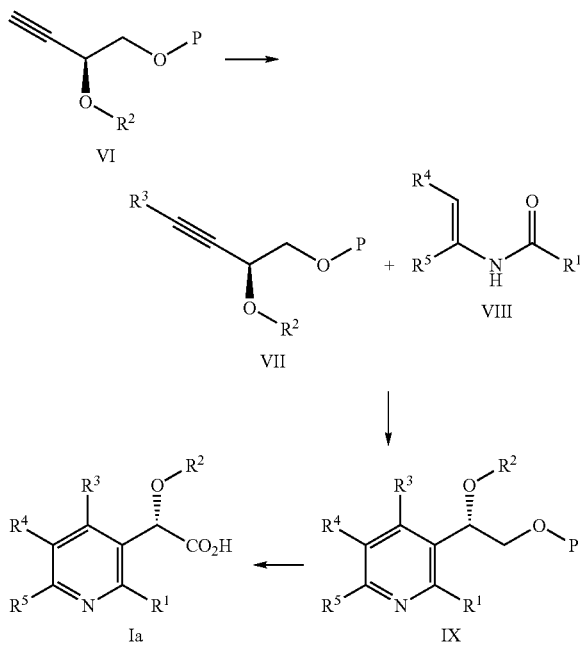

Intermediates VI and VIII, wherein $R^1$, $R^2$, $R^3$, $R^4$ and $R^5$ are as defined herein and P is a suitable protecting group, well known in the art, are commercially available or are prepared by reactions well known in the art or as set forth in the examples below. Intermediates VI are conveniently transformed to intermediates VII using conditions well-known to those skilled in the art, including but not limited to a Sonogashira coupling between intermediates $V^1$ and $R^3$—I. Intermediates VII and VIII undergo a cyclocondensation reaction under well known conditions, including but not limited to reaction with $(CF_3SO_2)_2O$ (triflic anhydride) in the presence of 2-chloropyridine to give intermediates IX. Deprotection of intermediate IX, followed by oxidation of the primary alcohol using conditions well known in the art, including but not limited to oxidation with Dess-Martin periodinane followed by sodium chlorite oxidation, provides compounds of formula (Ia).

It will be apparent to one skilled in the art that a compound of formula (I), or any of the intermediates II to XI involved in its preparation, wherein any of the substituents a, $R^1$, $R^2$, $R^3$, $R^4$, $R^5$ and $R^6$ has one meaning as defined herein, may be transformed to another compound of formula (I), or to any of the intermediates II to XI involved in its preparation as appropriate, wherein any of the substituents a, $R^1$, $R^2$, $R^3$, $R^4$, $R^5$ and $R^6$ has a different meaning as defined herein, at any chemically convenient step in the preparation. Examples of such transformations include but are not limited to alkylation, conversion of an aromatic primary amino group to a chloro or bromo substituent using a Sandmeyer reaction, and reductive dehalogenation. In addition, the substituents $R^1$, $R^2$, $R^3$, $R^4$, $R^5$ and $R^6$ may be protected and/or deprotected at intermediate steps in the preparation of a compound of formula (I), as will be recognized by the skilled person.

EXAMPLES

Other features of the present invention will become apparent from the following non-limiting examples which illustrate, by way of example, the principles of the invention. It will be apparent to a skilled person that the procedures exemplified below may be used, with appropriate modifications, to prepare other compounds of the invention as described herein.

As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel (SiO2) according to the procedure of W. C. Still et al., J. Org. Chem., (1978), 43, 2923. Mass spectral analyses are recorded using electrospray mass spectrometry. A number of intermediate and final products are purified using CombiFlash®Companion or RF apparatus, purchased from Teledyne Isco Inc, employing pre-packed silica gel cartridges and EtOAc and hexanes as solvents. These cartridges are available either from Silicycle Inc (SiliaFlash, 40-63 μm silica) or from Teledyne Isco (RediSep, 40-63 μm silica). Preparative HPLC is carried out under standard conditions using a SunFire™ Prep C18 OBD 5 μm reverse phase column, 19×50 mm and a linear gradient employing 0.1% TFA/acetonitrile and 0.1% TFA/water as solvents. Compounds are isolated as TFA salts when applicable.

Alternatively, preparative HPLC is carried out under standard conditions using a SunFire™ Prep C18 OBD 5 μm reverse phase column, 19×50 mm and a linear gradient employing 10 mM ammonium formate in $H_2O$ (pH=3.8); and MeOH. Alternatively, preparative HPLC is carried out under standard conditions using a XBridge™ Prep C18 OBD 5 μm reverse phase column, 19×50 mm and a linear gradient employing 10 mM ammonium bicarbonate in $H_2O$ (pH=10.0); and MeOH.

Analytical HPLC is carried out under standard conditions using a SunFire™ C18 (3.5 μm, 4.6×30 mm) reverse phase column at 220 nm, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
| --- | --- | --- | --- |
| 0 | 2.5 | 98 | 2 |
| 0.5 | 2.5 | 98 | 2 |
| 6.0 | 2.5 | 50 | 50 |
| 10.5 | 3.0 | 0 | 100 |
| 11.5 | 3.0 | 0 | 100 |

Alternatively, analytical HPLC is carried out under standard conditions using a SunFire™ C18 (3.5 μm, 4.6×30 mm) reverse phase column at 220 nm, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 2.5 | 98 | 2 |
| 0.6 | 2.5 | 98 | 2 |
| 5.5 | 2.5 | 50 | 50 |
| 7.3 | 3.0 | 0 | 100 |
| 7.9 | 3.0 | 0 | 100 |

Alternatively, analytical HPLC is carried out under standard conditions using a SunFire™ C18 (3.5 μm, 4.6×30 mm) reverse phase column at 220 nm, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 2.5 | 98 | 2 |
| 0.6 | 2.5 | 98 | 2 |
| 3.4 | 2.5 | 50 | 50 |
| 4.5 | 3.0 | 0 | 100 |
| 4.9 | 3.0 | 0 | 100 |

Alternatively, analytical HPLC is carried out under standard conditions using a SunFire™ C18 (3.5 μm, 4.6×30 mm) reverse phase column at 220 nm, elution with a linear gradient as described in the following table (Solvent A 10 mM Ammonium Formate in $H_2O$ (pH=3.8); solvent B MeOH):

| Time (min) | Flow (mL/min) | Solvent A (%) | Solvent B (%) |
|---|---|---|---|
| 0 | 4.0 | 98 | 2 |
| 2.85 | 4.0 | 0 | 100 |
| 2.86 | 5.0 | 0 | 100 |
| 3.60 | 5.0 | 0 | 100 |

Alternatively, analytical HPLC is carried out using a shorter run time using an Aquity™ HSST3 (1.8 μm, 2.1×50 mm) reverse phase column at 220 nm, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 0.9 | 98 | 2 |
| 1.5 | 0.9 | 50 | 50 |
| 2.6 | 0.9 | 0 | 100 |

Alternatively, analytical UPLC is carried out using a shorter run time using an Aquity™ HSST3 (1.8 μm, 2.1×50 mm) reverse phase column at 220 nm, elution with a linear gradient as described in the following table (Solvent A 10 mM Ammonium Formate in $H_2O$ (pH=3.8); solvent B MeOH):

| Time (min) | Flow (mL/min) | Solvent A (%) | Solvent B (%) |
|---|---|---|---|
| 0 | 0.8 | 95 | 5 |
| 2.30 | 0.9 | 0 | 100 |
| 2.32 | 1.0 | 0 | 100 |
| 3.00 | 1.0 | 0 | 100 |

Abbreviations or symbols used herein include:
Ac: acetyl; AcOH: acetic acid; $Ac_2O$: acetic anhydride; BOC or Boc: tert-butyloxycarbonyl; BSA: bovine serum albumin; Bu: butyl; DABCO: 1,4-diazabicyclo[2.2.2]octane; DBU: 1,8-diazabicyclo[5.4.0]undec-7-ene; DCE: dichloroethane; DEAD: diethyl azodicarboxylate; DCM: dichloromethane; DIAD: diisopropyl azodicarboxylate; DIBAL: diisobutyl aluminum hydride; DMA: dimethyl acetamide; DMAP: N,N-dimethyl-4-aminopyridine; DME: 1,2-dimethoxyethane; DMF: N,N-dimethylformamide; DMSO: dimethylsulfoxide; DPPA: diphenylphosphoryl azide; Dppf: 1,1'-Bis(diphenylphosphino)ferrocene; $EC_{50}$: 50% effective concentration; eq: equivalent; Et: ethyl; $Et_3N$: triethylamine; $Et_2O$: diethyl ether; EtOAc: ethyl acetate; EtOH: ethanol; HPLC: high performance liquid chromatography; $IC_{50}$: 50% inhibitory concentration; $^iPr$ or i-Pr: 1-methylethyl (iso-propyl); LiHMDS: lithium hexamethyldisilazide; Me: methyl; MeCN: acetonitrile; MeOH: methanol; MOI: multiplicity of infection; MS: mass spectrometry (ES: electrospray); n-BuONa: sodium n-butoxide; n-BuOH: n-butanol; n-BuLi: n-butyl lithium; NMP: N-methylpyrrolidone; NMR: nuclear magnetic resonance spectroscopy; Ph: phenyl; PhMe: toluene; PG: protecting group; Pr: propyl; RPMI: Roswell Park Memorial Institute (cell culture medium); RT: room temperature (approximately 18° C. to 25° C.); SM: starting material; TBTU: 2-(1H-Benzotriazole-1-yl)-1,1,3,3-tetramethyluronium tetrafluoroborate; tert-butyl or t-butyl: 1,1-dimethylethyl; Tf: trifluoromethanesulfonyl; $Tf_2O$: trifluoromethanesulfonic anhydride; TFA: trifluoroacetic acid; THF: tetrahydrofuran; TLC: thin layer chromatography; and UPLC: ultra high performance liquid chromatography.

Example 1

Synthesis of Compound 1029 (Table 1)

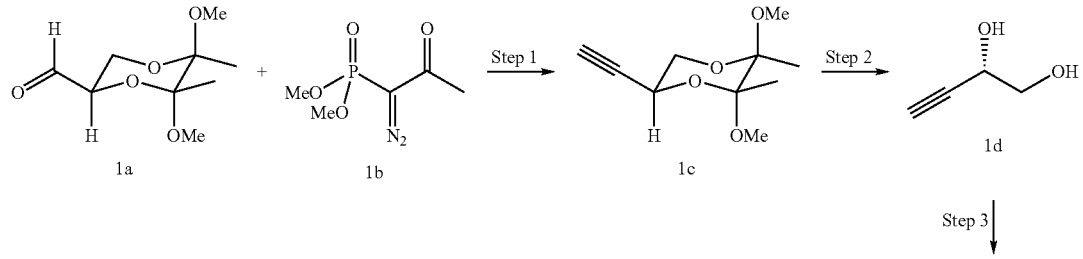

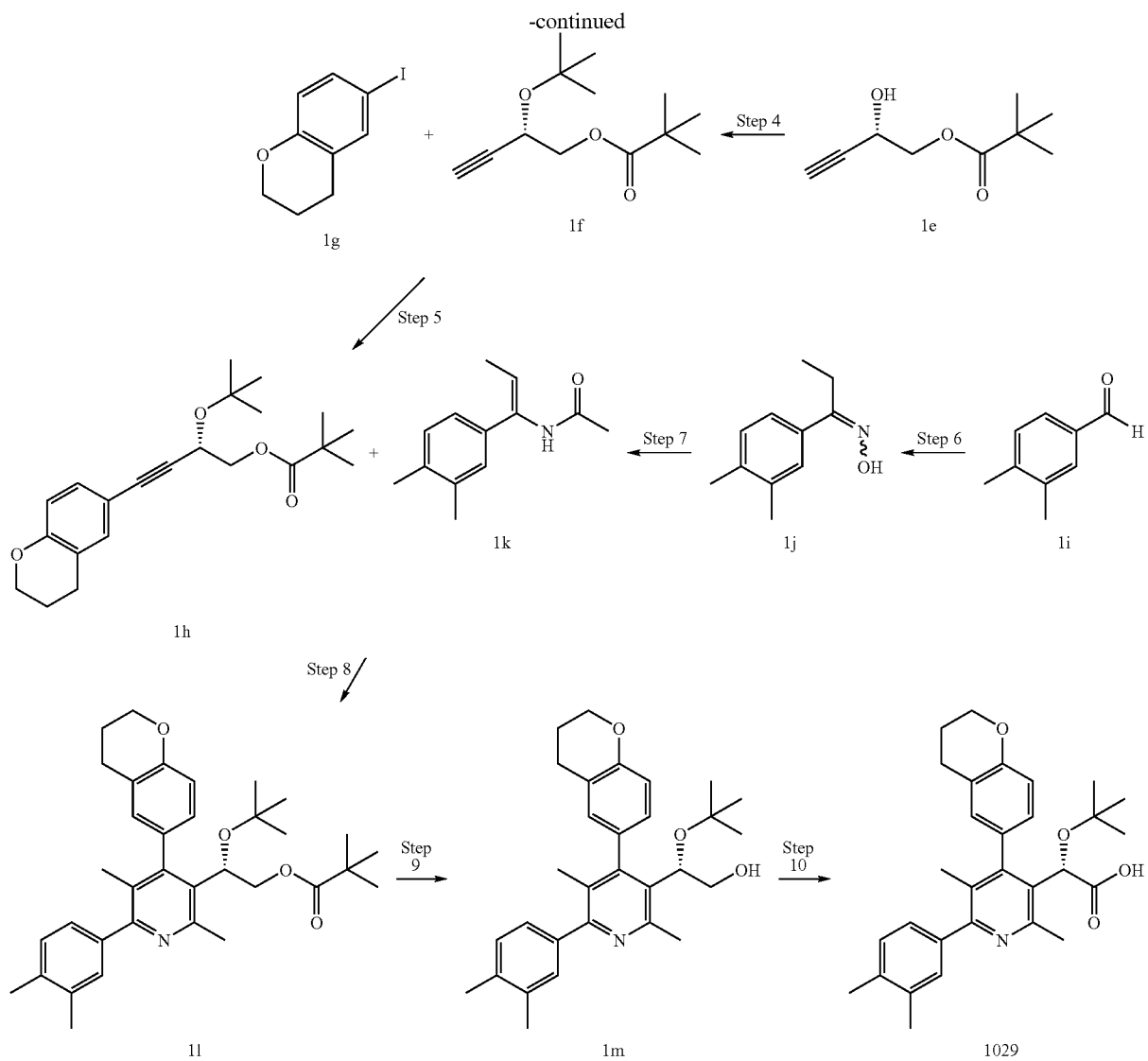

Step 1:

A mixture of aldehyde 1a (5.85 g, 28.6 mmol; prepared according to Michel, P. and Ley, S. V. *Synthesis* 2003, 10, 1598-1602), phoshonate 1b (6.6 g, 34 mmol) and $K_2CO_3$ (8.8 g, 64 mmol) in MeOH (125 mL) is stirred overnight at RT. The mixture is concentrated nearly to dryness and the residue is partitioned between $H_2O$ (250 mL) and EtOAc (500 mL). The aqueous layer is washed with EtOAc (2×250 mL), and the combined organic layers are dried over anhydrous $Na_2SO_4$ and concentrated to give alkyne 1c.

Step 2:

A mixture of alkyne 1c (5.0 g, 25 mmol) in TFA (35 mL) and water (3.6 mL) is stirred at RT for about 30 min. The mixture is concentrated under reduced pressure and the residue is purified by CombiFlash® Companion to give diol 1d.

Step 3:

A solution of diol 1d (1.2 g, 14 mmol) and $Et_3N$ (1.7 mL, 12 mmol) in DCM (80 mL) is cooled to 0° C. under $N_2$. Trimethylacetyl chloride is added dropwise and the resulting mixture is allowed to stir overnight at RT. The reaction is quenched with MeOH (100 mL) and stirring is continued for about 20 min. The mixture is concentrated under reduced pressure and the residue is purified by CombiFlash® Companion to give the desired mono ester 1e.

Step 4:

In a sealable reaction flask, a solution of the propargylic alcohol 1e (375 mg, 2.20 mmol) and Amberlyst® H-15 resin (150 mg) in hexane (3 mL) is cooled to −78° C. Isobutene is then bubbled through the solution until the volume approximately doubles. The tube is then sealed, brought to RT and is stirred overnight. The tube is then cooled to −78° C., is opened and brought back to RT. The mixture is then filtered through a plug of $SiO_2$ (EtOAc wash) and concentrated under reduced pressure to provide pure tert-butyl ether 1f.

Step 5:

Solid $Pd(PPh_3)_4$ (444 mg, 0.385 mmol) and CuI (146 mg, 0.769 mmol) are added successively to a mixture of 1g (10 g, 34 mmol) and alkyne 1f (11 g, 55 mmol) in DMF (23 mL) and $Et_2NH$ (115 mL). The reaction mixture is stirred overnight at RT and then concentrated, diluted with EtOAc (300 mL) and washed successively with brine, 1 N aqueous HCl and water. The organic layer is dried over $Na_2SO_4$ and the residue purified by CombiFlash® Companion to give alkyne 1 h.

Step 6:

To a mixture of 3,4-dimethylbenzaldehyde (1i; 500 mg, 3.73 mmol) and Et$_2$O (12 mL) is added ethylmagnesium bromide (3M, 1.4 mL, 1.2 mmol) dropwise. After 15 min, the reaction is quenched with saturated aqueous NH$_4$Cl (50 mL) and the layers are separated. The organic layer is washed with saturated aqueous NH$_4$Cl (50 mL), dried over Na$_2$SO$_4$ and concentrated to give the intermediate benzyl alcohol. To a mixture of this material and DCM (28 mL) is added silica gel (2.2 g) followed by pyridinium chlorochromate (1.5 g, 7.2 mmol). The mixture is stirred for 45 min and the mixture is filtered through a plug of silica (3×1.5 cm) which is then washed with DCM (total of 50 mL). The filtrate is evaporated to dryness to give the intermediate ketone. This material is combined with sodium acetate (102 mg, 1.25 mmol) and hydroxylamine hydrochloride (87 mg, 1.25 mmol) in MeOH (0.8 mL) and is heated to 85° C. in a sealed tube. After 1 h, the reaction is allowed to cool to room temperature and concentrated onto silica gel (2 g). The product is purified by CombiFlash® Companion to give the oxime 1j as a mixture of cis- and trans-isomers.

Step 7:

A mixture of oxime 1j (130 mg, 0.73 mmol) and PhMe (1.7 mL) is degassed by bubbling N$_2$ gas through the solution for 30 min. Ph$_3$P (0.23 g, 0.88 mmol) is added and the mixture stirred for 10 min at RT. Ac$_2$O (84 μL, 0.89 mmol) is added and the mixture is stirred at reflux for 16 h, cooled to room temperature and concentrated in vacuo. A mixture of the residue, MeOH (3 mL) and excess K$_2$CO$_3$ (200 mg) is stirred for 1 h and the methanol is removed in vacuo. The residue is dissolved in EtOAc (10 mL) and water (5 mL). The organic layer is washed with water, concentrated and purified by CombiFlash® Companion to give amide 1k as a mixture of cis- and trans-isomers.

Step 8:

Tf$_2$O (48 μL, 0.29 mmol) is added via syringe over 1 min to a stirred mixture of amide 1k (55 mg, 0.27 mmol) and 2-chloropyridine (34 μL, 0.36 mmol) in DCM (0.7 mL) at −78° C. After 5 min, the reaction flask is placed in an ice-water bath and warmed to 0° C. Alkyne 1h (69 mg, 0.19 mmol) in DCM (0.7 mL) is added via syringe and the mixture is allowed to warm to RT. After stirring for 30 min, Et$_3$N (1 mL) is added and the mixture is evaporated to dryness. The residue is dissolved in EtOAc (10 mL) and washed with water. The organic layer is dried over Na$_2$SO$_4$ and concentrated and the residue is purified by CombiFlash® Companion giving pyridine 1l.

Step 9:

LiBH$_4$ in THF (2 M, 470 μL, 0.940 mmol) is added to a solution of ester 1l (51 mg, 0.094 mmol) dissolved in THF (0.85 mL) and the reaction mixture is heated to 85° C. and stirred for 30 min. Excess reagent is quenched with HCl (2 mL) and the mixture neutralized with NaHCO$_3$ (10 mL) and extracted with EtOAc (3×10 mL). The combined organic layers are dried over Na$_2$SO$_4$ and concentrated to give alcohol 1m.

Step 10:

Dess-Martin periodinane (71 mg, 0.17 mmol) is added to a mixture of alcohol 1m (43 mg, 0.094 mmol) and DCM (1.7 mL). After 2 h, the reaction mixture is concentrated, the residue is dissolved in 1:1 THF/tBuOH (2 mL), and 2,3-dimethyl-2-butene (1M in THF, 0.75 mL, 0.75 mmol) is added. A separate mixture of NaClO$_2$ (71 mg, 0.79 mmol) and NaH$_2$PO$_4$ (71 mg, 0.59 mmol) in water (1 mL) is added to the first mixture and the mixture is stirred at RT. After 30 min, the mixture is diluted with water (5 mL) and extracted with EtOAc (3×10 mL). The organic layer is dried over Na$_2$SO$_4$ and concentrated. The residue is purified by preparative HPLC to give compound 1029 (Table 1).

Example 2

Synthesis of Intermediate 2h

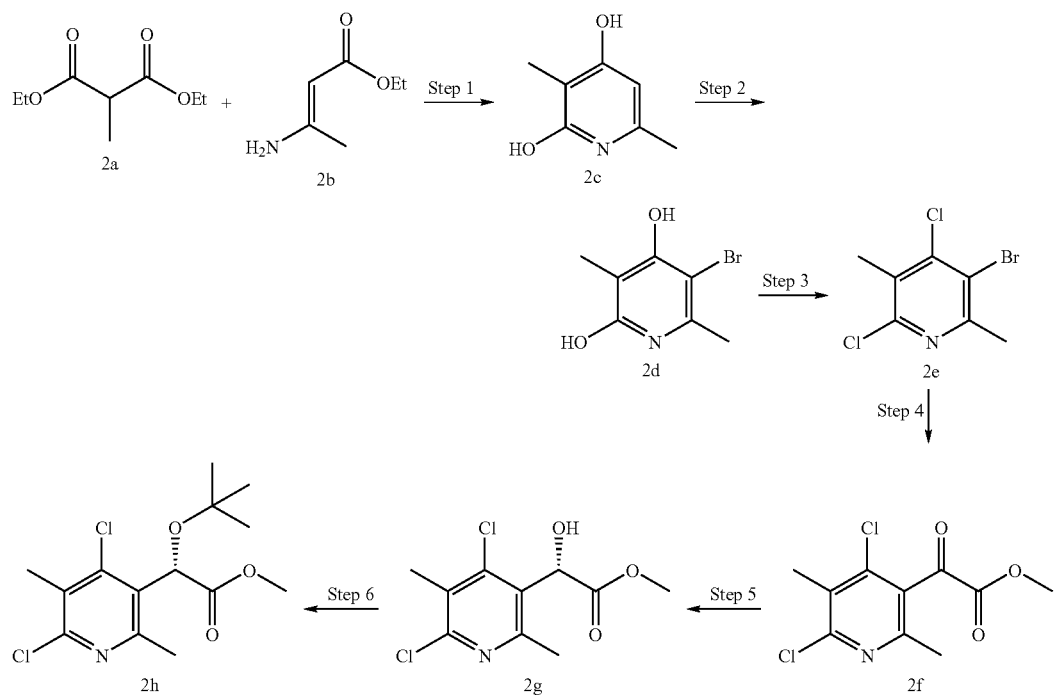

Step 1:

To a solution of sodium ethoxide (1.48 L, 3.74 mol, 21% w/w in EtOH) at RT is added a solution of diethyl methylmalonate 2a (645 mL, 3.72 mol) in anhydrous PhMe (330 mL). The resulting solution is stirred for 30 min and a solution of ethyl 3-aminocrotonate 2b (485 mL, 3.71 mol) in anhydrous PhMe (490 mL) is added. The mixture is stirred at reflux for 39 h, EtOH (1-1.5 L) is removed by vacuum distillation, the mixture is cooled and water (1.6 L) is added. The mixture is stirred at 40° C. for ~2 h, then is cooled and the phases are separated. The aqueous phase is washed with PhMe (2×50 mL) and then adjusted to pH 5-6 with conc. HCl. The solid is filtered and dried to afford dihydroxypyridine 2c.

Step 2:

To a mixture of dihydroxypyridine 2c (100 g, 0.718 mol) and DCM (800 mL) at ambient temperature is added dropwise $Br_2$ (37 mL, 150 g, 0.72 mol) in DCM (550 mL) over 16 min. The resulting mixture is stirred at RT for 1 h and intermediate 2d is collected by filtration (HBr salt).

Step 3:

The bromopyridine 2d (191 g, HBr salt) is heated at reflux in $POCl_3$ (850 mL) for 18 h and cooled to RT. The excess $POCl_3$ is removed by evaporation and the residue is poured onto ice. The mixture is adjusted to basic pH using 10 N NaOH and solid $NaHCO_3$. The mixture is filtered and the filtrate extracted with DCM (3×800 mL) and dried over $Na_2SO_4$. The solution is passed through a $SiO_2$ (600 g) column and concentrated to afford 2e.

Alternative Procedure for Step 3:

Bromopyridine 2d (370 g, HBr salt) is heated at reflux in $POCl_3$ (1.25 L) for 18 h. The mixture is cooled and excess $POCl_3$ is evaporated. To the residue is added $PhPOCl_2$ (1.2 L) and the mixture is heated at 150° C. for 28 h. The mixture is allowed to cool to RT and poured onto ice, then adjusted to basic pH with solid $Na_2CO_3$. The mixture is filtered and the filtrate is extracted with EtOAc (3×1500 mL), dried over $Na_2SO_4$ and filtered. The filtrate is passed through a $SiO_2$ (600 g) column and concentrated, and the residue is triturated with EtOAc to give 2e (196 g). The filtrate is concentrated and purified by CombiFlash® Companion to give a second crop of 2e.

Step 4:

To a solution of bromide 2e (105 g, 0.411 mol) in anhydrous THF (1.14 L) is added Cu(I)Br (15 g, 0.1 mol). To the resulting mixture at RT is added iPrMgCl—LiCl (400 mL, 0.52 mol, 1.3 M in THF) over 30 min. The mixture is allowed to stir for 1 h, methyl chlorooxoacetate (80 mL, 0.87 mol) is added and stirring is continued for 1 h. The reaction is quenched with saturated $NaHCO_3$ and solid $NaHCO_3$ and the mixture extracted with EtOAc (3×1.2 L). The organic extract is dried over $Na_2SO_4$, and filtered. The extract is passed through a $SiO_2$ (300 g) column, concentrated and the residue is purified by CombiFlash® Companion (EtOAc/hexanes) to afford 2f.

Step 5:

To a mixture of ester 2f (65 g, 0.248 mol) in anhydrous PhMe (400 mL) in a 3 necked 5 L round bottom flask equipped with a magnetic stir bar, addition funnel, thermometer and gas-inlet is added (R)-2-methyl-CBS-oxazoborolidine (1 M solution in toluene, 50 mL, 50 mmol) with stirring. The mixture is cooled to −35° C. and a solution of catecholoborane (36 mL, 40.5 g, 338 mmol) in toluene (240 mL) is added over a 2 h period. Stirring is continued at −35° C. for 30 min. The mixture is allowed to warm to −15° C. and is diluted with EtOAc (400 mL) and aqueous $Na_2CO_3$ (15 wt %, 800 mL). The mixture is stirred vigorously for 30 min, and the organic phase is separated and washed with aqueous $Na_2CO_3$ (15 wt %, 2×200 mL; vigorous stirring for 30 min each time) and aqueous $NH_4Cl$ (15 wt %, 2×300 mL; vigorous stirring for 30 min each time). The organic layer is separated, passed through $SiO_2$ (300 g) eluting with EtOAc, and concentrated in vacuo. The residue is purified by CombiFlash® Companion to afford 2g.

Step 6:

A mixture of 2g (33.8 g, 0.128 mol) and t-butyl acetate (2.4 L) is cooled in an ice bath, and perchloric acid (70% aq) (300 mL) is added quickly. The flask is sealed and allowed to stir for 6 h at ~0-5° C. The reaction is quenched with a saturated solution of $Na_2CO_3$ (850 mL) and the mixture is adjusted to pH 8-9 with solid $Na_2CO_3$. The mixture is filtered, the organic layer is separated and the aqueous layer extracted with EtOAc (3×750 mL), dried over $Na_2SO_4$, filtered and concentrated. DCM is added to the residue and the mixture is filtered. The organic phase is concentrated and purified using the CombiFlash® Companion (hexane/EtOAc: 1% to 30%) to afford 2h (>98% ee by chiral HPLC) and recovered starting material 2g.

Example 3

Synthesis of Intermediates 3g and 3h

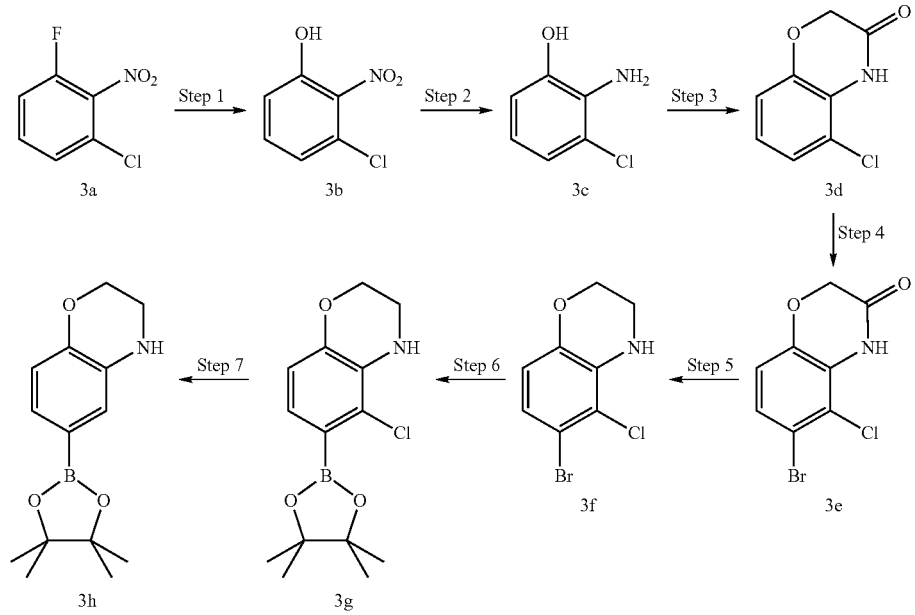

Step 1:
To a mixture of 2-chloro-6-fluoronitrobenzene 3a (6.62 g, 37.7 mmol) and LiOH.H$_2$O (6.33 g, 151 mmol) in THF (45 mL) and water (65 mL) is added aqueous H$_2$O$_2$ (30%, 8.6 mL, 80.0 mmol). The mixture is sealed and is heated to 60° C. with rapid stirring. After 3 days, the mixture is cooled, added to half-saturated aqueous sodium thiosulfate (200 mL) and shaken vigorously in a separatory funnel. The mixture is acidified to pH<3 with 1 N HCl, extracted with EtOAc (500 mL) and washed with brine (400 mL). The combined extracts are dried over magnesium sulfate, filtered and evaporated to give phenol 3b.

Step 2:
To a mixture of phenol 3b (6.37 g, 36.7 mmol) and THF (100 mL) is added tin powder (17.4 g, 147 mmol) followed by 1 N HCl (220 mL, 220 mmol) and the mixture is stirred vigorously at RT for 16 h. The mixture is cooled to 0° C. and neutralized with 10 N NaOH (22 mL), and stirred vigorously for about 15 min. The mixture is filtered through a pad of Celite® and the solids are washed thoroughly with EtOAc (4×200 mL). The filtrate is acidified with 1 N HCl (4 mL) and diluted with brine (400 mL) and the organic phase is washed with brine (400 mL). The extract is dried over sodium sulfate, filtered and concentrated to afford aminophenol 3c.

Step 3:
Chloroacetyl chloride (1.94 mL, 24.3 mmol) is added to an ice-cold mixture of aminophenol 3c (2.91 g, 20.3 mmol) and K$_2$CO$_3$ (8.40 g, 60.8 mmol) in anhydrous DMF (200 mL) under a N$_2$ atmosphere. After 5 min, the reaction is allowed to warm to RT and, after a further 45 min, is heated to 50° C. After 15 h, the reaction is cooled and extracted with EtOAc (600 mL), and washed with water/brine (1 L), half-saturated sodium bicarbonate (1 L) and brine (600 mL). The organic phase is then dried over MgSO$_4$, filtered and concentrated to afford lactam 3d.

Step 4:
Bromine (1.8 mL, 35 mmol) is slowly added dropwise to a stirred mixture of lactam 3d (3.15 g; 17.1 mmol) in anhydrous DCM (40 mL) at RT. After 3 h, the mixture is slowly added to saturated aqueous sodium thiosulfate (200 mL) and extracted with DCM (4×100 mL). The combined extracts are washed with brine (200 mL), dried over MgSO$_4$, filtered and evaporated to afford the bromide 3e.

Step 5:
A solution of borane in THF (1.0 M, 18.5 mL, 18.5 mmol) is added dropwise to an ice-cold mixture of lactam 3e (4.00 g, 15.2 mmol) in anhydrous THF (75 mL), and the reaction is allowed to warm to RT. After about 30 min, the solution is heated to gentle reflux under a N$_2$ atmosphere. After 2 h, the mixture is cooled to 0° C., carefully quenched with 1N NaOH (19 mL) and stirred for about 15 min. The mixture is diluted with water (30 mL) and the THF is evaporated. The aqueous residue is extracted with EtOAc (400 mL+50 mL) and washed with water/brine (200 mL), 0.5 N NaOH (200 mL) and brine (100 mL). The combined extracts are dried over magnesium sulfate, filtered and evaporated to afford the morpholine derivative 3f.

Step 6:
Anhydrous DMF (30 mL) is added to a flask charged with aryl bromide 3f (1.84 g, 7.42 mmol), bis(pinacolato)diborane (2.83 g, 11.1 mmol) and potassium acetate (2.47 g, 26.0 mmol) and the mixture is deoxygenated by bubbling a stream of N$_2$ gas through the mixture for about 15 min. 1,1'-bis(diphenylphosphino)ferrocene (909 mg, 1.11 mmol) is added, and the mixture is deoxygenated for about a further 5 min and then heated to 95° C. After about 16 h, the reaction mixture is cooled, extracted with EtOAc (300 mL) and the extract is washed with 1:1 water/brine (500 mL) and brine (200 mL), dried over MgSO$_4$, filtered and concentrated. The residue is purified by chromatography over silica gel (EtOAc/hexanes) to afford the boronate 3g contaminated with 0.8 eq of the diboron reagent.

Step 7:
Palladium on activated charcoal (10% Pd by weight, 1.08 g) is added to a mixture of aryl chloride 3g (3.0 g, 10 mmol) and ammonium formate (6.4 g, 0.10 mol) in MeOH (75 mL). The mixture is heated at reflux for 30 min, cooled to RT and filtered through Celite®. The filter cake is rinsed with MeOH, the filtrate is concentrated to dryness and the residue is partitioned between water (50 mL) and EtOAc (100 mL). The organic layer is washed with brine (20 mL), dried over anhydrous MgSO$_4$ and concentrated to obtain boronic ester 3h.

Example 4

Synthesis of Compound 1163 (Table 1)

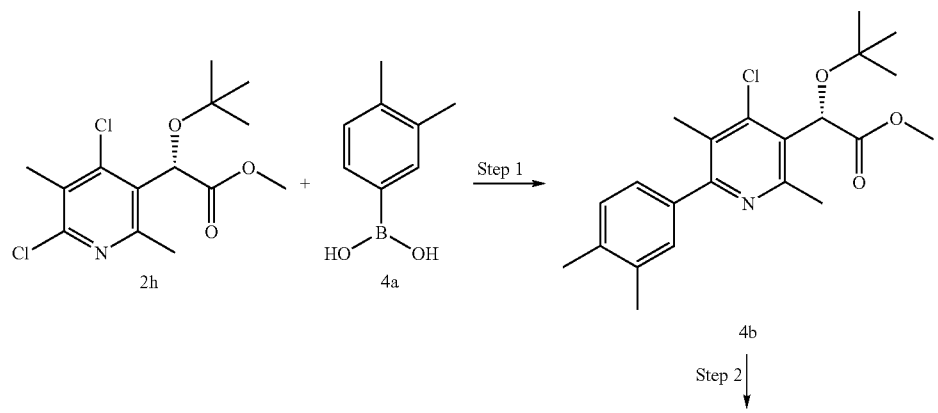

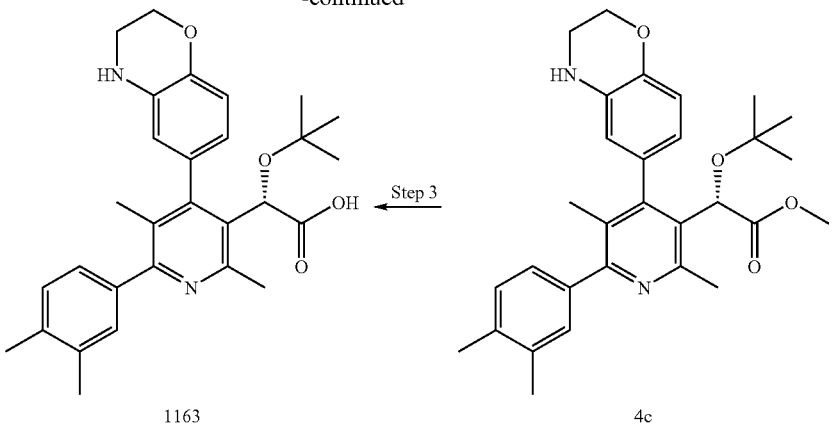

1163

4c

Step 1:

To a solution of the dichloropyridine 2h (Example 2) (2.0 g, 6.25 mmol) and 3,4-dimethylphenylboronic acid 4a (1.12 g, 7.5 mmol) in DMF (20 mL) is added 2M $Na_2CO_3$ (7.8 mL, 16 mmol) followed by $PdCl_2(PPh_3)_2$ (440 mg, 0.62 mmol). The reaction mixture is degassed by bubbling with argon (10 min), the reaction vessel is sealed and the mixture is heated at 110° C. for 16 h. The cooled mixture is diluted with EtOAc, washed with water and brine, dried over $MgSO_4$ and filtered. The residue is purified by CombiFlash® Companion (Hexanes/EtOAc) to give 4b.

Step 2:

To a mixture of chloropyridine 4b (250 mg, 0.64 mmol) in DMA (5.6 mL) is added boronate ester 3h (Example 3) (218 mg, 0.83 mmol), Pd([P(t-Bu)$_3$]$_2$ (33 mg, 0.064 mmol), and $NaHCO_3$ (269 mg, 3.2 mmol), followed by water (565 µL). The mixture is degassed by bubbling with argon under sonication for 10 min, the reaction vessel is sealed and the mixture is heated at 130° C. for 16 h. The reaction mixture is diluted with EtOAc (30 mL) and washed with brine (2×), water, and brine, dried over $MgSO_4$, filtered and concentrated and the residue is purified by CombiFlash® Companion (30% EtOAc/hexanes) to afford 4c.

Step 3:

To a mixture of ester 4c (191 mg, 0.39 mmol) and THF (8 mL)/MeOH (4 mL) is added 1.0N NaOH (4 mL, 4.0 mmol) at RT. The mixture is stirred at 50° C. for 18 h, cooled to RT, quenched with AcOH and diluted with EtOAc. The mixture is washed with water and brine, dried ($MgSO_4$), filtered and concentrated under vacuum. The residue is purified by CombiFlash® Companion (DCM/MeOH, 0-5%) and the product is diluted with MeCN/$H_2O$, frozen and lyophilized to give compound 1163 (Table 1).

Example 5

Synthesis of Compound 2003 (Table 2)

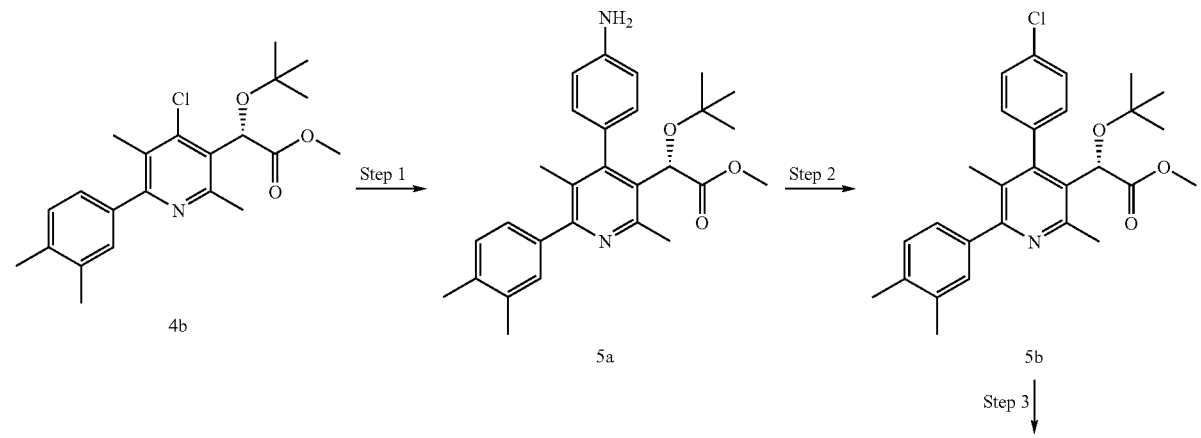

4b

5a

5b

Step 3

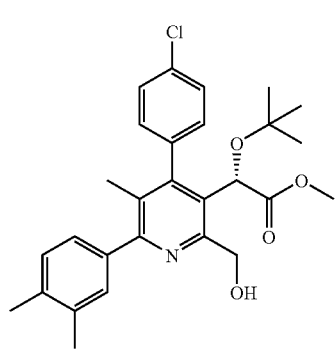 5e

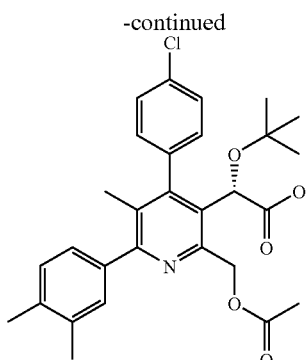 5d

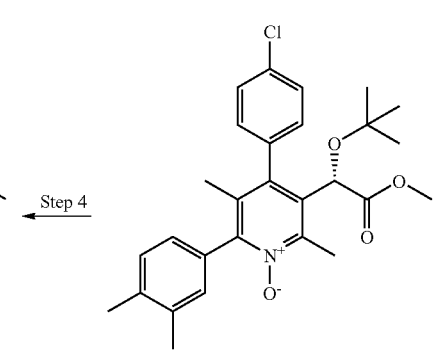 5c

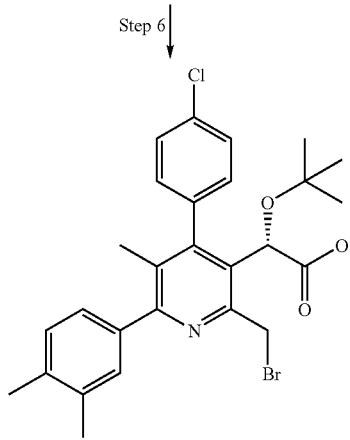 5f

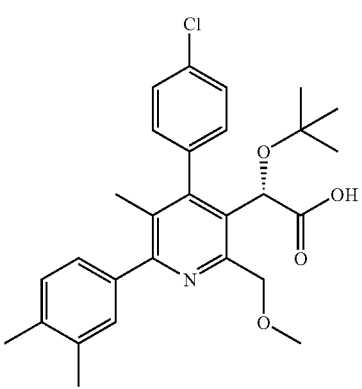 2003

Step 1:

To a solution of chloropyridine 4b (Example 4) (2.0 g, 5.1 mmol) in DMA (40 mL) is added 4-(4,4,5,5-tetramethyl-1,2,3-dioxaborolan-2-yl)aniline (1.6 g; 7.2 mmol) followed by NaHCO$_3$ (2.2 g, 26 mmol) and distilled water (3 mL). The mixture is split into two microwave flasks and streams of argon gas are bubbled through the vigorously stirred mixtures for 30 min. bis-(Tri-tert-butylphosphine) palladium(0) catalyst (131 mg; 0.256 mmol) is added to each flask and the argon bubbling is continued for 10 min. The flasks are sealed and heated at 130° C. for 16 h. The two reaction mixtures are pooled together, diluted with EtOAc (300 mL), and washed with water/brine (1:1 v/v; 5×100 mL) and brine (2×100 mL). The organic phase is dried over MgSO$_4$, filtered and concentrated. The residue is purified with CombiFlash® Companion to yield intermediate 5a.

Step 2:

To a mixture of copper (II) chloride (558 mg, 4.15 mmol) and dry MeCN (20 mL) at 0° C. under nitrogen atmosphere is added, dropwise, t-butyl nitrite (0.55 mL; 4.17 mmol). A solution of aniline 5a (1.3 g, 2.9 mmol) in dry MeCN (20 mL) is added dropwise over 5 min and the ice bath removed after 15 min. After 16 h, the solvent is evaporated and the residue is adsorbed onto silica gel, purified by CombiFlash® Companion and dried under high vacuum to afford intermediate 5b.

Step 3:

Meta-chloroperbenzoic acid (80%, 455 mg, 2.11 mmol) is added to a stirred mixture of pyridine 5b (546 mg, 1.17 mmol) in anhydrous DCM (10 mL) and the reaction is allowed to stir at ambient temperature. After 2 days, additional meta-chloroperbenzoic acid (200 mg) and DCM (2 mL) are added and the stirring continued. After an additional day, the mixture is extracted with EtOAc (2×50 mL), and washed with saturated NaHCO$_3$ and brine. The combined organic phases are dried over MgSO$_4$ and concentrated to afford the N-oxide 5c.

Step 4:

Pyridine N-oxide 5c (1.17 mmol) is dissolved in Ac$_2$O (7.5 mL, 79 mmol) and the resulting solution is heated to 60° C. under a nitrogen atmosphere. After 2 h, the solution is concentrated under high vacuum and the residue is dried under high vacuum for 1 h. The residue is extracted with EtOAc (100 mL) and washed with saturated NaHCO$_3$ and brine. The extract is dried over MgSO$_4$ and concentrated to afford intermediate 5d.

Step 5:

HCl in dioxane (4N, 1.0 mL, 4.0 mmol) is added to a stirred mixture of 5d (1.17 mmol) and dry MeOH (4.2 mL) cooled to 0° C., and the mixture is allowed to warm to ambient temperature. After 21 h, the mixture is extracted with EtOAc (80+20 mL) and washed with saturated NaHCO$_3$ and brine. The combined extracts are dried over MgSO$_4$ and evaporated to afford alcohol 5e.

Step 6:

To a stirred mixture of alcohol 5e (1.17 mmol) and anhydrous DCM (8 mL) at ambient temperature is added CBr$_4$ (427 mg, 1.3 mmol) followed by triphenylphosphine (339 mg; 1.3 mmol). The mixture is stirred at ambient temperature for 16 h, then diluted with DCM, absorbed onto silica gel and purified by CombiFlash® Companion to afford bromide 5f.

Step 7:

NaH (60% oil dispersion; ca. 2 mg) is added to a mixture of bromide 5f (30 mg, 0.055 mmol), anhydrous THF (0.5 mL)

and anhydrous MeOH (50 μL, 1.2 mmol) and the mixture is stirred in a sealed vial at ambient temperature. After 2 h, additional NaH (ca. 2 mg) is added and the stirring continued. After 17 h, the reaction mixture is acidified with acetic acid, diluted with water, filtered through a Millex filter, divided into two portions and purified by preparatory HPLC. The relevant fractions are pooled and lyophilized to afford compound 2003 (Table 2, TFA salt).

Example 6

Synthesis of Compound 2004 (Table 2)

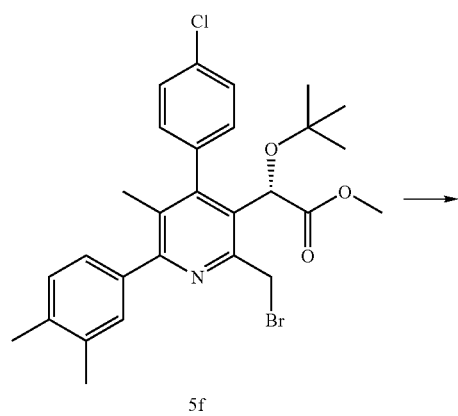

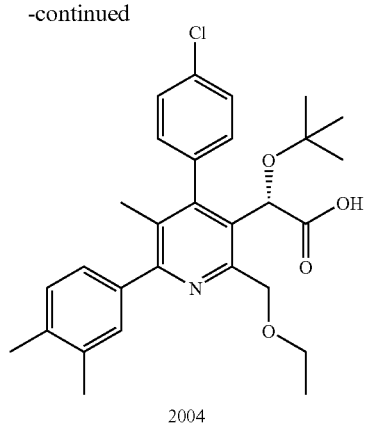

Intermediate 5f (Example 5) is transformed to compound 2004 (Table 2) using the procedure described in step 7 of Example 5, except that MeOH is replaced with absolute EtOH.

Example 7

Synthesis of Compound 2002 (Table 2)

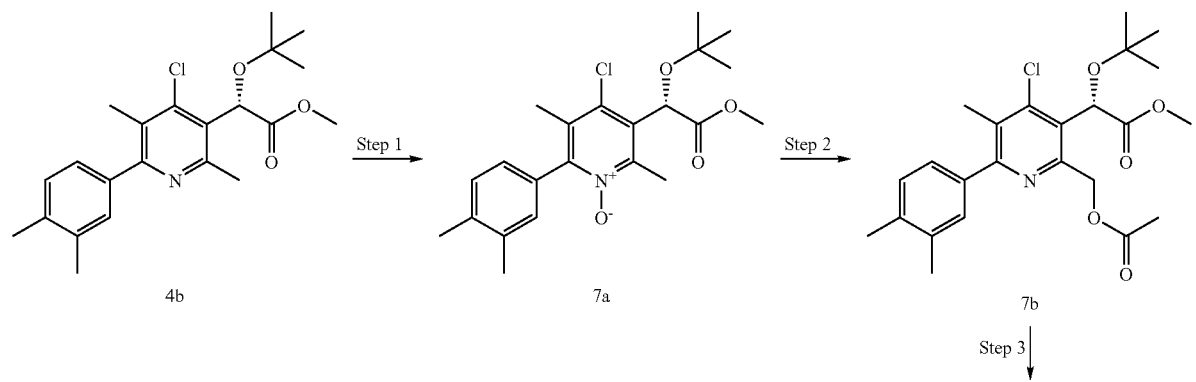

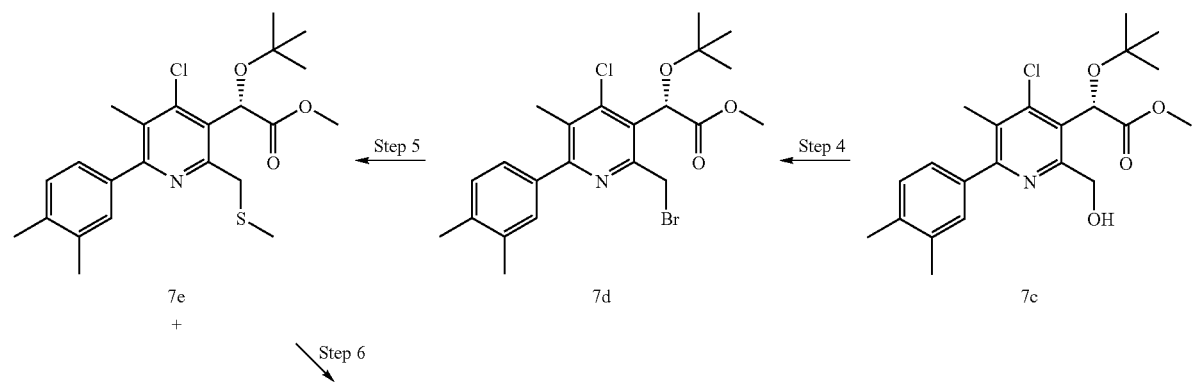

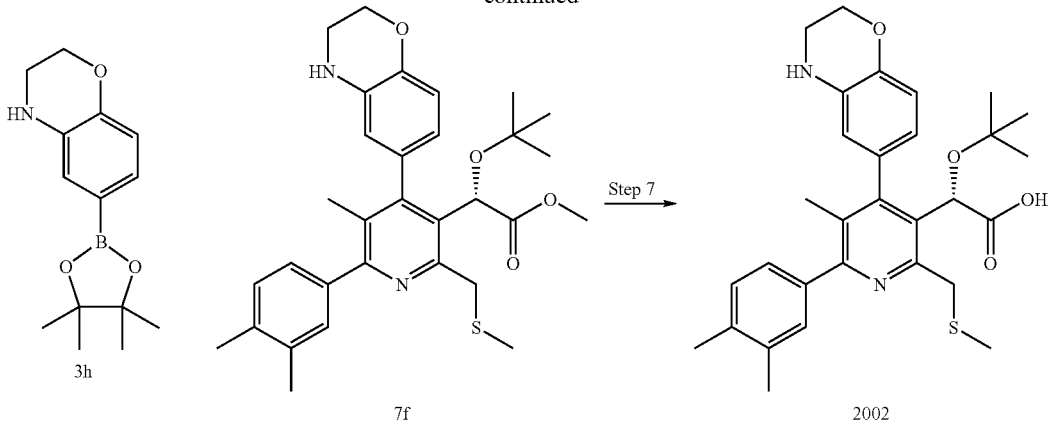

Step 1 to Step 4:
Intermediate 4b (Example 4) is transformed to intermediate 7d using the procedures described in steps 3 to 6 of Example 5.

Step 5:
To a stirred solution of bromide 7d (314 mg, 0.67 mmol) in anhydrous DMF (2.0 mL) at ambient temperature is added sodium thiomethoxide (57 mg, 0.81 mmol). Stirring is continued for 1 h and the solution is extracted with EtOAc (75 mL) and washed with saturated NaHCO₃ and brine. The extract is dried over MgSO₄ and concentrated and the residue is purified by CombiFlash®Companion to afford the thioether 7e.

Step 6:
To a mixture of chloropyridine 7e (63 mg, 0.14 mmol), boronate ester 3h (Example 3) (53 mg, 0.20 mmol), bis-(tri-tert-butylphosphine) palladium(0) catalyst (16 mg; 0.031 mmol), Dave-Phos ligand (24 mg, 0.061 mmol) and NaHCO₃ (60 mg, 0.71 mmol) in DMA (1.3 mL) in a microwave vial is added distilled water (0.13 mL), and the mixture is deoxygenated by bubbling argon for 15 min. The vial is sealed and heated to 130° C. After 16 h, the mixture is extracted with EtOAc (40 mL) and washed with water and brine. The extract is dried over MgSO₄ and concentrated, and the residue is purified by CombiFlash®Companion to afford intermediate 7f.

Step 7:
To a mixture of ester 7f (15 mg, 0.028 mmol) and LiOH.H₂O (10 mg, 0.24 mmol) is added THF (0.70 mL) followed by distilled water (0.15 mL) and MeOH (0.1 mL), and the mixture is heated to 45° C. After 16 h, the mixture is acidified with AcOH, diluted with MeCN/water, split into two portions and purified by preparatory HPLC. The relevant fractions are pooled and lyophilized to yield compound 2002 (Table 2) (TFA salt).

Example 8

Synthesis of Compound 2007 (Table 2)

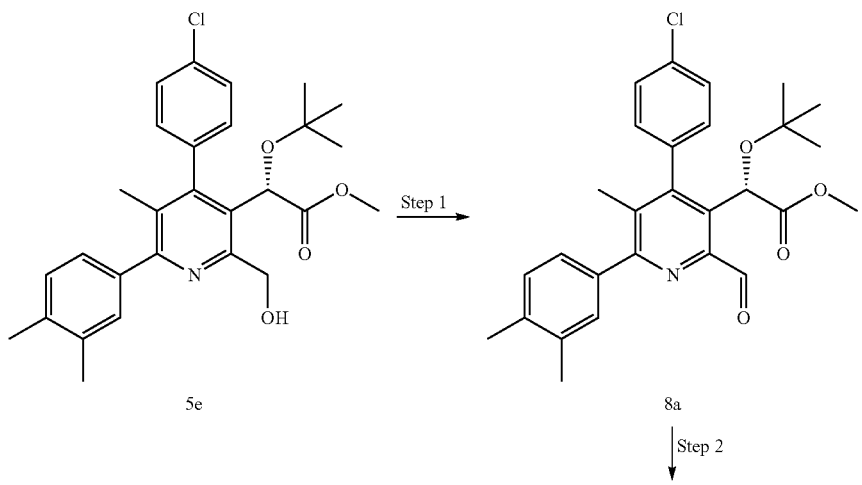

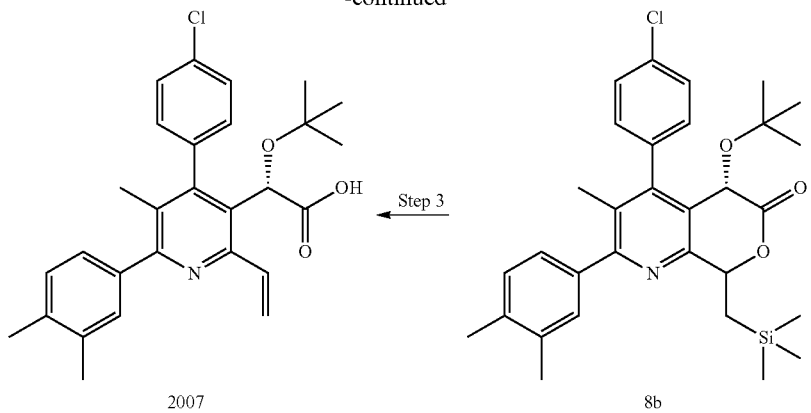

2007 → Step 3 → 8b

Step 1:

A mixture of alcohol 5e (Example 5) (200 mg, 0.49 mmol), Dess-Martin periodinane (251 mg; 0.59 mmol) and anhydrous DCM (6 mL) is stirred at RT under a nitrogen atmosphere for 18 h. The reaction mixture is vigorously stirred with saturated $NaHCO_3/Na_2S_2O_3$ (1:1, v/v, 12 mL) for 20 min and is extracted with DCM. The combined extracts are washed with saturated $NaHCO_3$, dried over $MgSO_4$ and concentrated to afford the aldehyde 8a.

Step 2:

Trimethylsilylmethylmagnesium bromide (90%, 1M solution in $Et_2O$, 0.34 mL, 0.31 mmol) is added dropwise to a stirred solution of aldehyde 8a (125 mg, 0.26 mmol) in anhydrous THF (2.0 mL) cooled to −35° C. under a nitrogen atmosphere. After 1 h, additional trimethylsilylmethyl magnesium bromide solution (0.26 mL; 0.23 mmol) is added. After a further 2 h, the reaction is quenched with saturated $NH_4Cl$ (1 mL) and the mixture is extracted with EtOAc (20 mL), and washed with 5% $NaHCO_3$ and brine. The extract is dried over $MgSO_4$, filtered and evaporated and the residue is purified by CombiFlash® Companion to afford lactone 8b.

Step 3:

To a stirred mixture of lactone 8b (98 mg; 0.183 mmol) and anhydrous THF (3.0 mL) under a nitrogen atmosphere is added dropwise tetrabutylammonium fluoride solution (1 M solution in THF; 0.27 mL; 0.27 mmol). The mixture is allowed to stir at 0° C. for 30 min, then is allowed to warm to ambient temperature. After 1 h, the reaction is concentrated to dryness and the residue is dissolved in MeCN (10 mL). An aliquot (1 mL) is set aside and the remaining solution is adsorbed onto silica gel and purified by CombiFlash® to afford compound 2007 (Table 2). The 1 ml aliquot is purified by preparatory HPLC to yield compound 2007 (Table 2) (TFA salt).

Example 9

Synthesis of Compound 2008 (Table 2)

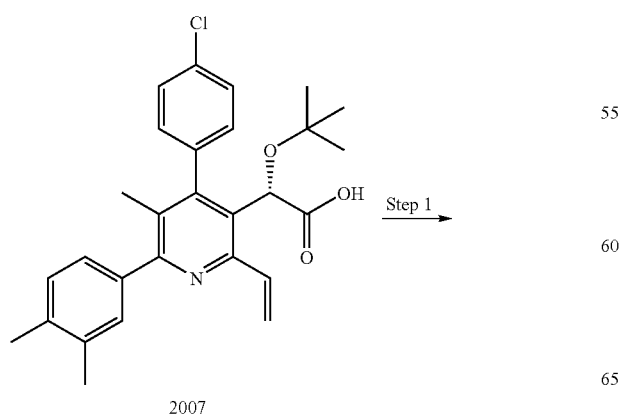

2007 → Step 1

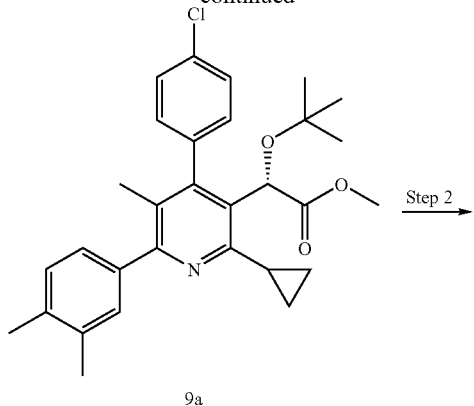

9a → Step 2

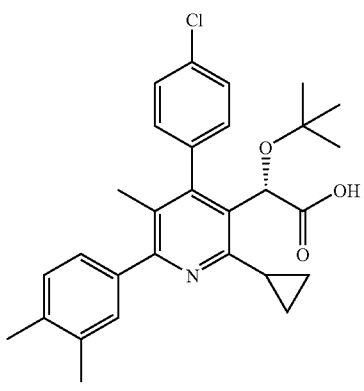

2008

Step 1:

To a stirred, ice cold solution of compound 2007 (Example 8) (12 mg, 0.026 mmol) is added dropwise a solution of diazomethane in $Et_2O$ (ca. 0.7 M, 2 mL) via a plastic pipette. After 5 min, palladium(II) acetate (5 mg, 0.02 mmol) is added and the mixture is stirred for 15 min. Nitrogen gas is bubbled through the solution to remove excess diazomethane and the residue is dried under high vacuum for 10 min to yield intermediate 9a.

Step 2:

Intermediate 9a is converted to compound 2008 using the procedure described in step 7 of Example 7.

Example 10

Synthesis of Intermediate 10B

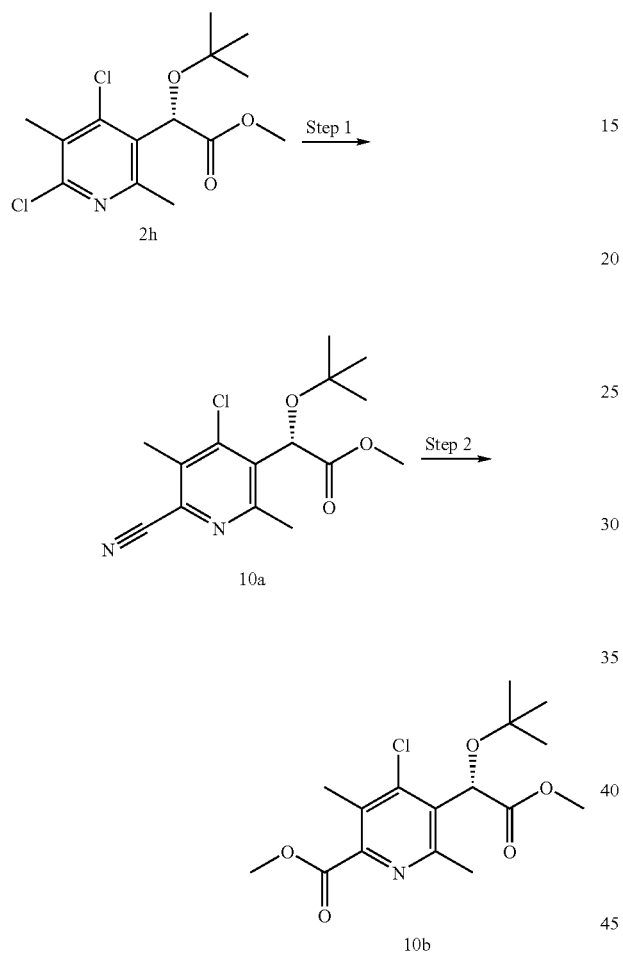

Step 1:

Dichloropyridine 2h (Example 2) (11 g, 33 mmol), Zn(CN)$_2$ (7.8 g, 66 mmol) and Pd[PPh$_3$]$_4$ (1.9 g, 1.6 mmol) are combined in DMA (100 mL) and heated in a sealed tube to 115° C. After 6 h, the reaction is cooled to RT, Pd[PPh$_3$]$_4$ (1.9 g, 1.6 mmol) is added and the reaction allowed to continue for 1 h. The mixture is cooled to RT, diluted with EtOAc (250 mL) and washed with water (250 mL). The aqueous layer is washed with EtOAc (100 mL) and the combined organic layers are washed with water (250 mL). The organic layer is dried over Na$_2$SO$_4$ and concentrated. The residue is purified by CombiFlash® Companion to give 10a.

Step 2:

A mixture of nitrile 10a (1.0 g, 3.2 mmol), aqueous NaOH (10 N, 3.4 mL, 32 mmol) and EtOH (3.2 mL) is heated at 90° C. in a sealed tube for 16 h. The mixture is cooled to RT and diluted with concentrated aqueous HCl (12N, 4 mL, 48 mmol) and water (50 mL). The mixture is extracted with EtOAc (3×50 mL) and the combined organic layers are dried over Na$_2$SO$_4$ and concentrated to dryness. The residue is taken up in MeOH (1 mL) and Et$_2$O (10 mL) and treated slowly with a hexane solution of TMSCH$_2$N$_2$ (2M, 3.5 mL, 7.0 mmol), and the mixture stirred for 10 min. The mixture is evaporated to dryness and the product is purified by CombiFlash®Companion to give the diester 10b.

Example 11

Alternative Synthesis of Intermediate 10B

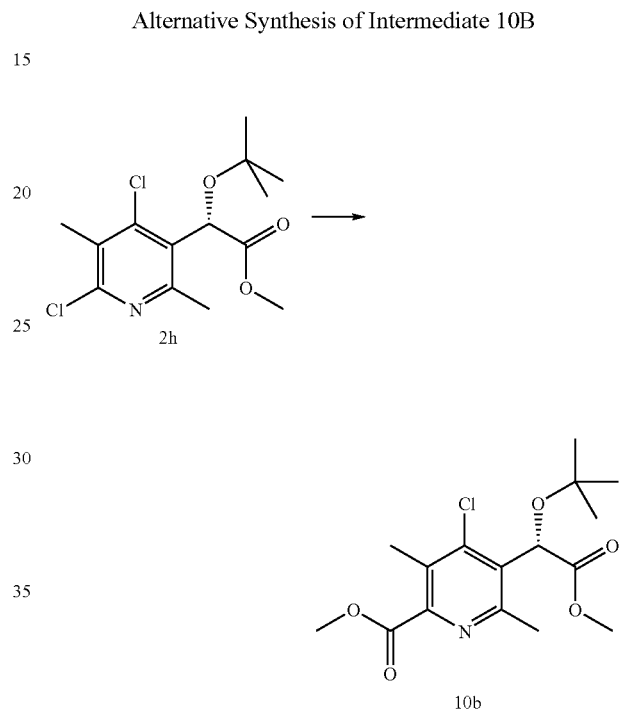

A mixture of Pd(OAc)$_2$ (70 mg, 0.31 mmol), 1,3-propylene bis(dicyclohexylphos-phonium tetrafluoroborate (0.38 g, 0.63 mmol), dichloropyridine 2h (Example 2) (2.0 g, 6.2 mmol) and potassium carbonate (1.3 g, 9.4 mmol) is added to dried 4 Å molecular sieves (3.0 g) in an oven-dried round bottom flask (100 mL) equipped with Teflon® coated magnetic stir bar, sealed with a rubber septum and cooled under vacuum. The rubber septum is secured by wrapping with electrical tape and DMF (20 mL) and MeOH (2.5 mL, 62 mmol) are added via syringe. A balloon of CO is connected to the reaction vessel using a short length of rubber tubing (~1 in.), a needle adapter and a 20 G needle. The inert atmosphere is then exchanged for carbon monoxide by briefly exposing the reaction vessel to vacuum (1-2 sec) and backfilling with carbon monoxide (3 times). The reaction mixture is heated at 120° C. and stirred vigorously for 16 h, then is allowed to cool to room temperature, and is diluted with EtOAc (20 mL), combined and filtered through a plug of Celite (eluting with EtOAc). The filtrate is washed with water and brine, dried over MgSO$_4$, filtered and concentrated. The residue is purified by CombiFlash® Companion (EtOAc/hexanes) to give the diester 10b.

Example 12

Synthesis of Compound 1187 (Table 1)

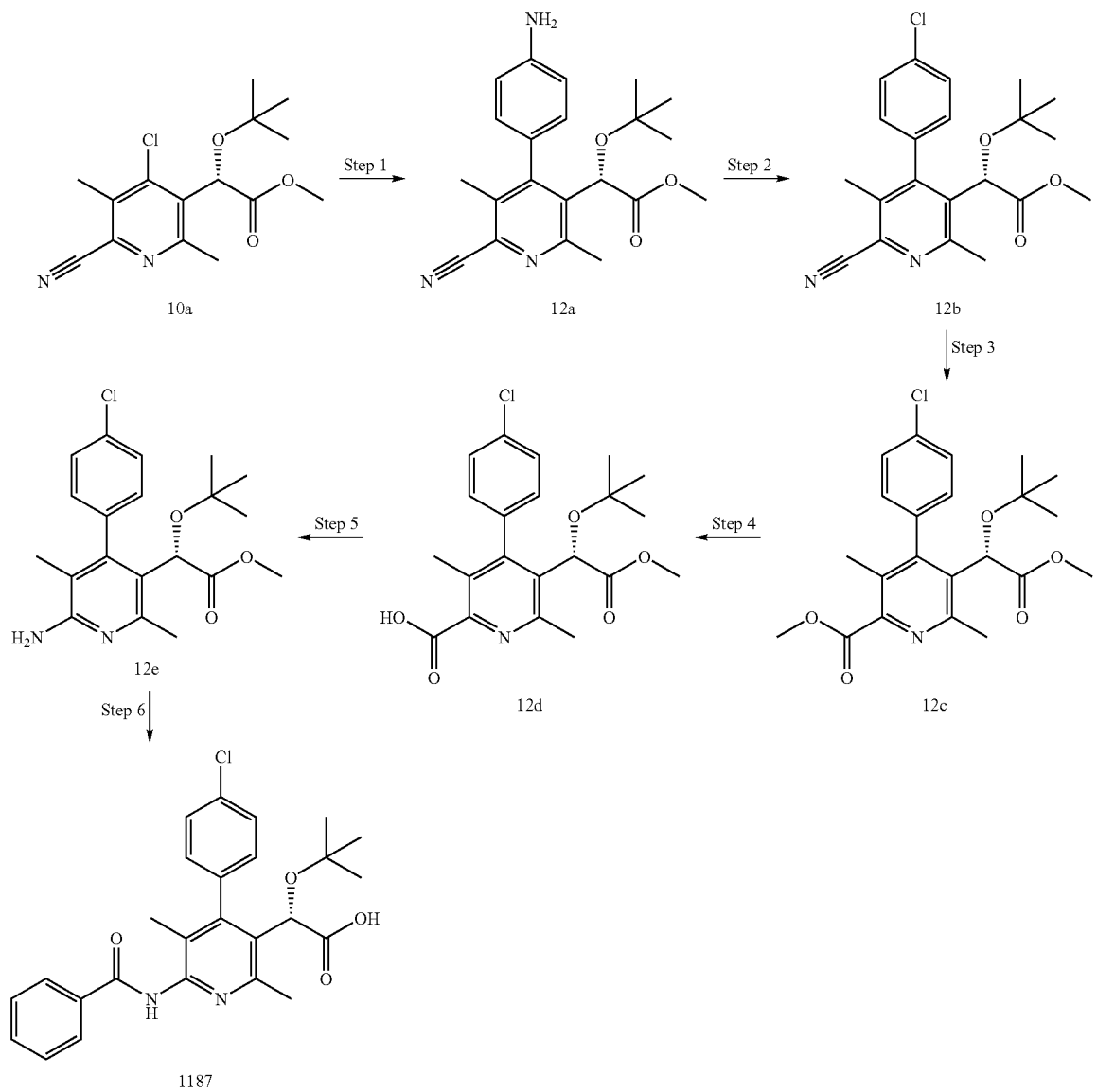

Step 1:
A mixture of nitrile 10a (Example 10) (1.7 g, 5.4 mmol), 2-aminophenylboronic acid (1.0 g, 7.3 mmol), bis[tri-t-butylphosphine]palladium(0) (276 mg, 0.54 mmol), NaHCO$_3$ (2.25 g, 26.7 mmol), DMA (50 mL) and water (5 mL) is degassed by bubbling Ar(g) under sonication for 5 min. The mixture is heated to 130° C. and stirred for 15 h, then cooled to RT and partitioned between EtOAc (225 mL) and water (200 mL). The aqueous layer is extracted with EtOAc (2×100 mL) and the combined organic layers are washed with water, dried over Na$_2$SO$_4$ and concentrated. The residue is purified by CombiFlash® Companion to give the aniline 12a.

Step 2:
Aniline 12a is converted to intermediate 12b using the procedure described in step 2 of Example 5.

Step 3:
A mixture of 12b (3.8 g, 9.8 mmol), aqueous NaOH (10N, 9.8 mL, 98 mmol) and EtOH (10 mL) is heated at 90° C. in a sealed tube for 16 h. The mixture is cooled to RT and diluted with concentrated HCl (12N, 10 mL, 120 mmol) and water (500 mL). The mixture is extracted with EtOAc (3×500 mL) and the combined organic layers are dried over Na$_2$SO$_4$ and concentrated to dryness. The residue is taken up in MeOH (5 mL) and Et$_2$O (50 mL) and treated slowly with a hexane solution of TMSCH$_2$N$_2$ (2M, 3.5 mL, 15.0 mmol), and the mixture is stirred for 10 min, then evaporated to dryness. The residue is purified by CombiFlash® Companion to give the diester 12c.

Step 4:

A mixture of diester 12c (2.9 g, 6.9 mmol), THF (9 mL) and MeOH (3 mL) is treated with LiOH (1N, 9.7 mL, 9.7 mmol). The mixture is stirred for 10 min, then is acidified with aqueous HCl (1N, 15 mL, 15 mmol), diluted with brine and extracted with EtOAc (3×50 mL). The combined organic layers are dried over $Na_2SO_4$ and concentrated to give carboxylic acid 12d.

Step 5:

To a mixture of 12d (1.9 g, 4.6 mmol) and $Et_3N$ (1.3 mL, 9.3 mmol) in PhMe (63 mL) is added water (0.4 mL, 23 mmol) followed by DPPA (2.0 mL, 9.3 mmol). The mixture is heated at 90° C. for 30 min, and then a further portion of DPPA (500 μL, 2.3 mmol) is added. Stirring is continued for 40 min and the mixture is cooled to RT, diluted with EtOAc (100 mL), and washed with saturated aqueous $NaHCO_3$, water and brine. The organic layer is dried over $Na_2SO_4$ and concentrated and the residue is purified by CombiFlash® Companion to give intermediate 12e.

Step 6:

A mixture of aminopyridine 12e (30 mg, 0.08 mmol) in THF (2 mL) is treated with $Et_3N$ (22 μL, 0.16 mmol) followed by benzoyl chloride (12 μL, 0.10 mmol) and the mixture is heated at 50° C. for 2 h. The mixture is diluted with MeOH (0.5 mL), aqueous NaOH (5N, 80 μL, 0.40 mmol) is added, and the mixture is stirred at 55° C. for 2 h. The mixture is concentrated nearly to dryness and diluted with AcOH (1.5 mL) and DMF (0.5 mL), and purified by preparative HPLC to give compound 1187 (Table 1).

Example 13

Synthesis of Compound 1268 (Table 1)

Step 1:

A mixture of nitrile 12b (Example 12) (6 g, 15.4 mmol) and AcOH (100 mL) is treated with 10% Pd/C (1.64 g, 1.54 mmol). The mixture is purged with hydrogen gas and stirred at RT for 1.5 h. The flask is evacuated several times and the catalyst is removed by filtration through Celite® with EtOAc washes. The mixture is concentrated in vacuo and the residue is taken up in EtOAc, washed with saturated $NaHCO_3$ and saturated brine, dried over $MgSO_4$, and concentrated. The residue is purified by CombiFlash® Companion (1-10% MeOH/DCM gradient with 1% $Et_3N$) to afford after concentration, amine 13a.

Step 2:

To a solution of amine 13a (85 mg, 0.22 mmol) in DCM (2 mL) is added $Et_3N$ (61 μL, 0.44 mmol) followed by t-butylacetyl chloride (34 μL, 0.24 mmol). The mixture is stirred at RT for 2 h and concentrated to dryness. The crude material containing amide 13b is used in the following step.

Step 3:

A mixture of 13b (106 mg, 0.22 mmol), MeOH (0.5 mL) and THF (1.5 mL) is treated with 5N NaOH (217 μL, 1.08 mmol). The mixture is stirred at 50° C. for 16 h and concentrated to dryness. The residue is dissolved in AcOH/DMSO (1 mL each) and purified by preparative HPLC to afford after freezing and lyophilization, compound 1268 (Table 1).

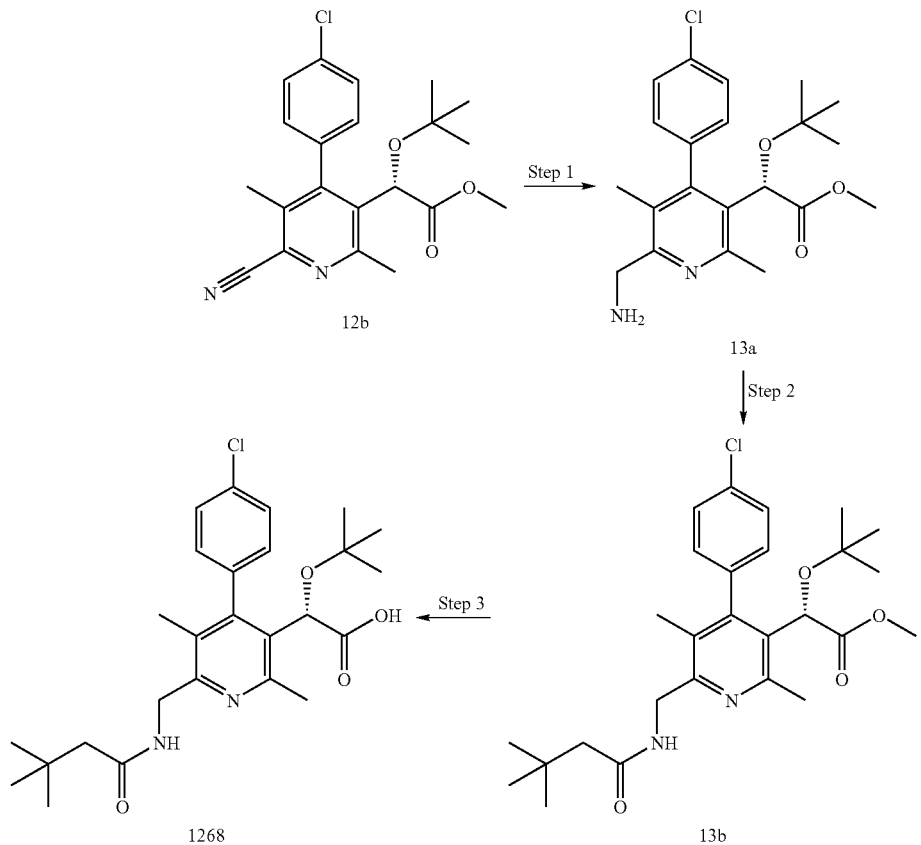

Example 14

Synthesis of Compound 3010 (Table 3)

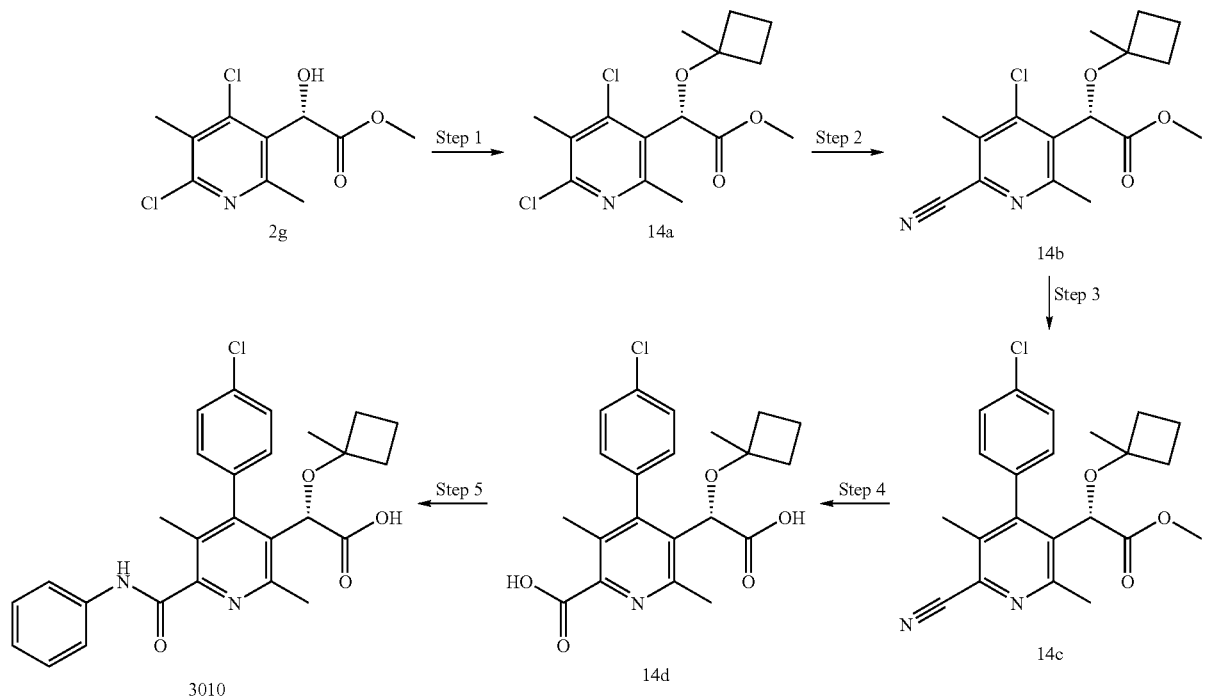

Step 1:

To solid $P_2O_5$ (652 mg, 4.6 mmol) in a dry RB flask is slowly added 85% $H_3PO_4$ (503 µL, 7.34 mmol) via syringe. This mixture is allowed to stir a few minutes; DCM (20 mL) is then added followed by alcohol 2g (Example 2) (970 mg, 3.67 mmol). To this mixture is added $BF_3.Et_2O$ (931 µL, 7.34 mmol) and methylenecyclobutane (3.4 mL, 37 mmol). The mixture is stirred at RT for 2 h then is quenched rapidly with aqueous $NaHCO_3$. The reaction mixture is diluted with EtOAc, washed with saturated brine, dried ($MgSO_4$), filtered and concentrated. The residue is purified using the Combi-Flash® Companion (hexanes/EtOAc) to give ether 14a and recovered starting alcohol 1g.

Step 2:

A mixture of 14a (825 mg, 2.48 mmol), $Zn(CN)_2$ (583 mg, 5 mmol), $Pd(PPh_3)_4$ (430 mg, 0.37 mmol) and DMA (12 mL) is sealed in a microwave vessel and heated in the microwave at 125° C. (10 min) using a Biotage Initiator Sixty. The reaction mixture is cooled, poured into EtOAc and washed with saturated brine. The organic phase is dried over $MgSO_4$, filtered and concentrated and the residue is purified by Combi-Flash® Companion (hexanes/EtOAc) to give nitrile 14b.

Step 3:

Intermediate 14b is transformed to intermediate 14c using the procedure described in steps 1 and 2 of Example 12.

Step 4:

To nitrile 14c (176 mg, 0.44 mmol) in MeOH (4 mL) is added 5 N NaOH (441 µL, 4.4 mmol). The mixture is heated at 65° C. (24 h), cooled to RT, acidified with 1N HCl (pH ~1-2) and extracted with EtOAc (3×). The combined organic phases are dried ($MgSO_4$), filtered and concentrated to give diacid 14d.

Step 5:

To a solution of diacid 14d (181 mg, 0.45 mmol) in anhydrous THF (8 mL) is added $Et_3N$ (263 µL, 1.9 mmol) and pivaloyl chloride (116 µL, 0.94 mmol) at RT and the mixture is stirred for 1 h. To a portion of this stock solution (2 mL, 0.11 mmol) is added aniline (11.3 µL, 0.12 mmol) and the mixture is allowed to stir at RT for 16 h. The reaction mixture is treated with 10 N NaOH (112 µL, 1.12 mmol) for 4 h and concentrated to dryness, purified by preparative HPLC and lyophilized to give compound 3010 (Table 3).

Example 15

Synthesis of Intermediate 15f

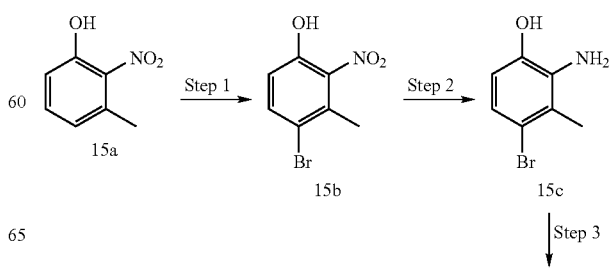

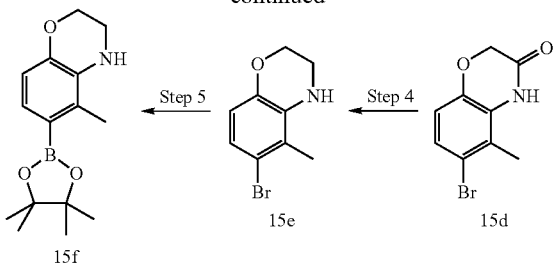

Step 1:

A mixture of nitrophenol 15a (5.23 g, 34.1 mmol) and AcOH (20 mL) is cooled in an ice bath and bromine (1.75 mL, 34.15 mmol, dissolved in 5 mL AcOH) is added dropwise with stirring. The mixture is stirred for about 1 h at 0° C. and poured into ice water (250 mL). The mixture is extracted with EtOAc (2×100 mL), washed with 5% NaHCO$_3$, dried over anhydrous MgSO$_4$, filtered and concentrated to give 15b. This material is used in the next step without further purification.

Step 2:

To a well stirred ethanol solution (75 mL) of 15b (8.1 g, 34.9 mmol) is added SnCl$_2$ (20 g, 105 mmol) and the reaction mixture is stirred at reflux for 2.5 h. A further portion of SnCl$_2$ (2 g, 10 mmol) is added and heating at reflux is continued for 1 h. The mixture is cooled to RT and poured onto ice (250 g), and the pH is adjusted to approximately 7.5 with aqueous 5% NaHCO$_3$. The mixture is extracted with EtOAc (3×100 mL) and the organic extract is washed with brine, dried over anhydrous MgSO$_4$, filtered and concentrated to dryness to give the aniline intermediate 15c.

Step 3:

To a stirred, ice cold, mixture of K$_2$CO$_3$ (2.05 g, 14.8 mmol), aniline 15c (750 mg, 3.71 mmol) and DMF (5 mL) under nitrogen, is added chloroacetyl chloride (355 µL, 4.45 mmol) dropwise. The mixture is allowed to warm to RT over a period of about 15 min and is then heated to 60° C. for 1 h. The mixture is allowed to cool to RT, is poured into a mixture of ice/water (250 mL) and is stirred for approximately 15 min. The suspension is centrifuged, and the supernatant is discarded. The solid material is left drying under suction overnight to give intermediate 15d.

Step 4:

To an ice cold mixture of the cyclic amide 15d (280 mg, 1.16 mmol) and THF (6 mL) under nitrogen is slowly added a borane-THF solution (1M in THF, 1.74 mL, 1.74 mmol). The reaction mixture is slowly allowed to warm to RT, then is stirred at RT for 1.5 h and then gently heated to reflux for 1 h. The mixture is cooled in an ice bath and is carefully quenched with aqueous 1 M NaOH (4 mL) over about 10 min. The reaction mixture is partitioned between EtOAc (150 mL) and water (25 mL). The organic layer is washed with aqueous 1 N NaOH (20 mL) and saturated aqueous NaCl, and dried over anhydrous MgSO$_4$, filtered and concentrated to give 15e.

Step 5:

A well stirred mixture of the arylbromide 15e (0.50 g, 2.2 mmol), potassium acetate (728 mg, 7.7 mmol) and bis(pinacolato)diborane (0.83 g, 3.3 mmol) in DMF (15 mL) is degassed by bubbling Ar through the solution for about 20 min. PdCl$_2$(dppf)-DCM (320 mg, 0.44 mmol) is added and degassing is continued for about 15 min. The system is sealed (teflon screw cap vessel) under Ar and heated to 90° C. for 5 h. The reaction mixture is allowed to cool to RT, diluted with EtOAc (150 mL), washed with brine and water, dried over anhydrous MgSO$_4$, filtered and concentrated to dryness. The residue is purified by CombiFlash® Companion (EtOAc/hexanes) to give the desired boronate 15f.

Example 16

Synthesis of Intermediate 16c

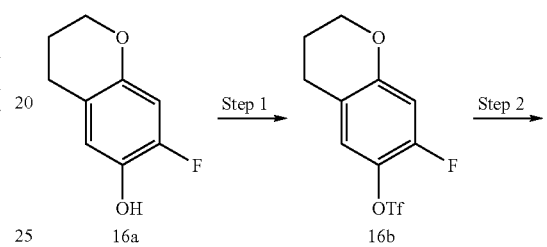

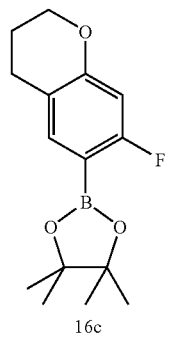

Step 1:

Neat Tf$_2$O (0.56 mL, 3.3 mmol) is added dropwise to a cooled (0° C.) mixture of phenol 16a (350 mg, 2.1 mmol; prepared according to Doi et al *Bull. Chem. Soc. Jpn.* 2004 77, 2257-2263) and pyridine (0.91 mL, 11 mmol) in DCM (10 mL) under an Ar atmosphere. The mixture is allowed to warm to RT and is stirred for 2 h. The reaction is quenched by the addition of a 10% citric acid solution (20 mL) and the mixture is extracted with DCM (3×20 mL). The combined organic layers are washed with water, dried over MgSO$_4$, filtered and concentrated to dryness. The residue is purified by CombiFlash® Companion to provide triflate 16b.

Step 2:

A mixture of the triflate 16b (510 mg, 1.7 mmol), bis[pinacolato]diborane (560 mg, 2.2 mmol) and potassium acetate (500 mg, 5.1 mmol) in DMF (18 mL) is degassed with Ar for 5 min, and PdCl$_2$dppf-DCM complex (140 mg, 0.17 mmol) is added. The reaction mixture is degassed for an additional 5 min and heated to 100° C. by microwave irradiation for 10 min, then cooled to RT. The mixture is diluted with EtOAc (60 mL) and washed with brine, dried over MgSO$_4$, filtered and concentrated. The residue is further purified by CombiFlash® Companion to afford boronic ester 16c.

Example 17

Synthesis of Intermediate 17f

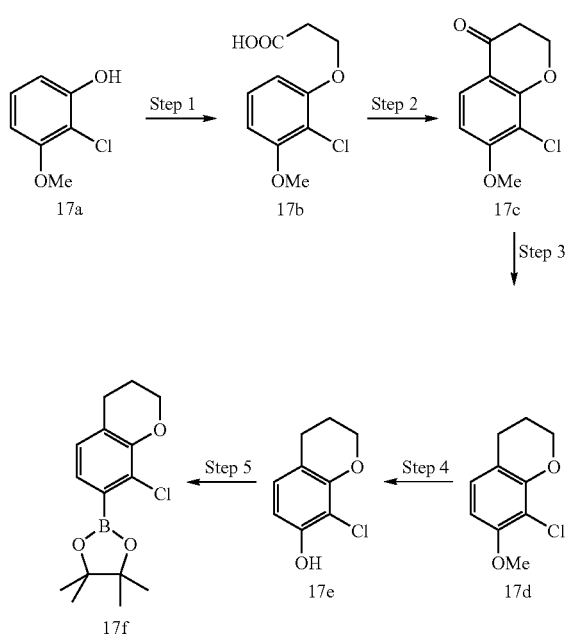

Step 1:
A solution of phenol 17a (0.91 g, 5.74 mmol) in dry DMF (1 mL) is added dropwise to a mixture of NaH (60% in oil, 0.60 g, 15 mmol) in dry DMF (1 mL) cooled to 15° C. and the mixture is stirred for 20 min. A solution of 3-bromopropionic acid (1.1 g, 6.9 mmol) in dry DMF (0.5 mL) is added dropwise and the mixture is stirred at RT overnight. After 16 h, MeOH (1.2 mL) is added and the reaction mixture is added to dilute HCl (12 mL of 1 N HCl in 100 mL water) and extracted with EtOAc (80 mL; the pH of the aqueous phase is adjusted to pH<3). The organic layer is dried over anhydrous $Na_2SO_4$, filtered and concentrated to give 17b contaminated with some unreacted starting material.

Step 2:
A mixture of 17b (1.53 g, 6.63 mmol) and polyphosphoric acid (7 g) is heated to 75° C. After 4 h, the reaction is cooled, and ice and water are slowly added with rapid stirring. The mixture is extracted with EtOAc (100 mL) and the organic extract is washed with water, saturated $NaHCO_3$ and brine, dried over anhydrous $MgSO_4$ and concentrated to give 17c (crude).

Step 3:
AcOH (80 mL) is added to a mixture of chromanone 17c (6.2 g, 29 mmol) and freshly activated zinc powder (38 g, 580 mmol). The mixture is stirred at 100° C. for 15 h and filtered through Celite, and the Celite pad is rinsed repeatedly with EtOAc (4×25 mL). The filtrate is concentrated and extracted with EtOAc (400 mL) and the organic extract is washed with saturated $NaHCO_3$ (2×400 mL) and brine (200 mL). The organic phase is dried over $MgSO_4$ and evaporated to provide crude chromane 17d.

Step 4:
A mixture of anisole 17d (4.0 g, 20 mmol) and dry dichloromethane (40 mL) is cooled to −78° C. A $BBr_3$ solution (1M in DCM, 44 mL, 44 mmol) is added dropwise and then the reaction mixture is removed from the dry ice bath. After 45 min, the mixture is cooled (ca. 0° C.) and the reaction is quenched with water (25 mL) added dropwise. The mixture is diluted with water (400 mL) and is carefully neutralized with saturated aqueous $NaHCO_3$ (final pH ca 8). This mixture is then extracted with DCM (300 mL and then 100 mL) and the combined organic layers are dried over $Na_2SO_4$ and evaporated to dryness. The product is purified by CombiFlash® Companion to provide phenol 17e.

Step 5:
Compound 17e is transformed to compound 17f using the procedure described in steps 1 and 2 of Example 16.

Example 18

Synthesis of Compound 1356 (Table 1)

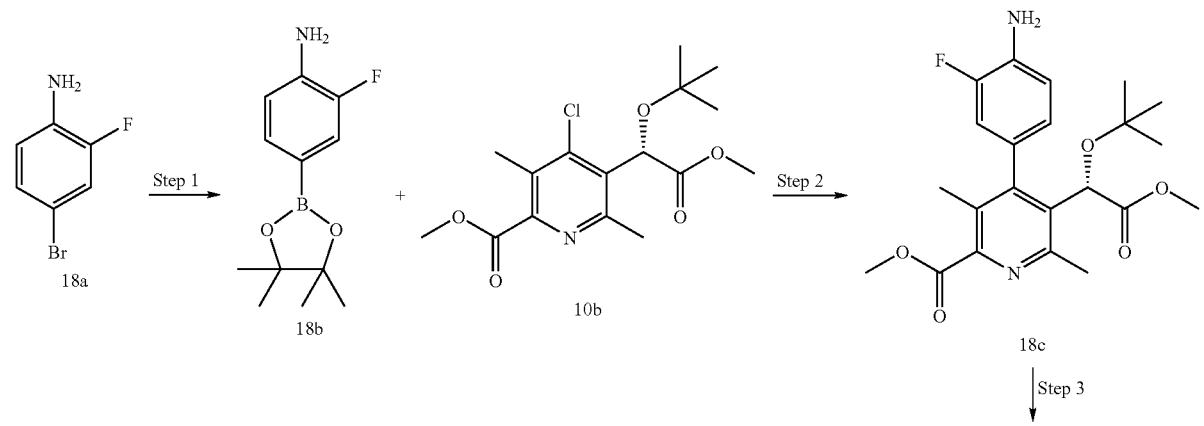

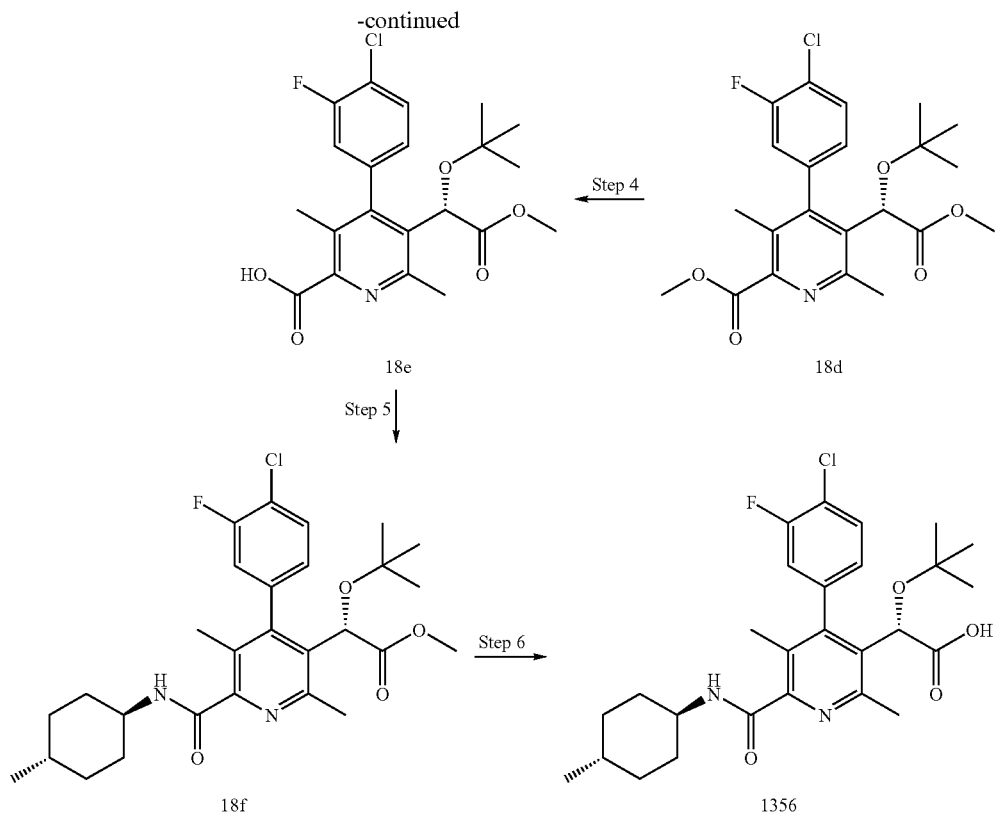

Step 1:

To a mixture of bromide 18a (1.0 g, 5.3 mmol), bis-(pinacolato)diboron (1.9 g, 7.4 mmol) and potassium acetate (1.6 g, 16 mmol) is added anhydrous DMF (20 mL) and the mixture is deoxygenated by bubbling a stream of $N_2$ gas through the mixture for about 25 min. 1,1'-Bis(diphenylphosphino)ferrocene (0.58 mg, 0.79 mmol) is added and the mixture is deoxygenated for approximately a further 5 min, then heated to 95° C. After 5 h, the reaction mixture is cooled, diluted with EtOAc (200 mL) and washed with brine (2×100 mL). The layers are filtered through a pad of Celite and reseparated. The organic phase is dried over anhydrous $MgSO_4$, filtered and concentrated and the residue is purified by CombiFlash® Companion (EtOAc/hexanes) to afford the boronate 18b.

Step 2:

Intermediate 18b is coupled to intermediate 10b (Example 10) using the procedure described in step 1 of Example 12 to give intermediate 18c.

Step 3:

Intermediate 18c is transformed to intermediate 18d using the procedure described in step 2 of Example 5.

Step 4:

Intermediate 18d is transformed to intermediate 18e using procedure described in step 4 of Example 12.

Step 5:

A mixture of carboxylic acid 18e (44 mg, 0.10 mmol) in NMP is treated with $Et_3N$ (58 μL, 0.42 mmol) and TBTU (67 mg, 0.21 mmol). The mixture is stirred for 5 min and trans-4-methylcyclohexylamine (35 μL, 0.31 mmol) is added. The mixture is stirred for 1 h, diluted with EtOAc (40 mL), washed with water and brine, dried over $MgSO_4$, filtered and concentrated. The crude mixture is purified by CombiFlash® Companion using a gradient of EtOAc/hexanes to afford the desired amide 18f.

Step 6:

A mixture of amide 18f (42 mg, 0.080 mmol), THF (1.5 mL) and MeOH (0.75 mL) is treated with 1.0 N LiOH (0.75 mL, 0.75 mmol). The mixture is stirred at 55° C. for 1 h, neutralized with AcOH and purified by preparative HPLC. A mixture of the product and DCM (3 mL) is adjusted to pH>10 with 1N NaOH and neutralized with AcOH. The mixture is passed through a phase separator filter and the organic layer is concentrated in vacuo, diluted with a mixture of MeCN/water and lyophilized to give compound 1356.

Example 19

Synthesis of Intermediate 19d

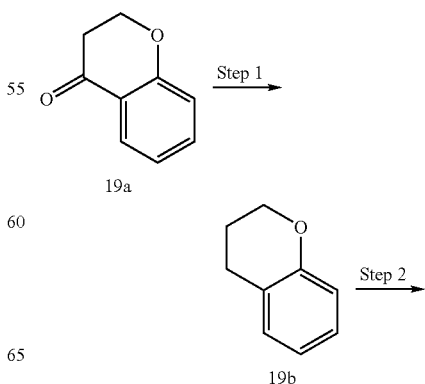

-continued

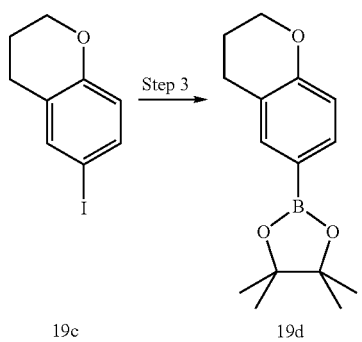

Step 1:

A mixture of chromanone 19a (9.78 g, 66.0 mmol) and AcOH (20 mL) is added to a mixture of zinc dust (108 g, 1.65 mol) in AcOH (150 mL). The mixture is heated to 100° C. and is stirred overnight, then filtered through Celite® (washed with EtOAc, 100 mL), diluted with PhMe (300 mL) and concentrated to give intermediate 19b.

Step 2:

AgNO$_3$ (12.0 g, 70.6 mmol) and I$_2$ (15.8 g, 62.3 mmol) are added sequentially to a mixture of 19b (8.45 g, 63.0 mmol) and MeOH (225 mL). The mixture is allowed to stir for about 1 h and filtered through Celite®, and the filtrate is concentrated under reduced pressure. The residue is diluted with EtOAc (250 mL) and washed with saturated sodium thiosulfate (250 mL). The organic layer is washed with water (200 mL), dried over Na$_2$SO$_4$, filtered and concentrated. The residue is further purified by CombiFlash® Companion to give 6-iodochroman 19c.

Step 3:

A mixture of the 6-iodochroman 19c (1.0 g, 3.85 mmol), bis[pinacolato]diborane (1.22 g, 4.81 mmol) and potassium acetate (1.10 g, 11.5 mmol) in DMF (36 mL) is degassed with Ar for about 5 min followed by the addition of the PdCl$_2$dppf-DCM complex (314 mg, 0.38 mmol). The reaction mixture is then degassed for about an additional 5 min and heated to 95° C. for 5 h. The mixture is then cooled to RT, diluted with water and extracted with EtOAc (3×100 mL). The combined organic extracts are washed with water (100 mL) and brine (100 mL), dried over MgSO$_4$, filtered and concentrated. The residue is further purified by CombiFlash® Companion using a gradient of EtOAc/hexanes to afford intermediate 19d.

Example 20

Synthesis of Intermediate 20h

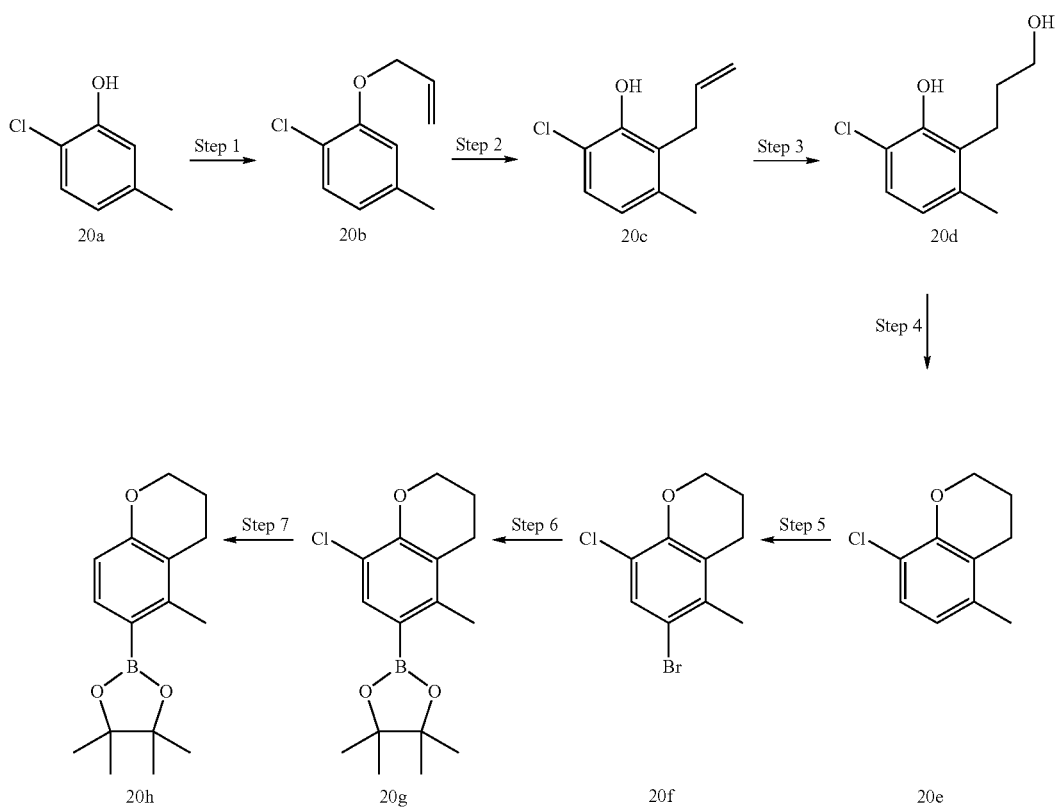

Step 1:

A mixture of phenol 20a (6.75 g, 47.3 mmol) and DMF (270 mL) is treated with allyl bromide (6.55 mL, 75.7 mmol). To this mixture, NaH (60%, 4 g, 99.4 mmol) is added portionwise and stirring is continued overnight. The reaction mixture is diluted with EtOAc (500 mL) and washed with $H_2O$. The organic layer is dried over $MgSO_4$, filtered and concentrated to dryness to obtain the desired product 20b.

Step 2:

The ether 20b (8.6 g) is stirred and heated at 240° C. for 20 min in a microwave vial to provide 20c.

Step 3:

To a mixture of the allyl intermediate 20c (9.3 g, 45.8 mmol) in anhydrous THF (300 mL) at 0° C. is added borane (1 M in THF, 96 mL, 96 mmol, 2.1 eq). The mixture is allowed to warm to RT and then is stirred for 2.5 h. The mixture is then cooled to 0° C. and treated with 10 N NaOH dropwise, followed by slow addition of 30% $H_2O_2$ (104 ml, 916 mmol). The resulting mixture is allowed to warm to RT and is stirred at RT for 1 h. The reaction mixture is diluted with HCl (10%, 100 mL) and extracted with EtOAc (3×200 mL). The combined organic phases are dried over $MgSO_4$ and concentrated. The residue is purified by CombiFlash® Companion to give 20d.

Step 4:

To a mixture of the diol 20d (7.1 g, 35.3 mmol) in THF (500 mL) are added $PPh_3$ (12 g, 45.9 mmol), followed by DEAD (7.2 mL, 45.9 mmol). The mixture is stirred at RT for 4 h. The reaction mixture is concentrated under reduced pressure and purified by CombiFlash® Companion to obtain the desired product 20e.

Step 5:

A mixture of the chroman derivative 20e (5.26 g, 28.8 mmol) and AcOH (70 mL) is treated with $Br_2$ (19.2 mL, 37.4 mmol) in AcOH (40 mL). The mixture is stirred at RT for 15 min, then diluted with toluene and concentrated to dryness. The residue is taken up in EtOAc (25 mL) and washed with saturated $Na_2S_2O_3$ (25 mL) and saturated $NaHCO_3$ (25 mL). The organic layer is dried over $MgSO_4$, concentrated and purified by CombiFlash® Companion to obtain the desired product 20f.

Step 6:

A mixture of bromide 20f (2.71 g, 10.4 mmol) and DMF (120 mL) is treated with bispinacolatoborane (4 g, 15.5 mmol) and potassium acetate (3.45 g, 36.3 mmol). The mixture is degassed (using an Ar balloon) and $PdCl_2dppf$ (845 mg, 1.04 mmol) is added. The mixture is degassed again (using an Ar balloon) and heated at 95° C. for 16 h. The mixture is cooled to RT, diluted with $H_2O$ (300 mL) and extracted with EtOAc (2×300 mL). The combined organic layers are washed with water, dried over $MgSO_4$, filtered and concentrated. The residue is purified by CombiFlash® Companion and is triturated with hexanes to provide intermediate 20g.

Step 7:

Palladium on activated charcoal (10% Pd by weight, 0.63 mg, 0.59 mmol) is added to a solution of aryl chloride 20g (0.91 g, 2.95 mmol) and ammonium formate (1.92 g, 30.4 mmol) dissolved in MeOH and the mixture is heated to reflux. After 15 min, the reaction is cooled to RT and filtered through Celite®, and the Celite® pad is rinsed with MeOH. The filtrate is concentrated to dryness and the residue partitioned between water and EtOAc (10 mL each). The organic layer is dried over anhydrous $MgSO_4$ and concentrated to obtain boronic ester 20h.

Example 21

Synthesis of Intermediate 21e

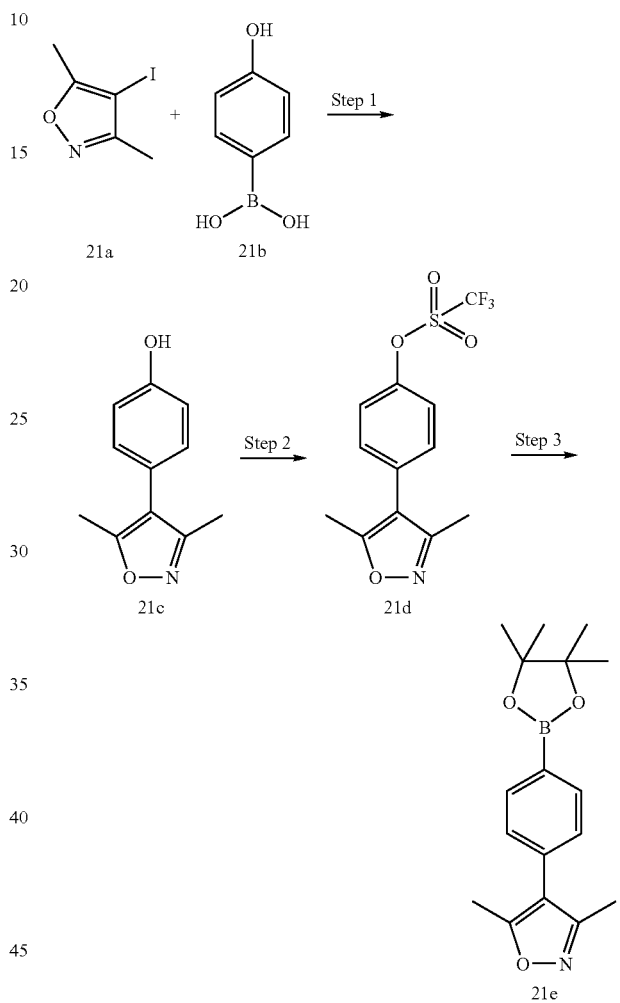

Step 1:

A mixture of 21a (1.0 g, 4.5 mmol), 21b (0.72 g, 5.2 mmol), potassium carbonate (1.6 g, 12 mmol) and trans-dichlorobis (triphenylphosphine)palladium (II) (0.36 g, 0.62 mmol) in DMF (8.3 mL) and water (0.88 mL) is heated under microwave for 15 min at 130° C. The mixture is partitioned between EtOAc (25 mL) and water (25 mL) and the organic layer is washed with water, dried over $Na_2SO_4$, filtered and concentrated. The residue is purified by CombiFlash® Companion using a gradient of EtOAc/hexanes to afford the desired alcohol 21c.

Step 2:

A mixture of alcohol 21c (0.70 g, 3.7 mmol) in pyridine (15 mL) is treated with $Tf_2O$ (0.95 mL, 5.6 mmol) and stirred at 23° C. for 30 min. The mixture is concentrated and the residue is partitioned between DCM (50 mL) and 10% HCl (50 mL). The organic layer is washed with 10% HCl and saturated $NaHCO_3$ solution and passed through a phase separator. Evaporation of the organic layer gives the triflate 21d.

Step 3:

A solution of the triflate 21d (1.2 g, 3.7 mmol), bis(pinacolato)diborane (1.4 g, 5.5 mmol) and potassium acetate (1.2 g, 13 mmol) in DMF (50 mL) is degassed with Ar for about 5 min followed by the addition of the PdCl$_2$dppf-DCM complex (0.39 mg, 0.48 mmol). The reaction mixture is then degassed for about an additional 5 min before being heated to 95° C. overnight. The reaction mixture is then cooled to RT, diluted with water (150 mL) and extracted with EtOAc (3×100 mL). The combined organic extracts are washed with water, dried over Na$_2$SO$_4$, filtered and concentrated. The residue is purified by CombiFlash® Companion using a gradient of EtOAc/hexanes to give borane 21e.

Example 22

Synthesis of Compound 2006 (Table 2)

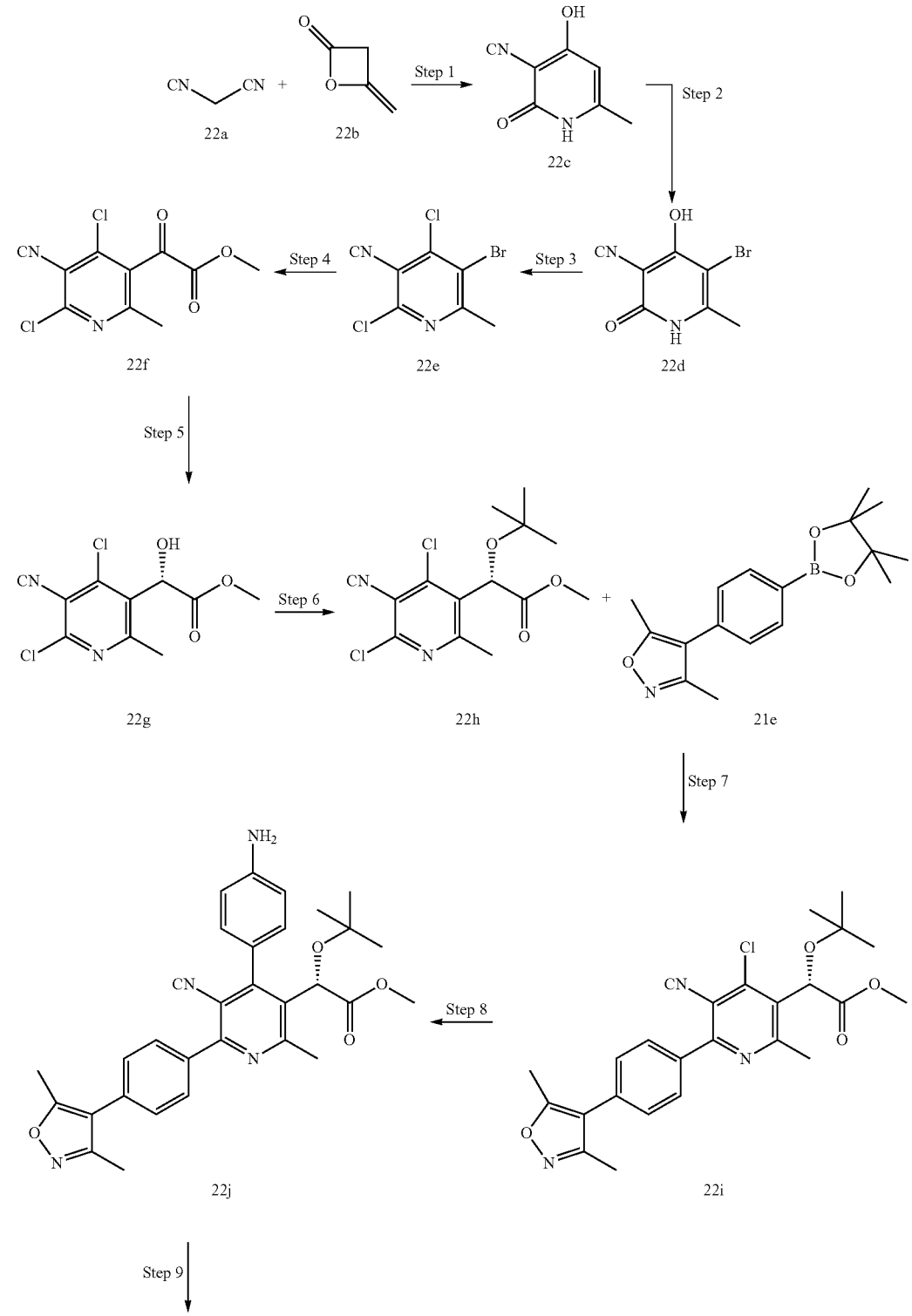

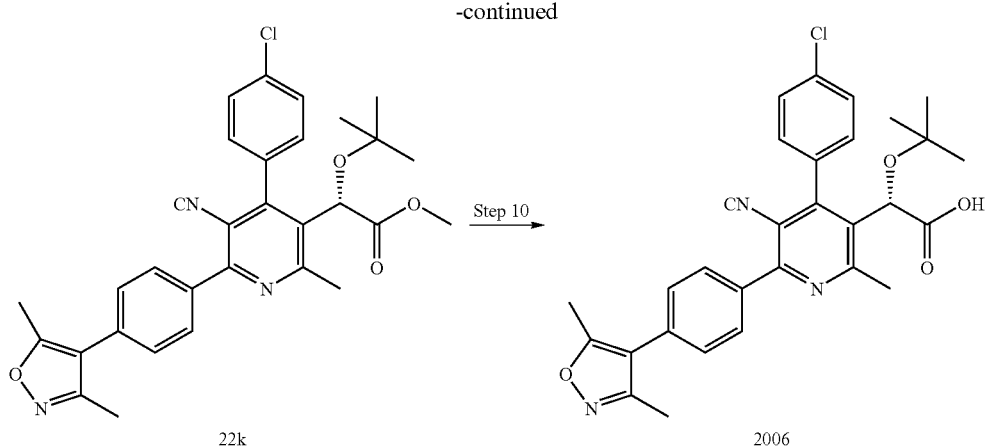

Step 1:
4-Hydroxypyridone 22c is synthesized using the procedure described by T. Kato; Y. Kubota; M. Tanaka; H. Takahashi and T. Chiba; *Heterocycles* 1978, 9, 811.

Step 2:
Intermediate 22c is transformed to intermediate 22d using procedures described in step 2 of Example 2.

Step 3:
Intermediate 22d is transformed to intermediate 22e using procedures described in step 3 of Example 2.

Step 4:
Intermediate 22e is transformed to intermediate 22f using procedures described in step 4 of Example 2.

Step 5:
Intermediate 22f is transformed to intermediate 22g using procedures described in step 5 of Example 2.

Step 6:
Intermediate 22g is transformed to intermediate 22h using procedures described in step 6 of Example 2.

Step 7:
Intermediate 22h is transformed to intermediate 22i using procedures described in step 1 of Example 4.

Step 8:
Intermediate 22i is transformed to intermediate 22j using procedures described in step 1 of Example 5.

Step 9:
Intermediate 22j is transformed to intermediate 22k using procedures described in step 2 of Example 5.

Step 10:
Intermediate 22j is transformed to compound 2006 using procedures described in step 3 of Example 4.

Example 23

Synthesis of Intermediate 23k

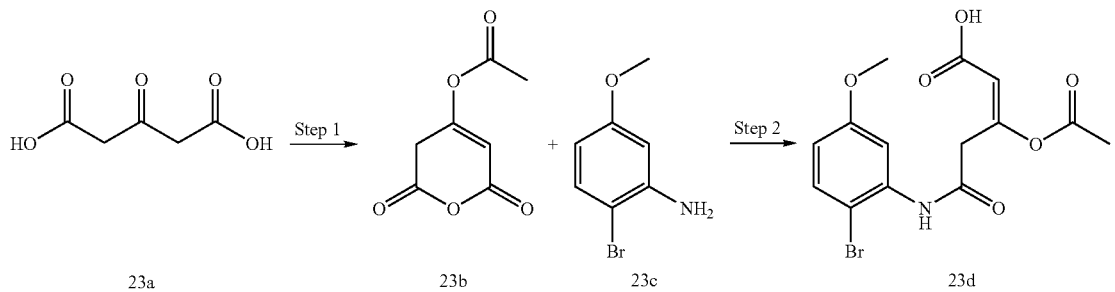

-continued

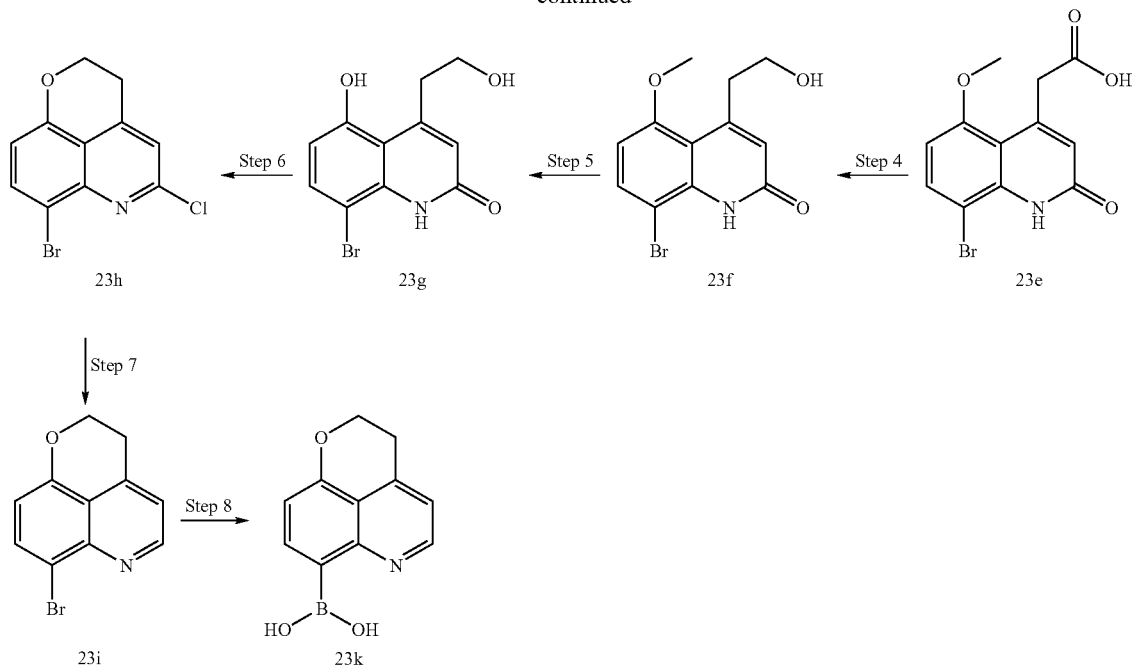

Step 1:

1,3-acetonedicarboxylic acid 23a (30 g; 205.3 mmol) is added in portions to Ac$_2$O (55 g; 587.7 mmol) and the mixture is stirred at 35° C. for 23 h, then filtered. The filtrate is diluted with benzene (200 mL) and the solution stored at 5° C. for 3 h. The precipitate is filtered and dried under vacuum to give intermediate 23b.

Step 2:

To a stirred solution of aniline 23c (7.5 g, 44 mmol) in AcOH (50 mL) is added 23b (8.0 g, 40 mmol) portionwise. The reaction mixture is warmed to 35° C. for 2 h, then cooled to room temperature and poured in ice/water (600 mL). The resulting precipitate is isolated by filtration, rinsed with water (100 mL) and dried under vacuum to give 23d.

Step 3:

Intermediate 23d (5.7 g, 15.4 mmol) is added portionwise to concentrated sulfuric acid (20 mL) at RT, so that the temperature of the reaction mixture is kept below 30° C. during addition. The mixture is stirred at RT for 30 min and poured in ice/water (400 mL). The resulting precipitate is isolated by filtration, rinsed with water and dried under vacuum to give 23e.

Step 4:

A solution of borane (1.0 M in THF, 10.5 ml, 10.5 mmol) is added dropwise to an ice cold solution of quinolone 23e (1.5 g, 4.8 mmol) in dry THF (40 mL) under a N$_2$ atmosphere. The mixture is allowed to warm to RT and stirred for 22 h. An additional equivalent of BH$_3$ is added at 0° C. and the reaction mixture is heated to 45° C. for 2 h. The reaction is carefully quenched witn 1.0 N NaOH (10 mL) and THF is removed under vacuum. The mixture is poured in EtOAc (100 mL) and the precipitate is collected by filtration and dried under vacuum to provide 23f.

Step 5:

To a mixture of 23f (1.1 g, 3.8 mmol) and DCM (60 mL) at −78° C. is added dropwise a 1.0 M BBr$_3$ solution (23 mL, 23 mmol). The cooling bath is removed after 1 h and the mixture is stirred at RT for 16 h. The mixture is poured in ice/water (100 mL) and the precipitate is collected by filtration and dried under vacuum to give 23g.

Step 6:

To a solution of intermediate 23g (773 mg, 2.27 mmol) in THF (30 mL) is added PPh$_3$ (928 mg, 3.5 mmol) followed by DIAD (0.69 ml, 3.5 mmol) (dropwise), and the solution is stirred at RT for 2 h. The reaction mixture is concentrated under vacuum and the crude product is directly added portionwise to POCl$_3$ (2 mL) at RT. The reaction mixture is stirred at 100° C. for 45 min and then cooled to room temperature. The mixture is concentrated under vacuum and the crude product is diluted with DCM. The organic phase is washed with 1.0 N NaOH, water, and brine, dried (MgSO$_4$), filtered and concentrated under vacuum. The crude product is purified by CombiFlash® (Hex/EtOAc 9/1 to 1/1) to give 23h.

Step 7:

To a solution of chloroquinoline 23h (300 mg, 1 mmol) in TFA (10 mL) is added zinc (340 mg, 5 mmol) and the mixture is stirred at RT for 16 h. The mixture is filtered and concentrated under vacuum, and the residue is diluted with 1.0 N NaOH (50 mL) and extracted with DCM (3×). The combined organic extracts are washed with water and brine, dried (MgSO$_4$), filtered and concentrated under vacuum. The residue is purified by CombiFlash® (Hex/EtOAc 6/4 to 4/6) to give 23i.

Step 8:

A mixture of aryl halide 23i (5 g, 20 mmol) Et$_2$O (400 mL) under a nitrogen atmosphere is heated to 43° C. then cooled to −75° C. in a dry ice/acetone bath. n-Butyllithium solution (1.38 M in hexanes, 21.7 mL, 30 mmol) is added dropwise (4 min addition time, internal temp below 70° C.). The mixture is stirred for an additional min and n-butyllithium solution (880 μL, 1.2 mmol) is added. After 5 min, triisopropyl borate (16.9 mL, 72 mmoles) is added while the temperature is held at −74° C. The reaction mixture is allowed to warm to −42° C. and 5 mL (21 mmol) of triisopropylborate are added. The mixture is stirred for 10 min at −18° C., and 2.5 mL (11 mmol) of triisopropylborate followed by aqueous 2 N HCl (200 mL, 400 mmol) are added. The mixture is allowed to stir at room temperature for 2.5 h, then is diluted with Et₂O (50 mL) and 2N HCl (50 mL). (The layers are separated and the aqueous layer is adjusted to pH=7 with 10N NaOH (45 mL) and 1N NaOH (20 mL). The precipitate is filtered and dried for 16 h at high vacuum affording the desired compound 23k.

Example 24

Synthesis of Intermediate 24b

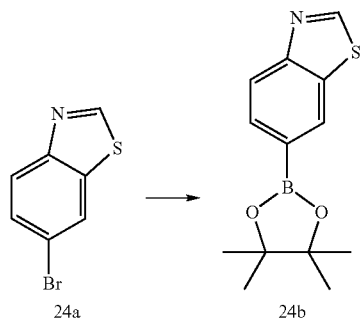

To a mixture of the bromide 24a (152 mg, 0.71 mmol) and DMF (5 mL) is added bis(pinacolato)diboron (234 mg, 0.92 mmol) and KOAc (210 mg, 2.13 mmol). The solution is degassed with argon gas under sonication (10 min) and dichloro[1,1'-bis(diphenylphosphino)ferrocene]palladium (II) DCM adduct (87 mg, 0.10 mmol) is added. The mixture is heated at 90° C. for 16 h and cooled to RT. The mixture is diluted with EtOAc, washed with saturated brine, dried (MgSO₄), filtered and concentrated. The residue is purified using the CombiFlash® Companion (hexanes/EtOAc) to give the boronate 24b.

Example 25

Synthesis of Intermediate 25e

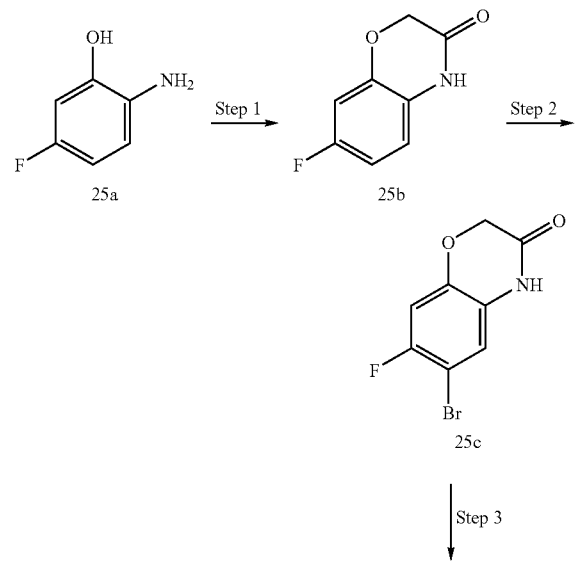

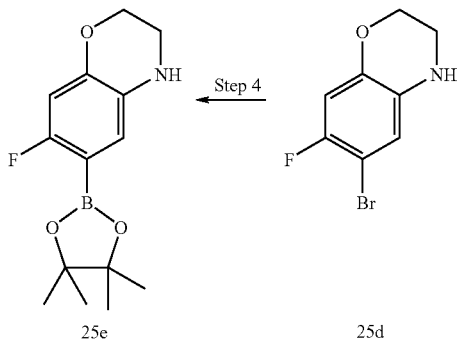

Step 1:

To a cold (0° C.) mixture of 25a (15.0 g, 118 mmol) and DMF (180 mL) is added K₂CO₃ (48.9 g, 354 mmol) followed by dropwise addition of chloroacetyl chloride (9.40 mL, 118 mmol). The reaction mixture is allowed to warm to RT and then heated to 60° C. for 2 h. The reaction mixture is cooled to RT, poured into ice-water (2.0 L) and stirred for 30 min. The mixture is filtered and the solid rinsed with water and dried under reduced pressure to provide 25b.

Step 2:

To a cooled (10° C.) mixture of 25b (12.4 g, 74.4 mmol), DCM (150 mL) and glacial Ac₂O (150 mL) is added dropwise over 1.5 hours, a solution of Br₂ (4.6 mL, 89 mmol) in DCM (75 mL). After 2 hours at 10° C., an additional amount of Br₂ (2.30 mL, 44.6 mmol) in DCM (40 mL) is added over 1 h with stirring at 10° C. Stirring is continued for 1 h and the reaction mixture is concentrated under reduced pressure. The residue is triturated with Et₂O (500 mL) to provide bromide 25c.

Step 3:

To a solution of 25c (13.4 g, 54.5 mmol) in THF (300 mL) is added slowly borane-methyl sulfide complex (55.0 mL, 2.0 M solution in THF, 110 mmol) at 0° C. The mixture is allowed to warm to room temperature and then stirred at reflux for 1 h. The reaction mixture is cooled to 0° C., quenched slowly with 1 M aqueous HCl (27 mL), and then refluxed for 1 h. The mixture is diluted with Et₂O, neutralized with 1 M aqueous NaOH and after further extraction is concentrated. The residue is purified by flash column chromatography (15 to 30% EtOAc/hexanes) to provide intermediate 25d.

Step 4:

A mixture of 25d (10.0 g, 43.1 mmol), bis(pinacolato)diboron (16.4 g, 64.7 mmol) and KOAc (12.7 g, 129 mmol) in 1,4-dioxane (430 mL) is degassed with nitrogen for 30 min at RT and heated at 100° C. under a nitrogen atmosphere. After 30 min, dichloro[1,1'-bis(diphenylphosphino)ferrocene]palladium (II) DCM adduct (3.5 g, 4.3 mmol) is added and stirring is continued at 100° C. (15 h). The reaction mixture is cooled to RT and filtered through a pad of Celite®. The Celite® pad is rinsed with EtOAc and the combined filtrate is concentrated under reduced pressure. The residue is purified by flash column chromatography (twice with 25% EtOAc/hexanes followed by 5% EtOAc/DCM) to provide 25e.

Example 26

Synthesis of Intermediate 26e

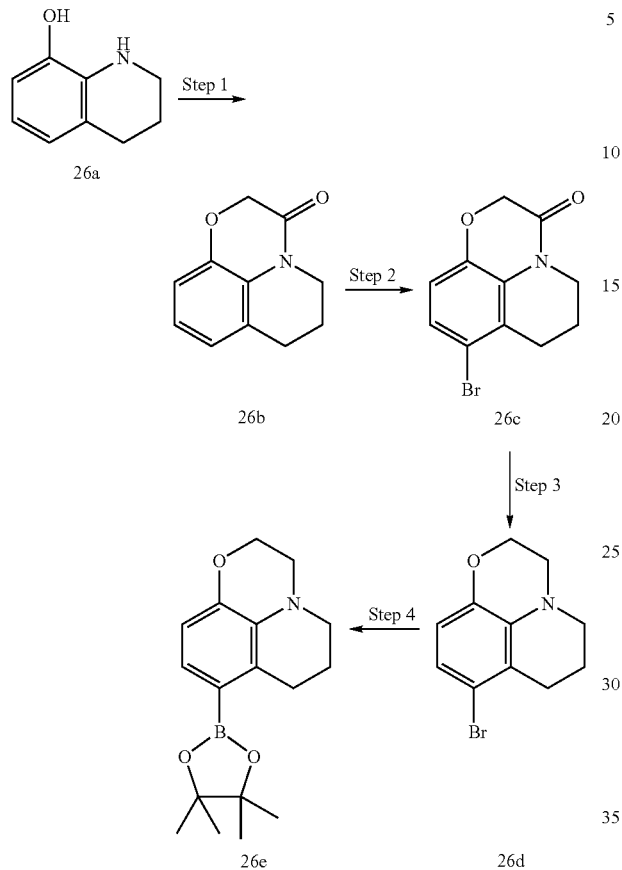

Step 1:

To a cold (0° C.) solution of 1,2,3,4-tetrahydroquinolin-8-ol 26a (6.00 g, 40 mmol) in DMF (60 mL) is added $K_2CO_3$ (16.7 g, 121 mmol) followed by dropwise addition of chloroacetyl chloride (4.25 mL, 53.6 mmol). The reaction mixture is warmed to RT and heated at 60° C. for 2 h. The reaction mixture is cooled to RT, poured into ice-water (1.5 L) and stirred for 30 min. The resulting mixture is filtered and the solid rinsed with water and dried under reduced pressure (16 h) to provide amide 26b.

Steps 2, 3, and 4:

Intermediate 26b is transformed to intermediate 26e using procedures described in steps 2 to 4 of Example 25.

Example 27

Synthesis of Intermediate 27e

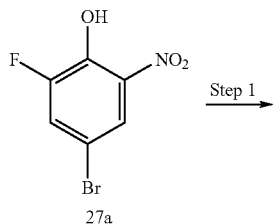

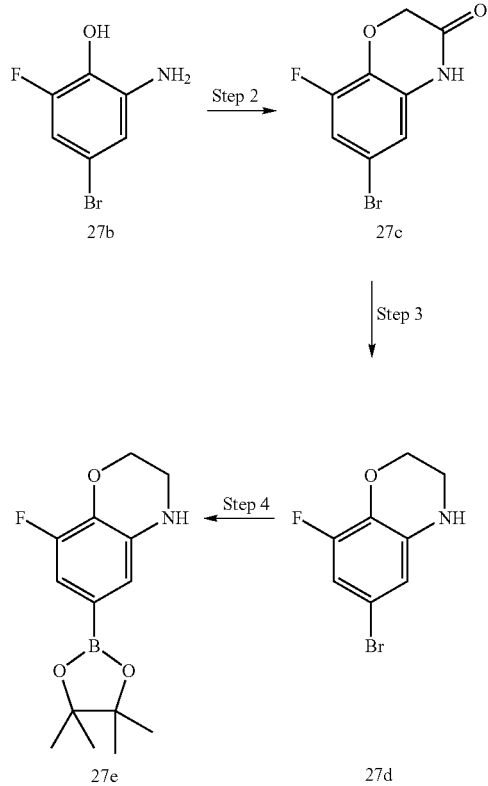

Step 1:

To a mixture of 4-bromo-2-fluoro-6-nitrophenol 27a (12.0 g, 51 mmol) and EtOH (375 mL) is added a solution of sodium dithionite (35.4 g, 203 mmol) in water (125 mL). The mixture is heated at reflux for 1 h, then cooled to 0° C. and slowly neutralized with saturated aqueous $NaHCO_3$ (150 mL). The mixture is concentrated and the residue is triturated with 10% MeOH/EtOAc (1.0 L) and filtered through a pad of Celite®. Concentration of the filtrate under reduced pressure provides aniline 27b.

Step 2:

Intermediate 27b is transformed to intermediate 27c using the procedure described in step 1 of Example 25.

Steps 3 and 4:

Intermediate 27c is transformed to intermediate 27e using the procedures described in steps 3 and 4 of Example 25.

Example 28

Synthesis of Intermediate 28e

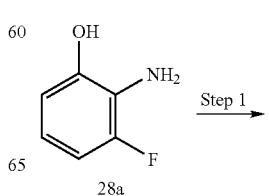

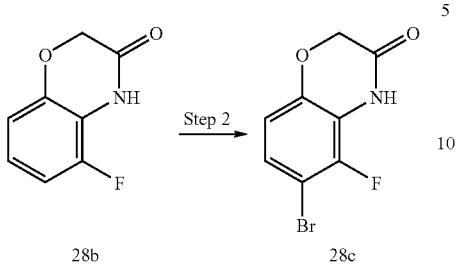
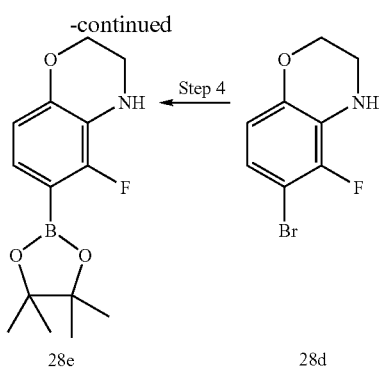
Steps 1 to 4:
Intermediate 28a is transformed to intermediate 28e using procedures described in steps 1 through 4 of Example 25.
Example 29
Synthesis of Compound 4007 (Table 4)
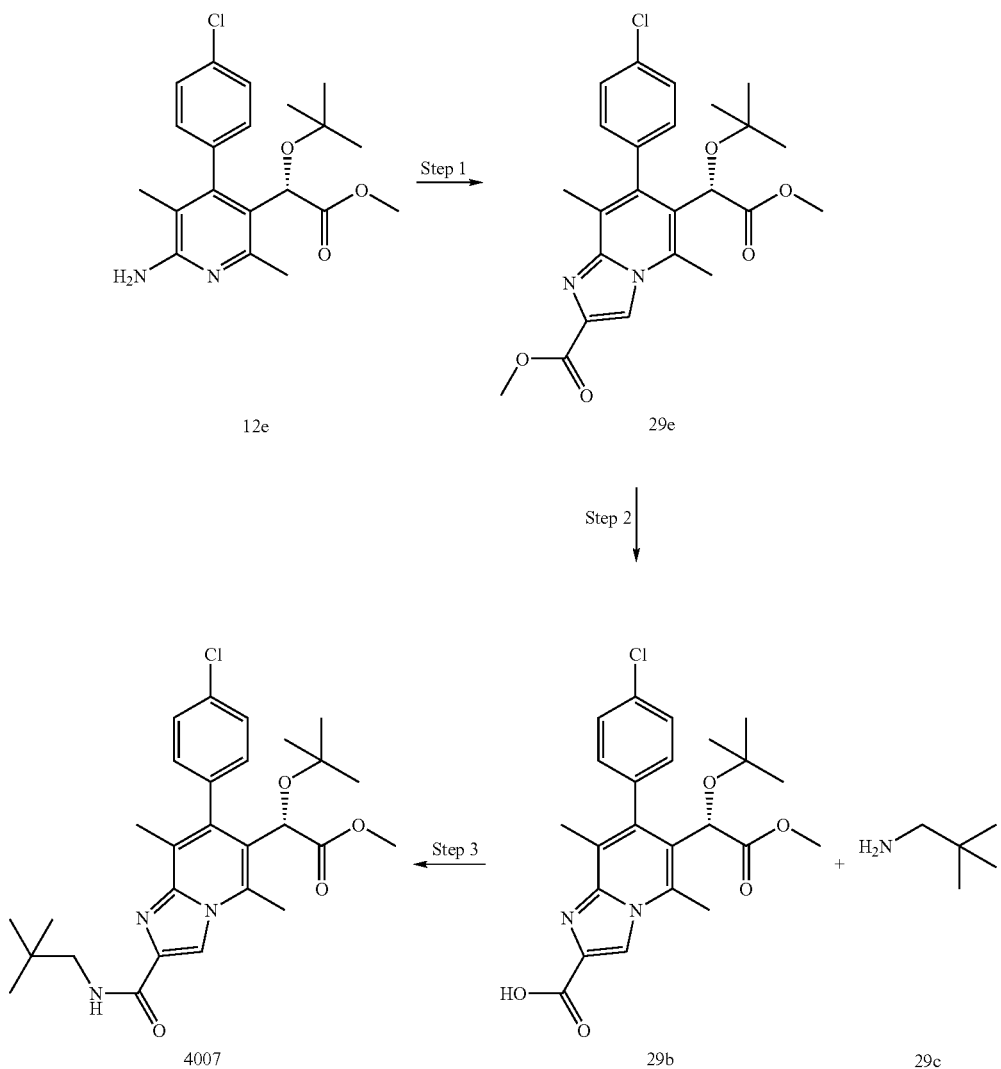

Step 1:

To a mixture of 12e (Example 12) (570 mg, 1.5 mmol), EtOH (11 mL) and acetone (2.2 mL) is added NaHCO₃ (197 mg, 1.6 mmol) and methyl bromopyruvate (177 µL, 1.7 mmol). The mixture is heated at 85° C. for 16 h and solvents are evaporated in vacuo. The residue is dissolved in DCM (20 mL), washed twice with water, dried over MgSO₄ and concentrated in vacuo giving 29a.

Step 2:

A mixture of 29a (620 mg, 1.4 mmol), THF (18.7 mL) and MeOH (6.2 mL) is treated with LiOH (1N, 1.4 mL, 1.4 mmol) at 23° C. for 15 h. A further portion of 1N LiOH (1.4 mL, 1.4 mmol) is added and the mixture is stirred for 4 h at 23° C. 1N NaOH (0.1 mL, 0.1 mmol) is then added and reaction is continued until complete conversion to product is detected by HPLC-MS. The mixture is adjusted to pH 1 with 1N HCl and extracted with DCM (3×), and the organic extract is dried over MgSO₄. The residue is purified by CombiFlash® (5% MeOH/94% DCM/1% AcOH) affording pure 29b.

Step 3:

To a mixture of 29b (50 mg, 0.11 mmol) and NMP (1 mL) is added Et₃N (63 L, 0.45 mmol), followed by N,N,N',N'-tetramethyl-O-(benzotriazol-1-yl)uronium tetrafluoroborate (72 mg, 0.22 mmol). The mixture is stirred for 10 min, treated with neopentylamine 29c (30 mg, 0.34 mmol) and stirred 16 h at 23° C. 1N NaOH (0.5 mL, 0.5 mmol) is added to the reaction mixture and stirring is continued for 2 h at 60° C. The solution is neutralized with AcOH and EtOAc (75 mL) is added. The organic layer is washed with water and brine, dried over MgSO₄, filtered and concenrated in vacuo and the residue is purified by prep HPLC. A mixture of the product and DCM (3 mL) is treated with 1N NaOH (pH>10) and neutralized with AcOH. The mixture is passed through a phase separator filter and the organic layer is concentrated in vacuo. The residue is diluted with a mixture of MeCN/water and lyophilized to give compound 4007.

Example 30

Synthesis of Compound 5002 (Table 5)

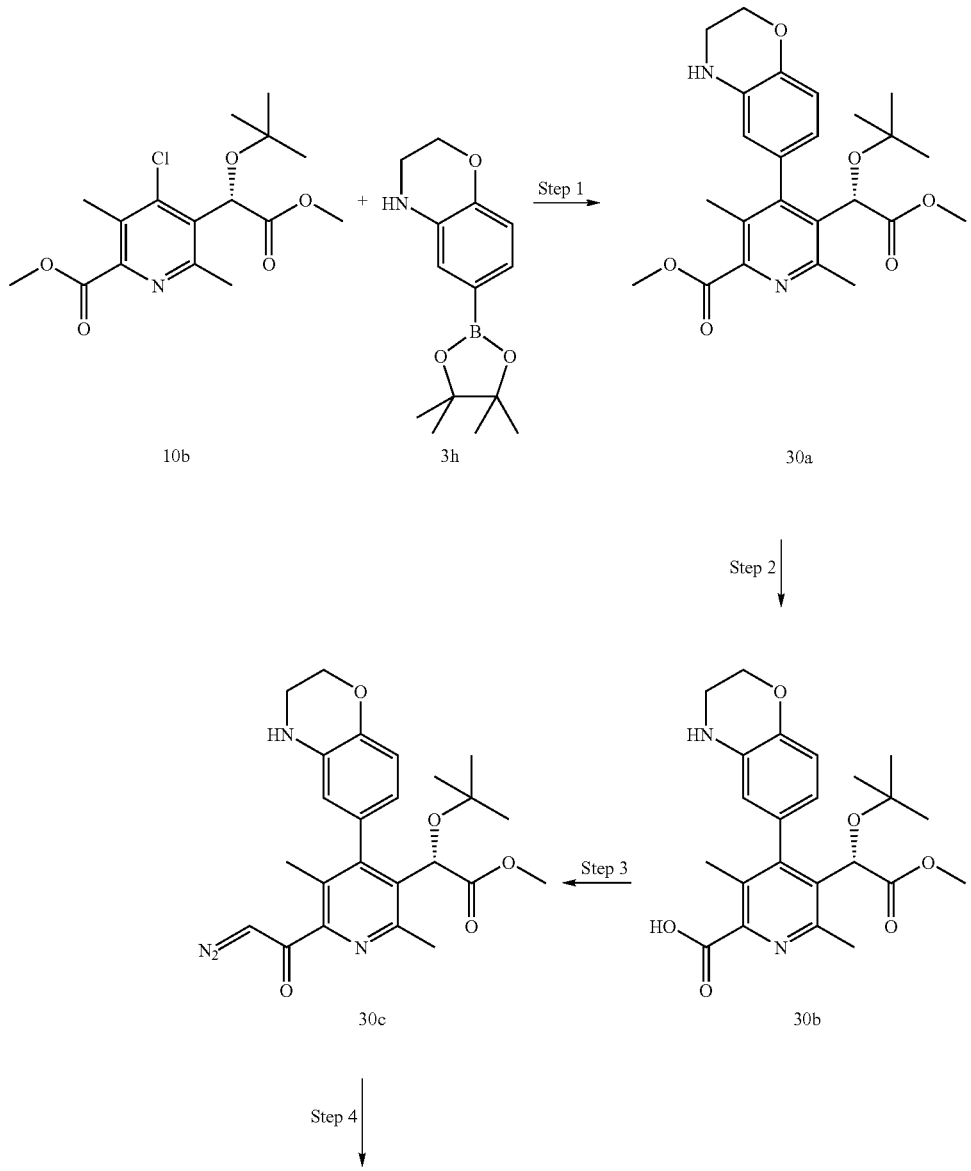

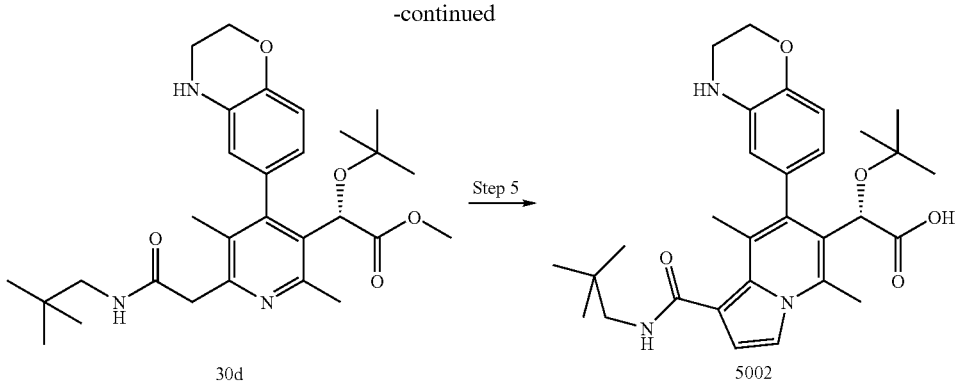

Step 1:
Intermediates 10b (Example 10) and 3h (Example 3) are transformed to intermediate 30a using the procedure described in step 2 of Example 4.

Step 2:
Intermediate 30a is transformed to intermediate 30b using the procedure described in step 4 of Example 12.

Step 3:
To a mixture of 30b (700 mg, 1.5 mmol), Et₃N (420 μL, 3.0 mmoles) and THF (15 mL) at 0° C. is added isobutyl chloroformate (205 μL, 1.6 mmol) dropwise. The mixture is stirred at 0° C. for 30 min, and diazomethane (0.67 M in Et₂O, 11.2 mL, 7.5 mmol) is added. The mixture is allowed to reach 23° C. and stirred for 2 h, then is concentrated in vacuo. A mixture of EtOAc and water is added to the residue, the layers are separated and the organic layer is washed with saturated NaHCO₃, water and brine, dried over Na₂SO₄, filtered and concentrated in vacuo affording 30c.

Step 4:
A mixture of 30c (125 mg, 0.28 mmol) and DCM (1 mL) is treated with neopentylamine 29c (Example 29) (65 μL, 0.55 mmol) and Et₃N (47 μL, 0.34 mmol), followed by addition of silver benzoate (16 mg, 0.07 mmol). The mixture is stirred at 23° C. for 16 h. The mixture is diluted with DCM, washed with saturated NH₄Cl, saturated NaHCO₃ and water, dried over Na₂SO₄, filtered and concentrated in vacuo providing 30d.

Step 5:
A mixture of 30d (40 mg, 0.08 mmol), chloroacetaldehyde (50% in water, 15 μL, 0.12 mmol) and NaHCO₃ (19.7 mg, 0.23 mmol) in EtOH (0.5 mL) is heated at reflux for 16 h. The mixture is cooled to 23° C. and filtered, and the solvent is evaporated in vacuo. The residue is mixed with THF (1 mL) and MeOH (0.3 mL), and 1N NaOH (0.3 mL, 0.3 mmol) is added. The mixture is stirred at 45° C. until the reaction is complete, then cooled to 23° C., adjusted to pH 5 with AcOH and purified by prep. HPLC to give compound 5002.

Example 31

Synthesis of Compound 6002 (Table 6)

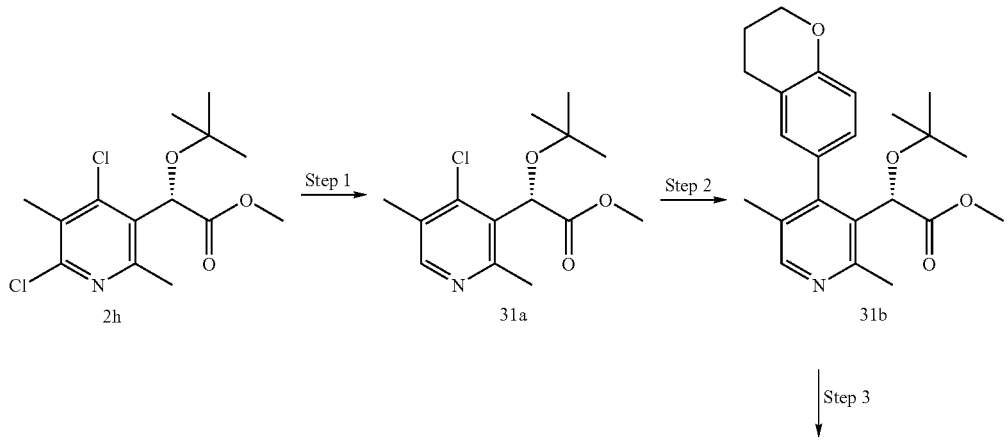

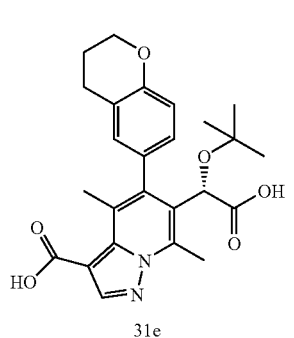 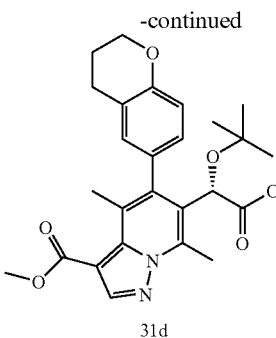 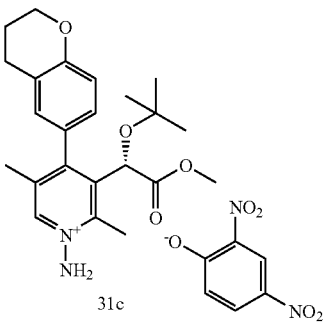

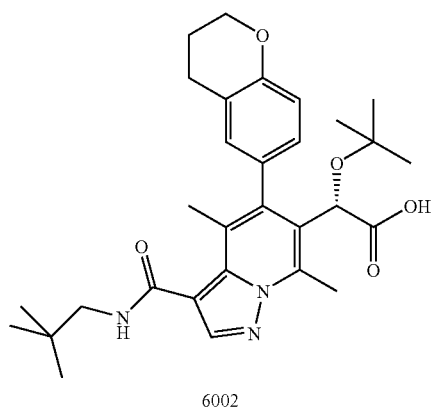

Step 1:

To a mixture of intermediate 2h (Example 2) (5 g, 15.6 mmol) in AcOH (100 mL) is added zinc (15.3 g, 234 mmoles). The mixture is stirred at 60° C. for 120 min, then is cooled to 23° C. and filtered through a Celite® pad, and the filtrate is concentrated in vacuo. The residue is slowly neutralized with saturated NaHCO$_3$ and extracted twice with EtOAc. The organic layers are combined, washed with water and brine, dried over MgSO$_4$, filtered and concentrated in vacuo to give the desired intermediate 31a.

Step 2:

A mixture of DMA (15.8 mL) and distilled water (1.58 mL) is degassed for 10 min with nitrogen and added by syringe to a mixture of the intermediate 31a (1 g, 3.5 mmol), 6-(4,4,5,5-tetramethyl-[1,3,2]dioxaborolan-2-yl)-chroman 19d (Example 19) (1 g, 3.85 mmol) and NaHCO$_3$ (1.47 gr, 17.5 mmol) under nitrogen atmosphere in a 48 mL resealeable vessel equipped with a magnetic stirring bar and fixed with a rubber septum. Bis(tri-t-butylphosphine)palladium (179 mg, 0.35 mmol) is added to the reaction mixture and the vessel is placed in a sonicator for 10 min while being purged with nitrogen. The vessel is sealed with a Teflon cap and heated at 130° C. for 4 h. The mixture is diluted with EtOAc and filtered through Celite®, and the organic extract is washed with water and brine, dried over MgSO$_4$ and concentrated in vacuo. The residue is purified by flash chromatography (10-25-100% ethyl acetate:hexanes) affording 31b.

Step 3:

To a 15 mL resealable vessel equipped with a magnetic stirring bar is added intermediate 31b (500 mg, 1.3 mmol), O-(2,4-dinitrophenyl)hydroxylamine (300 mg, 1.5 mmol; prepared as described in Tet. Lett 1972, 28, 3833-3843) and MeCN (1.7 mL). The reaction vessel is sealed with Teflon cap and the mixture is stirred at 40° C. for 24 h, then is cooled to 23° C. and concentrated in vacuo affording 31c.

Step 4:

To a mixture of 31c (521 mg, 1.3 mmol) and DMF (17.4 mL) is added K$_2$CO$_3$ (198 mg, 1.43 mmol). The reaction mixture is stirred for 5 min at 23° C. (exposed to air), then methyl proprionate (132 mg, 1.56 mmol) is added and stirring is continued for 18 h. The mixture is diluted with EtOAC and washed with saturated NaHCO$_3$, water and brine. The organic layer is dried over MgSO$_4$, filtered and concentrated in vacuo and the residue is purified by flash chromatography (10-100% ethyl acetate:hexanes) affording 31d.

Step 5:

A mixture of 31d (250 mg, 0.52 mmol), THF (2.5 mL) and MeOH (0.83 mL) is treated with a solution of 10 N NaOH (0.42 mL, 4.2 mmol) at 60° C. for 18 h. The mixture is adjusted to pH 1 with 1N HCl and extracted with DCM (3×). The combined organic layers are dried over MgSO$_4$, filtered and concentrated in vacuo affording intermediate 31e.

Step 6:

Intermediate 31e is transformed to compound 6002 using the procedure described in step 3 of Example 29.

Example 32

Synthesis of Intermediate 32a

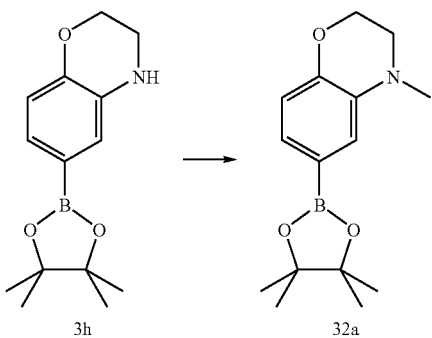

To a mixture of boronate 3h (Example 3) (0.80 g, 3.1 mmol) and acetone (20 mL) is added K$_2$CO$_3$ (5.23 g, 38 mmol) followed by methyl iodide (2.9 mL, 39 mmol). The reaction vessel is sealed and the reaction mixture stirred at RT (24 h). The mixture is diluted with EtOAc and saturated brine. The aqueous phase is extracted with EtOAc (2×) and the combined organic phases are dried (MgSO$_4$), filtered and concentrated to dryness to afford the desired boronate 32a.

Example 33

Synthesis of Intermediate 33c

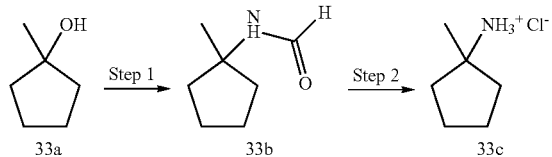

Step 1:

To a mixture of methylcyclopentanol 33a (2.0 g, 20 mmol) and AcOH (2.0 mL) is added KCN (1.43 g, 22 mmol) portionwise, followed by conc. H$_2$SO$_4$ (3.0 mL) added dropwise at a rate to keep the temperature at 30-35° C. The mixture is heated to 60° C. for 30 min and is then stirred at RT (16 h). Ice water (35 mL) is added, and the mixture is adjusted to basic pH with solid K$_2$CO$_3$ and extracted with Et$_2$O (5×). The combined organic phases are dried over MgSO$_4$, filtered and concentrated to give 33b.

Step 2:

A mixture of derivative 33b (1.5 g, 11.8 mmol) and dioxane (8 mL) is treated with 5N HCl (8.0 mL) and EtOH (4 mL). The mixture is heated at gentle reflux for 4 h, then ethanol and dioxane are removed under vacuum. The aqueous phase is washed with hexanes and then concentrated. Traces of water are removed by azeotropic removal with EtOH. The resulting solid is dried under high vacuum to give the amine hydrochloride salt 33c.

Example 34

Synthesis of Intermediate 34d

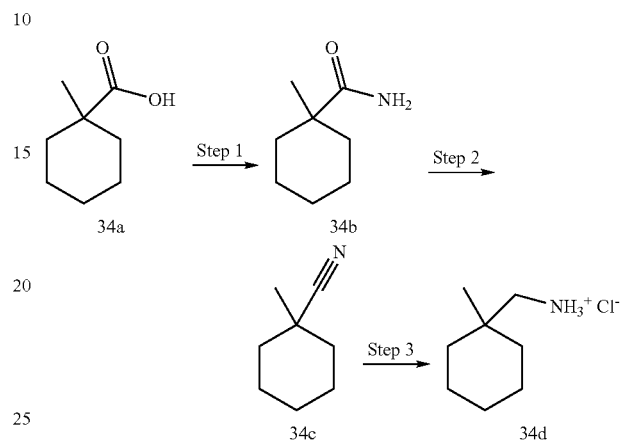

Step 1:

A mixture of 1-methylcyclohexane carboxylic acid 34a (25 g, 176 mmol) in DCM (125 mL) is cooled to 0° C. and a catalytic amount of DMF (250 µL) is added. Oxalyl chloride (20 mL, 228 mmol) is then added dropwise over 30 min and the mixture is allowed to stir for 45 min. The reaction mixture is then warmed to RT and stirred an additional 2.5 h. The mixture is concentrated to dryness and dried and the residue is mixed with 1,4-dioxane (125 mL). To this mixture is added portionwise a solution of 20% ammonium hydroxide (125 mL) at RT (1 h). The mixture is diluted with water (200 mL) and extracted with EtOAc (3×). The combined organic extracts are washed with saturated brine, dried (MgSO$_4$), filtered and concentrated to give a crude solid. This material is dissolved in hot hexanes (125 mL) and left at 4° C. (18 h). The solid formed is filtered and washed with cold hexanes to afford amide 34b.

Step 2:

In a 2 necked round bottomed flask equipped with a condenser is added 34b (18.0 g, 128 mmol) in thionyl chloride (12 mL, 106 mmol). The mixture is heated to reflux for 2 h until gas evolution ceases, then cooled to RT and diluted with Et$_2$O (125 mL) with careful addition of water (75 mL). The mixture is vigorously stirred for 5 min and then adjusted to basic pH with solid Na$_2$CO$_3$. The organic phase is separated and washed with saturated Na$_2$CO$_3$ and saturated brine, dried over MgSO$_4$, treated with charcoal and filtered through Celite®. The filtrate is concentrated under vacuum at RT to give 34c.

Step 3:

To a mixture of EtOH (50 mL) and HCl (g) (8.3 g, 0.23 mmol) at 0° C. is added 34c (14.7 g, 119 mmol) followed by platinum oxide (400 mg). The mixture is placed in a Parr shaker and treated with H$_2$(g) at 40 psi for 48 h. The atmosphere is flushed and the mixture filtered through Celite® and washed with EtOH. The filtrate is concentrated to dryness and the residue is washed with ether, filtered and dried to give the intermediate 34d as the hydrochloride salt.

Example 35

Synthesis of Compound 1363 (Table 1) Including Separation of Atropisomers

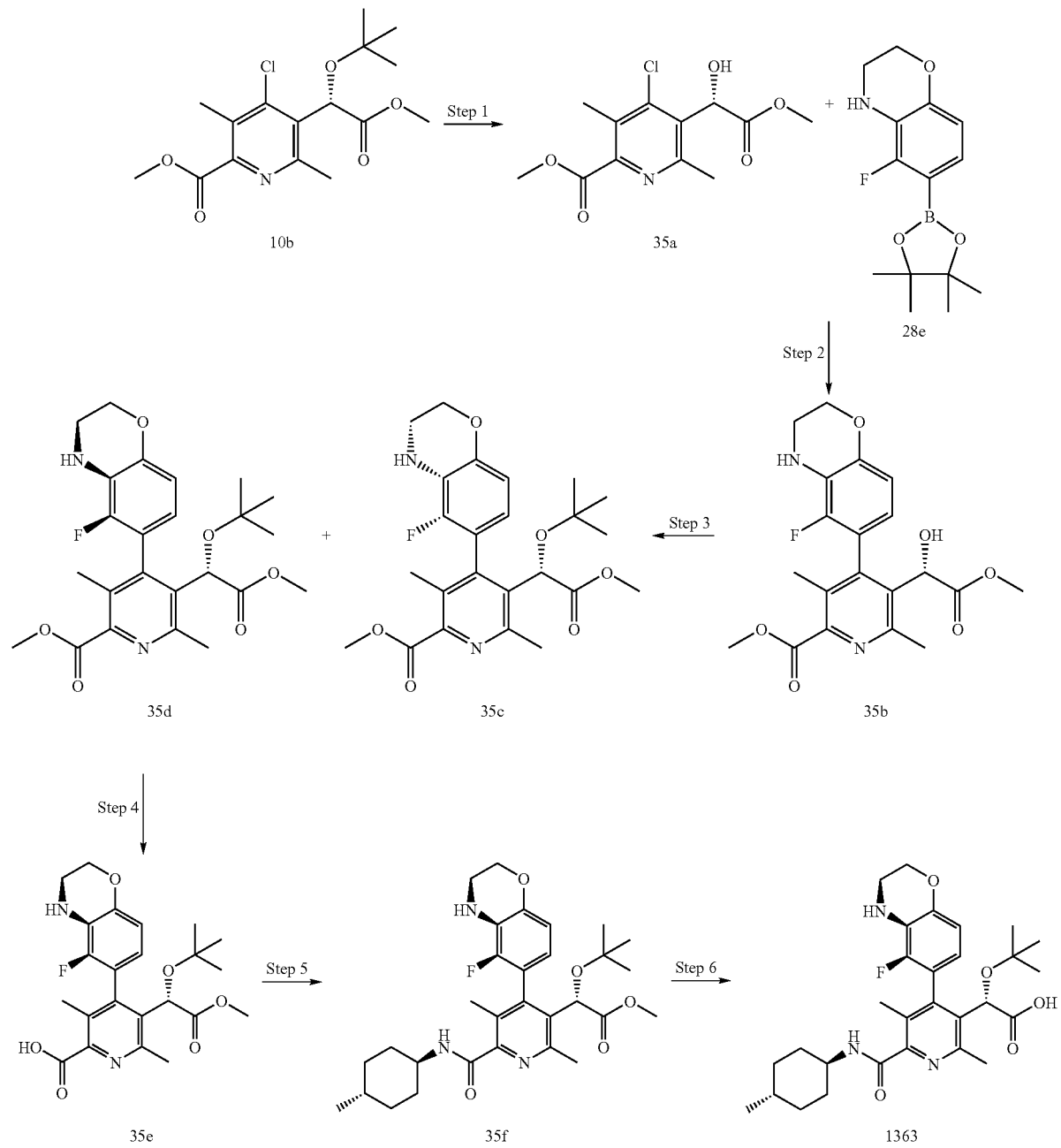

Step 1:

To a mixture of the diester 10b (1.0 g, 2.91 mmol), DCM (7 mL) and MeOH (0.25 mL) is added TFA (8 mL). The mixture is allowed to stir at RT for 2 h and is concentrated to dryness. The residue is taken up in EtOAc and washed with saturated NaHCO$_3$, dried (Na$_2$SO$_4$), filtered and concentrated to give alcohol 35a.

Step 2:

A mixture of boronate 28e (400 mg, 1.43 mmol), alcohol 35a (420 mg, 1.46 mmol), 2-dicyclohexylphosphino-2',6'-dimethoxybiphenyl (S-Phos, 59 mg, 0.1 mmol), tris(dibenzylideneacetone)dipalladium(0) (39 mg, 0.04 mmol) and Na$_2$CO$_3$ (607 mg, 5.7 mmol) in 2-methyl tetrahydrofuran (5.6 mL) and water (1.4 mL) is placed in a sealable vessel. The mixture is degassed by bubbling argon through the solution (10 min) and the vessel is sealed and heated at 75° C. (20 h). Further portions of the catalyst and ligand are added and the mixture is again heated at 75° C. (20 h). The cooled mixture is filtered, diluted with EtOAc, washed with brine, dried over Na₂SO₄, filtered and concentrated. The residue is purified by CombiFlash® Companion to give a mixture of isomers 35b.

Step 3:

The mixture of alcohols 35b (362 mg, 0.90 mmol) in tert-butyl acetate (7.1 mL, 53 mmol) is cooled to 0° C. in an ice bath and treated portionwise with perchloric acid (70% w/w in water, 1.2 mL, 13.4 mmol). The vessel is capped and the reaction mixture stirred at 0° C. until about 50% completion. The reaction is quenched with 1N NaOH (pH~9) and the mixture is extracted with EtOAc. The organic phase is washed with water and brine, dried over Na₂SO₄ and concentrated. The residue is purified by CombiFlash® Companion (20 to 100% EtOAc/hexanes) to give the separated isomers 35c and 35d plus unreacted starting alcohols 35b.

Step 4:

To a mixture of diester 35d (87 mg, 0.19 mmol), MeOH (0.4 mL) and THF (1.2 mL) is added 1N LiOH (0.21 mL, 0.21 mmol). The mixture is allowed to stir at RT (16 h) then is acidified with 1N HCl and extracted with EtOAc (2×). The organic extract is dried over Na₂SO₄, filtered and concentrated to give acid 35e.

Step 5:

A mixture of acid 35e (30 mg, 0.06 mmol) and NMP (1 mL) is treated with TBTU (40 mg, 0.12 mmol) and Et₃N (35 µL, 0.25 mmol). The mixture is allowed to stir at RT for 5 min then trans-4-methylcyclohexyl amine (25 µL, 0.19 mmol) is added. The reaction is allowed to stir at RT (2 h) and is then diluted with EtOAc. The organic phase is washed with saturated NH₄Cl, H₂O, and brine, dried over MgSO₄, filtered and concentrated to dryness to afford the amide 35f.

Step 6:

A mixture of amide 35f, THF (0.9 mL) and MeOH (0.3 mL) is treated with 1N NaOH (0.29 ml, 0.29 mmol) at 50° C. (1 h). The solution is acidified with AcOH and purified by preparative HPLC. The pure fractions are combined, concentrated to remove MeCN and then extracted into DCM. The organic phase is dried over Na₂SO₄, filtered and concentrated. This solid is re-dissolved in DCM and treated with 10 drops of 1N NaOH and then neutralized with AcOH. The phases are separated and the aqueous layer is extracted with DCM. The combined organic phases are concentrated and lyophilized to give compound 1363.

Example 36

Alternative Synthesis of Intermediate 12c

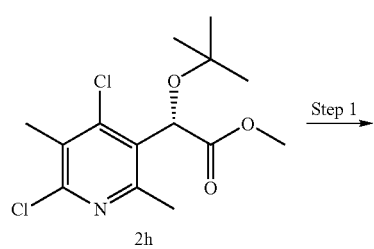

2h

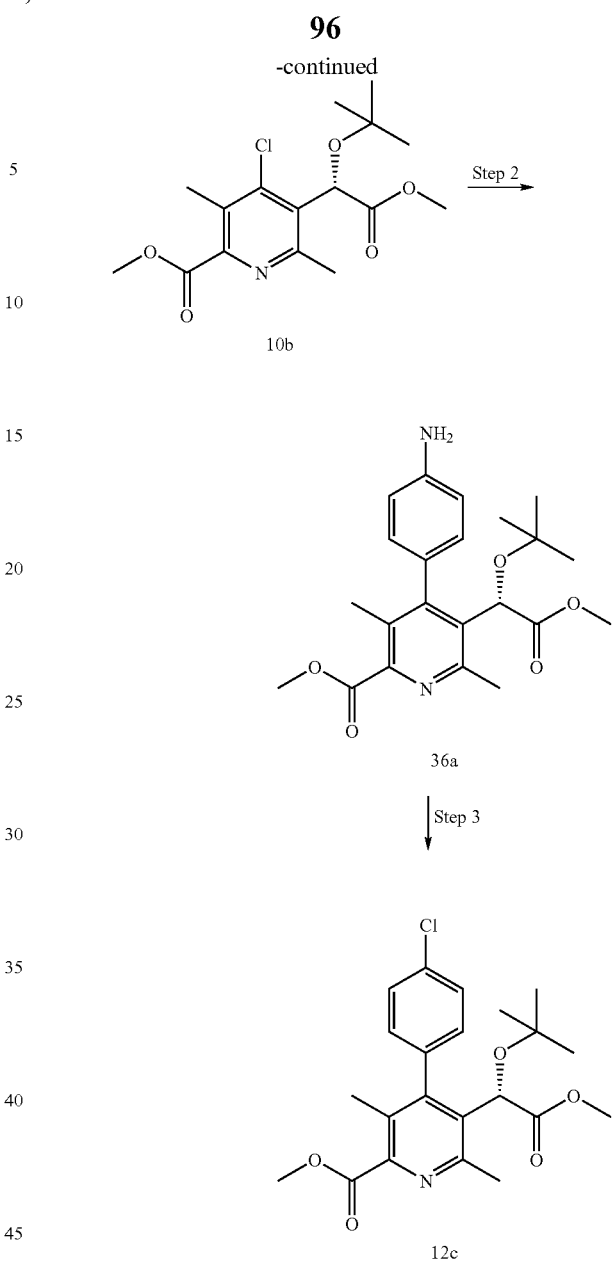

Step 1:

A steel bomb is charged with the compound 2h (11 g, 34.3 mmol), Pd(OAc)₂ (0.17 mg, 0.68 mmol), bis(diphenylphosphino)ferrocene (0.42 g, 0.76 mmol) and 2,6-lutidine (8.0 mL, 68.7 mmol). Degassed MeOH (50 mL) is added and the system is sealed. The system is purged with N₂ (2×) and CO (3×). The mixture is stirred at 110° C. under 200 psi of CO for 48 h. The reaction mixture is filtered, concentrated and purified by Combiflash® Companion to give 10b.

Step 2:

Intermediate 10b is transformed to intermediate 36a using the procedure described in step 1 of Example 12.

Step 3:

Intermediate 36a is transformed to intermediate 12c using the procedure described in step 2 of Example 5.

Example 37

Synthesis of Compound 1142 (Table 1)

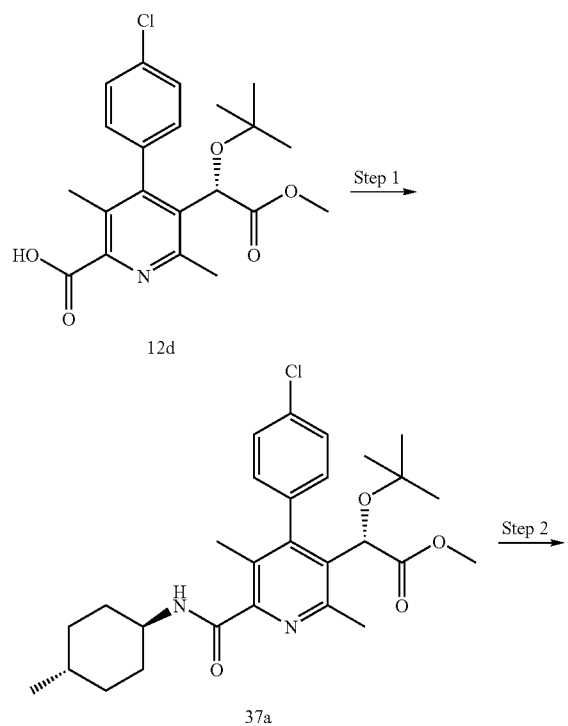

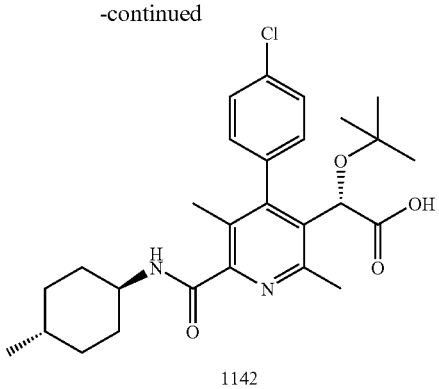

Step 1:
Intermediate 12d is transformed to intermediate 37a using the procedure described in step 5 of Example 35.

Step 2:
A mixture of amide 37a, (30 mg, 0.06 mmol), THF (2.5 mL) and MeOH (0.75 mL) is treated with 5N NaOH (65 µL, 0.33 mmol) at 60° C. (1 h). The solution is neutralized with AcOH (19 µL, 0.33 mmol) and evaporated to dryness. The residue is then purified by CombiFlash® Companion to give compound 1142.

Example 38

Synthesis of Compound 1438 (Table 1)

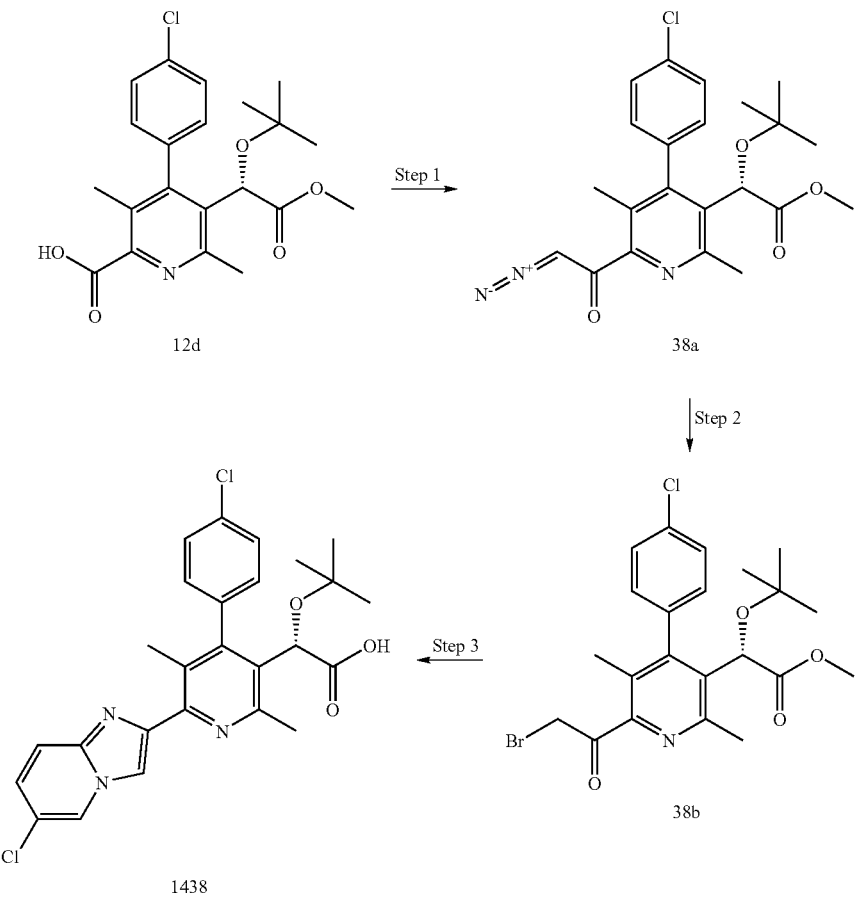

Step 1:

To 12d (1 g, 2.5 mmol) and Et$_3$N (481 µL, 3.5 mmol) in THF (13 mL) at 0° C. is added isobutyl chloroformate (448 µL, 3.5 mmol) dropwise. The mixture is stirred at 0° C. for 1 h. A diazomethane solution (0.67 M in diethyl ether, 37 mL, 25 mmol) is added slowly and the mixture is allowed to reach 23° C. After 1 h, the mixture is concentrated in vacuo and then EtOAc and water are added. The organic layer is washed with a saturated aqueous solution of NaHCO$_3$, water, brine, dried over Na$_2$SO$_4$, filtered and concentrated in vacuo. Crude product is purified by CombiFlash® Companion to give 38a.

Step 2:

To a solution of 38a (828 mg, 2.5 mmol) in THF (16 mL) at 0° C. is added dropwise an HBr solution (48% aq, 1.09 mL, 9.6 mmol). The mixture is stirred for 1 h at 0° C. The solution is diluted with EtOAc, washed with NaHCO$_3$ (sat), water, brine, dried over Na$_2$SO$_4$, filtered and concentrated in vacuo to provide 38b.

Step 3:

To 38b (50 mg, 0.1 mmol) in a mixture of EtOH (750 µL) and acetone (150 µL) is added NaHCO$_3$ (8.1 mg, 0.11 mmol) and 2-amino-5-chloropyridine (14.7 mg, 0.11 mmol) in a sealed tube. The mixture is heated at 85° C. for 30 min then concentrated in vacuo. The residue is diluted with THF (1 mL), MeOH (300 µL) and a NaOH solution (5 N, 103 µL, 0.52 mmol) and the resulting mixture is then stirred for 15 min at 60° C. The mixture is cooled to 23° C. and the pH is adjusted to ~5-6 with AcOH. The crude mixture is purified by prep HPLC (MeOH/water containing 10 mM ammonium bicarbonate (pH10)). The desired fractions are collected and concentrated under reduced pressure. The residue is dissolved in MeCN (1.5 mL) and freeze-dried to give 1438.

Example 39

Synthesis of Intermediate 39c

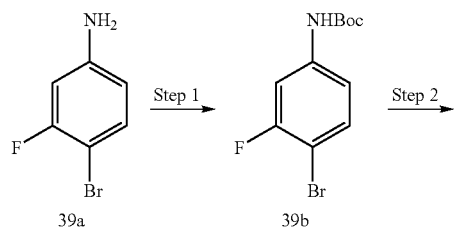

-continued

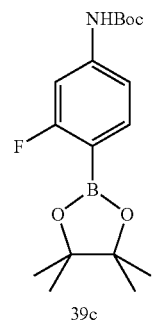

Step 1:

To a THF solution (90 mL) of 39a (7.2 g, 38 mmol) is added solid NaHCO$_3$ (16 g, 190 mmol) and water (9 mL) at RT. This mixture is stirred for 10 min before the portionwise addition of solid di-t-butyl dicarbonate (16.5 g, 76 mmol). The mixture is stirred at 55° C. for 16 h or until completion. The mixture is filtered and then partitioned between EtOAc and water. The aqueous phase is extracted with EtOAc and the combined organic phases are washed with brine, dried (MgSO$_4$) filtered and concentrated. The crude product is purified by CombiFlash® Companion to give 39b.

Step 2:

To 39b (11 g, 37.8 mmol) dissolved in dry 1,4-dioxane (120 mL) is added bis(pinacolato)diboron (13.7 g, 54 mmol) and potassium acetate (9.9 g, 101 mmol) before being deoxygenated by bubbling a stream of argon for 15 min. To this mixture is added 1,1'-bis(diphenylphosphino)ferrocene (2.75 g, 3.4 mmol). This mixture is degassed a further 5 min before being refluxed at 100° C. for 16 h. The cooled mixture is diluted with EtOAc and water and then filtered through Celite. The phases are separated and the organic layer is washed with water, brine, dried (MgSO$_4$), filtered and concentrated. The resulting residue is purified by CombiFlash® Companion to give intermediate 39c.

Example 40

Synthesis of Compound 1453 (Table 1)

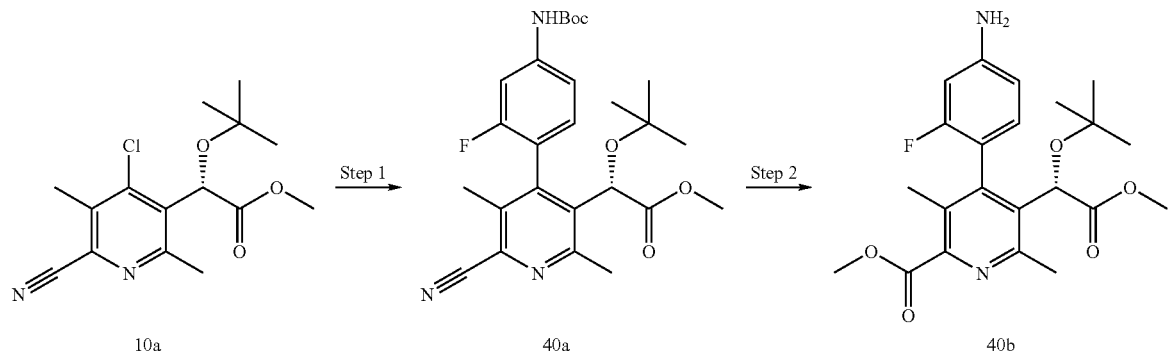

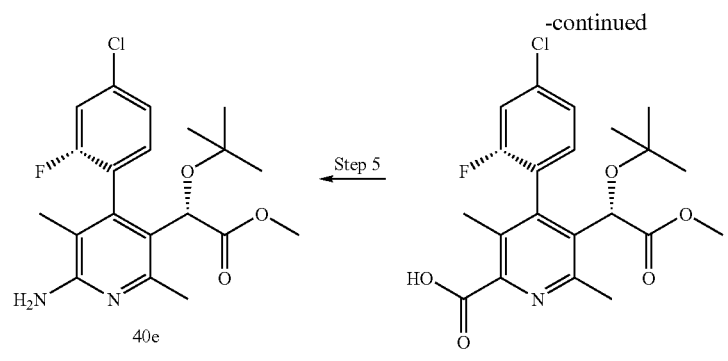

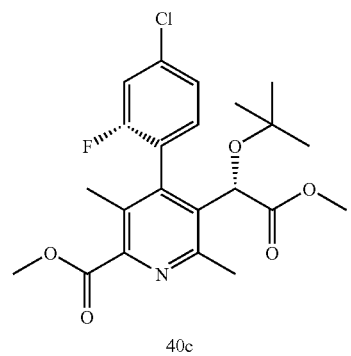

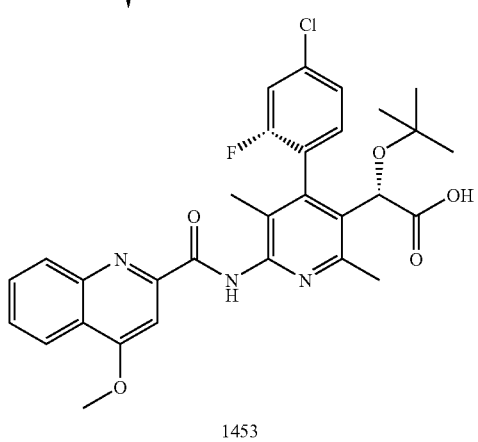

Step 1:
Intermediate 10a (4.0 g, 12.9 mmol) is treated with boronate 39c (5.2 g, 15.5 mmol) using the procedure described in step 1 of Example 12 to afford 40a.

Step 2:
Intermediate 40a is transformed to diester 40b using the procedure described in step 3 of Example 12.

Step 3:
Aniline 40b (2.86 g, 6.84 mmol) is converted to intermediate 40c using the procedure described in step 2 of Example 5. The atropisomers are separated at this stage by Combi-Flash® Companion to give 40c.

Step 4:
Diester 40c is converted to mono-acid 40d using the procedure described in step 4 of Example 12.

Step 5:
Intermediate 40d is transformed to intermediate 40e using the procedure described in step 5 of Example 12.

Step 6:
To a solution of 4-methoxy-2-quinoline carboxylic acid (302 mg, 1.5 mmol) and DMF (15 µL) in DCM (7 mL) is added oxalyl chloride as a 2M solution in DCM (968 µL, 1.94 mmol) dropwise at RT (with evolution of gas). After 20 min, the solution is concentrated to dryness and then dissolved in THF (2 mL). To this solution is added intermediate 40e (294 mg, 0.74 mmol) and DIPEA (650 µL, 3.72 mmol) then heated at 50° C. for 2 h. The cooled reaction mixture is diluted with EtOAC and washed consecutively with a NH$_4$Cl solution (sat), a NaHCO$_3$ solution (sat) and brine. The organic phase is dried (MgSO$_4$), filtered and concentrated to dryness. The solution of the crude ester (431 mg, 0.74 mmol) in THF (4 mL) and MeOH (2 mL) is heated at 50° C. before being treated with 5 N NaOH (743 µL, 3.72 mmol). The reaction is stopped after 1 h by quenching with AcOH (500 µL) and the mixture is concentrated to dryness. The residue is taken up into MeOH and purified by preparative HPLC to give, after lyophilization, compound 1453.

Example 41

Synthesis of Intermediate 41d

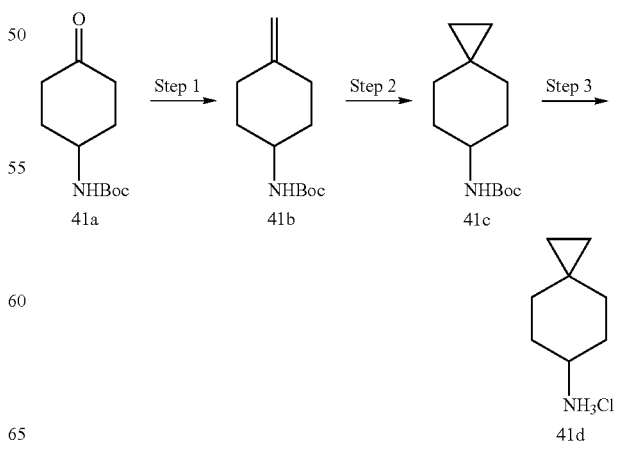

Step 1:
Compound 41a is converted to 41b using dimsyl sodium and methyl-triphenylphosphoium bromide as described in J. Am. Chem. Soc., 1980, 102, 1404-1408.

Step 2:
Intermediate 41b (250 mg, 1.18 mmol) is dissolved in diethyl ether (5 mL) and cooled to 0° C. before being treated with diazomethane in ether (40 mL, 2.8 mmol). To this cooled solution is added portionwise palladium (II) acetate (5×5 mg). This sequence is repeated until the reaction is complete by NMR analysis. The solution is filtered and concentrated to give 41c.

Step 3:
To 41c (261 mg, 1.16 mmol) is added 4M HCl/dioxane (5 mL, 20 mmol) and the mixture is allowed to stir at RT for 2 h. The solution is concentrated and then treated with diethyl ether. This mixture is sonicated to afford a solid which is filtered and dried to give 41d as the HCl salt.

Example 42

Synthesis of Compound 1440 (Table 1)

mixture is stirred at RT for 1 h. EtOAc (10 mL) is added and the solution is washed with brine, dried (MgSO$_4$), filtered and the solvent evaporated. The crude amide is dissolved in AcOH (4 mL) and heated at 80° C. (1 h). The solution is concentrated, EtOAc (10 mL) is added and the solution is washed with saturated NaHCO$_3$ and brine. The layers are separated and the organic layer is evaporated to give the crude benzimidazole. The product is purified by CombiFlash® Companion to afford 42a.

Step 2:
A solution of benzimidazole 42a (120 mg, 0.25 mmol) in DMF (1.5 mL) is treated with NaH (60% dispersion in mineral oil, 11 mg, 0.27 mmol) and the mixture is stirred for 15 min. Iodoethane (30 µL, 0.37 mmol) is added and the reaction is stirred for 1 h. The reaction is diluted with water (15 mL) and extracted with EtOAc (15 mL). The organic layer is dried (MgSO$_4$) and evaporated to dryness to give compound 42b.

Step 3:
A mixture of amide 42b (125 mg, 0.25 mmol) in THF (3.5 mL) and MeOH (0.5 mL) is treated with 5N NaOH (250 µL, 1.5 mmol) at 50° C. (3 h). The solution is acidified with AcOH

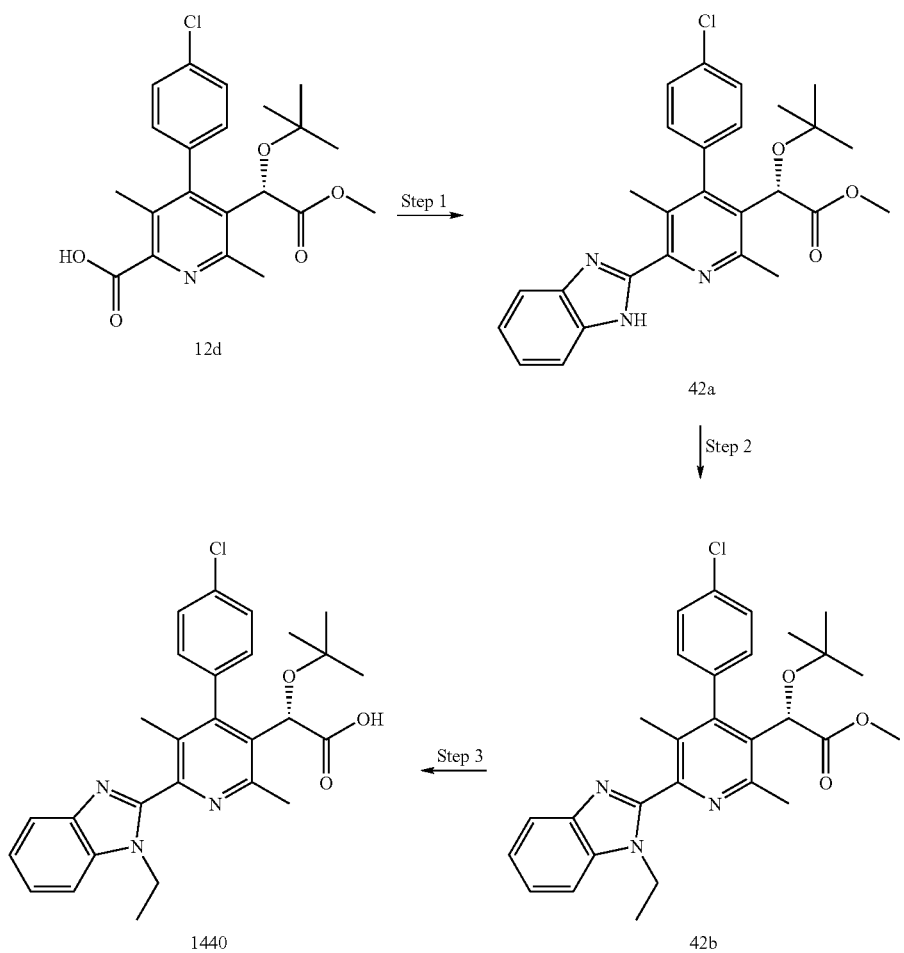

Step 1:
A solution of 2-aminoaniline (27 mg, 0.25 mmol), HATU (110 mg, 0.30 mmol) and 12d (0.10 g, 0.25 mmol) in DMF (3 mL) at RT is treated with Et$_3$N (0.10 mL, 0.74 mmol). This and evaporated to dryness. The residue is then dissolved in MeOH (1 mL) and purified by preparative HPLC. The fractions containing pure compound are pooled, evaporated to dryness, redissolved in 1:1 MeCN/water (50 mL), frozen and lyophilized to give compound 1440.

Example 43

Synthesis of Compound 1437 (Table 1)

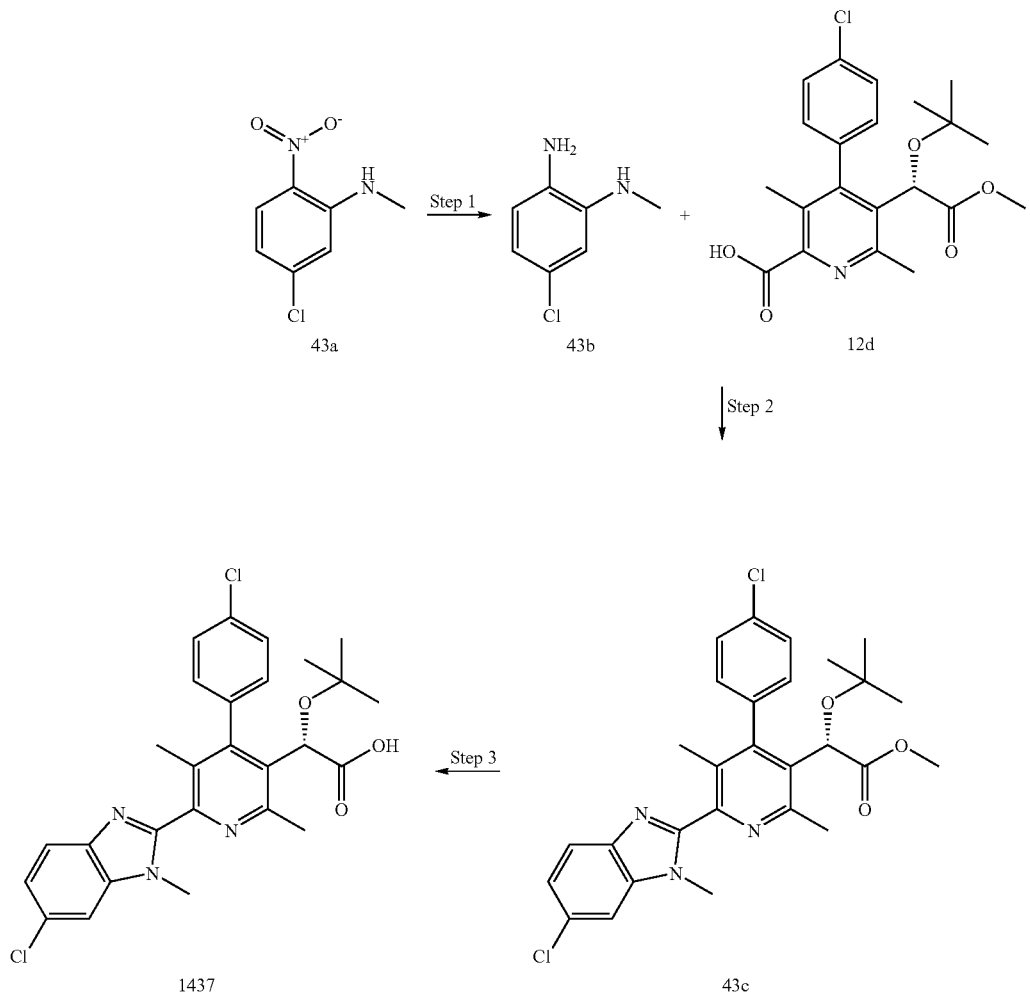

Step 1:

To a solution of compound 43a (1.9 g, 10 mmol) in THF is added tin powder and 1N HCl (50 mL, 50 mmol). After 1 h of vigorous stirring, 1 N NaOH (50 mL) is added slowly to the reaction. The mixture is filtered on Celite and the filter cake is washed with EtOAc (200 mL). The filtrate is extracted with EtOAc and the combined organic layers are dried (Na$_2$SO$_4$) and concentrated to dryness to give compound 43b.

Step 2:

Intermediates 43b and 12d are coupled to give intermediate 43c using the procedure described in step 1 of Example 42.

Step 3:

Intermediate 43c is transformed to compound 1437 using the procedure described in step 3 of Example 42.

Example 44

Synthesis of Compound 1450 (Table 1)

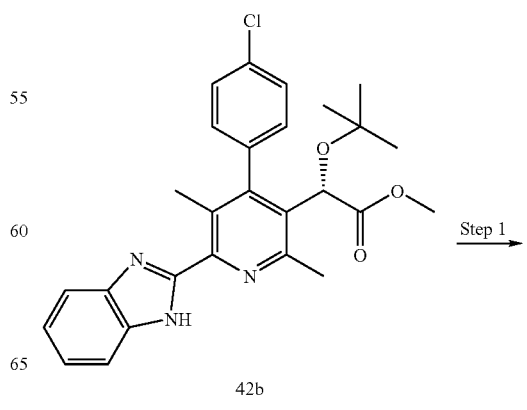

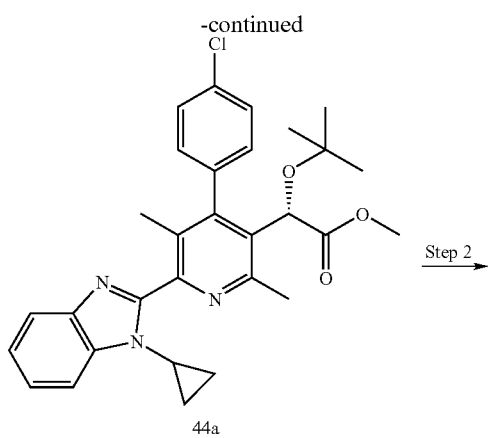

Step 2 →

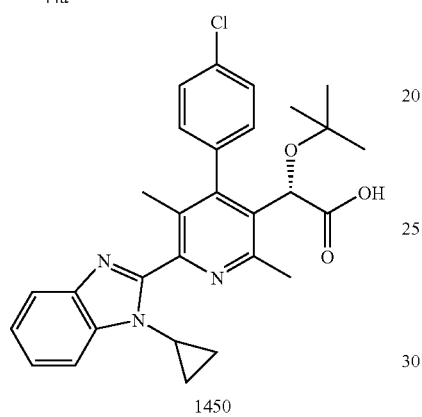

1450

Step 1:
A mixture of benzimidazole 42b (88 mg, 0.19 mmol), cyclopropyl boronic acid (32 mg, 0.37 mmol), copper acetate (34 mg, 0.19 mmol) 2,2-bipyridyl (29 mg, 0.19 mmol) and $Na_2CO_3$ (39 mg, 0.37 mmol) in DCE (3 ml) is heated to 70° C. for 18 h. The mixture is cooled to RT and washed with a mixture of water/saturated $NH_4Cl$ (15 mL each). The water layer is extracted with DCM, and the organic layer is washed with brine, dried ($MgSO_4$), filtered and concentrated to give compound 44a.

Step 2:
Intermediate 44a is transformed to compound 1450 using the procedure described in step 3 of Example 42.

Example 45

Synthesis of Compound 1447 (Table 1)

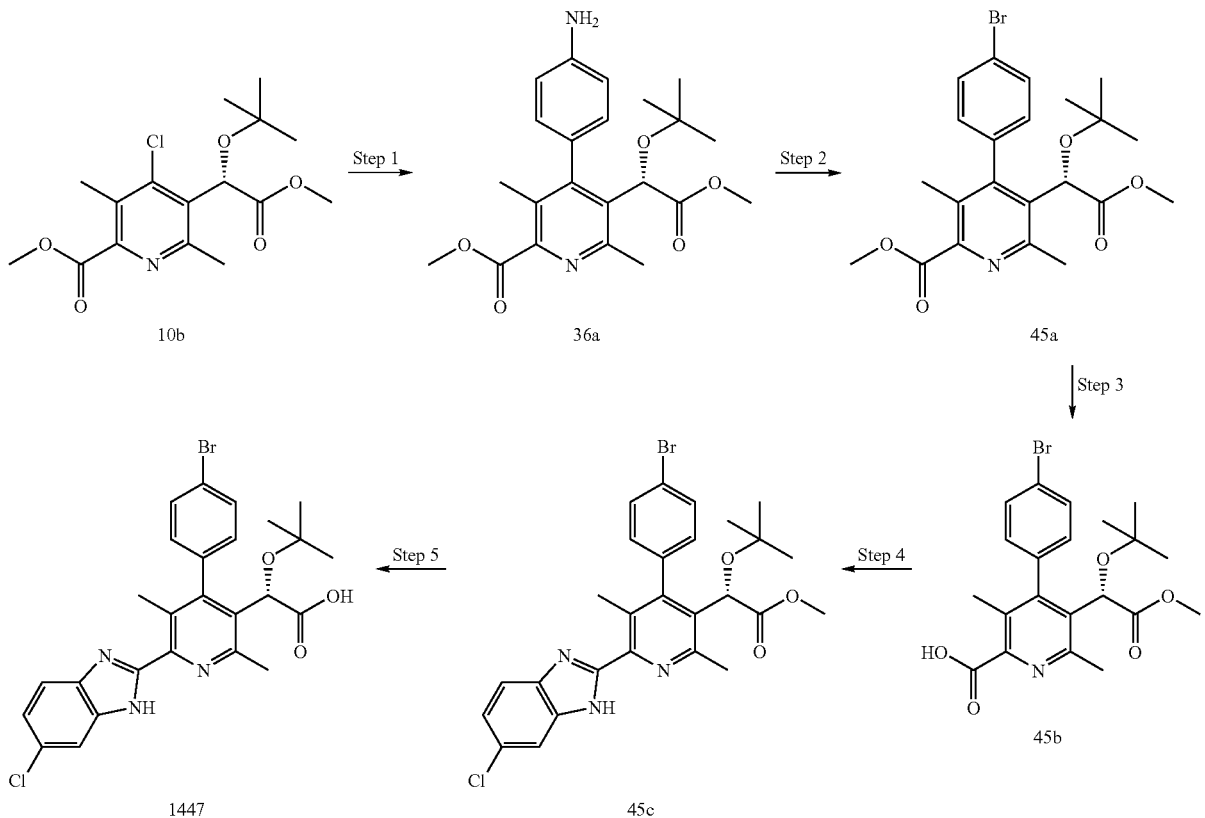

Step 1:

Intermediate 10b is transformed to intermediate 36a using the procedure described in step 1 of Example 12

Step 2:

t-Butyl nitrite (90% w/w, 1.0 mL, 7.9 mmol) is added to a stirred suspension of CuBr$_2$ (1.6 g, 7.3 mmol) in anhydrous, deoxygenated MeCN (12 mL) cooled to 0° C. under a nitrogen atmosphere. A solution of compound 36a in dry, deoxygenated MeCN (15 mL+5 mL rinse) is added dropwise and the reaction is allowed to warm to RT. After 4 h, additional t-butyl nitrite (0.3 mL, 2.4 mmol) is added and the stirring is continued. After 16 h, silica gel is added (30 g) and the solvent is evaporated. The product is purified by CombiFlash® Companion to afford intermediate 45a.

Step 3:

Intermediate 45a is transformed to intermediate 45b using the procedure described in step 4 of Example 12.

Step 4:

Intermediate 45c is transformed to intermediate 45c using the procedure described in step 1 of Example 42.

Step 5:

Intermediate 45c is transformed to intermediate 1447 using the procedure described in step 3 of Example 42.

Example 46

Synthesis of Compound 1443 (Table 1)

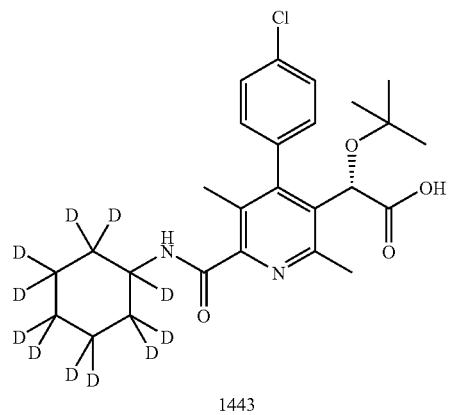

1443

Step 1:

Intermediate 12d and commercially available D-11 cyclohexylamine (CDN Isotopes) are coupled to give intermediate 46a using the procedure described in step 5 of Example 35.

Step 2:

Intermediate 46a is transformed to compound 1443 using the procedure described in step 2 of Example 37.

Example 47

Synthesis of Compound 1470 (Table 1)

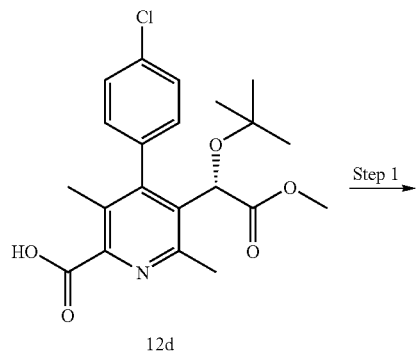

12d

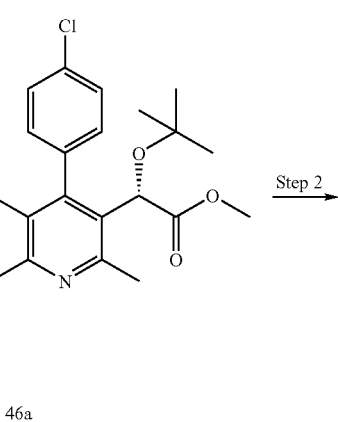

46a

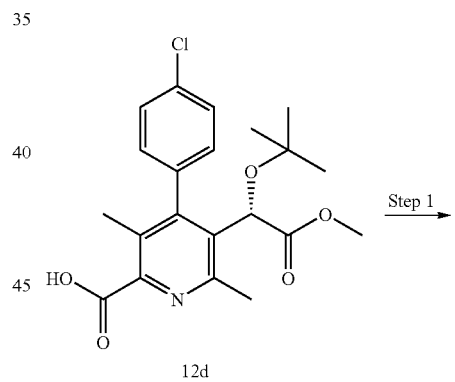

12d

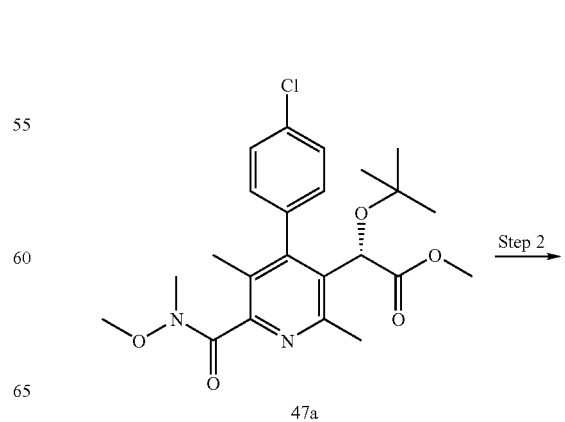

47a

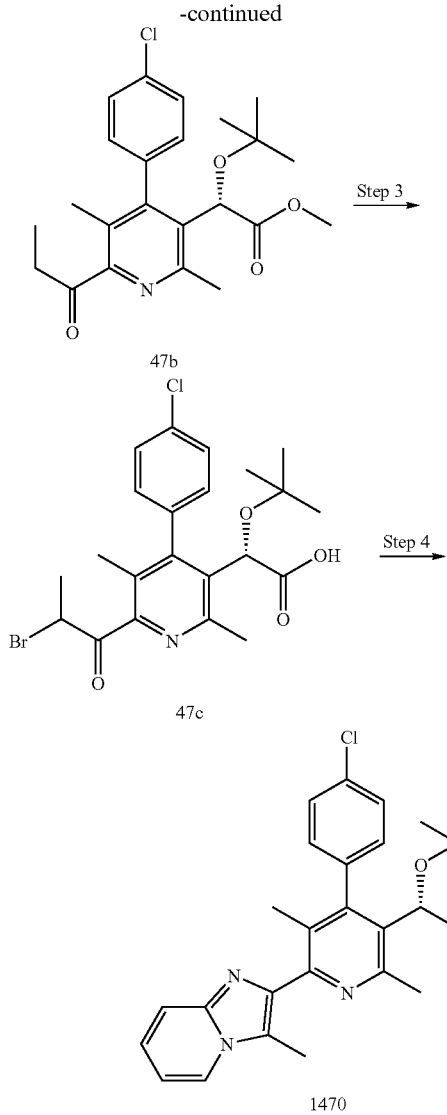

Step 1:
To 12d (200 mg, 0.49 mmol) in N-methylpyrrolidinone (2.5 mL) is added Et$_3$N (137 µL, 0.99 mmol) followed by N,N,N',N'-tetramethyl-O-(benzotriazol-1-yl)uronium tetrafluoroborate (320 mg, 0.99 mmol). The mixture is stirred for 10 min, treated with N,O-dimethylhydroxylamine hydrochloride (96 mg, 0.99 mmol) and then stirred for 60 h at 23° C. A saturated, aqueous solution of ammonium chloride is added to the mixture. The solution is diluted with water and extracted with EtOAc (2×). The combined organic layers are washed with water (2×), brine, dried over MgSO$_4$, filtered and evaporated in vacuo. The crude product is purified by CombiFlash®Companion with an eluting gradient of 20 to 100% EtOAc/hexanes to afford 47a.
Step 2:
To a solution of 47a (163 mg, 0.36 mmol) in THF (3.6 mL) at −78° C. is added dropwise an ethyl magnesium bromide solution (2.2 M in THF, 198 µL, 0.44 mmol). The mixture is stirred for 30 min at −40° C. A 1N HCl solution (~10-15 mL) is added to the reaction mixture and then the mixture is extracted with diethyl ether (2×). The combined organic layers are washed with brine, dried over Na$_2$SO$_4$, filtered and concentrated in vacuo. The crude product is purified by Com-biFlash® Companion with an eluting gradient of 5 to 20% EtOAc/hexanes affording pure 47b.
Step 3:
To 47b (100 mg, 0.24 mmol) in THF (1 mL) is added phenyl trimethylammonium tribromide (94.5 mg, 0.25 mmol). The reaction mixture is stirred at reflux for 20 h. The solution is taken up in EtOAc, washed with NaHCO$_3$ (sat), brine, dried over Na$_2$SO$_4$, filtered and concentrated in vacuo to give 47c.
Step 4:
To 47c (50 mg, 0.1 mmol) in a mixture of EtOH (729 µL) and acetone (145 µL) is added NaHCO$_3$ (8.8 mg, 0.11 mmol) and 2-aminopyridine (14.2 mg, 0.11 mmol) in a resealable tube. The mixture is heated at 85° C. for 2 h then concentrated in vacuo. The residue is diluted with THF (1 mL), MeOH (300 4), aqueous NaOH solution (5N, 140 µL, 0.70 mmol) and stirred for 60 h at 23° C. The pH of the mixture is adjusted to approximately 5-6 with AcOH. The crude mixture is purified by prep HPLC (MeOH: water containing 10 mM ammonium formate (pH 3.8)). The desired fractions are collected and concentrated under reduced pressure. The residues are dissolved in AcCN (1.5 mL) and freeze-dried to afford 1470.

Example 48

C8166 HIV-1 Luciferase Assay (EC$_{50}$)

C8166 cells are derived from a human T-lymphotrophic virus type 1 immortalized but nonexpressing line of cord blood lymphocytes (obtained from J. Sullivan and originally produced in the laboratory of R. Gallo, Virology 1983; 129: 51-64) and are highly permissive to HIV-1 infection. The pGL3 Basic LTR/TAR plasmid is made by introducing the HIV-1 HxB2 LTR sequence from nucleotide −138 to +80 (Sca1-HindIII) upstream of the luciferase gene in the pGL3 Basic Vector (a promoterless luciferase expression vector from Promega catalogue # E1751) with the gene for blasticidine resistance cloned in. The reporter cells are made by electroporating C8166 cells with pGL3 Basic LTR/TAR and selecting positive clones with blasticidine. Clone C8166-LTRluc #A8-F5-G7 is selected by 3 consecutive rounds of limiting dilution under blasticidine selection. Cultures are maintained in complete media (consisting of: Roswell Park Memorial Institute medium (RPMI) 1640+10% FBS+10$^{-5}$ M β-mercaptoethanol+10 µg/ml gentamycin) with 5 µg/ml blasticidine, however, blasticidine selection is removed from the cells before performing the viral replication assay.
Luciferase Assay Protocol
Preparation of Compounds
Serial dilutions of HIV-1 inhibitor compounds are prepared in complete media from 10 mM DMSO stock solutions. Eleven serial dilutions of 2.5× are made at 8× desired final concentration in a 1 mL deep well titer plate (96 wells). The 12$^{th}$ well contains complete media with no inhibitor and serves as the positive control. All samples contain the same concentration of DMSO (≦0.1% DMSO). A 25 µL aliquot of inhibitor is added, to triplicate wells, of a 96 well tissue culture treated clear view black microtiter plate (Corning Costar catalogue # 3904). The total volume per well is 200 µL of media containing cells and inhibitor. The last row is reserved for uninfected C8166 LTRluc cells to serve as the background blank control and the first row is media alone.
Infection of Cells
C8166 LTRluc cells are counted and placed in a minimal volume of complete RPMI 1640 in a tissue culture flask (ex. 30×10$^6$ cells in 10 mL media/25 cm$^2$ flask). Cells are infected with HIV-1 or virus with variant integrase generated as described below at a molecules of infection (moi) of 0.005. Cells are incubated for 1.5 hours at 37° C. on a rotating rack in a 5% $CO_2$ incubator and re-suspended in complete RPMI to give a final concentration of 25,000-cells/175 µL. 175 µL of cell mix is added to wells of a 96 well microtiter plate containing 25 µL 8× inhibitors. 25,000 uninfected C8166-LTR-luc cells/well in 200 µL complete RPMI are added to the last row for background control. Cells are incubated at 37° C. in 5% $CO_2$ incubator for 3 days.

Luciferase Assay

50 µL Steady Glo (luciferase substrate $T_{1/2}$=5 hours Promega catalogue # E2520) is added to each well of the 96 well plate. The relative light units (RLU) of luciferase is determined using the LUMIstar Galaxy luminometer (BMG LabTechnologies). Plates are read from the bottom for 2 seconds per well with a gain of 240.

The level of inhibition (% inhibition) of each well containing inhibitor is calculated as follows:

$$\% \cdot \text{inhibition} = \left(1 - \left[\frac{RLU \cdot \text{well} - RLU \cdot \text{blank}}{RLU \cdot \text{control} - RLU \cdot \text{blank}}\right]\right) * 100$$

The calculated % inhibition values are used to determine $EC_{50}$, slope factor (n) and maximum inhibition ($I_{max}$) by the non-linear regression routine NLIN procedure of SAS using the following equation:

$$\% \cdot \text{inhibition} = \frac{I_{max} \times [\text{inhibitor}]^n}{[\text{inhibitor}]^n + IC_{50}^n}$$

All compounds of Tables 1 to 6 have $EC_{50}$ values of 500 nM or less against the NL4.3 strain of HIV-1 integrase (SEQ ID NO: 1) as measured by the assay of Example 48. The potency of representative compounds is provided in Table 7.

Tables of Compounds

The following tables list compounds of the invention. Compounds of the invention are particularly effective at inhibiting HIV integrase. Retention times ($t_R$) for each compound are measured using the standard analytical HPLC or, where indicated, UPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions.

TABLE 1

| Cpd | R³ | R⁵ | $t_R$ (min) | MS (M + H)⁺ |
|---|---|---|---|---|
| 1001 | chroman-6-yl | phenyl | 5.0/5.1* | 446.2 |
| 1002 | 8-methylchroman-6-yl | phenyl | 5.2** | 460.3 |
| 1003 | chroman-6-yl | 3-(1-methyl-1H-pyrazol-5-yl)phenyl | 4.9/5.0* | 526.3 |

TABLE 1-continued
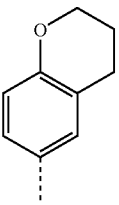
| Cpd | R³ | R⁵ | $t_R$ (min) | MS (M + H)⁺ |
|---|---|---|---|---|
| 1004 | 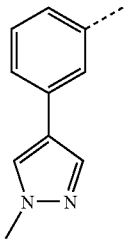 | 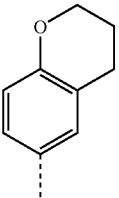 | 4.9/5.0* | 526.3 |
| 1005 | 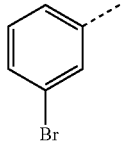 | 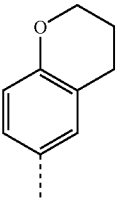 | 5.4/5.5* | 524.1 526.1 |
| 1006 | 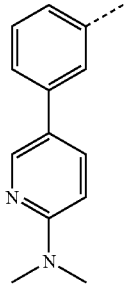 | 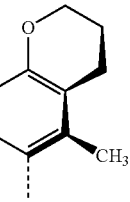 | 4.3/4.4* | 566.3 |
| 1007 | 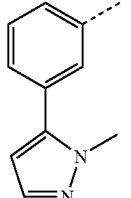 | 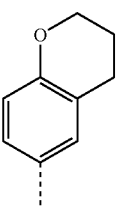 | 3.6 | 540.2 |
| 1008 | 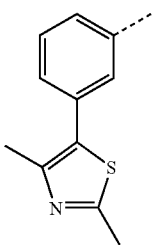 | | 3.4 | 557.2 |

TABLE 1-continued
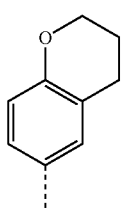
| Cpd | R³ | R⁵ | $t_R$ (min) | MS $(M + H)^+$ |
|---|---|---|---|---|
| 1009 | 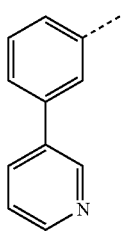 | 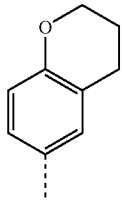 | 3.0 | 523.2 |
| 1010 | 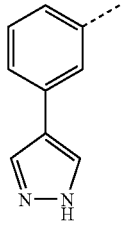 | 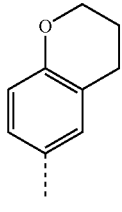 | 4.8 | 512.2 |
| 1011 | 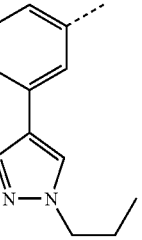 | 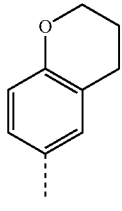 | 5.5 | 554.3 |
| 1012 | 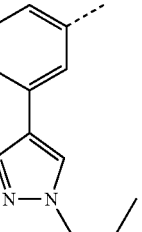 | 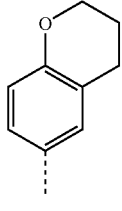 | 5.8 | 568.3 |
| 1013 | 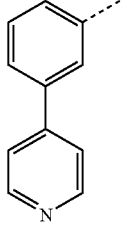 | 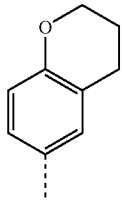 | 4.2 | 523.2 |

TABLE 1-continued
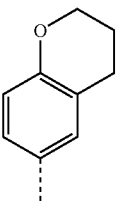
| Cpd | R³ | R⁵ | $t_R$ (min) | MS $(M + H)^+$ |
|---|---|---|---|---|
| 1014 | 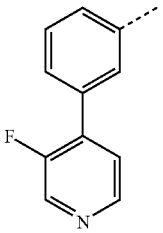 | 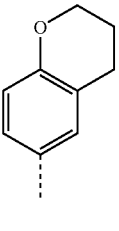 | 4.8 | 541.2 |
| 1015 | 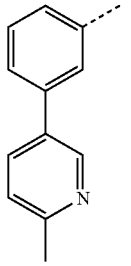 | 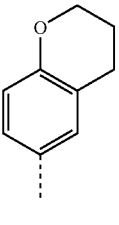 | 4.1/4.2* | 537.3 |
| 1016 | 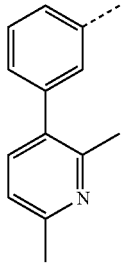 | 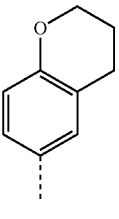 | 4.2 | 551.2 |
| 1017 | 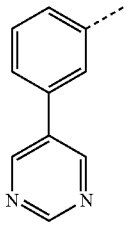 | 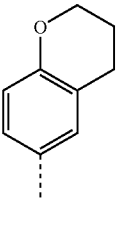 | 4.7/4.8* | 524.0 |
| 1018 | | 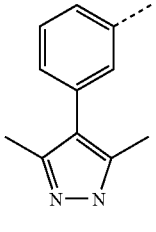 | 4.5 | 540.2 |

TABLE 1-continued
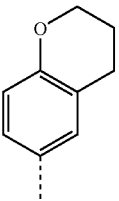
| Cpd | R³ | R⁵ | $t_R$ (min) | MS $(M + H)^+$ |
|---|---|---|---|---|
| 1019 | 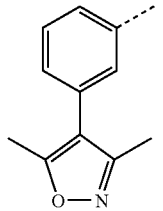 | 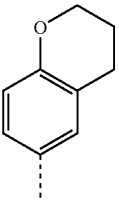 | 5.4 | 541.2 |
| 1020 | 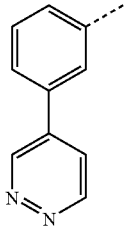 | 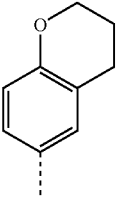 | 4.5/4.6* | 524.2 |
| 1021 | 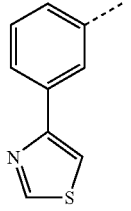 | 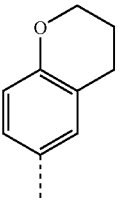 | 5.2/5.3* | 529.2 |
| 1022 | 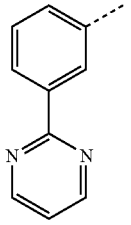 | 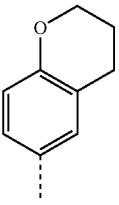 | 5.0/5.1* | 524.2 |
| 1023 | 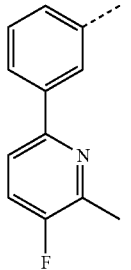 | | 5.7/5.8* | 555.2 |

TABLE 1-continued
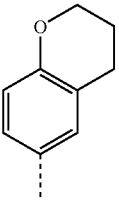
| Cpd | R³ | R⁵ | $t_R$ (min) | MS $(M + H)^+$ |
|---|---|---|---|---|
| 1024 | 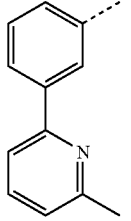 | 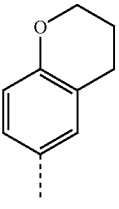 | 4.2/4.3* | 537.2 |
| 1025 | 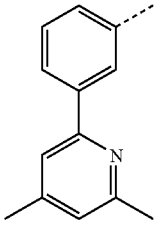 | 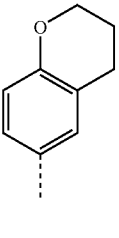 | 4.2/4.3* | 551.3 |
| 1026 | 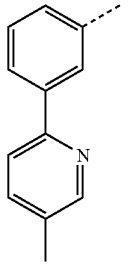 | 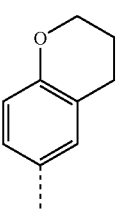 | 4.3/4.4* | 537.2 |
| 1027 | 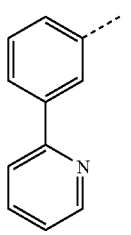 | 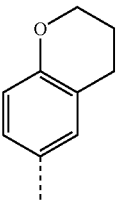 | 4.3/4.4* | 523.2 |
| 1028 | 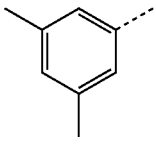 |  | 5.5/5.6* | 474.2 |

TABLE 1-continued
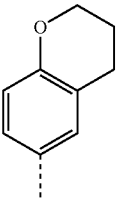
| Cpd | R³ | R⁵ | $t_R$ (min) | MS $(M + H)^+$ |
|---|---|---|---|---|
| 1029 | 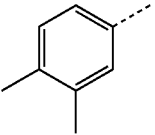 | 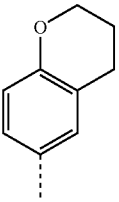 | 5.5/5.6* | 474.2 |
| 1030 | 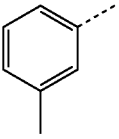 | 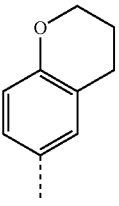 | 5.3/5.4* | 460.1 |
| 1031 | 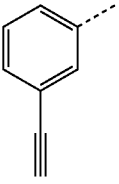 | 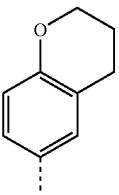 | 5.3/5.4* | 470.3 |
| 1032 | 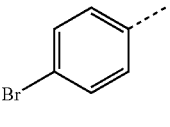 | 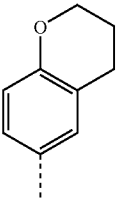 | 5.4/5.5* | 524.2/526.2 |
| 1033 | 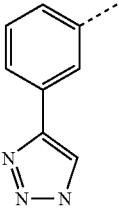 | 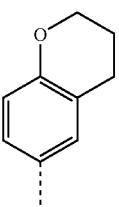 | 4.7/4.8* | 513.3 |
| 1034 | 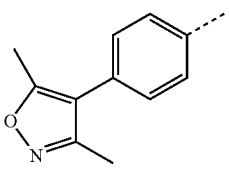 | | 5.3/5.4* | 541.4 |

TABLE 1-continued
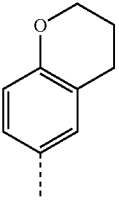
| Cpd | R³ | R⁵ | $t_R$ (min) | MS $(M + H)^+$ |
|---|---|---|---|---|
| 1035 | 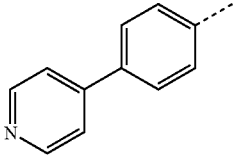 | 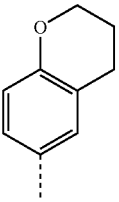 | 4.0/4.1* | 523.4 |
| 1036 | 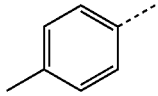 | 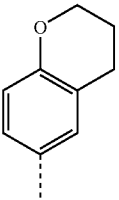 | 5.4 | 460.4 |
| 1037 | 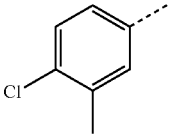 | 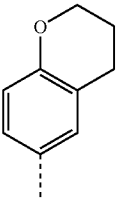 | 5.7 | 494.3 496.3 |
| 1038 | 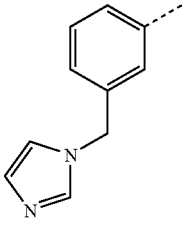 | 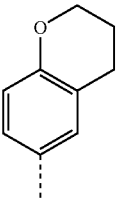 | 4.0 | 526.3 |
| 1039 | 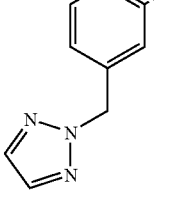 | 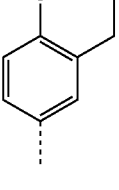 | 5.0 | 527.3 |
| 1040 | | 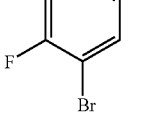 | 5.5/5.6* | 542.1/544.1 |

TABLE 1-continued
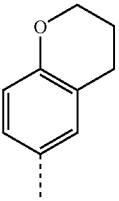
| Cpd | R³ | R⁵ | $t_R$ (min) | MS $(M + H)^+$ |
|---|---|---|---|---|
| 1041 | 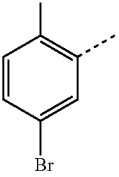 | 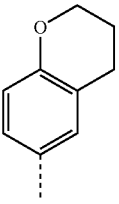 | 5.6/5.7* | 542.1/544.1 |
| 1042 | 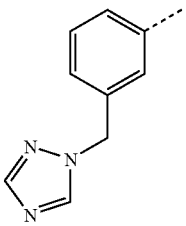 | 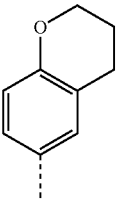 | 4.5 | 527.4 |
| 1043 | 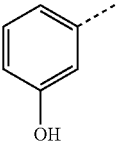 | 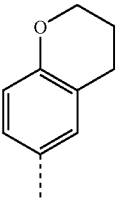 | 3.4 | 462.3 |
| 1044 | 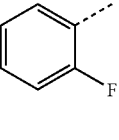 | 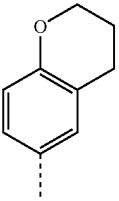 | 5.0 | 464.3 |
| 1045 | 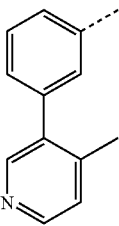 | 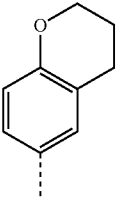 | 4.1/4.2* | 537.3 |
| 1046 | 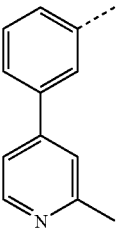 |  | 4.2 | 537.3 |

TABLE 1-continued
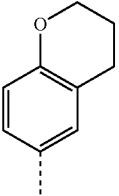
| Cpd | R³ | R⁵ | $t_R$ (min) | MS (M + H)⁺ |
|---|---|---|---|---|
| 1047 | 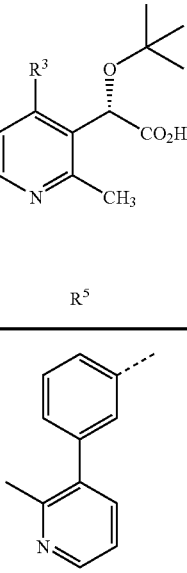 | 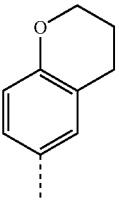 | 4.1/4.2* | 537.3 |
| 1048 | 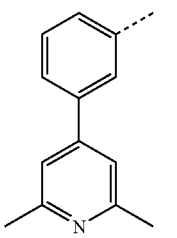 | 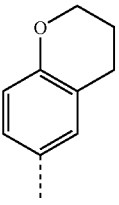 | 4.2/4.3* | 551.3 |
| 1049 | 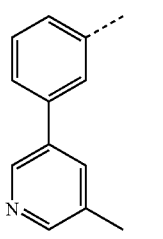 | 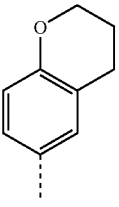 | 4.2/4.3* | 537.3 |
| 1050 | 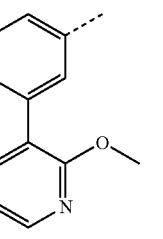 | 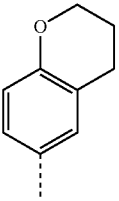 | 5.4/5.5* | 553.3 |
| 1051 | 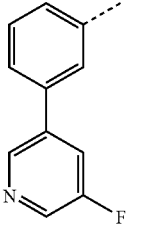 | | 5.1/5.2* | 541.3 |

TABLE 1-continued
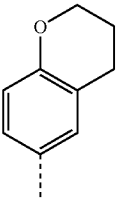
| Cpd | R³ | R⁵ | t_R (min) | MS (M + H)⁺ |
|---|---|---|---|---|
| 1052 | 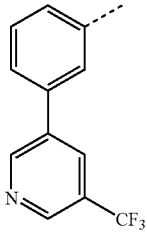 | 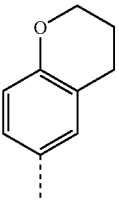 | 5.7 | 591.3 |
| 1053 | 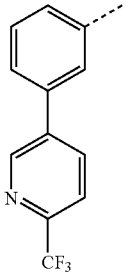 | 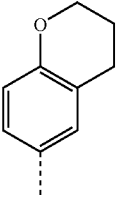 | 5.8 | 591.3 |
| 1054 | 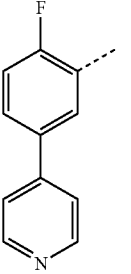 | 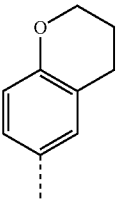 | 4.3 | 541.3 |
| 1055 | 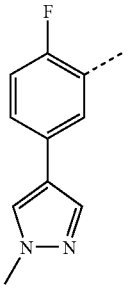 | | 5.1/5.2* | 544.3 |

TABLE 1-continued
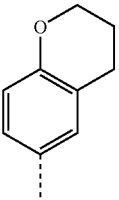
| Cpd | R³ | R⁵ | $t_R$ (min) | MS $(M + H)^+$ |
|---|---|---|---|---|
| 1056 | 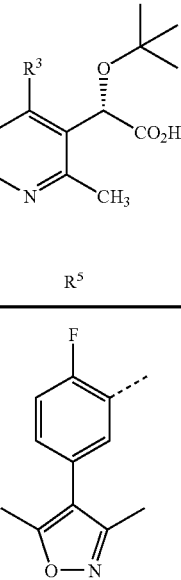 | 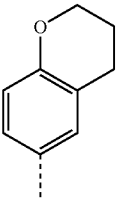 | 5.4/5.5* | 559.3 |
| 1057 | 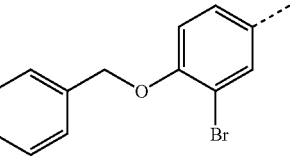 | 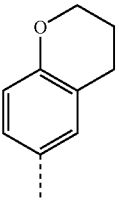 | 6.2 | 630.2/632.2 |
| 1058 | 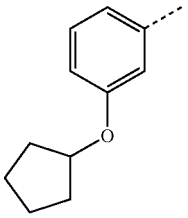 | 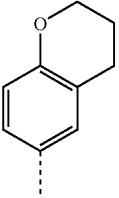 | 6.0 | 530.3 |
| 1059 | 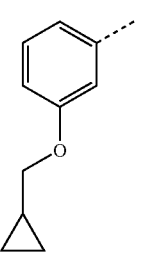 | 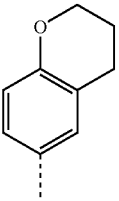 | 5.6 | 516.3 |
| 1060 | 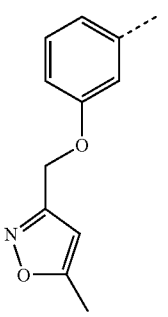 | | 5.3 | 557.3 |

TABLE 1-continued
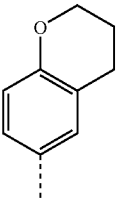
| Cpd | R³ | R⁵ | $t_R$ (min) | MS $(M + H)^+$ |
|---|---|---|---|---|
| 1061 | 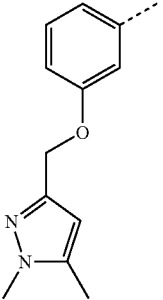 | 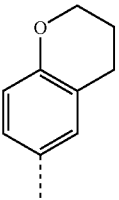 | 5.0 | 570.3 |
| 1062 | 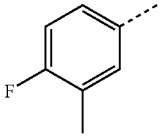 | 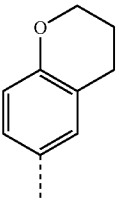 | 5.3/5.4* | 478.3 |
| 1063 | 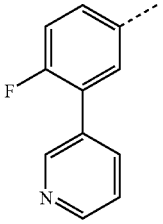 | 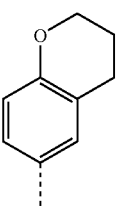 | 4.3 | 541.3 |
| 1064 | 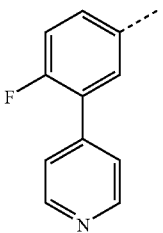 | 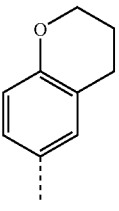 | 4.1/4.2* | 541.3 |
| 1065 | 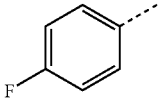 | | 5.1/5.2* | 464.3 |

TABLE 1-continued
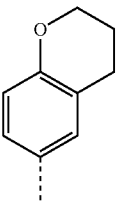
| Cpd | R³ | R⁵ | $t_R$ (min) | MS $(M + H)^+$ |
|---|---|---|---|---|
| 1066 | 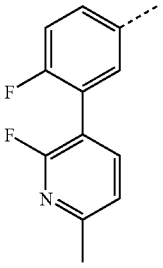 | 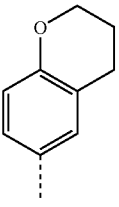 | 5.5/5.6* | 573.3 |
| 1067 | 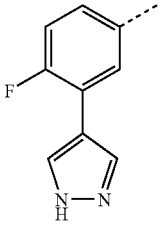 | 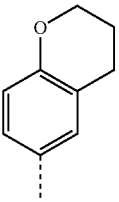 | 4.9/5.0* | 530.3 |
| 1068 | 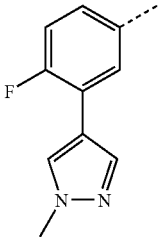 | 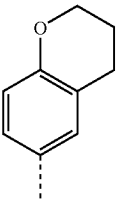 | 5.1/5.2* | 544.3 |
| 1069 | 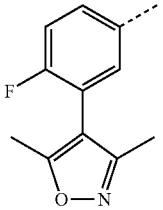 | 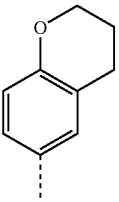 | 5.4/5.5* | 559.3 |
| 1070 | 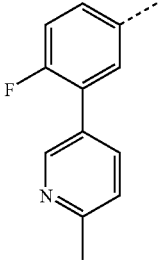 | | 4.3 | 555.3 |

TABLE 1-continued
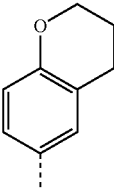
| Cpd | R³ | R⁵ | $t_R$ (min) | MS $(M + H)^+$ |
|---|---|---|---|---|
| 1071 | 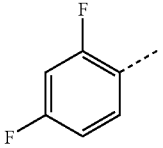 | 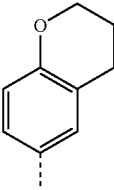 | 5.0 | 482.2 |
| 1072 | 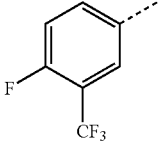 | 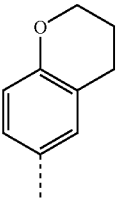 | 5.6 | 532.2 |
| 1073 | 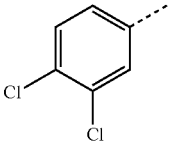 | 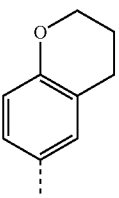 | 5.7/5.8* | 514.2/516.2 518.2 |
| 1074 | 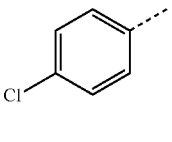 | 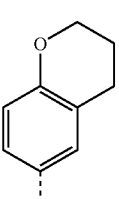 | 5.3/5.4* | 480.2/482.2 |
| 1075 | 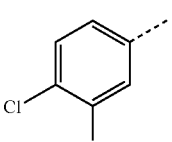 | 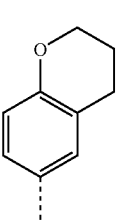 | 5.5/5.6* | 498.2 500.2 |
| 1076 | 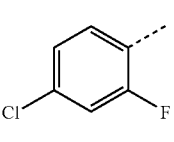 |  | 5.4/5.5* | 498.2/500.2 |

TABLE 1-continued
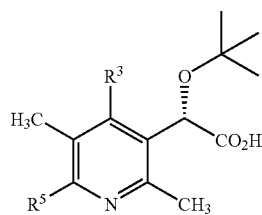
| Cpd | R³ | R⁵ | $t_R$ (min) | MS $(M + H)^+$ |
|---|---|---|---|---|
| 1077 | chroman-6-yl | 2-fluoro-5-(1-methyl-1H-pyrazol-5-yl)phenyl | 5.1 | 544.3 |
| 1078 | (S)-5-methylchroman-6-yl | 2-fluorophenyl | 5.3 | 478.2 |
| 1079 | (S)-5-methylchroman-6-yl | 4-bromo-2-fluorophenyl | 5.8 | 556.2/558.2 |
| 1080 | chroman-6-yl | 2-fluoro-5-methoxyphenyl | 6.0/6.1* | 494.2 |
| 1081 | chroman-6-yl | 2-chloro-4-fluorophenyl | 6.2 | 498.2/500.2 |
| 1082 | chroman-6-yl | 4-bromo-2-fluorophenyl | 5.6/5.7* | 542.2/544.2 |

TABLE 1-continued
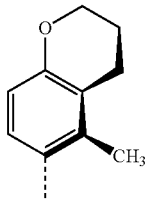
| Cpd | R³ | R⁵ | $t_R$ (min) | MS $(M + H)^+$ |
|---|---|---|---|---|
| 1083 | 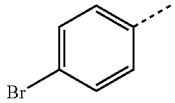 | 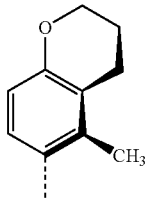 | 5.6 | 538.2/540.2 |
| 1084 | 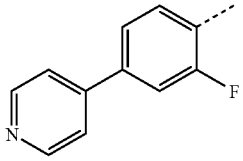 | 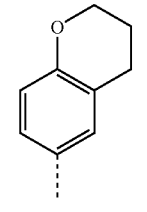 | 4.4 | 555.2 |
| 1085 | 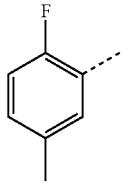 | 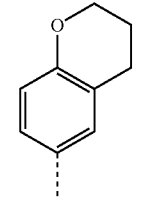 | 6.1 | 478.3 |
| 1086 | 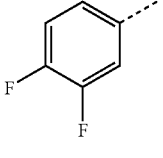 | 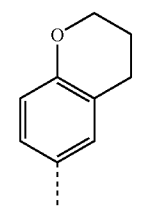 | 6.0 | 482.2 |
| 1087 | 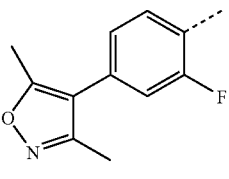 | 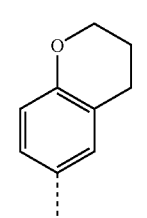 | 5.4/5.5* | 559.3 |
| 1088 | 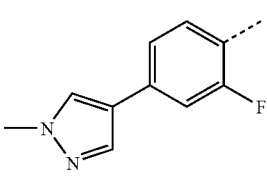 | | 5.1/5.2* | 544.3 |

TABLE 1-continued
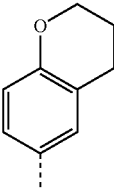
| Cpd | R³ | R⁵ | $t_R$ (min) | MS $(M + H)^+$ |
|---|---|---|---|---|
| 1089 | 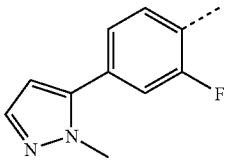 | 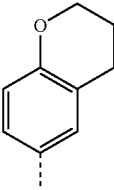 | 5.1/5.2* | 544.3 |
| 1090 | 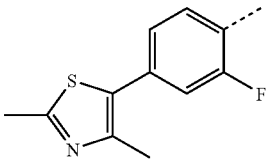 | 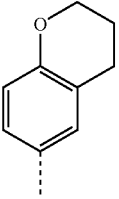 | 5.1/5.2* | 575.3 |
| 1091 | 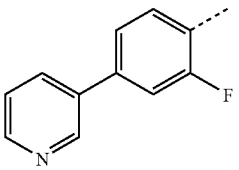 | 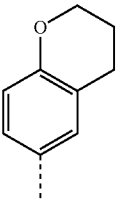 | 4.3 | 541.3 |
| 1092 | 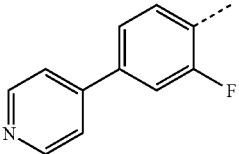 | 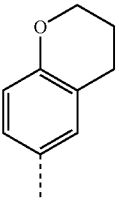 | 4.3 | 555.3 |
| 1093 | 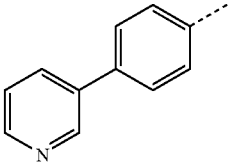 | 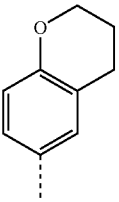 | 4.1 | 523.3 |
| 1094 | 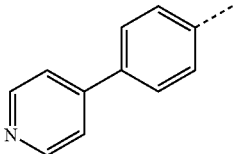 | | 4.2 | 537.3 |

TABLE 1-continued
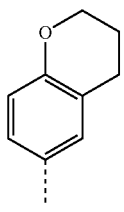
| Cpd | R³ | R⁵ | $t_R$ (min) | MS $(M + H)^+$ |
|---|---|---|---|---|
| 1095 | 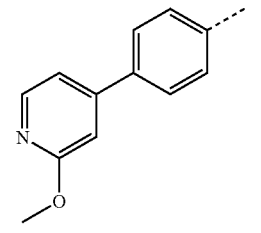 | 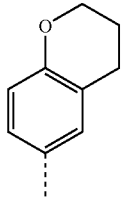 | 5.0/5.1* | 553.3 |
| 1096 | 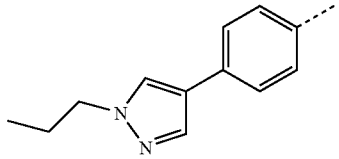 | 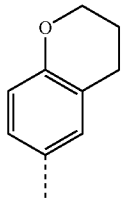 | 5.4/5.5* | 554.3 |
| 1097 | 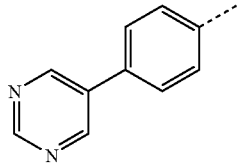 | 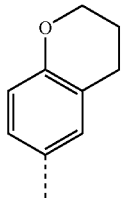 | 4.7/4.8* | 524.3 |
| 1098 | 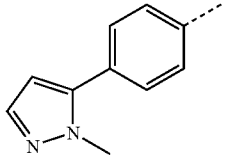 | 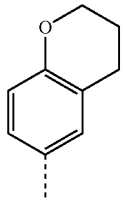 | 5.6 | 526.3 |
| 1099 | 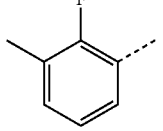 | 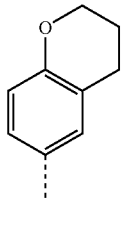 | 6.2 | 478.3 |
| 1100 | 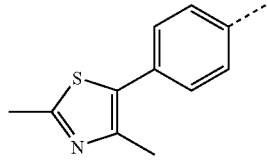 |  | 5.6 | 557.2 |

TABLE 1-continued
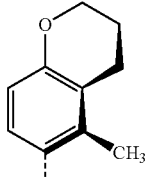
| Cpd | R³ | R⁵ | $t_R$ (min) | MS $(M + H)^+$ |
|---|---|---|---|---|
| 1101 | 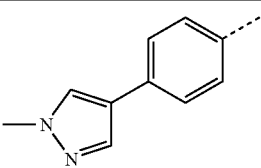 | 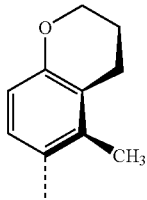 | 6.0 | 540.2 |
| 1102 | 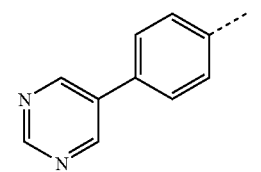 | 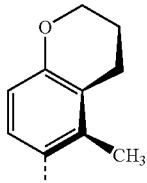 | 5.6 | 538.3 |
| 1103 | 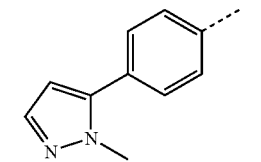 | 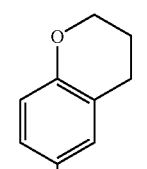 | 5.9 | 538.3 |
| 1104 | 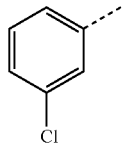 | 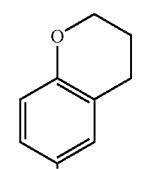 | 5.1 | 480.3 482.3 |
| 1105 | 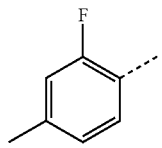 | 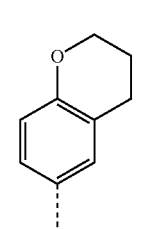 | 6.0 | 478.3 |
| 1106 | 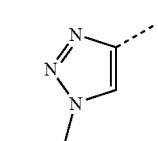 | | 5.3 | 513.3 |

TABLE 1-continued

| Cpd | R³ | R⁵ | t_R (min) | MS (M + H)⁺ |
|---|---|---|---|---|
| 1107 | benzothiazol-6-yl | 3,4-dimethylphenyl | 5.2 | 475.3 |
| 1108 | 4-methylphenyl (via CH₂) | 3,4-dimethylphenyl | 6.1 | 444.3 |
| 1109 | 5-chloro-8-amino-3,4-dihydro-2H-benzo[b][1,4]oxazin-6-yl | 3,4-dimethylphenyl | 5.3** | 509.3/511.3 |
| 1110 | 5-methylchroman-6-yl | 3,4-dimethylphenyl | 6.0** | 488.4 |
| 1111 | 4-chlorophenyl | 3,4-dimethylphenyl | 5.8 | 452.3/454.3 |
| 1112 | chroman-6-yl | 4-chloro-2-fluoro-5-methylphenyl | 5.7/5.8* | 512.2/514.2 |

TABLE 1-continued

| Cpd | R³ | R⁵ | t_R (min) | MS (M + H)⁺ |
|---|---|---|---|---|
| 1113 | | | 6.0** | 489.4 |
| 1114 | | | 6.0 | 494.4 |
| 1115 | | | 6.2 | 555.4 |
| 1116 | | | 4.7** | 511.3 |
| 1117 | | | 6.5** | 508.1 510.1 |
| 1118 | | | 6.5** | 492.4 |

TABLE 1-continued
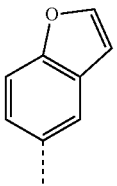
| Cpd | R³ | R⁵ | $t_R$ (min) | MS (M + H)⁺ |
|---|---|---|---|---|
| 1119 | 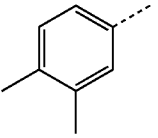 | 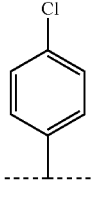 | 3.7* | 548.4 |
| 1120 | 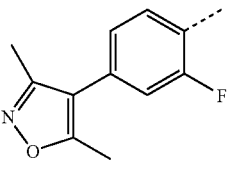 | 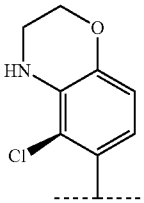 | 6.2 | 537.2/539.2 |
| 1121 | 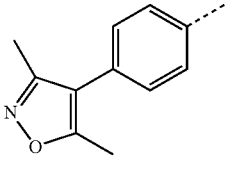 | 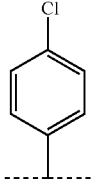 | 3.5** | 576.1/578.1 |
| 1122 | 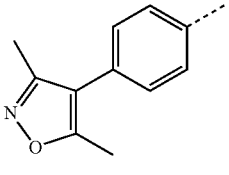 | 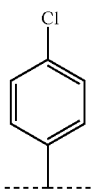 | 3.7 | 519.1/521.1 |
| 1124 | 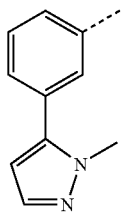 | 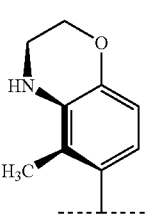 | 5.1 | 504.2/506.2 |
| 1125 | 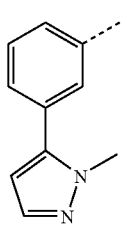 |  | 4.6** | 541.3 |

TABLE 1-continued
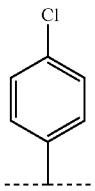
| Cpd | R³ | R⁵ | t_R (min) | MS (M + H)⁺ |
|---|---|---|---|---|
| 1126 | 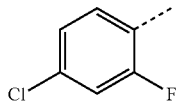 | 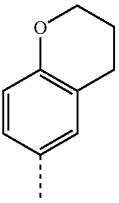 | 5.9 | 476.1/478.1/480.1 |
| 1127 | 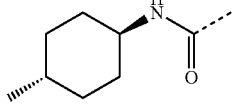 | 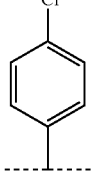 | 6.2* | 509.3 |
| 1128 | 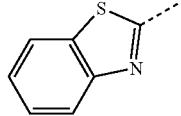 | 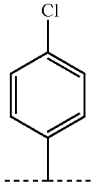 | 7.3 | 481.1/483.1 |
| 1129 | 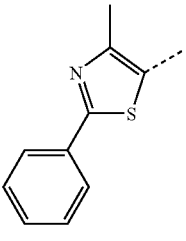 | 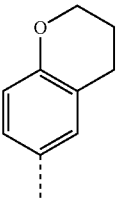 | 6.2 | 521.1/523.1 |
| 1130 |  | —CH₃ | 4.1/4.2* | 384.2 |
| 1131 | 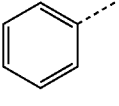 |  | 5.0 | 424.2/426.2 |

TABLE 1-continued
| Cpd | R³ | R⁵ | $t_R$ (min) | MS $(M + H)^+$ |
|---|---|---|---|---|
| 1132 | 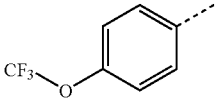 | 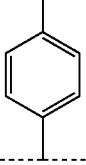 | 5.8 | 508.1/510.1 |
| 1133 | 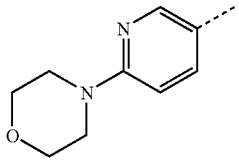 |  | 4.4 | 510.2/512.2 |
| 1134 | 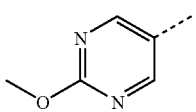 | 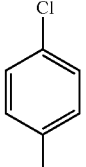 | 4.8 | 456.2/458.2 |
| 1135 |  | 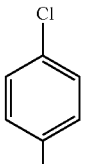 | 5.7 | 500.2/502.2 |
| 1136 | 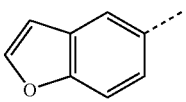 | 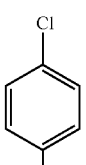 | 5.3 | 464.1/466.1 |
| 1137 | Cl | 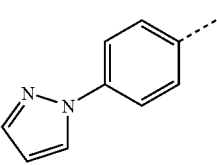 | 5.2 | 490.2/492.2 |

TABLE 1-continued
| Cpd | R³ | R⁵ | $t_R$ (min) | MS $(M + H)^+$ |
|---|---|---|---|---|
| 1138 | 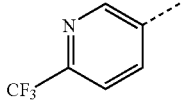 | 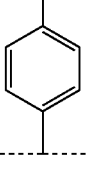 | 5.9 | 493.1/495.1 |
| 1139 | 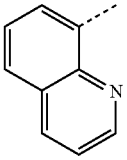 | 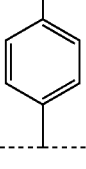 | 4.9 | 475.1/477.2 |
| 1140 | 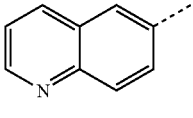 | 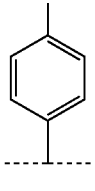 | 4.2 | 475.2/477.2 |
| 1141 | 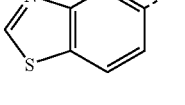 | 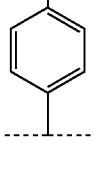 | 4.9 | 481.1/483.1 |
| 1142 | 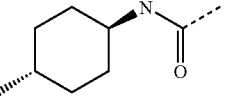 | 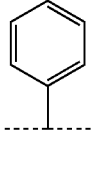 | 6.6 | 487.2/489.2 |
| 1143 | 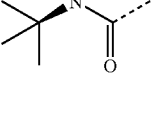 |  | 6.6 | 447.2/449.2 |

TABLE 1-continued
| Cpd | R³ | R⁵ | $t_R$ (min) | MS (M + H)⁺ |
|---|---|---|---|---|
| 1144 | 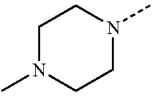 4-Cl-phenyl | 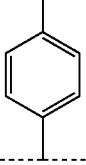 4-methylpiperazin-1-yl | 4.1 | 446.2/448.2 |
| 1145 | 4-Cl-phenyl | 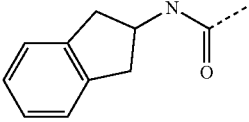 | 6.5 | 507.1/509.1 |
| 1146 | 4-Cl-phenyl | 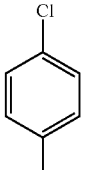 | 6.4 | 495.1/497.1 |
| 1147 | 4-Cl-phenyl | 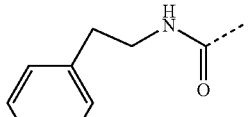 | 6.5 | 487.2/489.2 |
| 1148 | 4-Cl-phenyl | 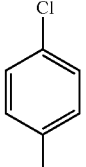 | 6.6 | 507.1/509.1 |
| 1149 | 4-Cl-phenyl | 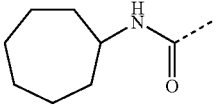 | 6.3 | 461.1/463.1 |

TABLE 1-continued

| Cpd | R³ | R⁵ | t_R (min) | MS (M + H)⁺ |
|---|---|---|---|---|
| 1150 | 4-Cl-phenyl | pyrrolidinyl-C(CH₃)₂-CH₂-NH-C(O)- | 4.8 | 516.2/518.2 |
| 1151 | 4-Cl-phenyl | PhCH=CH- | 5.5 | 450.1/452.1 |
| 1152 | 4-Cl-phenyl | cyclohexyl-CH(CH₃)-NH-C(O)- | 6.7 | 501.2/503.2 |
| 1153 | 4-Cl-phenyl | Ph-CH(CH₃)-NH-C(O)- | 6.5 | 465.1/497.1 |
| 1154 | 4-Cl-phenyl | Ph-C(CH₃)₂-NH-C(O)- | 6.6 | 509.2/511.2 |
| 1155 | 4-Cl-phenyl | Ph-CH(CH₃)-NH-C(O)- | 5.6 | 495.1/497.1 |

TABLE 1-continued
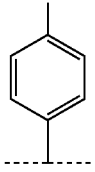
| Cpd | R³ | R⁵ | $t_R$ (min) | MS (M + H)⁺ |
|---|---|---|---|---|
| 1156 | 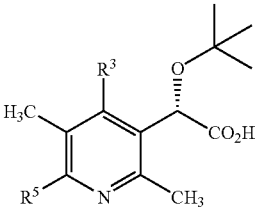 | 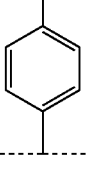 | 6.1 | 458.1/460.1 |
| 1157 | 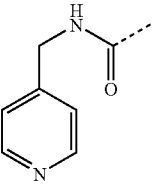 | 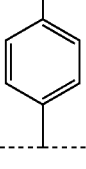 | 4.4 | 482.2/484.2 |
| 1158 | 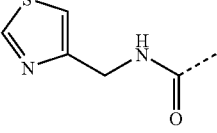 | 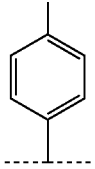 | 5.4 | 488.2/490.2 |
| 1159 | 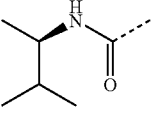 | 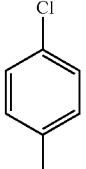 | 6.3 | 481.2/463.1 |
| 1160 | 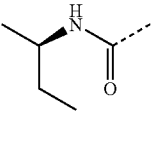 | 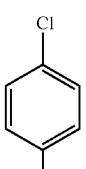 | 6.0 | 447.1/449.1 |
| 1161 | 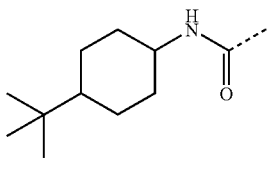 |  | 7.0 | 529.2/531.2 |

TABLE 1-continued
| Cpd | R³ | R⁵ | $t_R$ (min) | MS $(M+H)^+$ |
|---|---|---|---|---|
| 1162 | 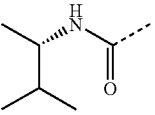 | 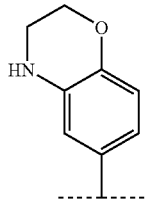 | 6.2 | 461.2/463.2 |
| 1163 | 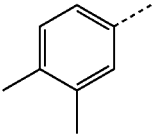 | 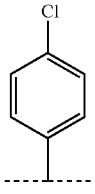 | 4.9/5.5* | 475.5 |
| 1164 | 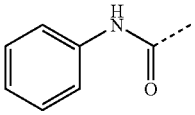 | 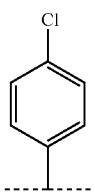 | 6.7 | 467.1/469.1 |
| 1165 | 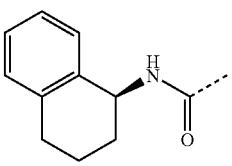 | 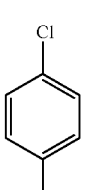 | 6.7 | 521.1/523.2 |
| 1166 | 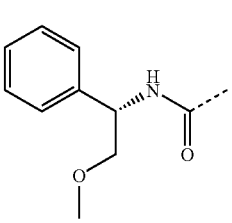 | 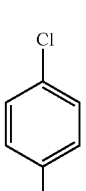 | 6.4 | 525.1/527.1 |
| 1167 | | 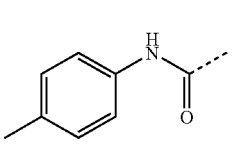 | 6.9 | 481.0/483.0 |

TABLE 1-continued
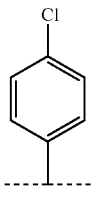
| Cpd | R³ | R⁵ | $t_R$ (min) | MS $(M + H)^+$ |
|---|---|---|---|---|
| 1168 | 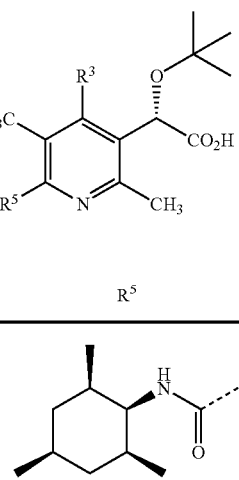 | 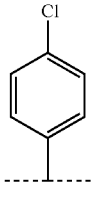 | 7.1 | 515.1/517.1 |
| 1169 | 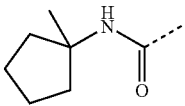 | 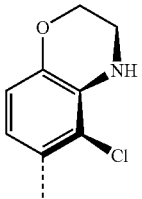 | 6.3 | 473.1/475.1 |
| 1170 | 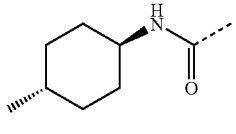 | 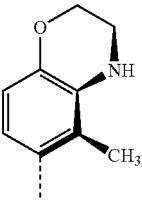 | 6.3* | 544.3/546.3 |
| 1171 | 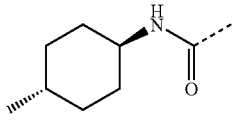 | 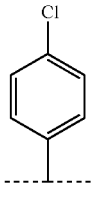 | 5.7* | 524.2 |
| 1172 | 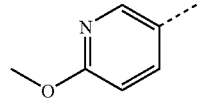 | 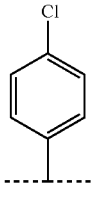 | 4.9 | 455.1/457.1 |
| 1173 | 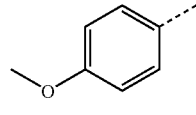 |  | 5.2 | 454.1/456.1 |

TABLE 1-continued
| Cpd | R³ | R⁵ | t_R (min) | MS (M + H)⁺ |
|---|---|---|---|---|
| 1174 | 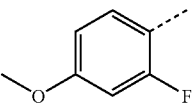 | 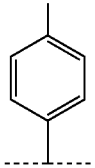 | 5.3 | 472.1/474.1 |
| 1175 | 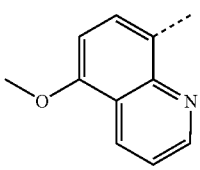 | 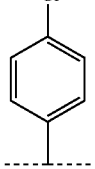 | 5.2 | 505.1/507.1 |
| 1176 | 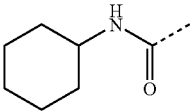 | 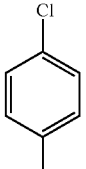 | 6.3 | 473.1/475.1 |
| 1177 | 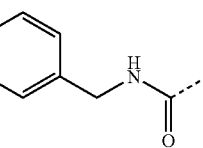 | 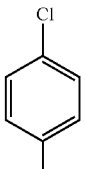 | 6.4 | 481.1/483.1 |
| 1178 | 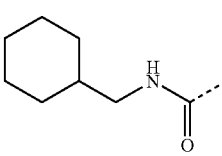 | 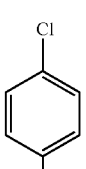 | 6.6 | 487.1/489.1 |
| 1179 | 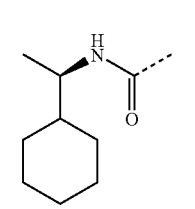 | | 6.8 | 501.1/503.1 |

TABLE 1-continued
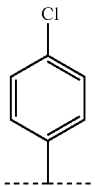
| Cpd | R³ | R⁵ | $t_R$ (min) | MS $(M + H)^+$ |
|---|---|---|---|---|
| 1180 | 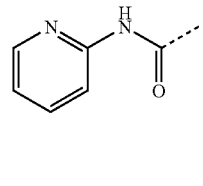 | 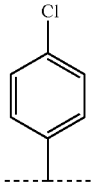 | 6.6 | 468.1/470.1 |
| 1181 | 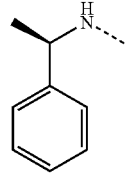 | 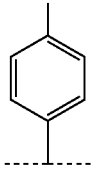 | 5.6 | 467.3/469.3 |
| 1182 | 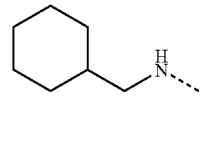 | 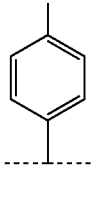 | 5.3 | 459.2/461.1 |
| 1183 | 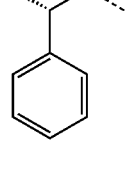 | 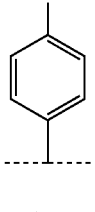 | 5.2 | 467.1/469.1 |
| 1184 | 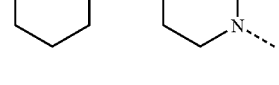 | 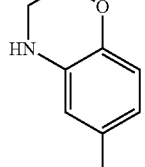 | 5.1 | 528.3/530.2 |
| 1185 | 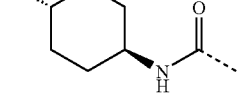 | | 5.2/5.6* | 510.3 |

TABLE 1-continued
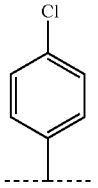
| Cpd | R³ | R⁵ | $t_R$ (min) | MS (M + H)⁺ |
|---|---|---|---|---|
| 1186 | 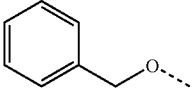 | 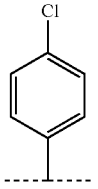 | 7.2 | 454.1/456.1 |
| 1187 | 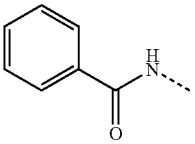 | 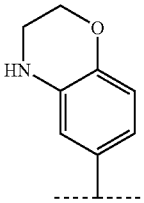 | 5.3 | 467.1/469.1 |
| 1188 | 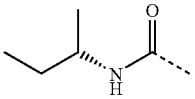 | 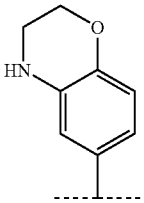 | 4.3/4.7* | 470.3 |
| 1189 | 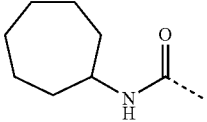 | 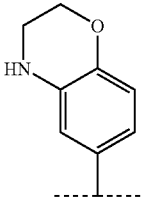 | 5.1/5.5* | 510.3 |
| 1190 | 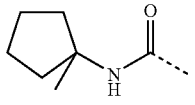 | 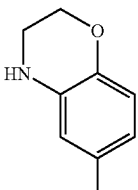 | 4.7/5.1* | 496.3 |
| 1191 | 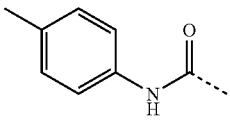 |  | 5.6/6.2* | 504.3 |

TABLE 1-continued

| Cpd | R³ | R⁵ | $t_R$ (min) | MS $(M+H)^+$ |
|---|---|---|---|---|
| 1192 | 5-methyl-3,4-dihydro-2H-benzo[b][1,4]oxazin-8-yl (HN, H₃C) | cycloheptyl-NHC(O)- | 5.6** | 524.2 |
| 1193 | 5-methyl-3,4-dihydro-2H-benzo[b][1,4]oxazin-8-yl | 1-methylcyclopentyl-NHC(O)- | 5.2** | 510.2 |
| 1194 | 5-methyl-3,4-dihydro-2H-benzo[b][1,4]oxazin-8-yl | 4-methylphenyl-NHC(O)- | 6.2** | 518.2 |
| 1195 | 4-chlorophenyl | (S)-sec-butyl-NHC(O)- | 5.3 | 447.1/449.1 |
| 1196 | 4-chlorophenyl | trans-4-methylcyclohexyl-NHC(O)- | 6.6 | 487.1/489.1 |
| 1197 | 4-chlorophenyl | 2,4,4-trimethylpentan-2-yl-NHC(O)- | 9.0 | 489.2/491.2 |

TABLE 1-continued
| Cpd | R³ | R⁵ | t_R (min) | MS (M + H)⁺ |
|---|---|---|---|---|
| 1198 | 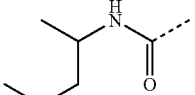 | 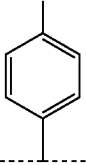 | 8.3 | 475.2/477.2 |
| 1199 | 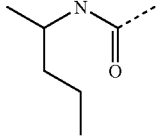 | 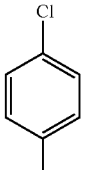 | 7.7 | 461.1/463.1 |
| 1200 | 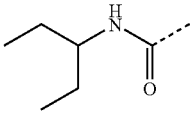 | 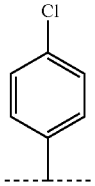 | 7.6 | 461.1/463.1 |
| 1201 | 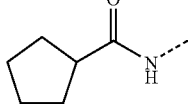 | 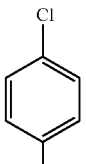 | 5.1 | 459.1/461.1 |
| 1202 | 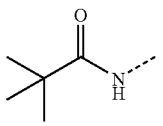 | 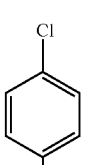 | 5.1 | 447.1/449.1 |
| 1203 | Cl (phenyl) | 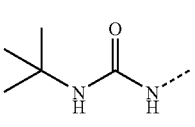 | 5.2 | 462.1/464.1 |

TABLE 1-continued
| Cpd | R³ | R⁵ | t_R (min) | MS (M + H)⁺ |
|---|---|---|---|---|
| 1205 | 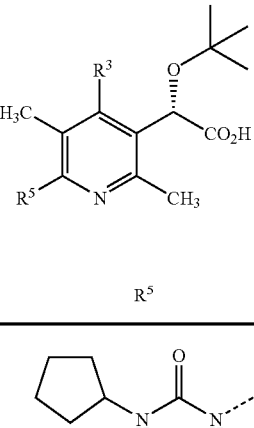 | 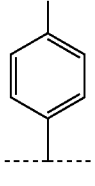 | 5.3 | 474.1/476.1 |
| 1206 | 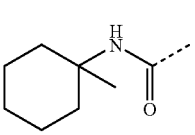 | 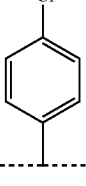 | 8.5 | 487.1/489.1 |
| 1207 | 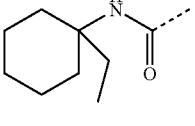 | 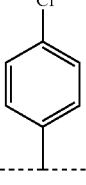 | 9.4 | 501.1/503.1 |
| 1208 | 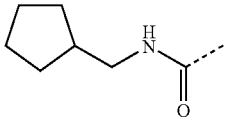 | 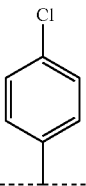 | 8.1 | 473.1/475.1 |
| 1209 | 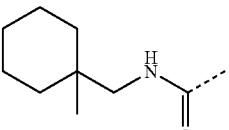 |  | 9.2 | 501.2/503.1 |
| 1210 | | 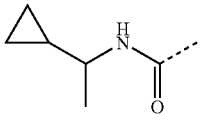 | 7.1 | 459.1/461.1 |

TABLE 1-continued
| Cpd | R³ | R⁵ | $t_R$ (min) | MS $(M + H)^+$ |
|---|---|---|---|---|
| 1211 | 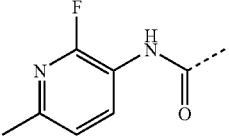 | 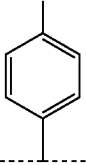 | 4.6 | 500.1/502.1 |
| 1212 | 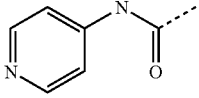 | 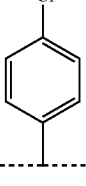 | 3.5 | 468.1/470.1 |
| 1213 | 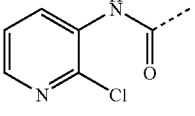 | 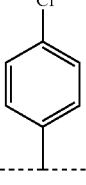 | 4.6 | 502.0/504.0/506.0 |
| 1214 | 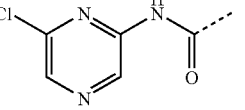 | 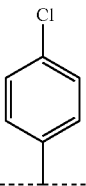 | 4.7 | 503.0/505.0/507.0 |
| 1215 | 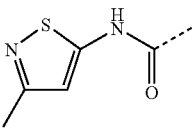 | 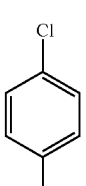 | 4.3 | 488.0/490.0 |
| 1216 | 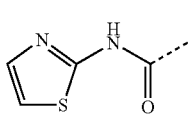 | | 4.4 | 474.0/476.0 |

TABLE 1-continued
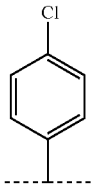
| Cpd | R³ | R⁵ | $t_R$ (min) | MS $(M + H)^+$ |
|---|---|---|---|---|
| 1217 | 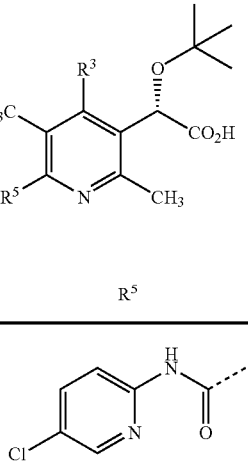 | 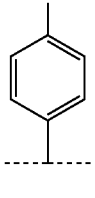 | 4.7 | 502.0/504.0/506.0 |
| 1218 | 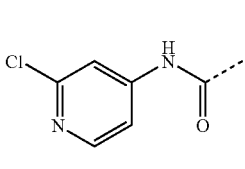 | 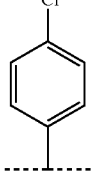 | 4.5 | 502.0/504.0/506.0 |
| 1219 | 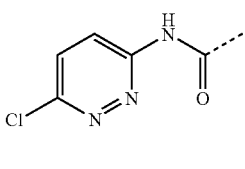 | 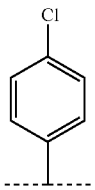 | 4.5 | 503.0/505.0/507.0 |
| 1220 | 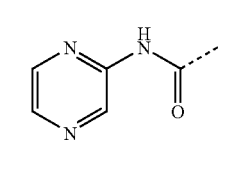 | 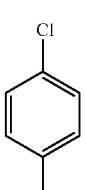 | 4.4 | 469.1/471.1 |
| 1221 | 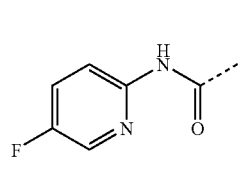 | 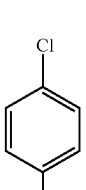 | 4.6 | 486.1/488.1 |
| 1222 | 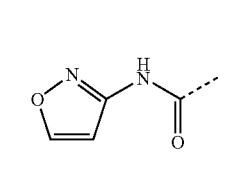 |  | 4.4 | 458.1/460.1 |

TABLE 1-continued
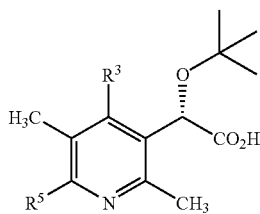
| Cpd | R³ | R⁵ | t_R (min) | MS (M + H)⁺ |
|---|---|---|---|---|
| 1223 | 4-Cl-C₆H₄- | 2-chloropyrimidin-5-yl-NHC(O)- | 4.5 | 503.0/505.0/507.0 |
| 1224 | 4-Cl-C₆H₄- | pyrimidin-4-yl-NHC(O)- | 4.2 | 469.1/471.1 |
| 1225 | 4-Cl-C₆H₄- | 6-methoxypyridin-3-yl-NHC(O)- | 4.3 | 498.1/500.1 |
| 1226 | 4-Cl-C₆H₄- | 6-fluoropyridin-2-yl-NHC(O)- | 4.6 | 486.0/488.0 |
| 1227 | 4-Cl-C₆H₄- | 5-methylthiazol-2-yl-NHC(O)- | 4.4 | 488.0/490.0 |
| 1228 | 4-Cl-C₆H₄- | 4-methylthiazol-2-yl-NHC(O)- | 4.4 | 488.0/490.0 |

TABLE 1-continued
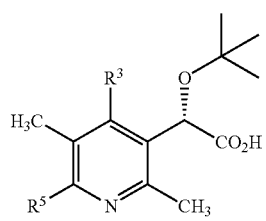
| Cpd | R³ | R⁵ | $t_R$ (min) | MS $(M + H)^+$ |
|---|---|---|---|---|
| 1229 | 4-chlorophenyl | N-(pyridin-3-yl)acetamide | 3.4 | 468.1/470.1 |
| 1230 | 4-chlorophenyl | N-(6-fluoro-2-methylpyridin-3-yl)acetamide | 4.5 | 500.1/502.1 |
| 1231 | 4-chlorophenyl | N-(2-methoxypyridin-4-yl)acetamide | 3.9 | 498.1/500.1 |
| 1232 | 4-chlorophenyl | N-(benzo[d]thiazol-5-yl)acetamide | 4.4 | 524.0/526.0 |
| 1233 | 5-chloro-3,4-dihydro-2H-benzo[b][1,4]oxazin-4-yl | N-(cycloheptyl)acetamide | 6.2** | 544.1/546.1 |
| 1234 | 5-chloro-3,4-dihydro-2H-benzo[b][1,4]oxazin-4-yl | N-(tert-pentyl)acetamide | 5.8** | 518.1/520.1 |

TABLE 1-continued

| Cpd | R³ | R⁵ | $t_R$ (min) | MS $(M + H)^+$ |
|---|---|---|---|---|
| 1235 | 4-chloro-3,4-dihydro-2H-benzo[b][1,4]oxazin-8-yl | (S)-1-phenylethylaminocarbonyl | 6.1** | 552.1/554.1 |
| 1236 | 4-chloro-3,4-dihydro-2H-benzo[b][1,4]oxazin-8-yl | 2-phenylethylaminocarbonyl | 6.0** | 552.1/554.1 |
| 1237 | 4-chlorophenyl | tert-pentylaminocarbonyl | 5.4 | 481.1/463.1 |
| 1238 | 4-chlorophenyl | (6-chloropyridin-3-yl)aminocarbonyl | 4.5 | 502.0/504.0/506.0 |
| 1239 | 4-chlorophenyl | benzo[d]thiazol-6-ylaminocarbonyl | 4.4 | 524.0/526.0 |
| 1240 | 4-chlorophenyl | benzo[c][1,2,5]oxadiazol-5-ylmethoxy | 7.2 | 496.0/498.0 |

TABLE 1-continued

| Cpd | R³ | R⁵ | t_R (min) | MS (M + H)⁺ |
|---|---|---|---|---|
| 1241 | 4-chlorophenyl | N-(pentan-3-yl)-2-oxyacetamide | 6.7 | 491.1/493.1 |
| 1242 | 8-chloro-3,4-dihydro-2H-benzo[b][1,4]oxazin-4-amine-5-yl | pivalamide | 4.7** | 504.1/506.1 |
| 1243 | 8-chloro-3,4-dihydro-2H-benzo[b][1,4]oxazin-4-amine-5-yl | 2,2-dimethylbutanamide | 4.9** | 518.1/520.1 |
| 1244 | benzo[d][1,3]dioxol-5-yl | trans-4-methylcyclohexyl acetamide | 4.2* | 497.2 |
| 1245 | 2,3-dihydrobenzo[b][1,4]dioxin-6-yl | trans-4-methylcyclohexyl acetamide | 4.2* | 511.2 |
| 1246 | 2,3-dihydrobenzofuran-5-yl | trans-4-methylcyclohexyl acetamide | 4.2* | 495.1 |

TABLE 1-continued
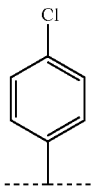
| Cpd | R³ | R⁵ | $t_R$ (min) | MS $(M + H)^+$ |
|---|---|---|---|---|
| 1247 | 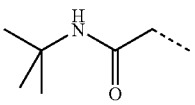 | 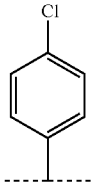 | 4.9 | 461.1/463.1 |
| 1248 | 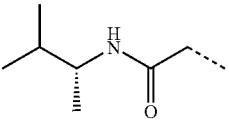 | 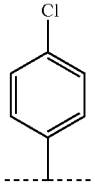 | 5.1 | 475.1/477.1 |
| 1249 | 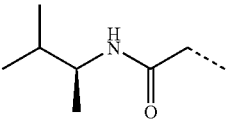 | 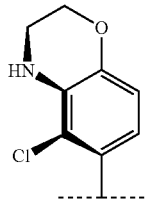 | 5.1 | 475.1/447.1 |
| 1250 | 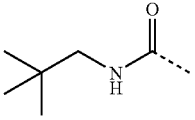 | 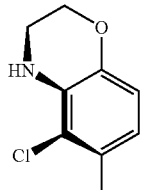 | 7.0** | 518.2/520.2 |
| 1251 | 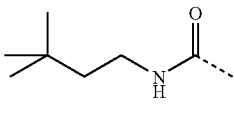 | 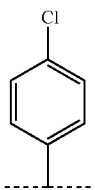 | 7.6** | 532.1/534.1 |
| 1252 | 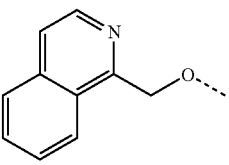 |  | 5.3 | 505.1/507.1 |

TABLE 1-continued

| Cpd | R³ | R⁵ | t_R (min) | MS (M + H)⁺ |
|---|---|---|---|---|
| 1253 | 4-chloro-3,4-dihydro-2H-benzo[b][1,4]oxazin-8-yl (HN, Cl substituted benzoxazine) | N-(3,3-dimethylbutan-2-yl)acetamide linker | 8.2** | 546.1/548.1 |
| 1254 | 4-chloro-3,4-dihydro-2H-benzo[b][1,4]oxazin-8-yl | N-(1-methylcyclohexyl)acetamide linker | 7.6** | 544.1/546.1 |
| 1255 | 4-chloro-3,4-dihydro-2H-benzo[b][1,4]oxazin-8-yl | N-((1-methylcyclohexyl)methyl)acetamide linker | 8.5** | 558.1/560.1 |
| 1256 | 4-chloro-3,4-dihydro-2H-benzo[b][1,4]oxazin-8-yl | N-(cyclopentylmethyl)acetamide linker | 7.1** | 530.1/532.1 |
| 1267 | 4-chlorophenyl | 1-tert-butyl-3-ethylurea linker | 4.7 | 476.1/478.1 |
| 1258 | 4-chlorophenyl | tert-butyl ethylcarbamate linker | 4.9 | 477.2/479.2 |

TABLE 1-continued
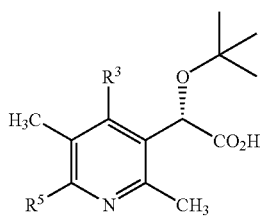
| Cpd | R³ | R⁵ | $t_R$ (min) | MS $(M + H)^+$ |
|---|---|---|---|---|
| 1259 | | | 6.3** | 581.1/583.0 |
| 1260 | | | 6.3** | 545.1/547.1 |
| 1261 | | | 6.0** | 555.1/557.1 |
| 1262 | | | 5.8** | 530.2/532.2 |
| 1263 | | | 5.7** | 530.2/532.2 |
| 1264 | | | 5.1** | 555.1/557.1 |

TABLE 1-continued
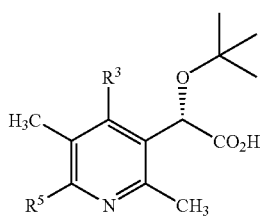
| Cpd | R³ | R⁵ | $t_R$ (min) | MS (M + H)⁺ |
|---|---|---|---|---|
| 1265 | | | 4.4** | 525.1/527.2 |
| 1266 | | | 4.7/5.2* | 496.3 |
| 1267 | | | 5.3/5.8* | 532.3 |
| 1268 | | | 4.8 | 475.2/477.2 |
| 1269 | | | 4.9 | 487.2/489.2 |
| 1270 | | | 5.3** | 546.2 |

TABLE 1-continued
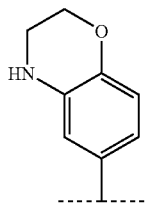
| Cpd | R³ | R⁵ | $t_R$ (min) | MS $(M + H)^+$ |
|---|---|---|---|---|
| 1271 | 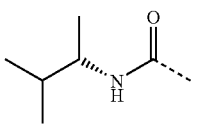 | 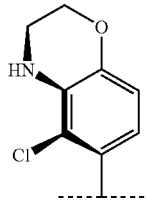 | 4.6/5.1* | 484.3 |
| 1272 | 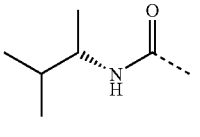 | 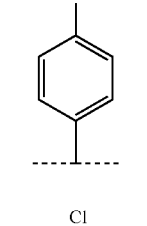 | 5.7** | 518.2/520.2 |
| 1273 | 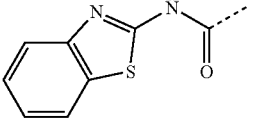 | 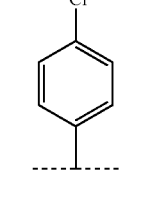 | 7.1 | 524.1/526.1 |
| 1274 | 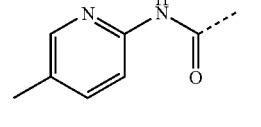 | 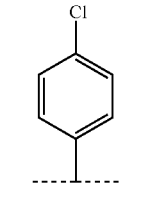 | 5.8 | 482.2/484.2 |
| 1275 | 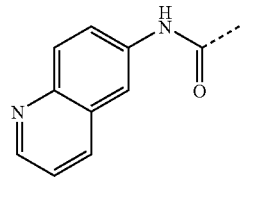 | 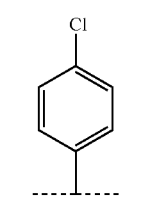 | 5.1 | 518.2/520.2 |
| 1276 | | 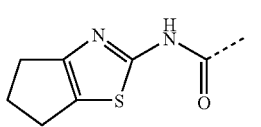 | 6.9 | 514.1/516.1 |

TABLE 1-continued
| Cpd | R³ | R⁵ | $t_R$ (min) | MS $(M + H)^+$ |
|---|---|---|---|---|
| 1277 | 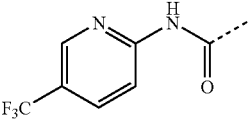 | 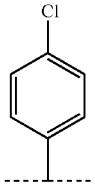 | 7.2 | 536.1/538.1 |
| 1278 | 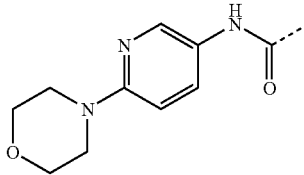 | 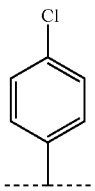 | 4.9 | 553.2/555.2 |
| 1279 | 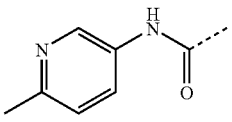 | 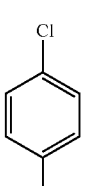 | 4.8 | 482.2/484.2 |
| 1280 | 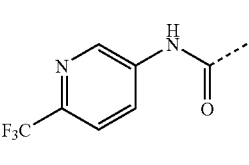 | 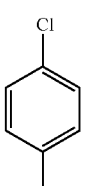 | 6.9 | 536.1/538.1 |
| 1281 | 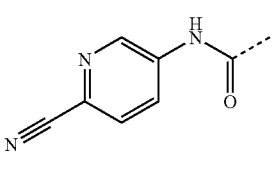 | 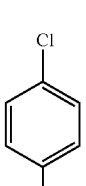 | 6.7 | 493.1/495.1 |
| 1282 | | 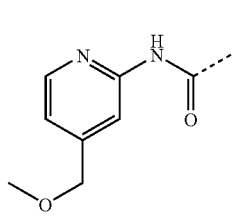 | 5.8 | 512.2/514.2 |

TABLE 1-continued
| Cpd | R³ | R⁵ | $t_R$ (min) | MS (M + H)⁺ |
|---|---|---|---|---|
| 1283 | 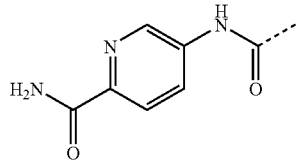 | 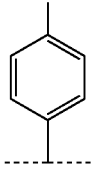 | 5.9 | 511.2/513.2 |
| 1284 | 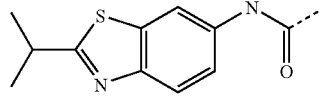 | 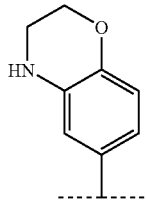 | 7.1 | 566.2/568.2 |
| 1285 | 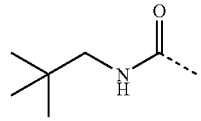 | 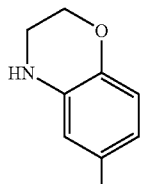 | 5.8/6.4* | 484.3 |
| 1286 | 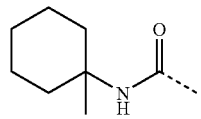 | 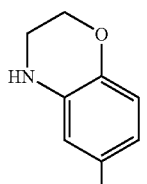 | 6.2/6.8* | 510.3 |
| 1287 | 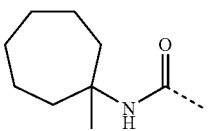 | 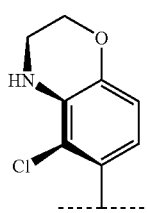 | 6.5/7.3* | 524.3 |
| 1288 | 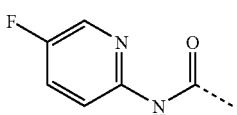 | | 4.4** | 543.2/545.2 |

TABLE 1-continued
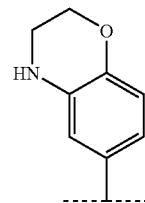
| Cpd | R³ | R⁵ | $t_R$ (min) | MS $(M + H)^+$ |
|---|---|---|---|---|
| 1289 | 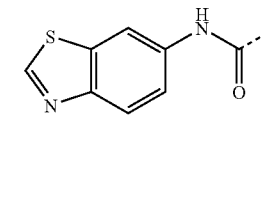 | 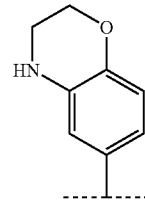 | 3.8/4.1* | 574.2 |
| 1290 | 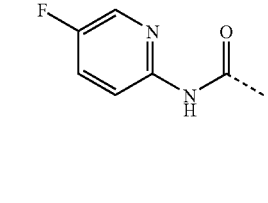 | 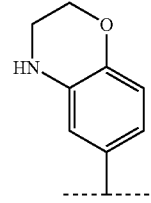 | 4.0/4.3* | 509.2 |
| 1291 | 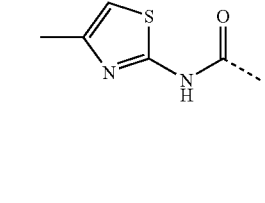 | 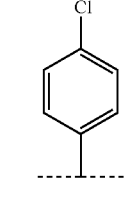 | 3.8/4.1* | 511.2 |
| 1292 | 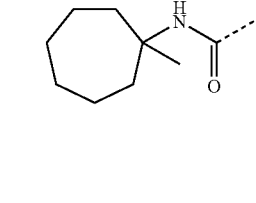 | 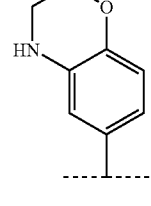 | 9.3 | 501.1/503.1 |
| 1293 | 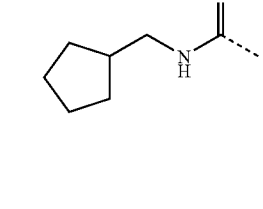 | 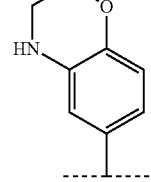 | 5.9/6.5* | 496.2 |
| 1294 | 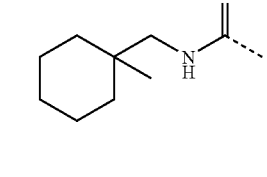 |  | 6.8/7.7* | 524.2 |

TABLE 1-continued
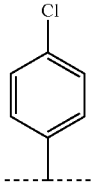
| Cpd | R³ | R⁵ | t_R (min) | MS (M + H)⁺ |
|---|---|---|---|---|
| 1295 | 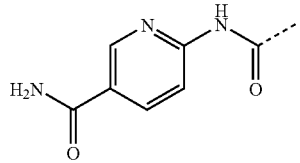 | 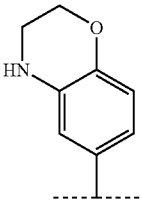 | 5.9 | 511.2/513.2 |
| 1296 | 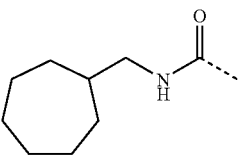 | 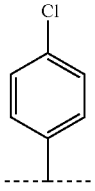 | 5.6/6.0* | 524.2 |
| 1297 | 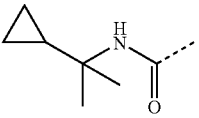 | 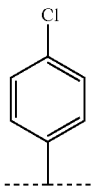 | 6.2 | 473.1/475.1 |
| 1298 | 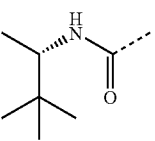 | 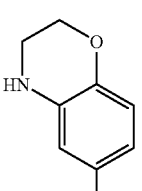 | 6.5 | 475.3/477.2 |
| 1299 | 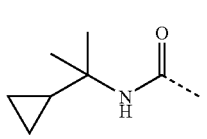 | 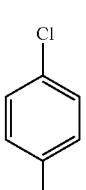 | 4.7/5.1* | 496.3 |
| 1300 | 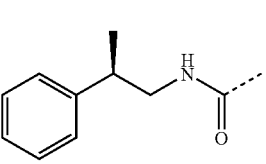 |  | 6.5 | 509.0/511.0 |

TABLE 1-continued
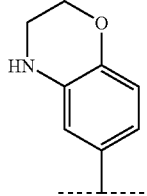
| Cpd | R³ | R⁵ | $t_R$ (min) | MS (M + H)⁺ |
|---|---|---|---|---|
| 1301 | 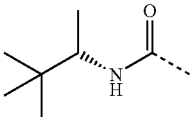 | 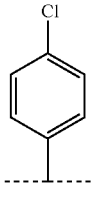 | 4.9/5.4* | 498.1 |
| 1302 | 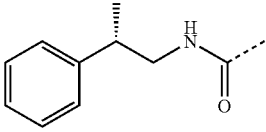 | 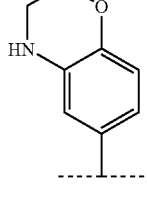 | 6.5 | 509.0 511.0 |
| 1303 | 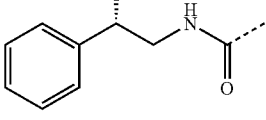 | 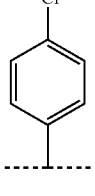 | 5.1/5.6* | 532.3 |
| 1304 | 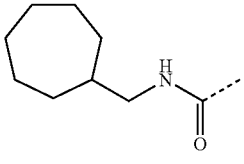 | 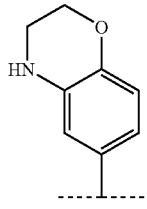 | 6.8 | 501.1/503.1 |
| 1305 | 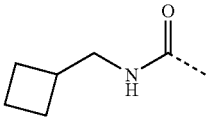 | 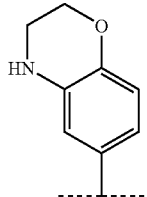 | 4.5/5.0* | 482.3 |
| 1306 | 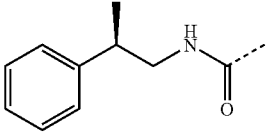 | | 5.1/5.5* | 532.3 |

TABLE 1-continued
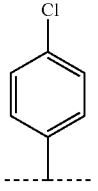
| Cpd | R³ | R⁵ | t_R (min) | MS (M + H)⁺ |
|---|---|---|---|---|
| 1307 | 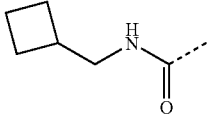 | 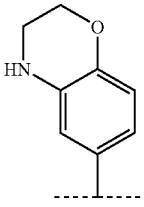 | 6.2 | 459.1/461.0 |
| 1308 | 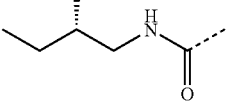 | 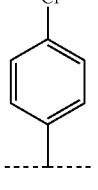 | 4.8/5.2* | 484.3 |
| 1309 | 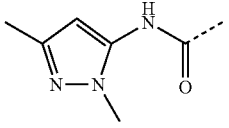 | 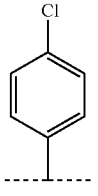 | 6.0 | 485.2/487.2 |
| 1310 | 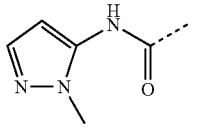 | 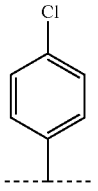 | 6.0 | 471.2/473.2 |
| 1311 | 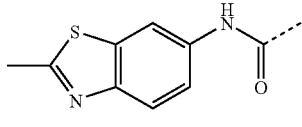 | 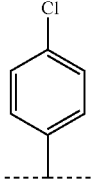 | 6.7 | 538.1/540.2 |
| 1312 | | 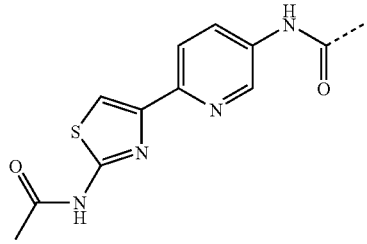 | 5.4 | 608.2/610.2 |

TABLE 1-continued
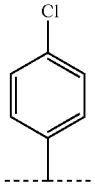
| Cpd | R³ | R⁵ | t_R (min) | MS (M + H)⁺ |
|---|---|---|---|---|
| 1313 | 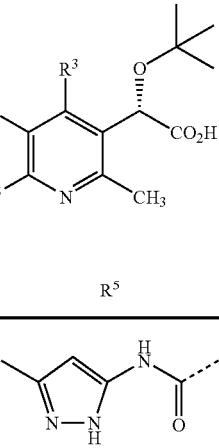 | 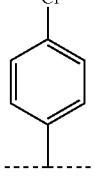 | 5.6 | 471.1/473.1 |
| 1314 | 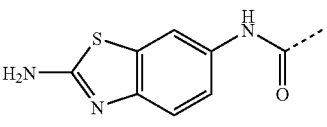 | 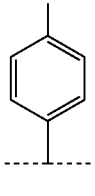 | 5.0 | 539.1/541.1 |
| 1315 | 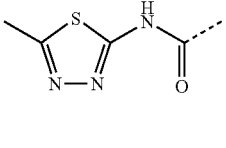 | 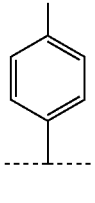 | 6.4 | 489.0/491.0 |
| 1316 | 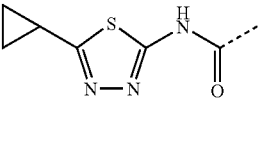 | 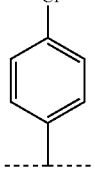 | 6.7 | 515.0/517.0 |
| 1317 | 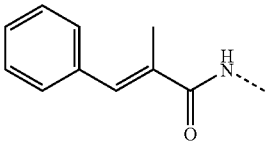 |  | 6.2 | 507.0/509.0 |
| 1318 | 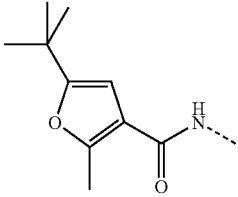 | | 6.2 | 527.1/529.1 |

TABLE 1-continued
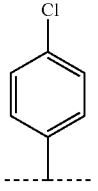
| Cpd | R³ | R⁵ | t_R (min) | MS (M + H)⁺ |
|---|---|---|---|---|
| 1319 | 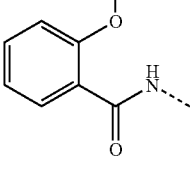 | 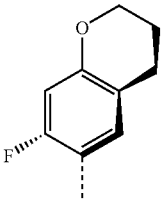 | 5.3 | 497.0/499.0 |
| 1320 | 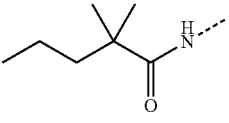 | 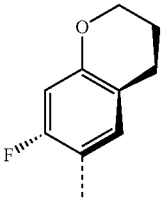 | 6.1 | 475.1/477.1 |
| 1321 | 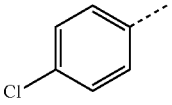 | 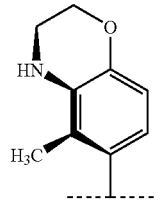 | 5.6** | 498.1 500.1 |
| 1322 | 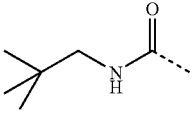 | 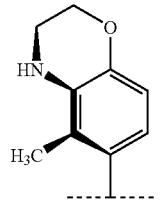 | 6.1** | 498.3 |
| 1323 | 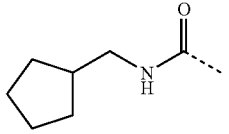 | 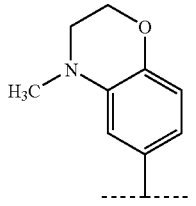 | 6.2** | 510.3 |
| 1324 | 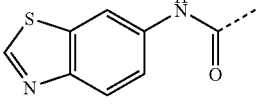 |  | 4.2/4.3* | 561.2 |

TABLE 1-continued
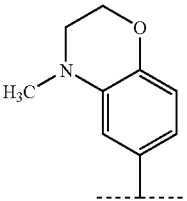
| Cpd | R³ | R⁵ | $t_R$ (min) | MS $(M + H)^+$ |
|---|---|---|---|---|
| 1325 | 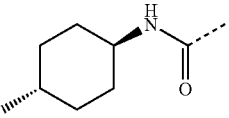 | 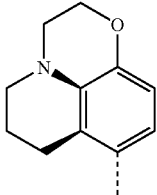 | 4.1/4.2* | 524.3 |
| 1326 | 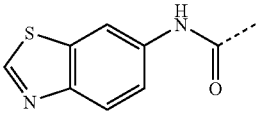 | 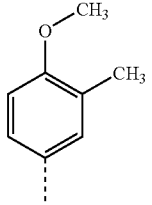 | 7.9** | 587.3 |
| 1327 | 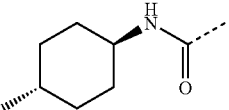 | 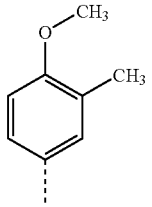 | 7.5/7.8* | 497.2 |
| 1328 | 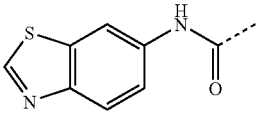 | 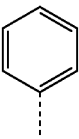 | 7.8/8.2* | 534.1 |
| 1329 | 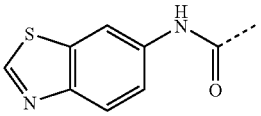 | 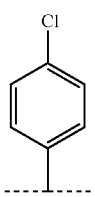 | 7.5 | 490.1 |
| 1330 | 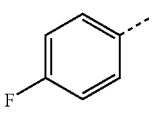 |  | 5.2 | 442/1/ 444.1 |

TABLE 1-continued
| Cpd | R³ | R⁵ | t_R (min) | MS (M + H)⁺ |
|---|---|---|---|---|
| 1331 | 4-chlorophenyl | 4-(methylthio)phenyl | 5.5 | 470.2/472.1 |
| 1332 | 4-chlorophenyl | 4-(methylsulfonyl)phenyl | 4.9 | 502.2/504.1 |
| 1333 | 4-chlorophenyl | 4-(ethylsulfonyl)phenyl | 5.1 | 516.2/518.1 |
| 1335 | 4-chlorophenyl | 4-isopropoxyphenyl | 5.7 | 482.2/484.2 |
| 1336 | 4-chlorophenyl | 3,4-dichlorophenyl | 5.5 | 458.1/460.1/462.1 |
| 1337 | 4-chlorophenyl | benzothiazol-6-yl | 4.9 | 481.1/483.1 |

TABLE 1-continued

| Cpd | R³ | R⁵ | t_R (min) | MS (M + H)⁺ |
|---|---|---|---|---|
| 1338 | 3,4-dihydro-2H-benzo[b][1,4]oxazin-6-yl | cyclooctylaminocarbonyl | 6.1/6.7* | 524.3 |
| 1339 | 3,4-dihydro-2H-benzo[b][1,4]oxazin-6-yl | benzo[d]thiazol-5-ylaminocarbonyl | 3.7/4.0* | 547.2 |
| 1340 | (S)-5-methyl-3,4-dihydro-2H-benzo[b][1,4]oxazin-6-yl | benzo[d]thiazol-6-ylaminocarbonyl | 4.1** | 561.2 |
| 1341 | benzo[d][1,3]dioxol-5-yl | benzo[d]thiazol-6-ylaminocarbonyl | 4.2 | 534.2 |
| 1342 | 4,5-dimethyl-3,4-dihydro-2H-benzo[b][1,4]oxazin-6-yl | trans-4-methylcyclohexylaminocarbonyl | 5.7** | 538.2 |
| 1343 | 4-methyl-3,4-dihydro-2H-benzo[b][1,4]oxazin-6-yl | (S)-2-methylbutylaminocarbonyl | 5.5/5.7* | 498.1 |

TABLE 1-continued
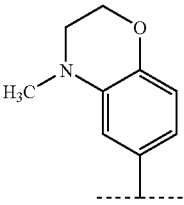
| Cpd | R³ | R⁵ | t_R (min) | MS (M + H)⁺ |
|---|---|---|---|---|
| 1344 | 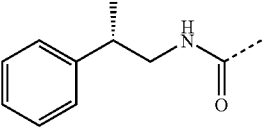 | 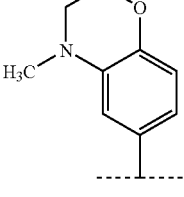 | 5.8/6.0* | 546.1 |
| 1345 | 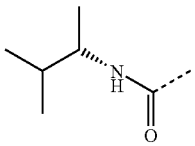 | 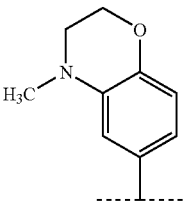 | 5.3/5.5* | 498.1 |
| 1346 | 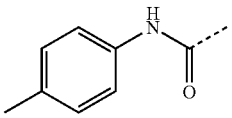 | 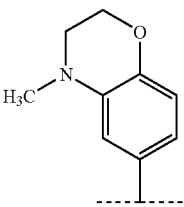 | 6.4/6.5* | 518.1 |
| 1347 | 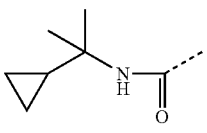 | 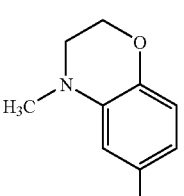 | 5.4/5.5* | 510.1 |
| 1348 | 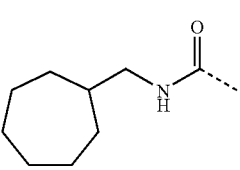 | 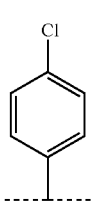 | 6.2/6.4* | 538.2 |
| 1349 | 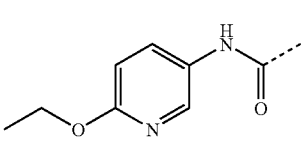 | | 6.6 | 512.2/514.2 |

TABLE 1-continued
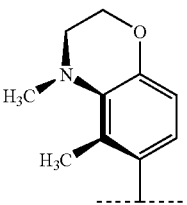
| Cpd | R³ | R⁵ | t_R (min) | MS (M + H)⁺ |
|---|---|---|---|---|
| 1350 | 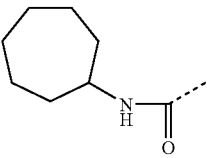 | 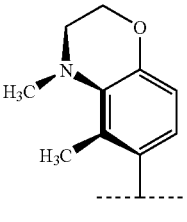 | 5.6** | 538.3 |
| 1351 | 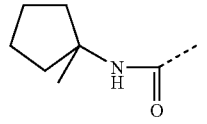 | 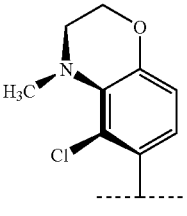 | 5.2** | 524.3 |
| 1352 | 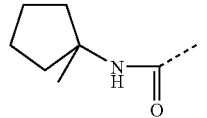 | 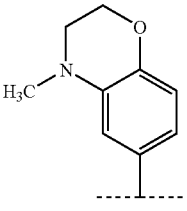 | 5.8** | 544.3/546.3 |
| 1353 | 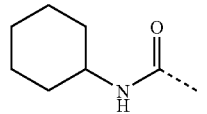 | 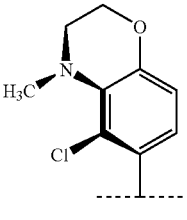 | 5.4/5.6* | 510.3 |
| 1354 | 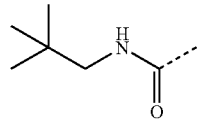 | 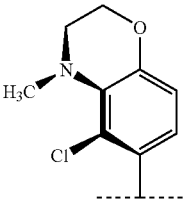 | 7.1** | 532.2/534.2 |
| 1355 | 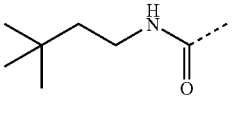 | | 7.8** | 546.2/548.2 |

TABLE 1-continued
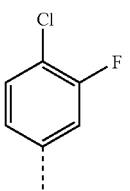
| Cpd | R³ | R⁵ | t_R (min) | MS (M + H)⁺ |
|---|---|---|---|---|
| 1356 | 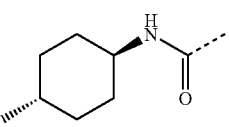 | 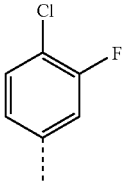 | 8.9 | 515.1/507.1 |
| 1357 | 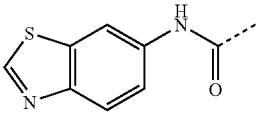 | 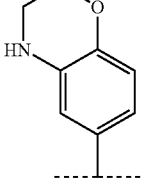 | 8.6 | 542.0/544.0 |
| 1358 | 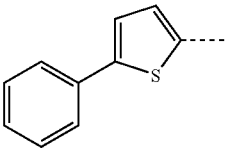 | 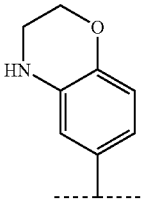 | 5.4/5.9* | 529.2 |
| 1359 | 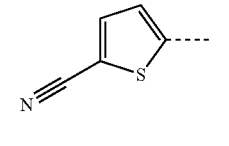 | 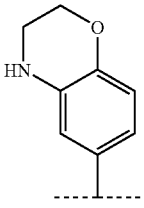 | 5.2/5.8* | 476.2 |
| 1360 | 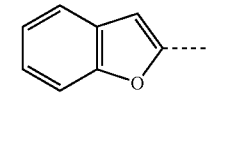 | 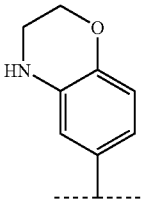 | 4.7/5.2* | 487.2 |
| 1361 | 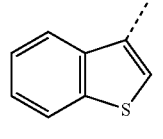 |  | 4.7/5.1* | 503.2 |

TABLE 1-continued

| Cpd | R³ | R⁵ | t_R (min) | MS (M + H)⁺ |
|---|---|---|---|---|
| 1362 | | | 7.1** | 565.2 |
| 1363 | | | 7.3** | 528.3 |
| 1364 | | | 7.1/7.4* | 538.3 |
| 1365 | | | 6.3/6.6* | 498.3 |
| 1666 | | | 5.3/5.5* | 501.2 |
| 1367 | | | 4.3/4.7* | 493.3 |

TABLE 1-continued

| Cpd | R³ | R⁵ | $t_R$ (min) | MS $(M + H)^+$ |
|---|---|---|---|---|
| 1368 | chroman-6-yl | 4-CF₃-piperidin-1-yl-carbonyl | 5.6 | 549.3 |
| 1369 | chroman-6-yl | N-methyl-N-cyclohexyl-aminocarbonyl | 4.6 | 509.3 |
| 1370 | 4-chlorophenyl | tert-butyl-CH₂-C(O)NH- | 1.9$ | 461.2/463.2 |
| 1371 | 4-chlorophenyl | pyridin-2-yl-C(O)NH- | 1.9$ | 486.1/470.1 |
| 1372 | 4-chlorophenyl | naphthalen-2-yl-C(O)NH- | 2.1$ | 517.2/419.2 |
| 1373 | 4-chlorophenyl | naphthalen-1-yl-C(O)NH- | 2.1$ | 517.2/519.2 |

TABLE 1-continued
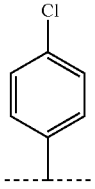
| Cpd | R³ | R⁵ | $t_R$ (min) | MS $(M + H)^+$ |
|---|---|---|---|---|
| 1374 | 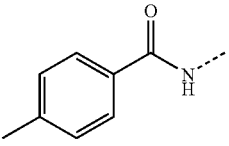 | 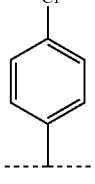 | 2.0$ | 581.2/483.1 |
| 1375 | 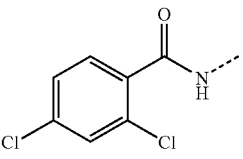 | 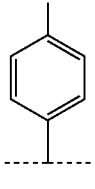 | 2.2$ | 537.0/539.0 |
| 1376 | 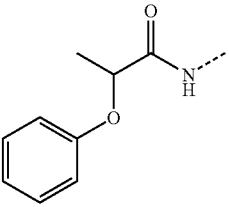 | 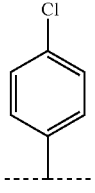 | 2.1$ | 511.2/513.1 |
| 1377 | 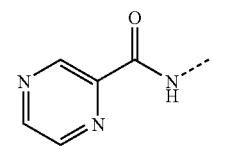 | 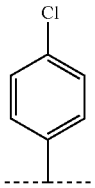 | 1.8$ | 469.1/471.1 |
| 1378 | 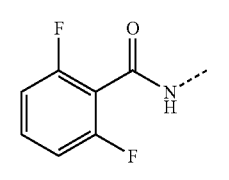 |  | 2.0$ | 503.1/505.1 |
| 1379 | | 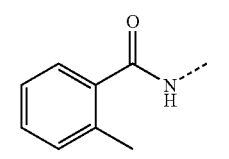 | 2.0$ | 481.1/483.1 |

TABLE 1-continued
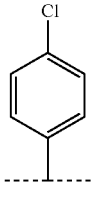
| Cpd | R³ | R⁵ | $t_R$ (min) | MS $(M + H)^+$ |
|---|---|---|---|---|
| 1380 | 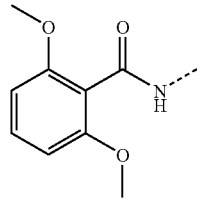 | 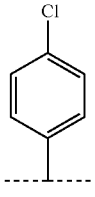 | 1.9$ | 527.1/529.1 |
| 1381 | 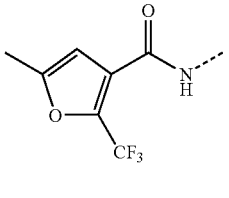 | 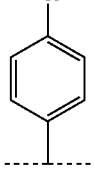 | 2.1$ | 539.1/541.1 |
| 1382 | 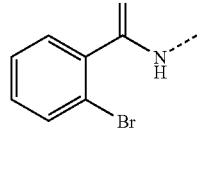 | 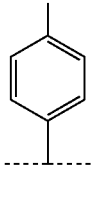 | 2.0$ | 546.2/548.0 |
| 1383 | 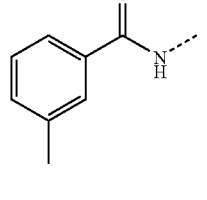 | 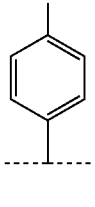 | 2.0$ | 481.2/483.1 |
| 1384 | 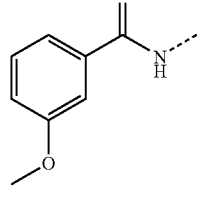 | 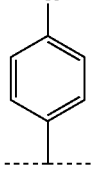 | 2.0$ | 497.1/499.1 |
| 1385 | 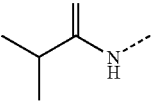 |  | 1.7$ | 433.2/435.1 |

TABLE 1-continued
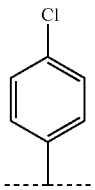
| Cpd | R³ | R⁵ | $t_R$ (min) | MS $(M+H)^+$ |
|---|---|---|---|---|
| 1386 | 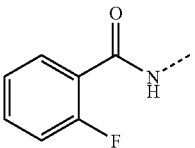 | 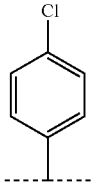 | 2.0$ | 485.1/487.1 |
| 1387 | 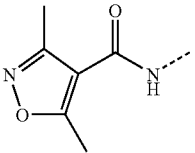 | 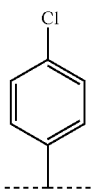 | 1.9$ | 486.1/488.1 |
| 1388 | 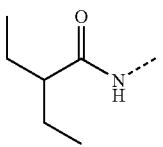 | 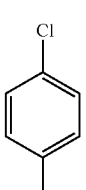 | 1.9$ | 461.2/463.2 |
| 1389 | 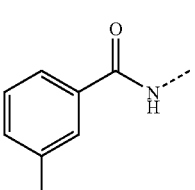 | 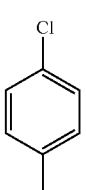 | 2.0$ | 492.1/494.1 |
| 1390 | 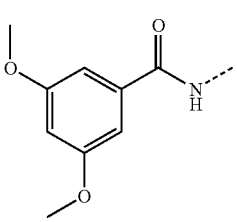 | 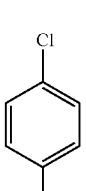 | 2.0$ | 527.1/529.1 |
| 1391 | | 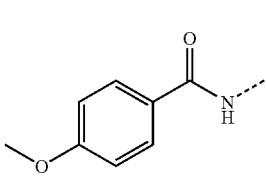 | 1.9$ | 497.1/499.1 |

TABLE 1-continued
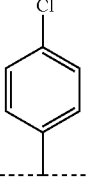
| Cpd | R³ | R⁵ | t_R (min) | MS (M + H)⁺ |
|---|---|---|---|---|
| 1392 | 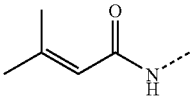 | 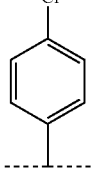 | 1.8$ | 445.2/447.2 |
| 1393 | 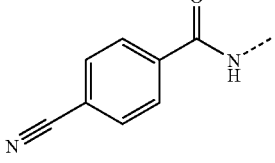 |  | 2.0$ | 492.1/494.1 |
| 1394 | 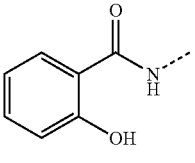 |  | 1.9$ | 483.1/485.1 |
| 1395 | 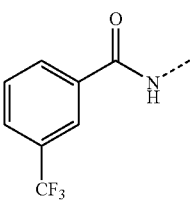 | 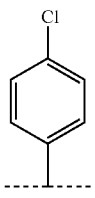 | 2.1$ | 535.1/537.1 |
| 1396 | 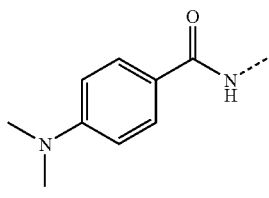 | 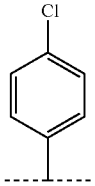 | 2.0$ | 510.2/512.1 |
| 1397 | 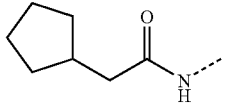 |  | 2.0$ | 473.2/475.2 |

TABLE 1-continued
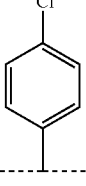
| Cpd | R³ | R⁵ | $t_R$ (min) | MS (M + H)⁺ |
|---|---|---|---|---|
| 1398 | 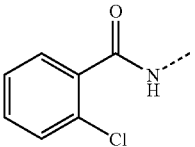 | 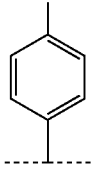 | 2.0$ | 501.1/503.1 |
| 1399 | 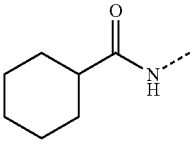 |  | 2.0$ | 473.2/475.2 |
| 1400 | 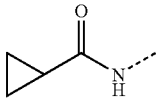 | 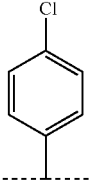 | 1.7$ | 431.2/433.1 |
| 1401 | 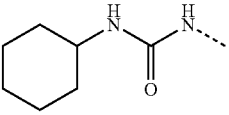 | 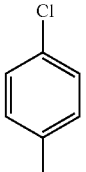 | 2.0$ | 488.2/490.2 |
| 1402 | 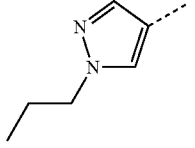 | 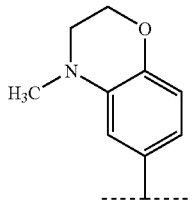 | 4.0/4.4* | 497.1 |
| 1403 | 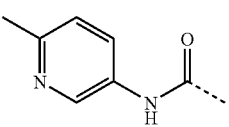 | | 4.4/4.5* | 519.2 |

TABLE 1-continued

| Cpd | R³ | R⁵ | t_R (min) | MS (M + H)⁺ |
|---|---|---|---|---|
| 1404 | 4-methyl-3,4-dihydro-2H-benzo[b][1,4]oxazine | quinolin-6-yl acetamide | 4.7/4.8* | 555.2 |
| 1405 | 4-methyl-3,4-dihydro-2H-benzo[b][1,4]oxazine | (4-(methoxymethyl)pyridin-2-yl)acetamide | 5.2/5.4* | 549.3 |
| 1406 | 3,4-dihydro-2H-benzo[b][1,4]oxazine | 2-methoxybenzamide | 4.5/4.8* | 520.2 |
| 1407 | 4-chlorophenyl | (5-methylpyridin-3-yl)acetamide | 4.9 | 482.2/484.2 |
| 1408 | 4-methyl-3,4-dihydro-2H-benzo[b][1,4]oxazine | 2-methoxybenzamide | 4.9/5.1* | 534.3 |
| 1409 | 4-ethyl-3,4-dihydro-2H-benzo[b][1,4]oxazine | cycloheptylacetamide | 6.1/6.2* | 538.4 |

TABLE 1-continued
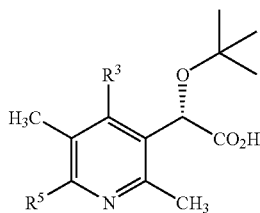
| Cpd | R³ | R⁵ | $t_R$ (min) | MS $(M + H)^+$ |
|---|---|---|---|---|
| 1410 | 4-ethyl-benzoxazine | benzothiazol-6-yl-NH-C(O)- | 6.3/6.4* | 575.3 |
| 1411 | 4-ethyl-benzoxazine | 1-methylcyclopentyl-NH-C(O)- | 5.7*5.8* | 524.4 |
| 1412 | 4-ethyl-benzoxazine | (1-methylcyclohexyl)methyl-NH-C(O)- | 6.6 | 552.4 |
| 1413 | 4-methyl-7-fluoro-benzoxazine | trans-4-methylcyclohexyl-NH-C(O)- | 6.5** | 542.4 |
| 1414 | 4-methyl-8-fluoro-benzoxazine | benzothiazol-6-yl-NH-C(O)- | 6.3/6.4* | 579.3 |
| 1415 | 4-methyl-8-fluoro-benzoxazine | trans-4-methylcyclohexyl-NH-C(O)- | 6.3/6.4* | 542.2 |

TABLE 1-continued
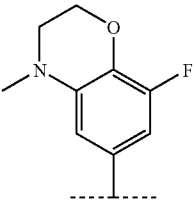
| Cpd | R³ | R⁵ | t_R (min) | MS (M + H)⁺ |
|---|---|---|---|---|
| 1416 | 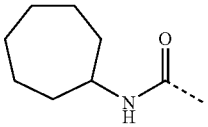 | 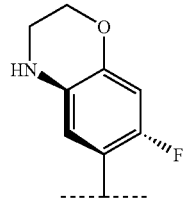 | 6.2/6.3* | 542.2 |
| 1417 | 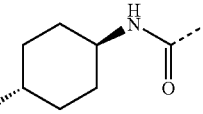 | 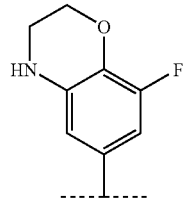 | 6.2** | 528.3 |
| 1418 | 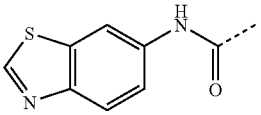 | 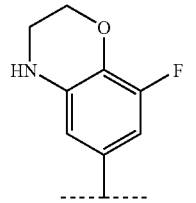 | 4.0/4.2* | 565.1 |
| 1419 | 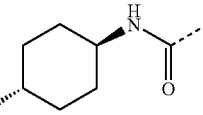 | 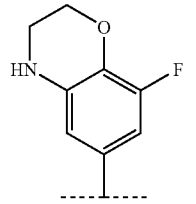 | 4.0/4.2* | 528.2 |
| 1420 | 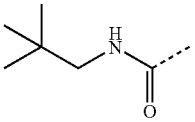 | 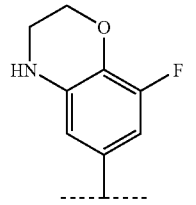 | 3.8/4.0* | 502.3 |
| 1421 | 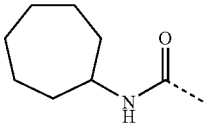 |  | 3.9/4.1* | 528.3 |

TABLE 1-continued
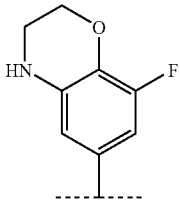
| Cpd | R³ | R⁵ | $t_R$ (min) | MS $(M + H)^+$ |
|---|---|---|---|---|
| 1422 | 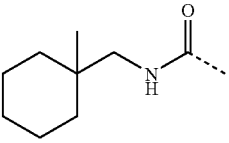 | 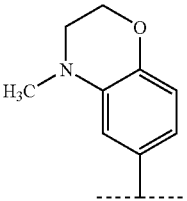 | 4.2/4.3* | 542.3 |
| 1423 | 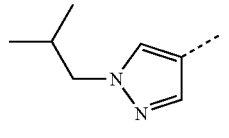 | 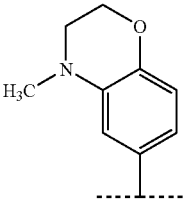 | 4.8/5.0* | 507.3 |
| 1424 | 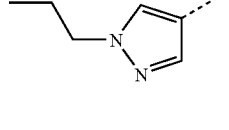 | 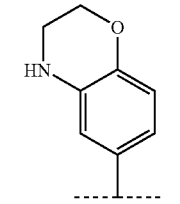 | 4.6/4.7* | 493.3 |
| 1425 | 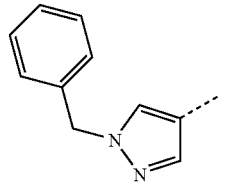 | 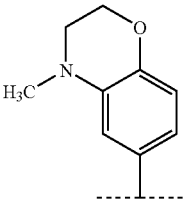 | 4.5/4.8* | 527.3 |
| 1426 | 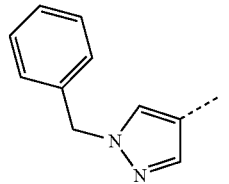 | 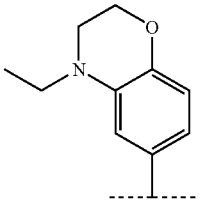 | 5.0/5.1* | 541.3 |
| 1427 | 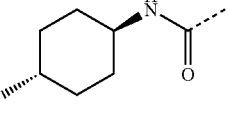 | | 6.3 | 538.4 |

TABLE 1-continued
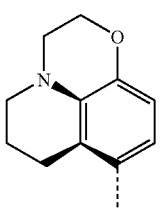
| Cpd | R[3] | R[5] | $t_R$ (min) | MS $(M + H)^+$ |
|---|---|---|---|---|
| 1428 | 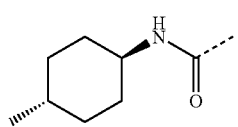 | 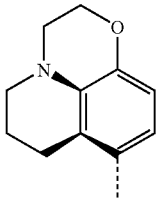 | 2.2[$] | 550.4 |
| 1429 | 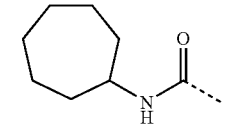 | 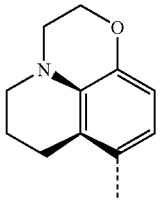 | 2.2[$] | 550.2 |
| 1430 | 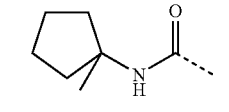 | 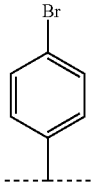 | 2.1[$] | 536.2 |
| 1431 | 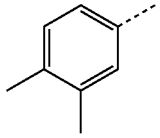 | 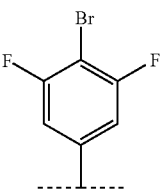 | 5.5 | 496.1/498.1 |
| 1432 | 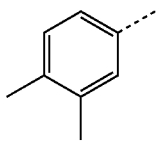 | 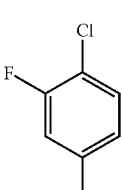 | 6.6 | 532.0/534.0 |
| 1433 | 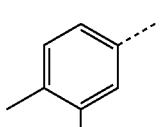 | | 6.0 | 470.1/472.1 |

TABLE 1-continued

| Cpd | R³ | R⁵ | t_R (min) | MS (M + H)⁺ |
|---|---|---|---|---|
| 1434 | 8-fluoro-4-methyl-3,4-dihydro-2H-benzo[1,4]oxazin-6-yl | 1-methylcyclopentyl-NH-C(O)- | 5.8/5.9* | 528.2 |
| 1435 | 8-fluoro-4-methyl-3,4-dihydro-2H-benzo[1,4]oxazin-6-yl | (1-methylcyclohexyl)methyl-NH-C(O)- | 6.6 | 556.3 |
| 1436 | 8-fluoro-4-methyl-3,4-dihydro-2H-benzo[1,4]oxazin-6-yl | neopentyl-NH-C(O)- | 6.0/6.1 | 516.2 |
| 1437 | 4-chlorophenyl | 5-chloro-1-methyl-1H-benzimidazol-2-yl | 2.0$ | 512.2/514.2/516.2 |
| 1438 | 4-chlorophenyl | 6-chloro-imidazo[1,2-a]pyridin-2-yl | 4.9 | 498.1/500.1 |
| 1439 | 4-chlorophenyl | 5-methoxy-1-methyl-1H-benzimidazol-2-yl | 2.1$ | 508.0/510.1 |

TABLE 1-continued
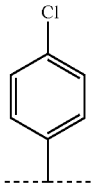
| Cpd | R³ | R⁵ | $t_R$ (min) | MS (M + H)⁺ |
|---|---|---|---|---|
| 1440 | 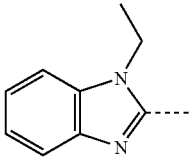 | 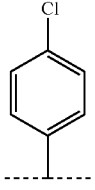 | 2.8$ | 492.1/494.1 |
| 1441 | 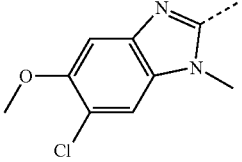 | 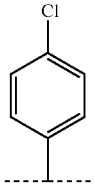 | 1.5$ | 542.2/544.2/546.2 |
| 1442 | 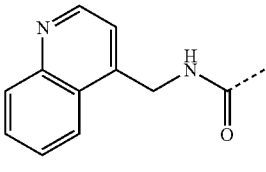 | 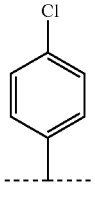 | 4.8 | 532.2/534.2 |
| 1443 | 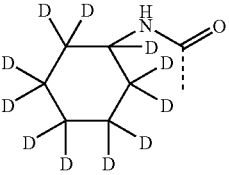 | 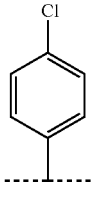 | 6.4 | 484.3/486.3 |
| 1444 | 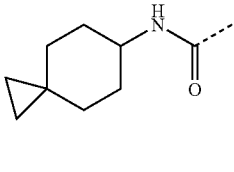 | 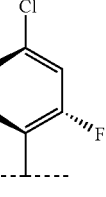 | 4.4 | 499.2/500.2 |
| 1445 |  | 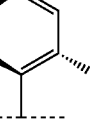 | 4.2** | 516.0/518.0/520.0 |
| 1446 | 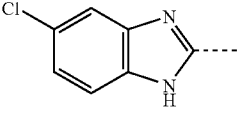 |  | 4.1** | 498.0/500.0/502.0 |

TABLE 1-continued
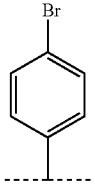
| Cpd | R³ | R⁵ | $t_R$ (min) | MS $(M + H)^+$ |
|---|---|---|---|---|
| 1447 | 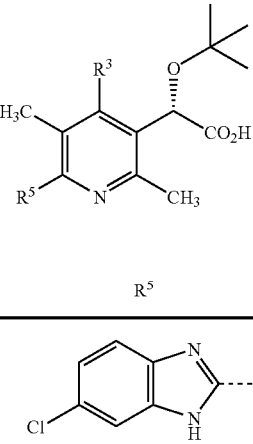 | 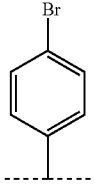 | 4.2 | 542.0/544.0/546.0 |
| 1448 | 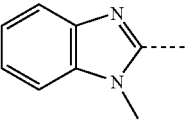 | 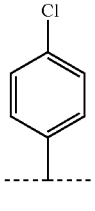 | 3.5 | 522.1/524.1 |
| 1449 | 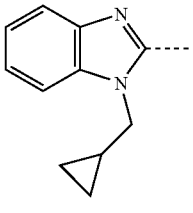 | 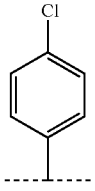 | 2.2$ | 518.2/520.2 |
| 1450 | 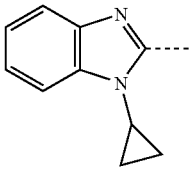 | 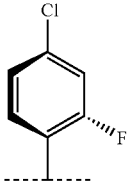 | 2.1$ | 504.0/506.0 |
| 1451 | 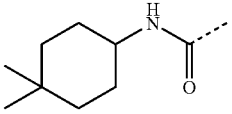 | 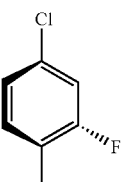 | 7.0** | 519.2/521.2 |
| 1452 | 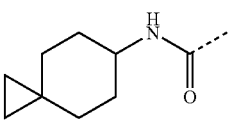 |  | 4.6** | 517.3/419.2 |

TABLE 1-continued

| Cpd | R³ | R⁵ | $t_R$ (min) | MS (M + H)⁺ |
|---|---|---|---|---|
| 1453 | | | 6.6** | 566.2/566.2 |
| 1454 | | | 2.9**$ | 505.2/507.2 |
| 1455 | | | 6.7** | 487.4/489.4 |
| 1456 | | | 5.4 | 531.2/533.2 |
| 1457 | | | 7.6 | 545.2/547.2 |
| 1458 | | | 7.4 | 543.2/545.2 |
| 1459 | | | 6.8 | 527.3 |

TABLE 1-continued

| Cpd | R³ | R⁵ | $t_R$ (min) | MS $(M + H)^+$ |
|---|---|---|---|---|
| 1460 | 2,3-dihydrobenzo[b][1,4]oxathiin-6-yl | (S)-N-(3,3-dimethylbutan-2-yl)amide | 6.6 | 512.2 |
| 1461 | 4-chlorophenyl | 4-methoxyquinoline-2-carboxamide | 6.7 | 548.3/550.2 |
| 1462 | 4-chlorophenyl | 4-chloro-2-methoxybenzamide | 2.0$ | 531.2/533.1/535.1 |
| 1463 | 4-chlorophenyl | 3-methylbenzofuran-2-carboxamide | 2.2$ | 521.3/523.3 |
| 1464 | 4-chlorophenyl | trans-4-methylcyclohexanecarboxamide | 2.0$ | 487.3/498.3 |
| 1465 | 4-chlorophenyl | 5-methyl-2-(trifluoromethyl)benzamide | 2.7$ | 549.0/551.0 |

TABLE 1-continued
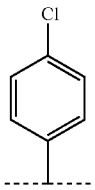
| Cpd | R³ | R⁵ | t_R (min) | MS (M + H)⁺ |
|---|---|---|---|---|
| 1466 | 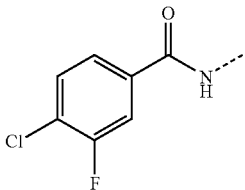 | 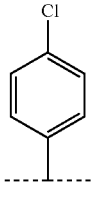 | 2.2$ | 519.1/521.1/523.1 |
| 1467 | 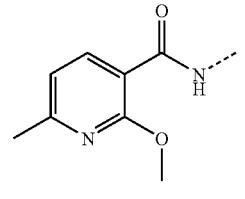 | 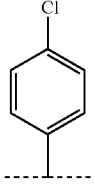 | 5.5 | 512.2/514.2 |
| 1468 | 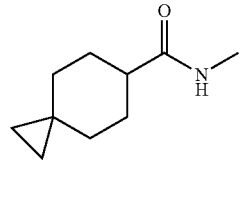 | 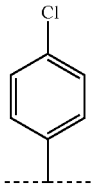 | 4.0 | 499.3/501.3 |
| 1469 | 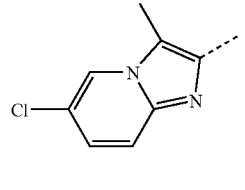 | 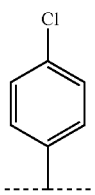 | 4.8 | 511.9/513.9 |
| 1470 | 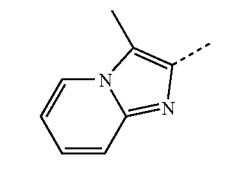 | 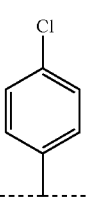 | 4.5 | 487.0/480.0 |
| 1471 | | 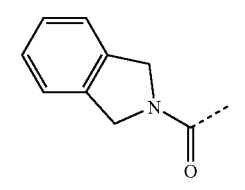 | 6.3 | 493.1/495.1 |
*presence of 2 inter-converting conformers by HPLC
**Most active atropisomer
$Retention time (t_R) measured by UPLC

TABLE 2

| Cpd | R¹ | R³ | R⁴ | R⁵ | $t_R$ (min) | MS (M + H)⁺ |
|---|---|---|---|---|---|---|
| 2001 | —CH₃ | chroman-6-yl | —CN | —CH₃ | 5.9 | 395.1 |
| 2002 | —CH₂SMe | 1,2,3,4-tetrahydroquinolin-6-yl | —CH₃ | 3,4-dimethylphenyl | 5.2/5.6* | 521.2 |
| 2003 | —CH₂OMe | 4-chlorophenyl | —CH₃ | 3,4-dimethylphenyl | 5.7 | 482.0/ 484.0 |
| 2004 | —CH₂OEt | 4-chlorophenyl | —CH₃ | 3,4-dimethylphenyl | 5.8 | 496.2/ 498.2 |
| 2005 | —CH₃ | 4-chlorophenyl | —CN | 4-(3,5-dimethylisoxazol-4-yl)phenyl | 8.5 | 530.2/ 532.2 |
| 2006 | —CH₃ | 1,2,3,4-tetrahydroquinolin-6-yl | —CN | 4-(3,5-dimethylisoxazol-4-yl)phenyl | 7.2* | 553.2 |

TABLE 2-continued
| Cpd | | | | $t_R$ (min) | MS $(M+H)^+$ |
|---|---|---|---|---|---|
| 2007 | —CH=CH$_2$ | 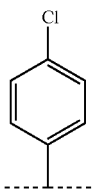 Cl | —CH$_3$ | 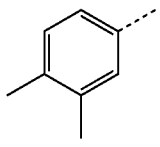 | 5.6 | 464.2/ 466.2 |
| 2008 |  | 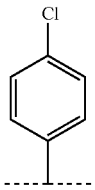 Cl | —CH$_3$ | 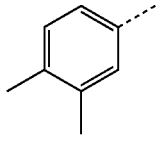 | 5.8 | 478.2/ 480.2 |
| 2009 | —CH$_3$ | 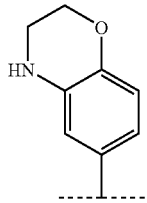 | —F | 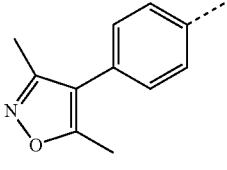 | 6.2 | 546.1 |
| 2010 | —CH$_2$OMe | 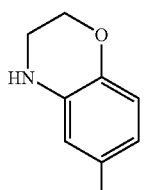 | —CH$_3$ | 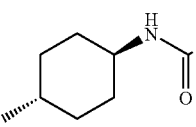 | 4.4/5.0 | 540.4 |
| 2011 | —CH$_2$OMe | 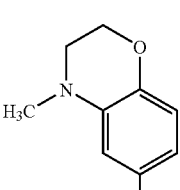 | —CH$_3$ | 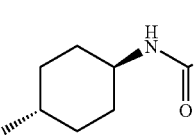 | 5.3/5.5* | 554.4 |
*presence of 2 inter-converting conformers by HPLC
**Most active atropisomer
TABLE 3
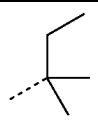
| Cpd | R$^2$ | R$^3$ | R$^5$ | $t_R$ (min) | MS $(M+H)^+$ |
|---|---|---|---|---|---|
| 3001 | 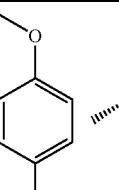 | 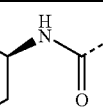 | | 5.7/6.2* | 524.3 |

TABLE 3-continued

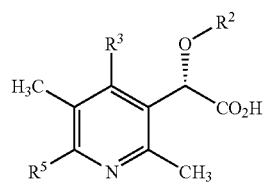

| Cpd | R² | R³ | R⁵ | $t_R$ (min) | MS (M + H)⁺ |
|---|---|---|---|---|---|
| 3002 | neopentyl | 3,4-dihydro-2H-benzo[b][1,4]oxazin-6-yl | N-phenylacetamide | 5.9/6.4* | 504.3 |
| 3003 | neopentyl | 3,4-dihydro-2H-benzo[b][1,4]oxazin-6-yl | N-cycloheptylacetamide | 5.6/6.1* | 524.3 |
| 3004 | neopentyl | 3,4-dihydro-2H-benzo[b][1,4]oxazin-6-yl | N-(1-methylcyclopentyl)acetamide | 5.1/6.6* | 510.2 |
| 3005 | neopentyl | 4-chlorophenyl | N-(trans-4-methylcyclohexyl)acetamide | 6.8 | 501.1/ 503.1 |
| 3006 | neopentyl | 4-chlorophenyl | N-phenylacetamide | 6.9 | 481.1/ 483.1 |
| 3007 | neopentyl | 4-chlorophenyl | N-cycloheptylacetamide | 6.8 | 501.1/ 503.1 |

TABLE 3-continued

| Cpd | R² | R³ | R⁵ | t_R (min) | MS (M + H)⁺ |
|---|---|---|---|---|---|
| 3008 | neopentyl | 4-Cl-phenyl | 1-methylcyclopentyl-NHC(O)- | 6.6 | 487.1/ 489.1 |
| 3009 | 1-methylcyclobutyl | 4-Cl-phenyl | trans-4-methylcyclohexyl-NHC(O)- | 6.8 | 499.1/ 501.1 |
| 3010 | 1-methylcyclobutyl | 4-Cl-phenyl | phenyl-NHC(O)- | 6.8 | 479.1/ 481.1 |
| 3011 | 1-methylcyclobutyl | 4-Cl-phenyl | cycloheptyl-NHC(O)- | 6.7 | 499.1/ 501.1 |
| 3012 | 1-methylcyclobutyl | 4-Cl-phenyl | 1-methylcyclopentyl-NHC(O)- | 6.5 | 485.1/ 487.1 |
| 3013 | 1-methylcyclobutyl | 3,4-dihydro-2H-benzo[1,4]oxazin-6-yl | 1-methylcyclopentyl-NHC(O)- | 4.9/5.0* | 508.2 |

TABLE 3-continued

[Structure: pyridine with R³, OR², CO₂H, H₃C, CH₃, R⁵, N]

| Cpd | R² | R³ | R⁵ | $t_R$ (min) | MS (M + H)⁺ |
|---|---|---|---|---|---|
| 3014 | 1-methylcyclobutyl | 4-chlorophenyl | 3,4-dimethylphenyl | 5.5 | 464.2 / 466.2 |

*presence of 2 inter-converting conformers by HPLC
**Most active atropisomer

TABLE 4

[Structure: imidazo-pyridine core with R³, O-tBu, CO₂H, H₃C, CH₃, R⁵¹]

| Cpd | R³ | R⁵¹ | $t_R$ (min) | MS (M + H)⁺ |
|---|---|---|---|---|
| 4001 | chroman-6-yl | cyclohexylmethyl | 6.3 | 505.2 |
| 4002 | chroman-6-yl | neopentyl | 5.4 | 479.2 |
| 4003 | chroman-6-yl | trans-4-methylcyclohexyl-NHC(O)- | 6.3 | 548.2 |
| 4004 | 4-chlorophenyl | trans-4-methylcyclohexyl-NHC(O)- | 7.1 | 526.1 / 528.1 |
| 4005 | 4-chlorophenyl | cycloheptyl-NHC(O)- | 6.9 | 526.1 / 528.1 |
| 4006 | 4-chlorophenyl | (1-methylcyclohexyl)methyl-NHC(O)- | 7.9 | 540.1 / 542.1 |

TABLE 4-continued

| Cpd | R³ | R⁵¹ | tR (min) | MS (M + H)⁺ |
|---|---|---|---|---|
| 4007 | 4-Cl-C₆H₄- | neopentyl-NH-C(O)- | 6.6 | 500.1/502.1 |
| 4008 | 4-Cl-C₆H₄- | 3,3-dimethylbutyl-NH-C(O)- | 7.0 | 514.1/516.1 |
| 4009 | 4-Cl-C₆H₄- | ethyl-NH-C(O)- | 5.3 | 458.1/460.1 |
| 4010 | 4-Cl-C₆H₄- | cyclopentylmethyl-NH-C(O)- | 6.7 | 512.1/514.1 |
| 4011 | 4-Cl-C₆H₄- | cyclobutylmethyl-NH-C(O)- | 6.3 | 498.1/500.1 |
| 4012 | 4-Cl-C₆H₄- | tert-butyl-NH-C(O)- | 6.1 | 486.1/488.1 |
| 4013 | 4-Cl-C₆H₄- | (S)-3,3-dimethylbut-2-yl-NH-C(O)- | 7.0 | 514.2/516.2 |
| 4014 | 4-Cl-C₆H₄- | isobutyl-NH-C(O)- | 6.1 | 486.1/488.1 |
| 4015 | 4-Cl-C₆H₄- | isobutyl-N(CH₃)-C(O)- | 5.5 | 500.1/502.1 |
| 4016 | 4-Cl-C₆H₄- | CF₃CH₂-NH-C(O)- | 4.7 | 512.2/514.2 |
| 4017 | 4-Cl-C₆H₄- | cyclopropylmethyl-NH-C(O)- | 4.5 | 484.3/486.3 |
| 4018 | 4-Cl-C₆H₄- | 2-cyclopropylpropan-2-yl-NH-C(O)- | 5.0 | 512.3/514.3 |

TABLE 4-continued
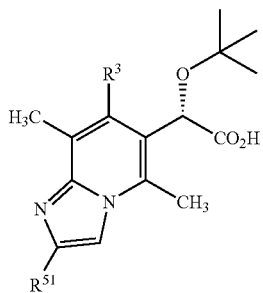
| Cpd | R³ | R⁵¹ | $t_R$ (min) | MS (M + H)⁺ |
|---|---|---|---|---|
| 4019 | Cl-phenyl | (S)-3,3-dimethyl-2-butyl-NHC(O)- | 5.1 | 514.2/ 516.2 |
TABLE 4-continued
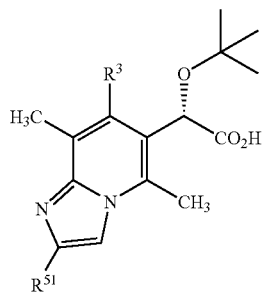
| Cpd | R³ | R⁵¹ | $t_R$ (min) | MS (M + H)⁺ |
|---|---|---|---|---|
| 4020 | Cl-phenyl | 1-methylcyclopentyl-NHC(O)- | 5.0 | 512.2/ 514.2 |
TABLE 5
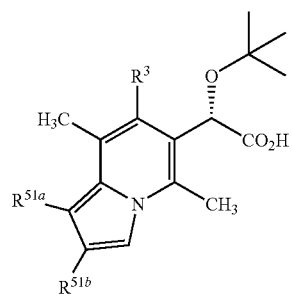
| Cpd | R³ | R⁵¹ᵃ | R⁵¹ᵇ | $t_R$ (min) | MS (M + H)⁺ |
|---|---|---|---|---|---|
| 5001 | 4-Cl-phenyl | cyclohexyl-NHC(O)- | H | 8.8 | 511.2/ 513.2 |
| 5002 | 3,4-dihydro-2H-benzo[b][1,4]oxazin-6-yl | neopentyl-NHC(O)- | H | 6.0/6.6* | 522.3 |
| 5003 | 3,4-dihydro-2H-benzo[b][1,4]oxazin-6-yl | trans-4-methylcyclohexyl-NHC(O)- | H | 6.5/7.3* | 548.4 |

TABLE 5-continued
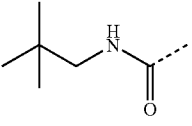
| Cpd | R³ | R⁵¹ᵃ | R⁵¹ᵇ | $t_R$ (min) | MS (M + H)⁺ |
|---|---|---|---|---|---|
| 5004 | 3,4-dihydro-2H-benzo[b][1,4]oxazin-6-yl (NH) | trans-4-methylcyclohexyl acetamide | —CF₃ | 7.9/8.7* | 616.3 |
*presence of 2 inter-converting conformers by HPLC
TABLE 6
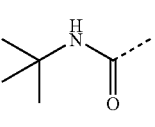
| Cpd | R³ | R⁵¹ | $t_R$ (min) | MS (M + H)⁺ |
|---|---|---|---|---|
| 6001 | chroman-6-yl | —COOMe | 8.2 | 467.1 |
| 6002 | chroman-6-yl | neopentyl acetamide | 7.8 | 522.2 |
| 6003 | chroman-6-yl | tert-butyl acetamide | 7.4/7.5* | 506.2 |

TABLE 6-continued

| Cpd | R³ | R⁵¹ | tR (min) | MS (M + H)⁺ |
|---|---|---|---|---|
| 6004 | chroman-6-yl | trans-4-methylcyclohexyl-NHC(O)- | 8.5/8.6 | 548.2 |
| 6005 | chroman-6-yl | cycloheptyl-NHC(O)- | 8.5 | 548.2 |
| 6006 | chroman-6-yl | (3,3-dimethylbutyl)-NHC(O)- | 8.4 | 536.2 |
| 6007 | chroman-6-yl | (cyclopentylmethyl)-NHC(O)- | 8.1 | 534.2 |
| 6008 | 4-methyl-3,4-dihydro-2H-benzo[b][1,4]oxazin-6-yl | neopentyl-NHC(O)- | 6.2/6.4* | 537.3 |
| 6009 | 4-methyl-3,4-dihydro-2H-benzo[b][1,4]oxazin-6-yl | trans-4-methylcyclohexyl-NHC(O)- | 6.5/6.6* | 563.2 |

TABLE 6-continued

| Cpd | R³ | R⁵¹ | $t_R$ (min) | MS $(M+H)^+$ |
|---|---|---|---|---|
| 6010 | 4-methyl-3,4-dihydro-2H-benzo[b][1,4]oxazin-7-yl | (1-methylcyclopentyl)aminocarbonyl | 6.3/6.5* | 549.2 |
| 6011 | 4-methyl-3,4-dihydro-2H-benzo[b][1,4]oxazin-7-yl | benzothiazol-6-ylaminocarbonyl | 6.0/6.2* | 600.1 |
| 6012 | 4-methyl-3,4-dihydro-2H-benzo[b][1,4]oxazin-7-yl | (2-cyclopropylpropan-2-yl)aminocarbonyl | 6.3/6.5* | 549.2 |
| 6013 | 4-methyl-3,4-dihydro-2H-benzo[b][1,4]oxazin-7-yl | ((1-methylcyclohexyl)methyl)aminocarbonyl | 6.7/6.8* | 577.2 |
| 6014 | 3,4-dihydro-2H-benzo[b][1,4]oxazin-7-yl | (2,2-dimethylpropyl)aminocarbonyl | 5.3/5.8* | 523.2 |
| 6015 | 3,4-dihydro-2H-benzo[b][1,4]oxazin-7-yl | (trans-4-methylcyclohexyl)aminocarbonyl | 5.6/5.8* | 549.2 |

TABLE 6-continued
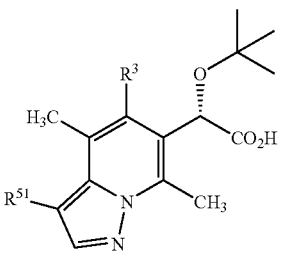
| Cpd | R³ | R⁵¹ | $t_R$ (min) | MS $(M+H)^+$ |
|---|---|---|---|---|
| 6016 | 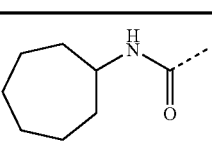 | 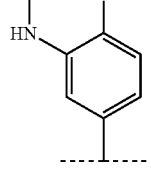 | 5.7/6.2* | 549.2 |
| 6017 | 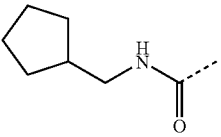 | 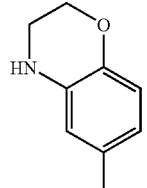 | 5.4/5.9* | 535.2 |
| 6018 | 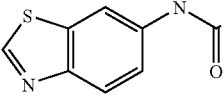 |  | 5.0/5.6* | 586.1 |
*presence of 2 inter-converting conformers by HPLC
TABLE 7
Antiviral potency
| Compound # | $EC_{50}$ nM |
|---|---|
| 1005 | 19 |
| 1009 | 20 |
| 1011 | 59 |
| 1017 | 21 |
| 1018 | 180 |
| 1020 | 49 |
| 1102 | 17 |
| 1111 | 15 |
| 1113 | 7.7 |
| 1116 | 13 |
| 1119 | 17 |
| 1124 | 81 |
| 1127 | 4.5 |
| 1132 | 9.4 |
| 1141 | 26 |
| 1142 | 7.9 |
| 1143 | 21 |
| 1145 | 35 |
| 1146 | 17 |
| 1147 | 6.9 |
| 1152 | 15 |
| 1153 | 22 |
| 1154 | 27 |
| 1160 | 16 |
| 1161 | 27 |
| 1167 | 9.3 |
| 1192 | 8.3 |
| 1202 | 31 |
| 1208 | 8.9 |
| 1242 | 220 |
| 1256 | 8.1 |
| 1275 | 4.5 |
| 1276 | 68 |
| 1280 | 22 |
| 1283 | 140 |
| 1290 | 11 |
| 1293 | 24 |
| 1307 | 17 |
| 1311 | 26 |
| 1316 | 47 |
| 1437 | 0.75 |
| 1438 | 0.94 |
| 1439 | 4.0 |
| 1440 | 2.4 |
| 1441 | 4.9 |
| 1442 | 16 |
| 1443 | 7.1 |
| 1444 | 9.2 |

TABLE 7-continued

| Antiviral potency | |
|---|---|
| Compound # | $EC_{50}$ nM |
| 1445 | 1.9 |
| 1446 | 1.9 |
| 1447 | 0.38 |
| 1448 | 1.4 |
| 1449 | 1.8 |
| 1450 | 7.7 |
| 1451 | 1.7 |
| 1452 | 5.7 |
| 1453 | 2.1 |
| 1454 | 3.7 |
| 1455 | 4.0 |
| 1456 | 4.2 |
| 1457 | 4.0 |
| 1458 | 6.9 |
| 1459 | 4.0 |
| 1460 | 1.7 |
| 1461 | 2.5 |
| 1462 | 1.2 |
| 1463 | 2.1 |
| 1464 | 6.2 |
| 1465 | 11 |
| 1466 | 4.9 |
| 1467 | 4.3 |
| 1468 | 15 |
| 1469 | 0.61 |
| 1470 | 5.9 |
| 1471 | 2.4 |
| 2003 | 17 |
| 2005 | 19 |
| 3005 | 9.3 |
| 3009 | 24 |
| 4002 | 73 |
| 6001 | 89 |

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A compound of Formula I

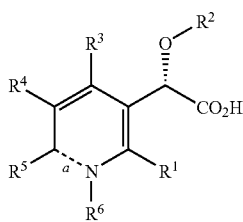

(I)

wherein

R$^1$ is (C$_{1-6}$)alkyl, (C$_{2-6}$)alkenyl or (C$_{3-6}$)cycloalkyl, wherein the (C$_{1-6}$)alkyl is optionally substituted with —O(C$_{1-6}$)alkyl or —S(C$_{1-6}$)alkyl;

R$^2$ is (C$_{1-8}$)alkyl or (C$_{3-8}$)cycloalkyl, wherein the (C$_{3-8}$)cycloalkyl is optionally substituted with (C$_{1-6}$)alkyl;

R$^3$ is aryl, wherein the aryl is optionally fused to one or more cycles, at least one of which is a heterocycle, to form a heteropolycycle, and wherein the aryl or heteropolycycle is optionally substituted with 1 to 4 substituents each independently selected from (C$_{1-6}$)alkyl, halo and —O(C$_{1-6}$)alkyl;

R$^4$ is (C$_{1-6}$)alkyl, —CN, halo, (C$_{1-6}$)haloalkyl, (C$_{3-5}$)cycloalkyl, or —O(C$_{1-6}$)alkyl; and a is a double bond, R$^6$ is absent and R$^5$ is R$^{51}$ or —(C$_{1-3}$)alkyl-R$^{51}$; or a is a single bond and R$^5$ and R$^6$ are joined, together with the atoms to which they are bonded, to form a 5-membered ring optionally having 1 to 3 further heteroatoms each independently selected from O, N and S, wherein the 5-membered ring is optionally substituted with 1 to 3 R$^{51}$ substituents;

wherein R$^{51}$ is in each case independently selected from R$^{52}$, —OR$^{53}$, —N(R$^{54}$)R$^{53}$, —C(=O)R$^{52}$, —C(=O)OR$^{53}$, —C(=O)N(R$^{54}$)R$^{53}$, —OC(=O)N(R$^{54}$)R$^{53}$, —N(R$^{54}$)C(=O)R$^{52}$, —N(R$^{54}$)C(=O)N(R$^{54}$)R$^{53}$ and —N(R$^{54}$)C(=O)OR$^{53}$; wherein R$^{52}$ is in each case independently selected from R$^{53}$, (C$_{2-8}$)alkenyl and (C$_{2-8}$)alkynyl, R$^{53}$ is in each case independently selected from (C$_{1-8}$)alkyl, (C$_{3-8}$)cycloalkyl, (C$_{3-8}$)cycloalkyl-(C$_{1-6}$)alkyl-, aryl, aryl-(C$_{1-6}$)alkyl-, Het, and Het-(C$_{1-6}$)alkyl-, and R$^{54}$ is in each case independently selected from H and (C$_{1-3}$)alkyl;

wherein each of R$^{52}$ and R$^{53}$ is optionally substituted with 1 to 3 substituents each independently selected from R$^{55}$, halo, —CN, —OR$^{56}$, —SR$^{56}$, —SOR$^{56}$, —SO$_2$R$^{56}$, —N(R$^{54}$)R$^{56}$, —N(R$^{54}$)C(=O)R$^{55}$, —N(R$^{54}$)C(=O)N(R$^{54}$)R$^{56}$, —N(R$^{54}$)C(=O)OR$^{56}$, —OC(=O)N(R$^{54}$)R$^{56}$, —C(=O)R$^{55}$, —C(=O)OR$^{56}$, and —CON(R$^{54}$)R$^{56}$, wherein R$^{55}$ is in each case independently selected from R$^{56}$, (C$_{2-8}$)alkenyl and (C$_{2-8}$)alkynyl, and R$^{56}$ is in each case independently selected from H, (C$_{1-8}$)alkyl, (C$_{3-8}$)cycloalkyl, (C$_{3-8}$)cycloalkyl-(C$_{1-6}$) alkyl-, aryl, aryl-(C$_{1-6}$)alkyl-, Het, and Het-(C$_{1-6}$) alkyl-, wherein each of R$^{55}$ and R$^{56}$ is, where possible, in each case independently optionally substituted with 1 to 3 substituents each independently selected from (C$_{1-6}$) alkyl, (C$_{1-6}$)haloalkyl, halo, —OH, —O(C$_{1-6}$)alkyl, —NH$_2$, —NH(C$_{1-6}$)alkyl, —N((C$_{1-6}$)alkyl)$_2$ and —NH(C=O)(C$_{1-6}$)alkyl;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S;

or a salt thereof.

2. A compound according to claim 1, or a pharmaceutically acceptable salt thereof, having the formula:

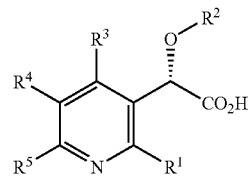

wherein R$^1$, R$^2$, R$^3$, R$^4$ and R$^5$ are as defined in claim 1.

3. A compound according to claim 1, or a pharmaceutically acceptable salt thereof, wherein R$^1$ is —CH$_3$, —CH$_2$OMe, —CH$_2$OEt, —CH$_2$SMe, —CH=CH$_2$ or

4. A compound according to claim 1, or a pharmaceutically acceptable salt thereof, wherein $R^2$ is.

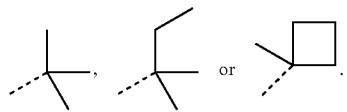

5. A compound according to claim 1, or a pharmaceutically acceptable salt thereof, wherein $R^3$ is phenyl or a heteropolycycle selected from:

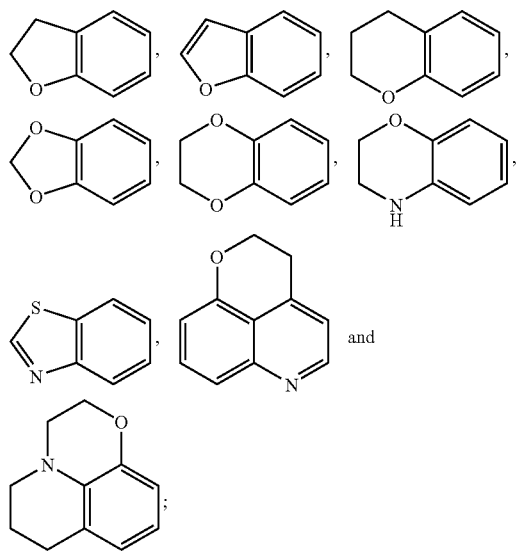

wherein the phenyl or heteropolycycle is optionally substituted with 1 to 4 substituents each independently selected from $(C_{1-6})$alkyl, halo and —O$(C_{1-6})$alkyl.

6. A compound according to claim 1, or a pharmaceutically acceptable salt thereof, wherein $R^4$ is $(C_{1-6})$alkyl, —CN, halo or $(C_{1-6})$haloalkyl.

7. A compound according to claim 1, or a pharmaceutically acceptable salt thereof, wherein $R^4$ is —CH$_3$.

8. A compound according to claim 1, or a pharmaceutically acceptable salt thereof, wherein a is a double bond, $R^6$ is absent and $R^5$ is $R^{51}$ or —$(C_{1-3})$alkyl-$R^{51}$;

wherein $R^{51}$ is selected from $R^{52}$, —OR$^{53}$, —C(=O)R$^{52}$, —C(=O)OR$^{53}$, —C(=O)N(R$^{54}$)R$^{53}$, —N(R$^{54}$)C(=O)R$^{52}$, —N(R$^{54}$)C(=O)N(R$^{54}$)R$^{53}$ and —N(R$^{54}$)C(=O)OR$^{53}$; wherein $R^{52}$ is selected from $R^{53}$ and $(C_{2-8})$alkenyl, and $R^{53}$ is selected from $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-, wherein Het and the Het portion of Het-$(C_{1-6})$alkyl- are in each case independently selected from:

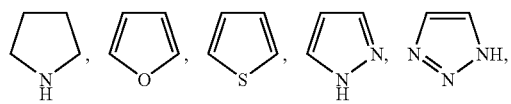

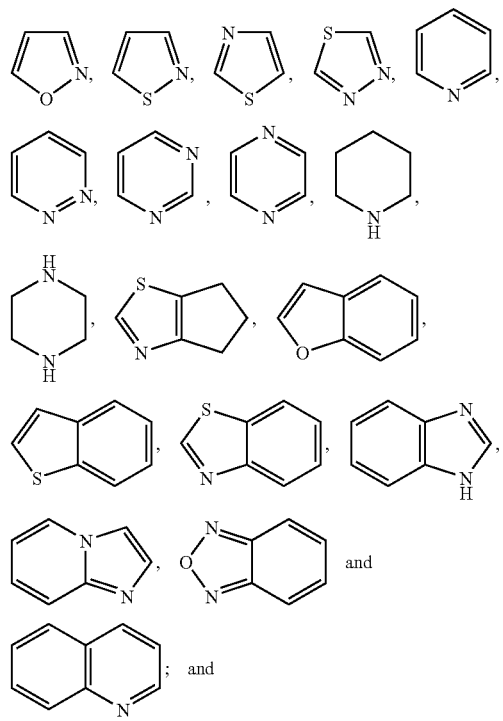

$R^{54}$ is in each case independently selected from H and $(C_{1-3})$alkyl;

wherein each of $R^{52}$ and $R^{53}$ is optionally substituted with 1 to 3 substituents each independently selected from $R^{56}$, halo, —CN, —OR$^{56}$, —SR$^{56}$, —SO$_2$R$^{56}$, —N(R$^{54}$)R$^{56}$ and —CON(R$^{54}$)R$^{56}$, wherein $R^{56}$ is in each case independently selected from H, $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-, wherein Het and the Het portion of Het-$(C_{1-6})$alkyl- are in each case independently selected from:

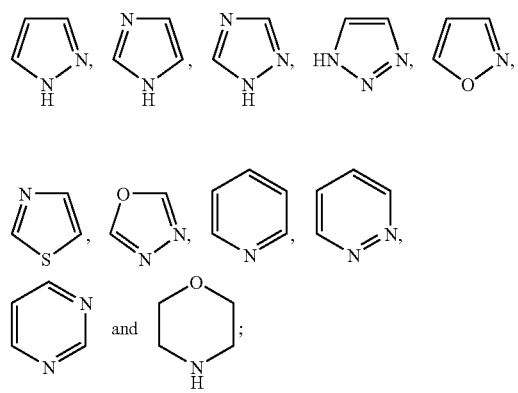

wherein $R^{56}$ is, where possible, in each case independently optionally substituted with 1 to 3 substituents each independently selected from $(C_{1-6})$alkyl, $(C_{1-6})$haloalkyl, halo, —O$(C_{1-6})$alkyl, —N($(C_{1-6})$alkyl)$_2$ and —NH(C=O)$(C_{1-6})$alkyl.

9. A compound of the formula:

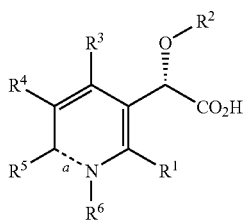

wherein
- $R^1$ is $(C_{1-6})$alkyl, $(C_{2-6})$alkenyl or $(C_{3-6})$cycloalkyl, wherein the $(C_{1-6})$alkyl is optionally substituted with —O$(C_{1-6})$alkyl or —S$(C_{1-6})$alkyl;
- $R^2$ is $(C_{1-8})$alkyl or $(C_{3-8})$cycloalkyl, wherein the $(C_{3-8})$ cycloalkyl is optionally substituted with $(C_{1-6})$alkyl;
- $R^3$ is aryl, wherein the aryl is optionally fused to one or more cycles, at least one of which is a heterocycle, to form a heteropolycycle, and wherein the aryl or heteropolycycle is optionally substituted with 1 to 4 substituents each independently selected from $(C_{1-6})$alkyl, halo and —O$(C_{1-6})$alkyl;
- $R^4$ is $(C_{1-6})$alkyl, —CN, halo, $(C_{1-6})$haloalkyl, $(C_{3-5})$cycloalkyl, or —O$(C_{1-6})$alkyl; and
- a is a double bond, $R^6$ is absent and $R^5$ is $R^{51}$ or —$(C_{1-3})$alkyl-$R^{51}$; or
- a is a single bond and $R^5$ and $R^6$ are joined, together with the atoms to which they are bonded, to form a 5-membered ring optionally having 1 to 3 further heteroatoms each independently selected from O, N and S, wherein the 5-membered ring is optionally substituted with 1 to 3 $R^{51}$ substituents;
- wherein $R^{51}$ is in each case independently selected from $R^{52}$, —OR$^{53}$, —N(R$^{54}$)R$^{53}$, —C(=O)R$^{52}$, —C(=O)OR$^{53}$, —C(=O)N(R$^{54}$)R$^{53}$, —OC(=O)N(R$^{54}$)R$^{53}$, —N(R$^{54}$)C(=O)R$^{52}$, —N(R$^{54}$)C(=O)N(R$^{54}$)R$^{53}$ and —N(R$^{54}$)C(=O)OR$^{53}$; wherein
- $R^{52}$ is in each case independently selected from $R^{53}$, $(C_{2-8})$alkenyl and $(C_{2-8})$alkynyl,
- $R^{53}$ is in each case independently selected from $(C_{1-8})$alkyl, $(C_{3-8})$cycloalkyl, $(C_{5-14})$spirocycloalkyl, $(C_{3-8})$cycloalkyl-$(C_{1-6})$alkyl-, aryl, aryl-$(C_{1-6})$alkyl-, Het, and Het-$(C_{1-6})$alkyl-, and
- $R^{54}$ is in each case independently selected from H and $(C_{1-3})$alkyl;
- wherein each of $R^{52}$ and $R^{53}$ is optionally substituted with 1 to 3 substituents each independently selected from $R^{55}$, halo, —CN, —OR$^{56}$, —SR$^{56}$, —SOR$^{56}$, —SO$_2$R$^{56}$, —N(R$^{54}$)R$^{56}$, —N(R$^{54}$)C(=O)R$^{55}$, —N(R$^{54}$)C(=O)N(R$^{54}$)R$^{56}$, —N(R$^{54}$)C(=O)OR$^{56}$, —OC(=O)N(R$^{54}$)R$^{56}$, —C(=O)R$^{55}$, —C(=O)OR$^{56}$, and —CON(R$^{54}$)R$^{56}$, wherein
- $R^{55}$ is in each case independently selected from $R^{56}$, $(C_{2-8})$alkenyl and $(C_{2-8})$alkynyl, and
- $R^{56}$ is in each case independently selected from H, $(C_{1-8})$alkyl, $(C_{3-8})$cycloalkyl, $(C_{3-8})$cycloalkyl-$(C_{1-6})$alkyl-, aryl, aryl-$(C_{1-6})$alkyl-, Het, and Het-$(C_{1-6})$alkyl-,
  - wherein each of $R^{55}$ and $R^{56}$ is, where possible, in each case independently optionally substituted with 1 to 3 substituents each independently selected from $(C_{1-6})$alkyl, $(C_{1-6})$haloalkyl, halo, —OH, —O$(C_{1-6})$alkyl, —NH$_2$, —NH$(C_{1-6})$alkyl, —N$((C_{1-6})$alkyl$)_2$ and —NH(C=O)$(C_{1-6})$alkyl;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S;

or a salt thereof.

10. A compound according to claim 1, or a pharmaceutically acceptable salt thereof, having the formula:

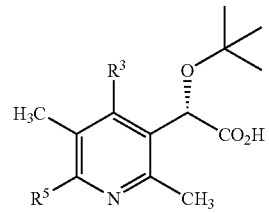

wherein $R^3$ and $R^5$ are defined as:

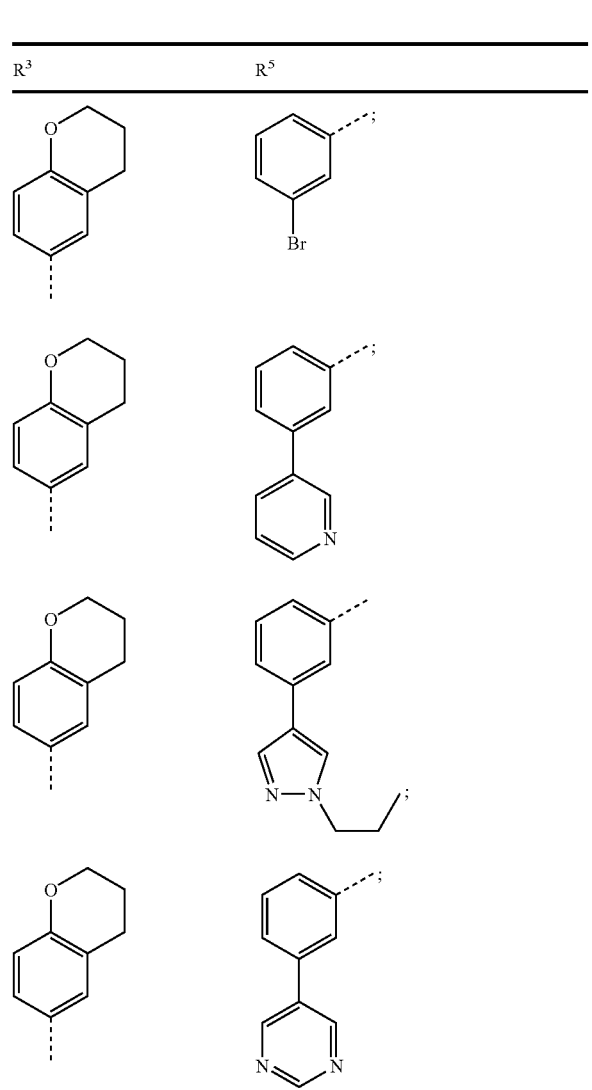

| 303 -continued | | 304 -continued | |
|---|---|---|---|
| R³ | R⁵ | R³ | R⁵ |
| 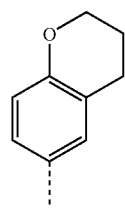 | 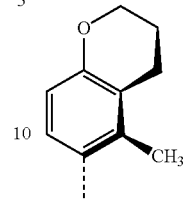 | 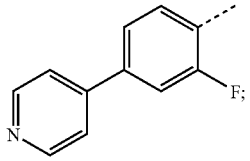 | 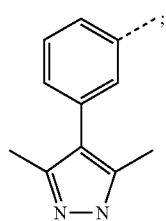 |
| 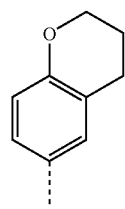 | 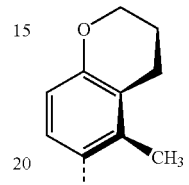 | 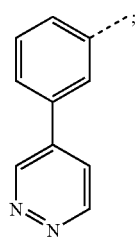 | 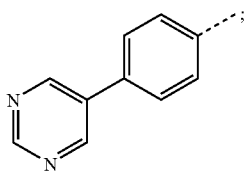 |
| 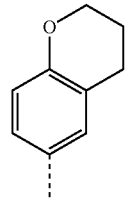 | 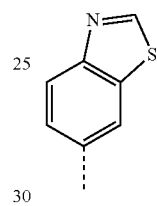 | 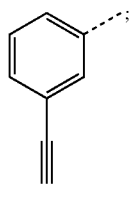 | 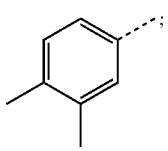 |
| 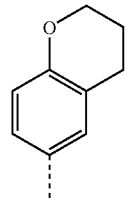 | 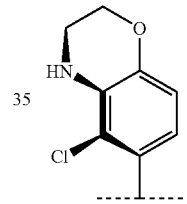 | 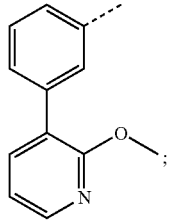 | 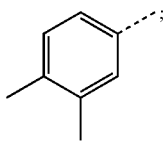 |
| 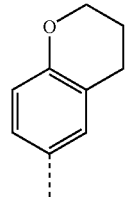 | 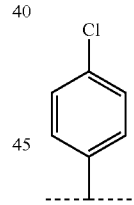 | 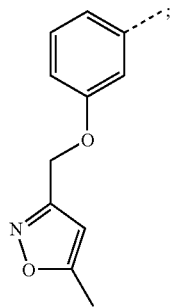 | 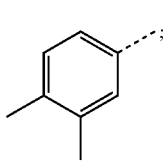 |
| 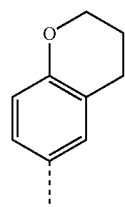 | 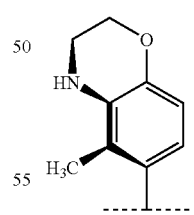 | 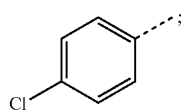 | 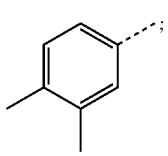 |
| | | 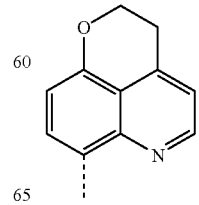 | 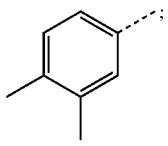 |

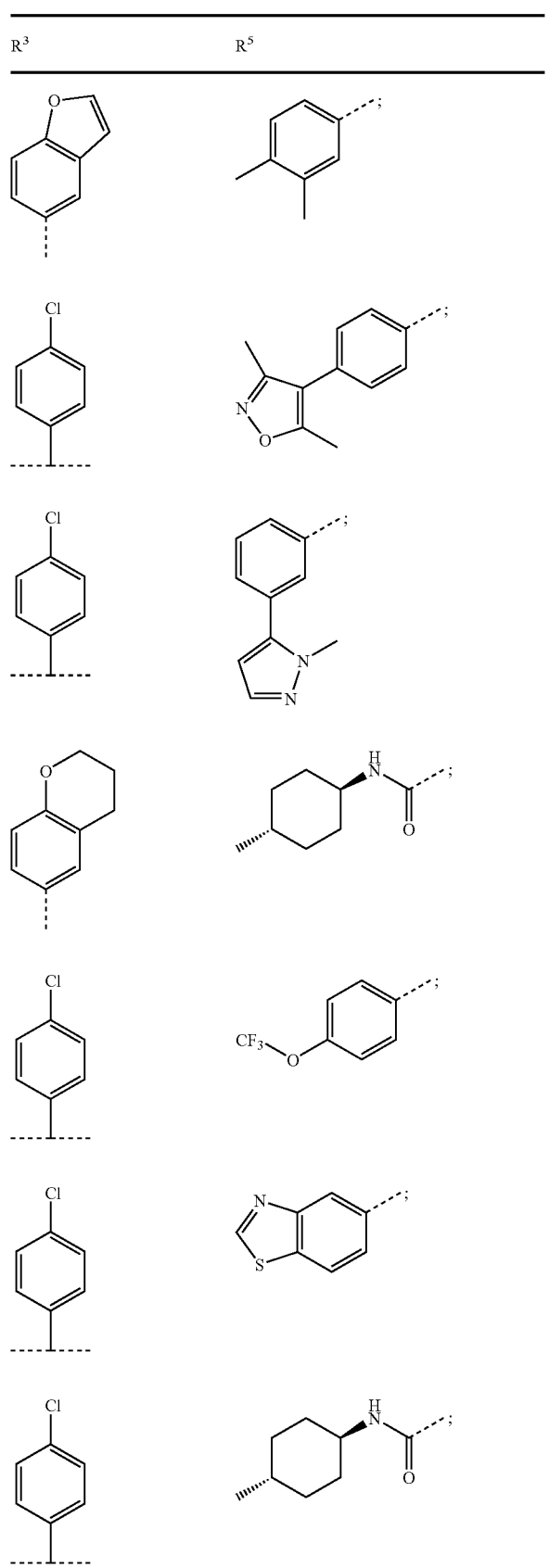
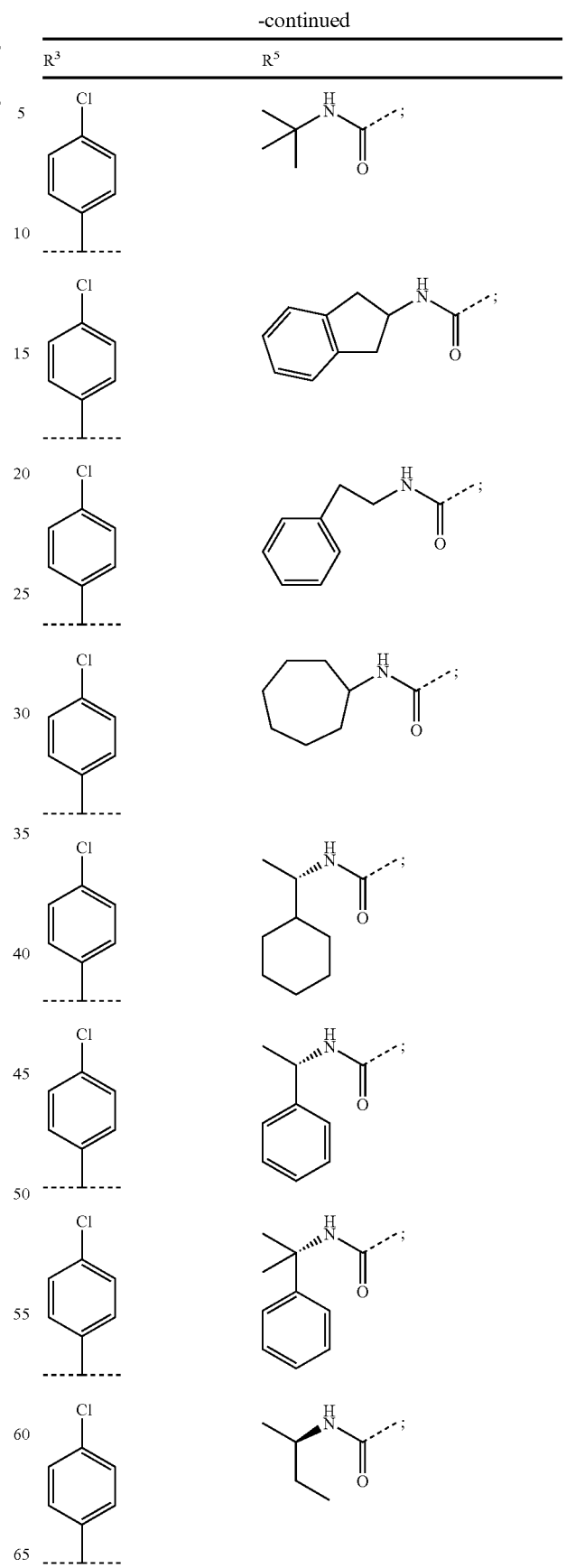

| 307 -continued | | 308 -continued | |
|---|---|---|---|
| R³ | R⁵ | R³ | R⁵ |
| 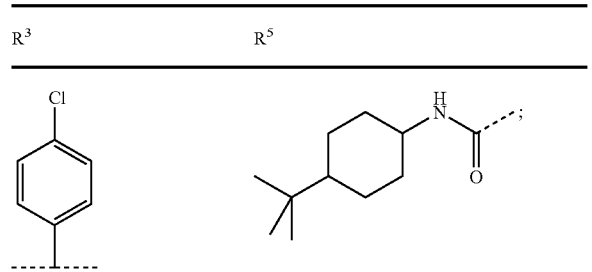 | | 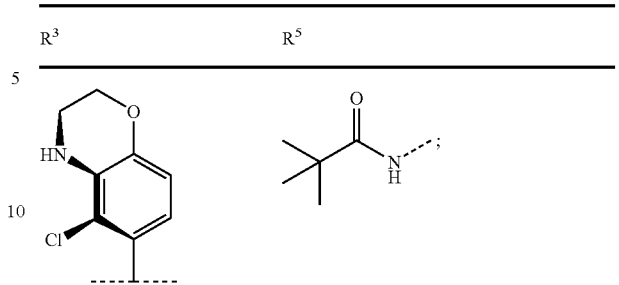 | |
| 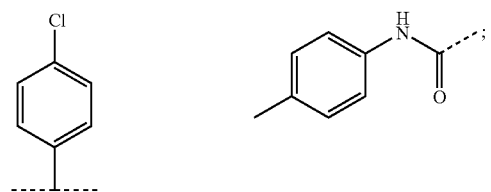 | | 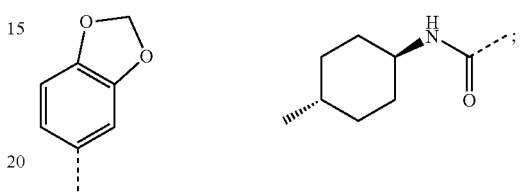 | |
| 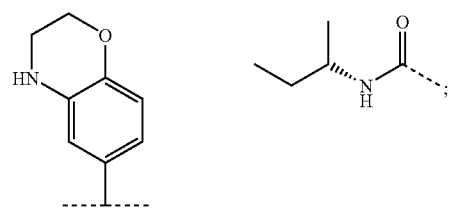 | | 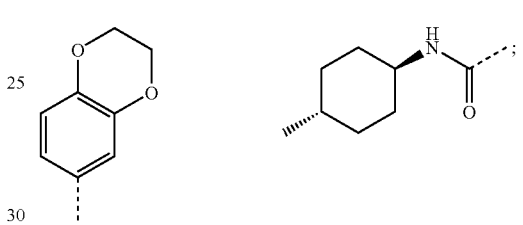 | |
| 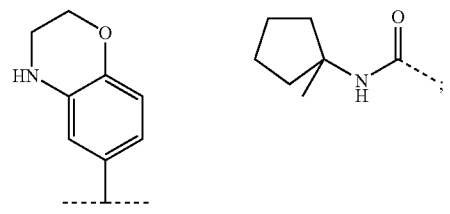 | | 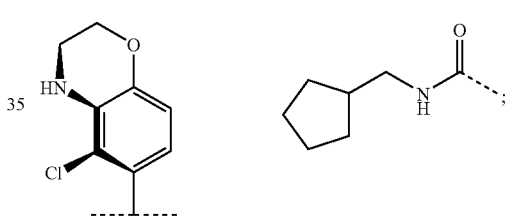 | |
| 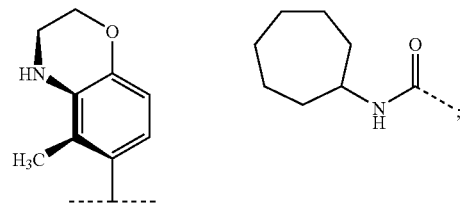 | | 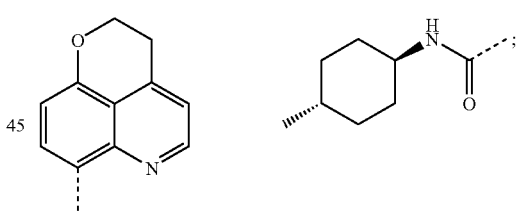 | |
| 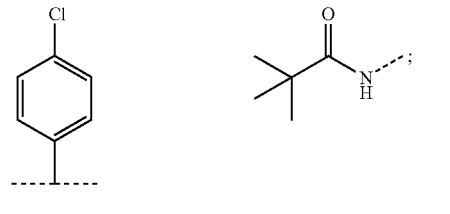 | | 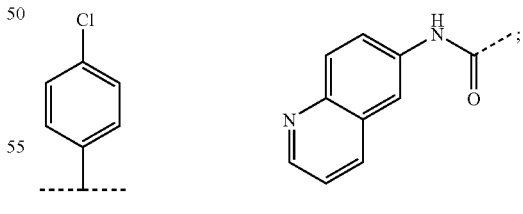 | |
| 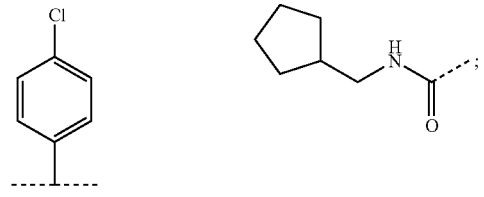 | | 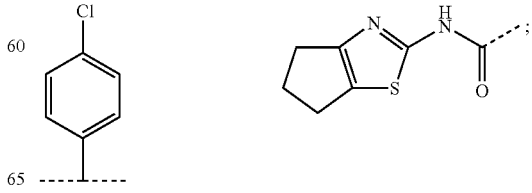 | |

| 309 -continued | | 310 -continued | |
|---|---|---|---|
| R³ | R⁵ | R³ | R⁵ |
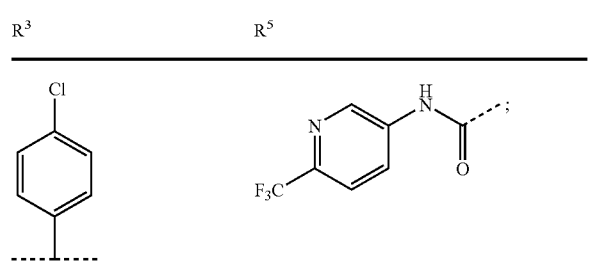
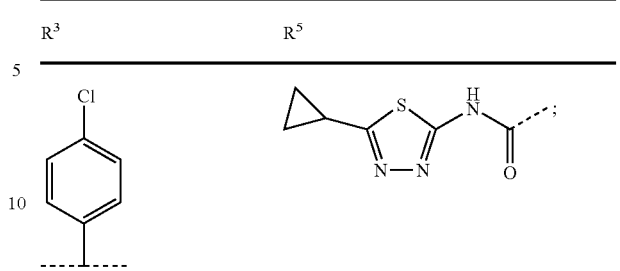
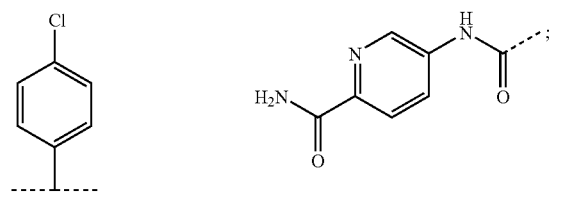
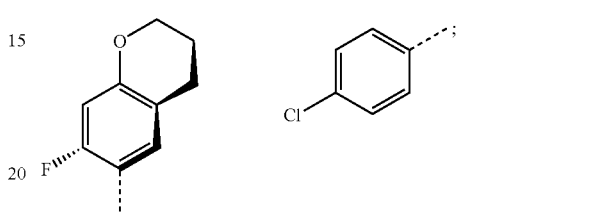
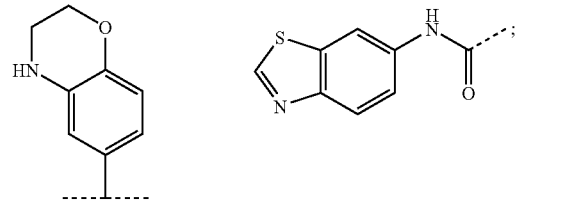
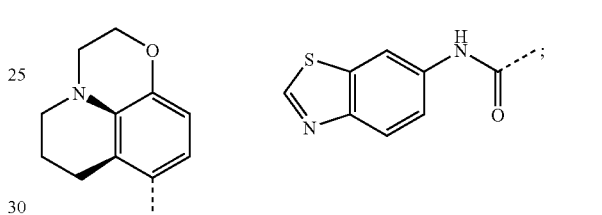
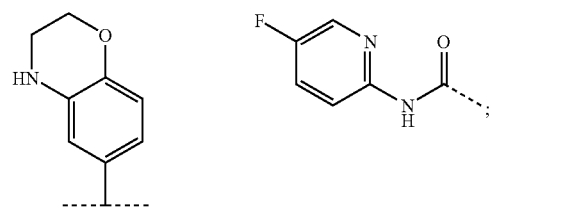
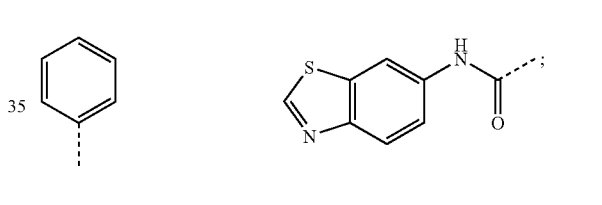
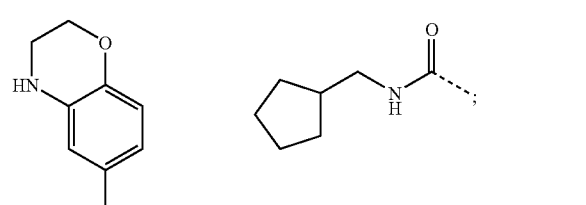
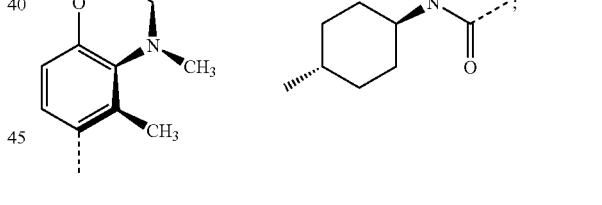
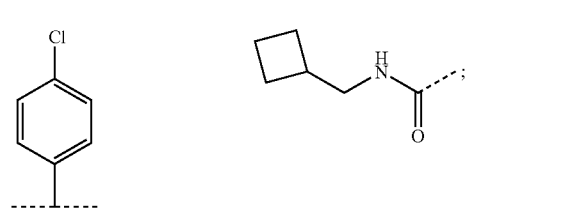
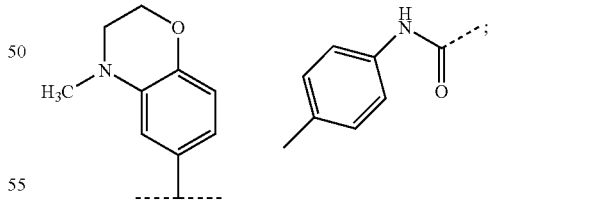
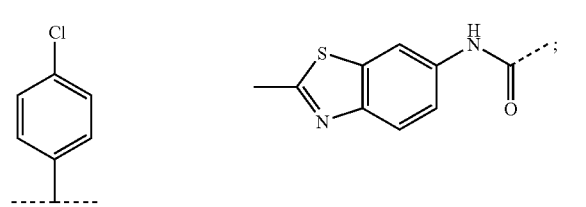
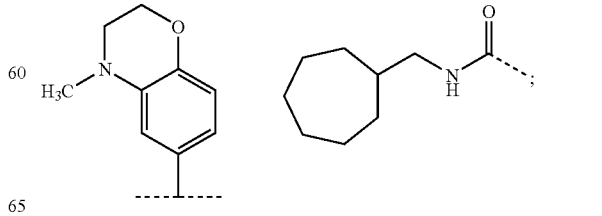

| 311-continued | | 312-continued | |
|---|---|---|---|
| R³ | R⁵ | R³ | R⁵ |
| 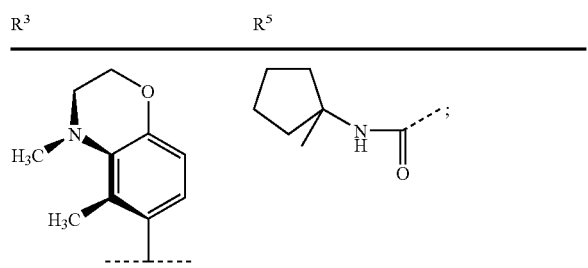 | | 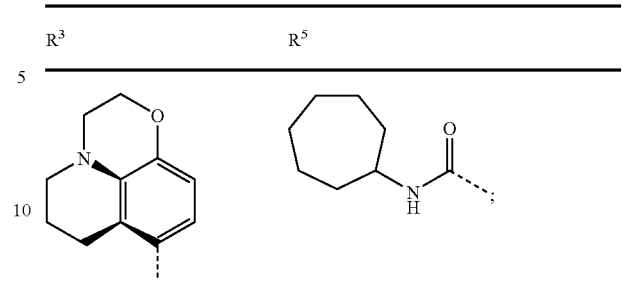 | |
| 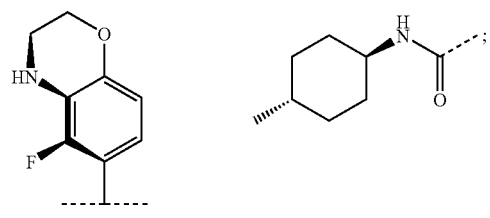 | | 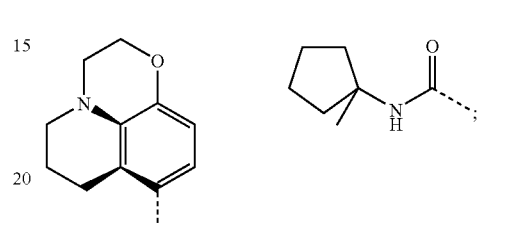 | |
| 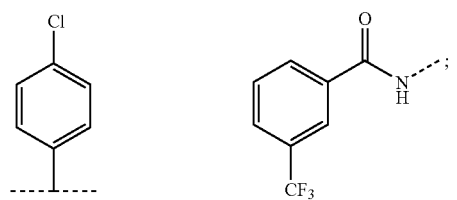 | | 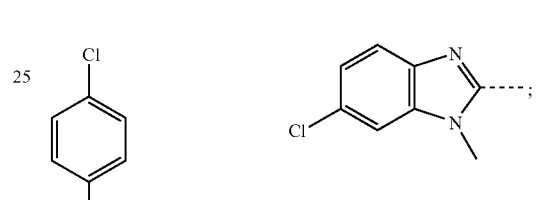 | |
| 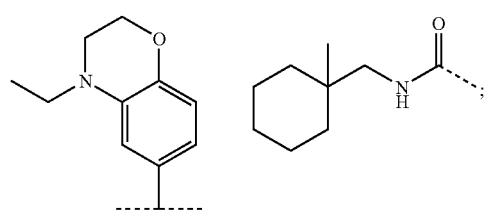 | | 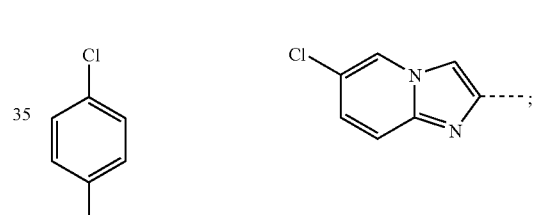 | |
| 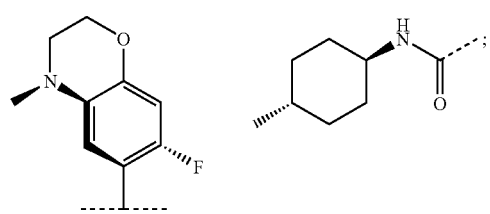 | | 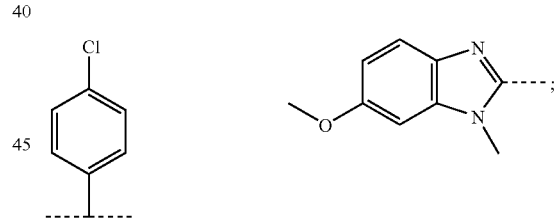 | |
| 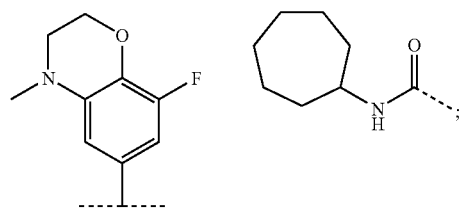 | | 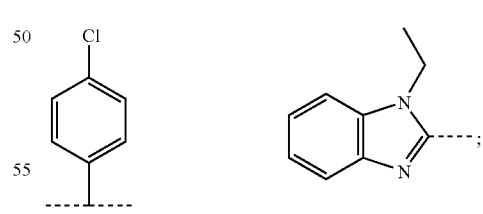 | |
| 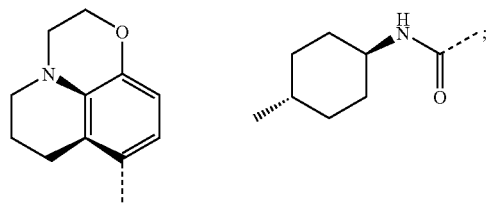 | | 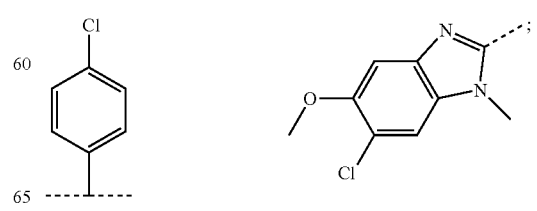 | |

-continued
| R³ | R⁵ | | R³ | R⁵ |
|---|---|---|---|---|
| 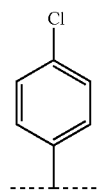 | 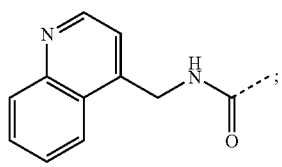 | | 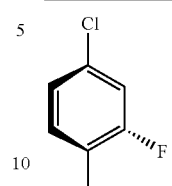 | 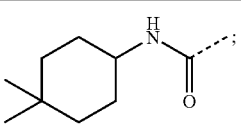 |
| 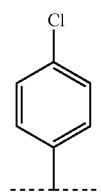 | 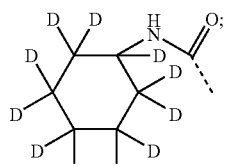 | | 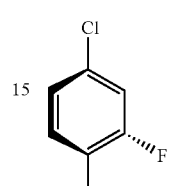 | 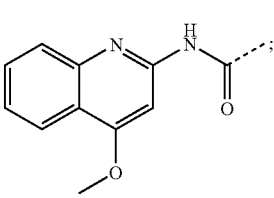 |
| 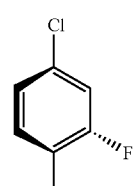 | 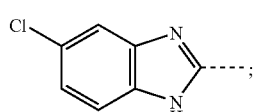 | | 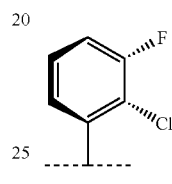 | 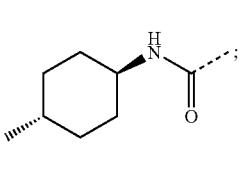 |
| 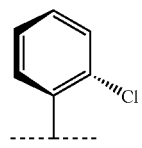 | 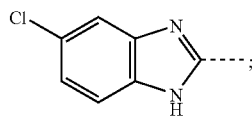 | | 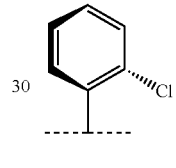 | 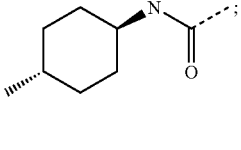 |
| 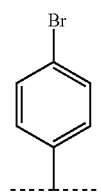 | 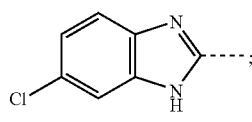 | | 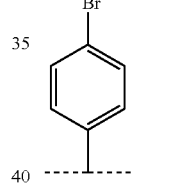 | 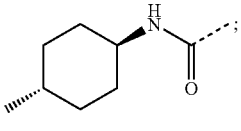 |
| 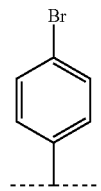 | 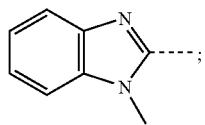 | | 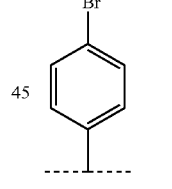 | 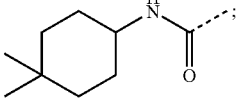 |
| 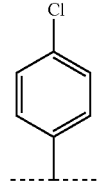 | 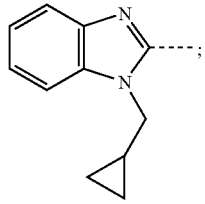 | | 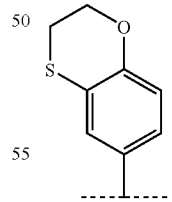 | 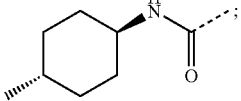 |
| 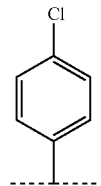 | 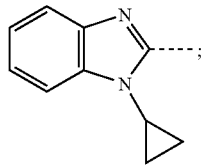 | | 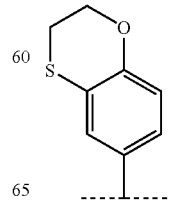 | 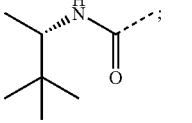 |

315
-continued

| R³ | R⁵ |
|---|---|

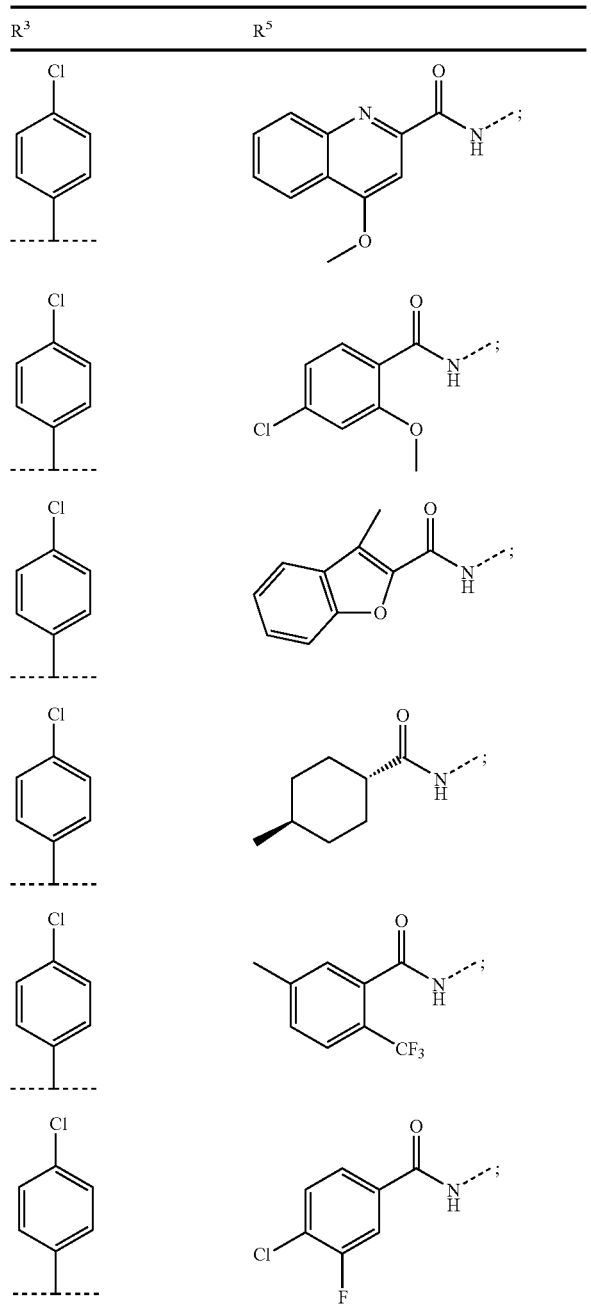

316
-continued

| R³ | R⁵ |
|---|---|

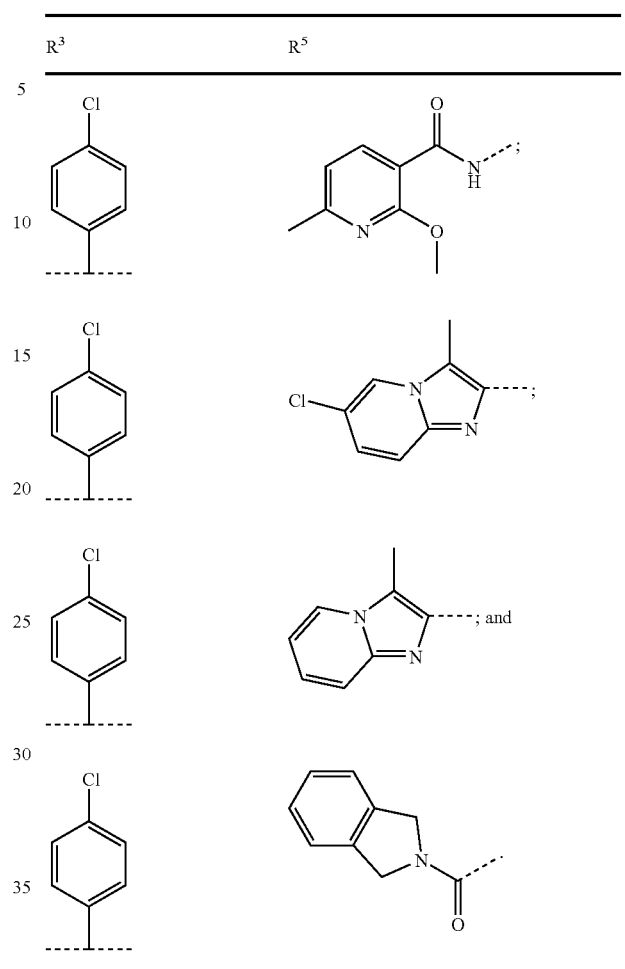

11. A pharmaceutical composition comprising a compound of formula (I) according to any one of claims 1 to 10, or a pharmaceutically acceptable salt thereof; and one or more pharmaceutically acceptable carriers.

12. A method of treating HIV infection which comprises administering to a host infected by HIV a therapeutically effective amount of a compound of formula (I) according to any one of claims 1 to 10, or a pharmaceutically acceptable salt thereof.

* * * * *